(12) United States Patent
Lindstedt et al.

(10) Patent No.: US 11,815,509 B2
(45) Date of Patent: Nov. 14, 2023

(54) CELL LINE AND USES THEREOF

(71) Applicant: SENZAGEN AB, Lund (SE)

(72) Inventors: Malin Marie Lindstedt, Sodra Sandby (SE); Carl A K Borrebaeck, Lund (SE); Henrik Johansson, Malmo (SE); Robin Gradin, Tjornarp (SE)

(73) Assignee: SENZAGEN AB, Lund (SE)

( * ) Notice: Subject to any disclaimer, the term of this patent is extended or adjusted under 35 U.S.C. 154(b) by 600 days.

(21) Appl. No.: 16/644,808

(22) PCT Filed: Sep. 24, 2018

(86) PCT No.: PCT/EP2018/075829
§ 371 (c)(1),
(2) Date: Mar. 5, 2020

(87) PCT Pub. No.: WO2019/057977
PCT Pub. Date: Mar. 28, 2019

(65) Prior Publication Data
US 2022/0178913 A1 Jun. 9, 2022

(30) Foreign Application Priority Data

Sep. 25, 2017 (GB) .................................... 1715445

(51) Int. Cl.
*G01N 33/50* (2006.01)
*C12N 5/09* (2010.01)
*C12Q 1/6876* (2018.01)

(52) U.S. Cl.
CPC ....... *G01N 33/5044* (2013.01); *C12N 5/0694* (2013.01); *C12Q 1/6876* (2013.01); *G01N 33/5023* (2013.01); *C12Q 2600/158* (2013.01)

(58) Field of Classification Search
CPC ........... G01N 33/5044; G01N 33/5023; C12N 5/0694; C12N 5/0639; C12Q 1/6876; C12Q 2600/158
See application file for complete search history.

(56) References Cited

U.S. PATENT DOCUMENTS

| | | | |
|---|---|---|---|
| 4,376,110 A | 3/1983 | David et al. | |
| 4,486,530 A | 12/1984 | David et al. | |
| 2015/0111771 A1* | 4/2015 | Lindstedt | G01N 33/5047 435/6.12 |

FOREIGN PATENT DOCUMENTS

| | | |
|---|---|---|
| WO | 2012/056236 A2 | 5/2012 |
| WO | 2013/160882 A1 | 10/2013 |
| WO | 2016/083604 A1 | 6/2016 |
| WO | 2017/162773 A1 | 9/2017 |

OTHER PUBLICATIONS

Brouwer (Human Immunology (2000) vol. 61, pp. 565-574).*

Johansson, et al., "Evaluation of the GARD assay in a blind Cosmetics Europe study" ALTEX (2017) 34(4):515-523.
Forreryd, et al., "From genome-wide arrays to tailor-made biomarker readout—Progress towards routine analysis of skin sensitizing chemicals with GARD" Toxicology in Vitro (2016) 37:178-188.
Johansson, et al., "Genomic Allergen Rapid Detection In-House Validation—A Proof of Concept" Toxicological Sci. (2014) 139(2):362-370.
Forreryd, et al., "Prediction of Chemical Respiratory Sensitizers Using GARD, a Novel In Vitro Assay Based on a Genomic Biomarker Signature" PLoS ONE (2015) 10(3): e0118808.
Zeller, et al., "The GARD Platform for Potency Assessment of Skin Sensitizing Chemicals" ALTEX (2017) 34 (4):539-559.
DSMZ, "MUTZ-3, ACC 295" Leibniz Institute, Braunschweig, Germany, available at https://www.dsmz.de/collection/catalogue/details/culture/ACC-295.
Schervish, M.J., "A Review of Multivariate Analysis" Statistical Science (1987) 2(4):396-413.
Burges, C.J.C., "A Tutorial on Support Vector Machines for Pattern Recognition" Data Mining and Knowledge Discovery (1998) 2:121-167.
The European Parliament and of the Council, "Regulation (EC) No. 1272/2008" (2008) available at http://echa.europa.eu/clp-2015.
Basketter, et al., "Categorization of Chemicals According to Their Relative Human Skin Sensitizing Potency" Dermatitis )2014) 25(1):11-21.
Basketter, et al., "Local lymph node assay—validation, conduct and use in practice" Food and Chemical Toxicology (2002) 40:593-598.
Magnusson, et al., "The Identification of Contact Allergens by Animal Assay. The Guinea Pig Maximization Test" J. Invest. Dermatol. (1969) 52(3):268-276.
Basketter, et al., "Evaluation of the skin sensitizing potency of chemicals by using the existing methods and considerations of relevance for elicitation" Contact Dermatitis (2005) 52:39-43.
Griem, et al., "Proposal for a risk assessment methodology for skin sensitization based on sensitization potency data" Regulatory Toxicology and Pharmacology (2003) 38:269-290.
World Health Organization, "Skin Sensitization in Chemical Risk Assessment" (2008) WHO Press, Geneva, Switzerland.
Fraker, et al., "Protein and cell membrane iodinations with a sparingly soluble chloroamide, 1,3,4,6-tetrachloro-3a,6a-diphenylglycoluril" Biochem. Biophys. Res. Comm. (1978) 80:849-857.
Jenkins, et al., "Arrays for protein expression profiling: Towards a viable alternative to two-dimensional gel electrophoresis?" Proteomics (2001) 1:13-29.
Lal, et al., "Antibody arrays: an embryonic but rapidly growing technology" Drug Discov. Today (2002) 7(18 Suppl): S143-9.
Zeller, et al., "An alternative biomarker-based approach for the prediction of proteins known to sensitize the respiratory tract" Toxicology in Vitro (2018) 46:155-162.

(Continued)

*Primary Examiner* — Valarie E Bertoglio
*Assistant Examiner* — Constantina E Stavrou
(74) *Attorney, Agent, or Firm* — Robert C. Netter, Jr.; Dann, Dorfman, Herrell & Skillman

(57) ABSTRACT

The present invention provides a non-naturally occurring dendritic-like myeloid leukaemia cell according to ATCC Patent Deposit Designation PTA-123875, and methods and kits utilising such cells.

2 Claims, 7 Drawing Sheets

(56) References Cited

OTHER PUBLICATIONS

Figure 1:
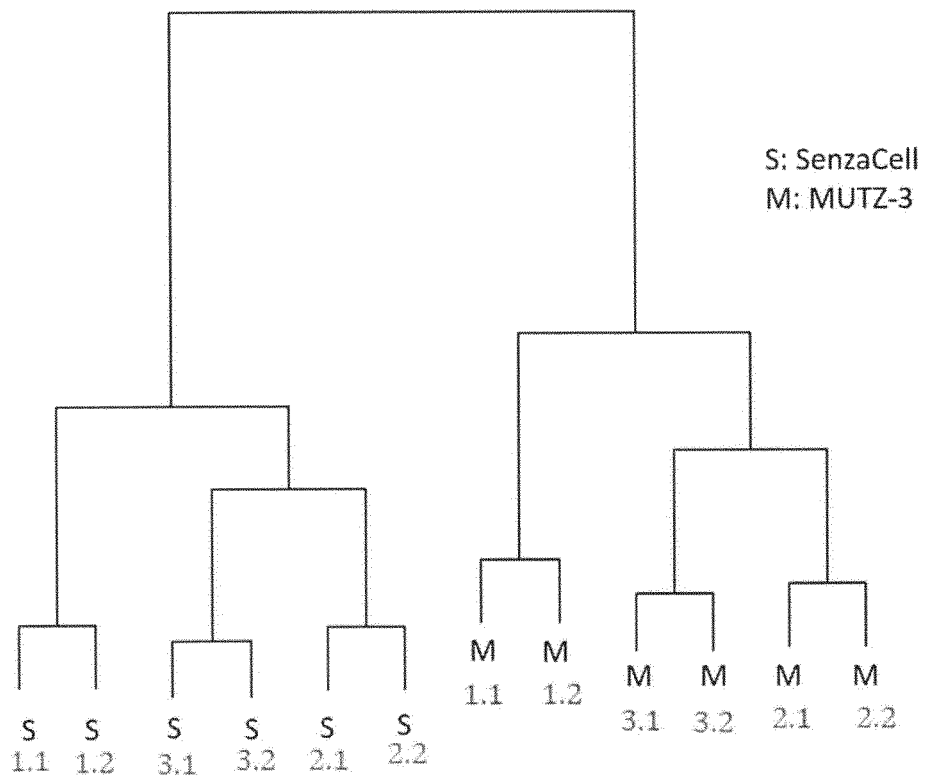

Peiser, et al., "Allergic contact dermatitis: epidemiology, molecular mechanisms, in vitro methods and regulatory aspects" Cell. Mol. Life Sci. (2012) 69:763-781.
Martin, S.F., "Allergic contact dermatitis: xenoinflammation of the skin" Current Opinion in Immunology (2012) 24:720-729.
Martin, S.F., "New concepts in cutaneous allergy" Contact Dermatitis (2015) 72:2-10.
McFadden, et al., "Why does allergic contact dermatitis exist?" British Journal of Dermatology (2013) 168:692-699.
Thyssen, et al., "The critical review of methodologies and approaches to assess the inherent skin sensitization potential (skin allergies) of chemicals: Part I" Contact Dermatitis (2012) 66(Suppl. 1):11-24.
Reisinger, et al., "Systematic evaluation of non-animal test methods for skin sensitisation safety assessment" Toxicology in Vitro (2015) 29:259-270.
Steiling, W., "Safety Evaluation of Cosmetic Ingredients Regarding Their Skin Sensitization Potential" Cosmetics (2016) 3:14.
Masterson, A.J., et al., "MUTZ-3, a human cell line model for the cytokine-induced differentiation of dendritic cells from CD34+ precursors" Blood (2002) 100:701-703.
Johansson, et al., "The GARD assay for assessment of chemical skin sensitizers" Toxicology in Vitro (2013) 27:1163-1169.
Johansson, et al., "A genomic biomarker signature can predict skin sensitizers using a cell-based in vitro alternative to animal tests" BMC Genomics (2011) 12:399.
Geraghty, et al., "Guidelines for the use of cell lines in biomedical research" British Journal of Cancer (2014) 111:1021-1046.
Dumont, et al., "Human cell lines for biopharmaceutical manufacturing: history, status, and future perspectives" Crit. Rev. Biotechnol. (2016) 36(6):1110-1122.
Kaur, et al., "Cell lines: Valuable tools or useless artifacts" Spermatogenesis (2012) 2:1.
Hughes, et al., "The costs of using unauthenticated, over-passaged cell lines: how much more data do we need?" Bio Techniques (2007) 43:575-586.
The R Foundation, "The R Project for Statistical Computing" (2020) available at https://www.r-project.org.
Hennig, C., "fpc: Flexible Procedures for Clustering" (2020) available at https://cran.r-project.org/web/packages/fpc/index.html.
McKenna, et al., "The Genome Analysis Toolkit: A MapReduce framework for analyzing next-generation DNA sequencing data" Genome Research (2010) 20:1297-1303.
Van Der Auwera, et al., "From FastQ data to high confidence variant calls: the Genome Analysis Toolkit best practices pipeline" Curr. Protoc. Bioinformatics (2013) 11(1110):11.10.1-11.10.33.
Congolani, et al., "A program for annotating and predicting the effects of single nucleotide polymorphisms, SnpEff SNPs in the genome of Drosophila melanogaster strain w1118; iso-2; iso-3" Fly (2012) 6:80-92.
Congolani, et al., "Using Drosophila melanogaster as a model for genotoxic chemical mutational studies with a new program, SnpSift" Frontiers in Genetics (2012) 3:35.
Carson, et al., "Effective filtering strategies to improve data quality from population-based whole exome sequencing studies" BMC Bioinformatics (2014) 15:125.
Mi, et al., "Large-scale gene function analysis with the PANTHER classification system" Nature Protocols (2013) 8 (8):1551-1566.
Trapnell, et al., "TopHat: discovering splice junctions with RNA-Seq" Bioinformatics (2009) 25(9):1105-1111.
Li, et al., "The Sequence Alignment/Map format and SAMtools" Bioinformatics (2009) 25(16):2078-2079.
Anders, et al., "HTSeq—a Python framework to work with high-throughput sequencing data" Bioinformatics (2015) 31(2):166-169.
Robinson, et al., "edgeR: a Bioconductor package for differential expression analysis of digital gene expression data" Bioinformatics (2010) 26(1):139-140.
Love, et al., "Moderated estimation of fold change and dispersion for RNA-Seq data with DESeq2" bioRxiv (2014) doi.org/10.1101/002832.
Tarca, et al., "A novel signaling pathway impact analysis" Bioinformatics (2009) 25(1):75-82.
Kanehisa, et al., KEGG as a reference resource for gene and protein annotation Nucleic Acids Research (2016) 44: D457-D462.
Kanehisa, et al., "KEGG: Kyoto Encyclopedia of Genes and Genomes" Nucleic Acids Research (2000) 28(1):27-30.
Kwiecien, et al., "Concordance Analysis: Part 16 of a Series on Evaluation of Scientific Publications" Dtsch. Arztebl. Int. (2011) 108(30):515-21.
Meyer, et al., "e1071: Misc Functions of the Department of Statistics, Probability Theory Group (Formerly: E1071)" (2019) available at https://cran.r-project_org/web/packages/e1071/index.html.
Haneke, et al., "ICCVAM Evaluation of the Murine Local Lymph Node Assay: Ill. Data Analyses Completed by the National Toxicology Program Interagency Center for the Evaluation of Alternative Toxicological Methods" Regulatory Toxicology and Pharmacology (2001) 34:274-286.
Uirbisch, et al., "Assessing skin sensitization hazard in mice and men using non-animal test methods" Regulatory Toxicology and Pharmacology (2015) 71:337-351.
Santegoets, et al., "A CD34+ human cell line model of myeloid dendritic cell differentiation: evidence for a CD14+CD11b+ Langerhans cell precursor" Journal of Leukocyte Biology (2006) 80:1337-1344.
Kim, et aL, "Impaired responses of leukemic dendritic cells derived from a human myeloid cell line to LPS stimulation" Experiment. Mol. Med. (2006) 38(1):72-84.
Rasaiyaah, et al., "Transcriptional and functional defects of dendritic cells derived from the MUTZ-3 leukaemia line" Immunology (2009) 127:429-441.
Fanger, et al., "Type I (CD64) and Type II (CD32) Fc Gamma Receptor-Mediated Phagocytosis by Human Blood Dendritic Cells" J. Immunol. (1996) 157:541-548.
Iwasaki, et al., "Toll-like receptor control of the adaptive immune responses" Nature Immunol. (2004) 5(10):987-995.
Medzhitov, et aL, "A human homologue of the Drosophila Toll protein signals activation of adaptive immunity" Nature (1997) 388:394-397.
Takeda, et al., "Toll-like receptors in innate immunity" International Immunology (2005) 17(1):1-14.
Gadhoum, et al., "Lewis x/CD15 expression in human myeloid cell differentiation is regulated by sialidase activity" Nat. Chem. Biol. (2008) 4(12):751-757.
THE 1000 Genomes Project Consortium, "A global reference for human genetic variation" Nature (2015) 526:68-74.
Nugoli, et al., "Genetic variability in MCF-7 sublines: evidence of rapid genomic and RNA expression profile modifications" BMC Cancer (2003) 3:13.
Ramsay, et al., "MYB function in normal and cancer cells" Nat. Reviews Cancer (2008) 8:523-534.
Logan, et al., "The WNT Signaling Pathway in Development and Disease" Annu. Rev. Cell Dev. Biol. (2004) 20:781-810.
Nusse, R., "Wnt signaling and stem cell control" Cell Research (2008) 18:523-527.
Polakis, P., "Wnt signaling and cancer" Genes & Development (2000) 14:1837-1851.
The Gene Ontology Consortium, "Gene Ontology Consortium: going forward" Nucleic Acids Research (2015) 43:D1049-D1056.
Pearson, et al., "Mitogen-Activated Protein (MAP) Kinase Pathways: Regulation and Physiological Functions" Endocrine Reviews (2001) 22(2): 153-183.
Lawrence, T., "The Nuclear Factor NF-kB Pathway in Inflammation" Cold Spring Harb. Perspect. Biol. (2009) 1: a001651.
PCT/EP2018/075829, International Search Report, dated 2018, pp. 1-4.

\* cited by examiner

2HA; 2-hydroxyethyl acrylate
DNCB; 2,4-dinitrochlorobenzene
unstim; unstimulated control

CELL LINE AND USES THEREOF

This application is a § 371 application of PCT/EP2018/075829, filed Sep. 24, 2018, which claims priority to GB 1715445.1, filed Sep. 25, 2017. The foregoing applications are incorporated by reference herein.

FIELD OF INVENTION

The present invention provides a non-naturally occurring dendritic-like cell line and methods and kits utilising such cells.

BACKGROUND

Dendritic cells (DCs) play key roles in the immune response by bridging the essential connections between innate and adaptive immunity. They can, upon triggering, rapidly produce large amounts of mediators, which influence migration and activation of other cells at the site of inflammation, and selectively respond to various pathogens and environmental factors, by fine-tuning the cellular response through antigen-presentation. Thus, exploring and utilizing the immunological decision-making by DCs during stimulation with sensitizers, can serve as a potent test strategy for prediction of sensitization.

However, multifaceted phenotypes and specialized functions of different DC subpopulations, as well as their wide and scarce distribution, are complicating factors, which impede the employment of primary DCs as a test platform. Hence, there is a real need to establish accurate and reliable in vitro assays that also circumvent the problems associated with variability of and difficulty in obtaining primary DCs, such as by utilising dendritic-like model cell lines.

The Genomic Allergen Rapid Detection (GARD) is an in vitro assay developed for the assessment of chemical and protein sensitizers and allergens. It uses transcriptional profiles from a dendritic cell-like cell line, to predict the sensitizing or allergenic potential of test agents (9). The transcriptional profiles consist of genes that were identified as having the greatest predicting performance in distinguishing sensitizers from non-sensitizers. Specifically, GARD has been developed to identify: skin sensitizers (WO 2012/056236; Johansson et al. (2017) Evaluation of the GARD assay in a blind Cosmetics Europe study. ALTEX Online first Feb. 17, 2017; Forreryd et al. (2016) From genome-wide arrays to tailor-made biomarker readout—Progress towards routine analysis of skin sensitizing chemicals with GARD. Toxicolgy In Vitro; Johansson et al. (2014) GARD in-house validation—A proof of concept. Tox Sci; Johansson et al., (2011) A genomic biomarker signature can predict skin sensitizers using a cell-based in vitro alternative to animal tests. BMC Genomics, 2011); respiratory sensitizers (WO 2013/160882; WO 2016/083604; Forreryd et al. (2015) Prediction of chemical Respiratory sensitizers using GARD, a novel in vitro assay based on a genomic biomarker signature. PLoS One 10(3)); the potency of skin sensitizers (PCT/EP2017/056878; Zeller et al. (2017) The GARD platform for potency assessment of skin sensitizing chemicals. ALTEX Online first published Apr. 12, 2017, version 2 https://doi.org/10.14573/altex.1701101); and the allergenicity of proteins.

SUMMARY OF INVENTION

The inventors now provide a non-naturally occurring dendritic-like myeloid leukemia cell line termed "SenzaCell" (ATCC Patent Deposit Designation PTA-123875) as a preferred dendritic cell-like cell line suitable for use in GARD assays. SenzaCell has been compared to the MUTZ-3 cell line which may also be used in GARD assays; MUTZ-3 cells are dendritic-like cells available from Deutsche Sammlung für Mikroorganismen und Zellkulturen GmbH (DSMZ), Braunschweig, Germany (www.dsmz.de; DSMZ No. ACC 295). MUTZ-3 cells are however protocolled to require culture with a feeder cell line which complicates their use. Therefore, there remains a need for alternatives to MUTZ-3 for use in methods such as the GARD assays.

The comparison between SenzaCell and MUTZ-3 included a phenotypic analysis where the expression of a panel of biomarkers were compared, a transcriptional analysis where the transcription levels of the cell lines were compared, a comparison of their DNA sequences and a functional analysis, which revealed many quantifiable differences in the phenotype and transcriptional profiles and yet showed shared functionality in the GARD assays.

Therefore, in a first aspect of the invention there is provided a non-naturally occurring dendritic-like myeloid leukaemia cell according to ATCC Patent Deposit Designation PTA-123875.

The cell is also referred to herein as "SenzaCell". SenzaCell (ATCC Patent Deposit Designation PTA-123875) was deposited at the American Type Culture Collection (ATCC), 10801 University Blvd, Manassas, VA 20110, USA, by SenzaGen AB on 9 Mar. 2017.

By "non-naturally occurring", we mean that the cell is different to, modified from, and/or a variant of, those which would be found in nature; in other words, they are not cells which would normally occur in nature. For example, different to, modified from, and/or a variant of, a naturally occurring human myeloid leukaemia cell or a naturally occurring dendritic cell.

In a second aspect of the invention there is provided a cell culture comprising a population of cells according to the first aspect.

In one embodiment the cell or population of cells comprises or consists of immortal or immortalised cells. By "immortal" we mean cells that are not limited by a point at which they can no longer continue to divide, which might otherwise be due to DNA damage or shortened telomeres. In an additional or alternative embodiment the cell or population of cells comprises or consists of undifferentiated cells.

In a third aspect of the invention there is provided an in vitro method for identifying agents capable of inducing sensitization and/or allergenicity in a mammal comprising or consisting of the steps of:

a) exposing a population of the dendritic-like cells according to the first or second aspect to a test agent; and b) measuring in the cells the expression of one or more biomarker(s) selected from the group defined in one or more of Tables A, B, C, D, and E;

wherein the expression in the cells of the one or more biomarkers measured in step (b) is indicative of the sensitizing and/or allergenic effect of the test agent.

In a fourth aspect of the invention there is provided an in vitro method for identifying agents capable of inducing sensitization of mammalian skin comprising or consisting of the steps of:

a) exposing a population of the dendritic-like cells according to the first or second aspect to a test agent; and b) measuring in the cells the expression of one or more biomarker(s) selected from the group defined in Table A;

wherein the expression in the cells of the one or more biomarkers measured in step (b) is indicative of the skin sensitizing effect of the test agent.

Methods for identifying agents capable of inducing sensitization of mammalian skin which may use the dendritic-like cells according to the invention are described in the functional analysis section of Example 1. The methods described in WO 2012/056236; Johansson et al. (2017) Evaluation of the GARD assay in a blind Cosmetics Europe study. ALTEX Online first Feb. 17, 2017; Forreryd et al. (2016) From genome-wide arrays to tailor-made biomarker readout—Progress towards routine analysis of skin sensitizing chemicals with GARD. Toxicolgy In Vitro; Johansson et al. (2014) GARD in-house validation—A proof of concept. Tox Sci; Johansson et al., (2011) A genomic biomarker signature can predict skin sensitizers using a cell-based in vitro alternative to animal tests. BMC Genomics, 2011, which are all incorporated herein by reference, may also be used.

In one embodiment, the method is for identifying agents capable of inducing a hypersensitivity response in human skin. Preferably, the hypersensitivity response is a cell-mediated hypersensitivity response, for example, a Type IV hypersensitivity response. Preferably, the hypersensitivity response is a Type IV delayed-type hypersensitivity reaction in a mammal. Preferably, the Type IV delayed-type hypersensitivity reaction is DC-mediated. Preferably, the method is for identifying agents capable of inducing allergic contact dermatitis (ACD) (i.e. the hypersensitivity response is ACD).

In one embodiment, the "agents capable of inducing sensitization of mammalian skin" is an agent capable of inducing and triggering a Type IV delayed-type hypersensitivity reaction at a site of epidermal contact in a mammal.

In a fifth aspect of the invention there is provided a method for identifying agents capable of inducing respiratory sensitization in a mammal comprising or consisting of the steps of:
  a) exposing a population of the dendritic-like cells according to the first or second aspect to a test agent; and
  b) measuring in the cells the expression of one or more biomarker(s) selected from the group defined in Table B;
  wherein the expression in the cells of the one or more biomarkers measured in step (b) is indicative of the respiratory sensitizing effect of the test agent.

In a sixth aspect of the invention there is provided a method for identifying agents capable of inducing respiratory sensitization in a mammal comprising or consisting of the steps of:
  a) exposing a population of the dendritic-like cells according to the first or second aspect to a test agent; and
  b) measuring in the cells the expression of one or more biomarker(s) selected from the group defined in Table C;
  wherein the expression in the cells of the one or more biomarkers measured in step (b) is indicative of the respiratory sensitizing effect of the test agent.

The methods of the fifth and sixth aspects may be combined such that step (b) comprises measuring in the cells the expression of one or more biomarker(s) selected from the group defined in Tables B and/or C.

Methods for identifying agents capable of inducing respiratory sensitization in a mammal which may use the dendritic-like cells according to the invention are discussed in Example 2. The methods described in WO 2013/160882; WO 2016/083604; and Forreryd et al. (2015) Prediction of chemical Respiratory sensitizers using GARD, a novel in vitro assay based on a genomic biomarker signature. PLoS One 10(3), which are all incorporated herein by reference, may also be used.

By "agents capable of inducing respiratory sensitization" we mean any agent capable of inducing and triggering a Type I immediate hypersensitivity reaction in the respiratory tract of a mammal. Preferably, the Type I immediate hypersensitivity reaction is DC-mediated and/or involves the differentiation of T cells into Th2 cells. Preferably the Type I immediate hypersensitivity reaction results in humoral immunity and/or respiratory allergy.

In one embodiment, the "agents capable of inducing sensitization of mammalian skin" is an agent capable of inducing and triggering a Type I immediate hypersensitivity reaction at a site of lung epithelium in a mammal. Preferably, the site of lung epithelium is in the respiratory zone of the lung, but may alternatively or additionally be in the conductive zone of the lung.

In a seventh aspect of the invention there is provided a method for determining the skin sensitizing potency of an agent comprising or consisting of the steps of:
  (a) providing a population of the dendritic-like cells according to the first or second aspect;
  (b) exposing the cells provided in step (a) to a test agent; and
  (c) measuring in the cells of step (b) the expression of one or more biomarkers selected from the group defined in Table D;
  wherein the expression of the one or more biomarkers measured in step (c) is indicative of the skin sensitizing potency of the test agent of step (b).

Methods for determining the skin sensitizing potency of an agent which may use the dendritic-like cells according to the invention are discussed in Example 3. The methods described in Zeller et al. (2017), The GARD platform for potency assessment of skin sensitizing chemicals. ALTEX Online first published Apr. 12, 2017, version 2 https://doi.org/10.14573/altex.1701101 and PCT/EP2017/056878, which is incorporated herein by reference, may also be used.

In an eighth aspect of the invention there is provided a method for identifying proteins which are allergenic in a mammal comprising or consisting of the steps of:
  (a) providing a population of the dendritic-like cells according to the first or second aspect;
  (b) exposing the cells provided in step (a) to a test protein; and
  (c) measuring in the cells of step (b) the expression of one or more biomarkers selected from the group defined in Table E;
  wherein the expression of the one or more biomarkers measured in step (c) is indicative of the allergenicity of the test protein of step (b).

Methods for identifying proteins which are allergenic in a mammal which may use the dendritic-like cells according to the invention are discussed in detail in Example 4.

In one embodiment the method according to any aspect of the invention further comprises:
  d) exposing a separate population of the dendritic-like cells according to the first or second aspect to one or more negative control agent that does not induce sensitization and/or allergy in a mammal; and
  e) measuring in the cells of step (d) the expression of the one or more biomarkers measured in step (b) or (c)
  wherein the test agent is identified as a sensitizer and/or as allergenic in the event that the expression of the one or more biomarkers measured in step (e) differs from the expression of the one or more biomarkers measured in step (b) or (c).

A vehicle control may be used as the negative control agent. The vehicle control may comprise DMSO and/or distilled water.

In an additional or alternative embodiment unstimulated cells may be used as the negative control. By "unstimulated cells" we include or mean cells which have not been exposed to a specific test agent.

In an additional or alternative embodiment the one or more negative control agent may comprise or consist of one or more agent selected from the group consisting of 1-Butanol; 2-Aminophenol; 2-Hydroxyethyl acrylate; 2-nitro-1, 4-Phenylenediamine; 4-Aminobenzoic acid; Chlorobenzene; Dimethyl formamide; Ethyl vanillin; Formaldehyde; Geraniol; Hexylcinnamic aldehyde; Isopropanol; Kathon CG*; Methyl salicylate; Penicillin G; Propylene glycol; Potassium Dichromate; Potassium permanganate; Tween 80; and Zinc sulphate.

In an additional or alternative embodiment the expression of the one or more biomarkers measured in step (b) or (c) is measured in the cells provided in step (a) prior to and following exposure to the test agent, and wherein the difference in expression between the one or more biomarkers prior to and following exposure to the test agent is indicative of the allergenicity and/or sensitizing effect of the test agent. Hence, the cells provided in step (a) may provide both the negative control and the test result.

By "differs from the expression of the one or more biomarkers measured in step (b) or (c)" and "difference in expression" we include that the presence and or amount in a first sample (e.g., a test agent sample) differs from that of a second sample (e.g., a control agent sample).

For example, the presence and/or amount in the test sample may differ from that of the one or more negative control sample in a statistically significant manner. Preferably the expression of the one or more biomarkers in the cell population exposed to the test agent is:

less than or equal to 80% of that of the cell population exposed to the negative control agent, for example, no more than 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or 0% of that of the cell population exposed to the negative control or negative control agent; or at least 120% of that of the cell population exposed to the negative control agent, for example, at least 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, 225%, 250%, 275%, 300%, 325%, 350%, 375%, 400%, 425%, 450%, 475% or at least 500% of that of the cell population exposed to the negative control or negative control agent By "differs from the expression of the one or more biomarkers measured in step (b) or (c)" we alternatively or additionally include that the test sample is classified as belonging to a different group as the one or more negative control sample. For example, where an SVM is used, the test sample is on the other side of the decision value threshold as the one or more negative control sample (e.g., if the test agent is classified as a protein allergen if one or more test (or replicate thereof) has an SVM decision value of ≤0, then the one or more positive control samples (or the majority thereof) should also have an SVM decision value of ≤0).

In an additional or alternative embodiment the method according to any aspect of the invention further comprises:
f) exposing a separate population of the dendritic-like cells according to the first or second aspect to one or more positive control agent that induces sensitization and/or is allergenic in a mammal; and
g) measuring in the cells of step (f) the expression of the one or more biomarkers measured in step (b) or (c)
wherein the test agent is identified as a sensitizer and/or as allergenic in the event that the expression of the one or more biomarkers measured in step (f) corresponds to the expression of the one or more biomarkers measured in step (b) or (c).

In an additional or alternative embodiment, the one or more positive control agent provided in step (f) comprises or consists of one or more agent selected from the group consisting of: Der p 1; and Der p 7.

In an additional or alternative embodiment, the one or more positive control agent may comprise or consist of one or more agent selected from the group consisting of Ammonium hexachloroplatinate; Ammonium persulfate; Ethylenediamine; Glutaraldehyde; Hexamethylen diisocyanate; Maleic Anhydride; Methylene diphenol diisocyanate; Phtalic Anhydride; Toluendiisocyanate; and Trimellitic anhydride.

By "corresponds to the expression of the one or more biomarkers measured in step (b) or (c)" we mean the expression of the one or more biomarkers in the cell population exposed to the test agent is identical to, or does not differ significantly from, that of the cell population exposed to the one more positive control agent. Preferably the expression of the one or more biomarkers in the cell population exposed to the test agent is between 81% and 119% of that of the cell population exposed to the one more positive control agent, for example, greater than or equal to 82%, 83%, 84%, 85%, 86%, 87%, 88%, 89%, 90%, 91%, 92%, 93%, 94%, 95%, 96%, 97%, 98% or 99% of that of the cell population exposed to the one more positive control agent, and less than or equal to 101%, 102%, 103%, 104%, 105%, 106%, 107%, 108%, 109%, 110%, 111%, 112%, 113%, 114%, 115%, 116%, 117%, 118% or 119% of that of the cell population exposed to the one more positive control agent.

By "corresponds to the expression of the one or more biomarkers measured in step (b) or (c)" we alternatively or additionally include that the test sample is classified as belonging to the same group as the one or more positive control sample. For example, where an SVM is used, the test sample is on the same side of the decision value threshold as the one or more positive control sample (e.g., if the test agent is classified as allergenic if one or more test (or replicate thereof) has an SVM decision value of >0, then the one or more positive control samples (or the majority thereof) should also have an SVM decision value of >0).

In an additional or alternative embodiment, the method is indicative of the allergenic and/or sensitizing potency of the agent to be tested. For example, the method may be used to predict the relative allergenic and/or sensitizing potency of a test agent compared to a positive control and/or compared to one or more additional test agents.

In an additional or alternative embodiment the methods comprises the further step of:

(h) identifying the allergenic and/or sensitizing effect of the test agent.

For example, step (h) may identify the test agent as being an allergen or a non-allergen and/or as a sensitizer or a non-sensitizer. Alternatively or additionally, step (h) may identify the relative allergenicity or allergenic potency and/or sensitizing effect or sensitizing potency of the test agent compared to a positive control and/or one or more additional test agents.

The identification may be performed using any suitable statistical method or machine learning algorithm known in the art, such as Random Forest (RF), Support Vector Machine (SVM), Principal Component Analysis (PCA), ordinary least squares (OLS), partial least squares regression (PLS), orthogonal partial least squares regression (O-PLS) and other multivariate statistical analyses (e.g., backward stepwise logistic regression model). For a review of multivariate statistical analysis see, for example, Schervish, Mark J. (November 1987). "A Review of Multivariate Analysis". Statistical Science 2 (4): 396-413 which is incorporated herein by reference. Preferably, Support Vector Machine (SVM) is used.

Typically, allergenic or sensitizing agents are identified using a support vector machine (SVM), such as those available from http://cran.r-project.org/web/packages/e1071/index.html (e.g. e1071 1.5-24). However, any other suitable means may also be used. SVMs may also be used to determine the ROC AUCs of biomarker signatures comprising or consisting of one or more biomarkers as defined herein.

Support vector machines (SVMs) are a set of related supervised learning methods used for classification and regression. Given a set of training examples, each marked as belonging to one of two categories, an SVM training algorithm builds a model that predicts whether a new example falls into one category or the other. Intuitively, an SVM model is a representation of the examples as points in space, mapped so that the examples of the separate categories are divided by a clear gap that is as wide as possible. New examples are then mapped into that same space and predicted to belong to a category based on which side of the gap they fall on.

More formally, a support vector machine constructs a hyperplane or set of hyperplanes in a high or infinite dimensional space, which can be used for classification, regression or other tasks. Intuitively, a good separation is achieved by the hyperplane that has the largest distance to the nearest training datapoints of any class (so-called functional margin), since in general the larger the margin the lower the generalization error of the classifier. For more information on SVMs, see for example, Burges, 1998, *Data Mining and Knowledge Discovery*, 2:121-167.

In one embodiment of the invention, the SVM is 'trained' prior to performing the methods of the invention using biomarker profiles of known agents (namely, known allergenic/sensitizer or non-allergenic/non-sensitizer agents). By running such training samples, the SVM is able to learn what biomarker profiles are associated with agents capable of inducing allergy and/or sensitization. Once the training process is complete, the SVM is then able to predict whether or not the biomarker sample tested is from an allergenic or non-allergenic/sensitizing or non-sensitizing agent.

Decision values for individual SVMs can be determined by the skilled person on a case-by-case basis. In one embodiment, the test agent is classified as allergenic and/or a sensitizer if one or more test (or replicate thereof) have an SVM decision value of >0. In one embodiment, the test agent is classified as non-allergenic and/or a non-sensitizer if one or more test (or replicate thereof) have an SVM decision value of ≤0. This allows test agents to be classified as allergenic or non-allergenic/sensitizing or non-sensitizing.

However, this training procedure can be by-passed by pre-programming the SVM with the necessary training parameters. For example, allergenic and/or sensitizing agents can be identified according to the known SVM parameters using the SVM algorithm described in WO 2012/056236, WO 2013/160882, or WO 2016/083604, based on the measurement of all the biomarkers listed in one or more of Tables A-E.

It will be appreciated by skilled persons that suitable SVM parameters can be determined for any combination of the biomarkers listed in Tables A-E by training an SVM machine with the appropriate selection of data (i.e. biomarker measurements from cells exposed to known allergenic and/or non-allergenic agents or sensitizing and/or non-sensitizing agents). Alternatively, the Table A-E biomarkers may be used to identify allergenic proteins and/or sensitizing agents according to any other suitable statistical method known in the art.

Alternatively, the Table A-E data may be used to identify agents capable of inducing allergy and/or sensitization according to any other suitable statistical method known in the art (e.g., ANOVA, ANCOVA, MANOVA, MANCOVA, Multivariate regression analysis, Principal components analysis (PCA), Factor analysis, Canonical correlation analysis, Canonical correlation analysis, Redundancy analysis Correspondence analysis (CA; reciprocal averaging), Multidimensional scaling, Discriminant analysis, Linear discriminant analysis (LDA), Clustering systems, Recursive partitioning and Artificial neural networks).

Preferably the methods of the invention are performed in vitro.

In an additional or alternative embodiment steps (b), (c), (e) and/or (g) of the methods of the invention comprise or consist of measuring the expression of two or more biomarkers listed in Tables A, B, C, D or E, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, or 391 of the biomarkers listed in Tables A, B, C, D or E. For example, steps (b), (c), (e) and/or (g) may comprise or consist of measuring the expression of all of the biomarkers listed in Tables A, B, C, D or E.

By "expression" we mean the presence, level and/or amount of the biomarker.

By "biomarker" we include any biological molecule, or component or fragment thereof, the measurement of which can provide information useful in determining the sensitizing effect and/or the allergenicity of a test agent. Thus, in the context of Tables A, B, C, D, and E, the biomarker may be a nucleic acid molecule, such as a mRNA or cDNA. Alternatively, the biomarker may be a protein encoded by the nucleic acid molecule or carbohydrate moiety, or an antigenic component or fragment thereof.

In an additional or alternative embodiment of the method of the seventh aspect the test agent is already known to be, or suspected of being, capable of inducing sensitization of the skin. For example, the test agent may already be known to be capable of inducing sensitization of the skin by using a method already known in the art, for instance a method described WO 2012/056236 and/or Johansson H et al. The GARD assay for assessment of chemical skin sensitizers. Toxicology in vitro 2013 which are incorporated herein by reference. In an alternative or additional embodiment, the method is for identifying skin sensitizer potency and skin sensitizer/non-sensitizer status of the test agent (i.e., identifying whether the test agent is a sensitizer or not and identifying its potency as a skin sensitizer). In an alternative or additional embodiment, the method comprises identifying whether the test agent is a sensitizer using the method described in WO 2012/056236 and/or Johansson H et al.

By "skin sensitizing potency" we include or mean the strength of the skin sensitizing ability of an agent. For example, the relative potency or strength of sensitizing ability of an agent might lead to the ordering of a group of test agents from most potent to least potent or vice versa, and/or it might lead to their categorization according to one or more known regulation or system. By "sensitization status" we include or mean whether or not a chemical entity (or mixture of chemical entities) is a sensitizer or not (e.g., a skin sensitizer and/or a respiratory sensitizer).

By "skin sensitizing" we mean any agent capable of inducing and triggering a Type IV delayed-type hypersensitivity reaction in a mammal. Preferably, the Type IV delayed-type hypersensitivity reaction is DC-mediated.

In an additional or alternative embodiment the skin sensitization potency determined by the method is categorised according to the European Classification, Labelling and Packaging (CLP) Regulation (EC) 1272/2008 (http://echa.europa.eu/clp-2015). This system is based on the United Nations' Globally Harmonised System (GHS) and from June 2015, the only legislation to apply to the classification and labelling of both substances and mixtures. It requires companies to classify, label and package their products appropriately before placing them on the market. It provides the categories: 1A (strong), 1B (weak), or no cat (no sensitizer).

For example, the method may provide:
(i) one or more agent of potency category 1A;
(ii) one or more agent of potency category 1B; and/or
(iii) one or more agent of potency category no category In an additional or alternative embodiment the skin sensitization potency determined by the method is categorised according to the system described in Basketter et al., 2014, 'Categorization of chemicals according to their relative human skin sensitizing potency,' Dermatitis, 25(1):11-21, i.e. categories 1 (strongest sensitizer), 2, 3, 4, 5, or 6 (true non-sensitizer) (e.g. Table 4, FIG. 4).

For example, the method may provide:
(i) one or more agent of potency category 1;
(ii) one or more agent of potency category 2;
(iii) one or more agent of potency category 3;
(iv) one or more agent of potency category 4;
(v) one or more agent of potency category 5; and/or
(vi) one or more agent of potency category 6 (e.g., see present Table 8 and/or Basketter et al., 2014 supra.).

In an additional or alternative embodiment skin sensitization potency is categorised according to the local lymph node assay (LLNA) classification, Guinea pig maximisation test (GPMT) or no observed-effect level (NOEL).

For a detailed description of LLNA see Basketter, D. A., et al., *Local lymph node assay—validation, conduct and use in practice*. Food Chem Toxicol, 2002. 40(5): p. 593-8 which is incorporated herein by reference. For a detailed description of the guinea pig maximization test see Magnusson, B. and A. M. Kligman, *The identification of contact allergens by animal assay. The guinea pig maximization test*. J Invest Dermatol, 1969. 52(3): p. 268-76, which is incorporated herein by reference. For a detailed description of the no observed-effects level (NOEL) test in relation to skin sensitizer potency see Basketter et al., 2005, 'Evaluation of the skin sensitizing potency of chemicals by using the existing methods and considerations of relevance for elicitation' *Contact Dermatitis*, 52(1):39-43; and Griem, P., et al., 2003, 'Proposal for a risk assessment methodology for skin sensitization based on sensitization potency data.' *Regul. Toxicol. Pharmacol.*, 38:269-290 which are incorporated herein by reference. For a correlation between NOEL and potency levels, see also WHO Library Cataloguing-in-Publication Data. Skin sensitization in chemical risk assessment. (IPCS harmonization project document: no. 5), ISBN 978 92 4 156360 4 (in particular, Table 1 on pages 26-28) which is incorporated herein by reference. For a detailed description of CLP, see (http://echa.europa.eu/clp-2015), which is incorporated herein by reference.

In an additional or alternative embodiment the expression of one or more biomarkers measured in step (c) is measured in the cells provided in step (a) prior to and following exposure to the skin sensitizing agent of predetermined potency, and wherein the difference in expression between the one or more biomarkers prior to and following exposure to the test agent is indicative of the potency of the skin sensitizing agent of step (b).

In an additional or alternative embodiment the expression of one or more biomarkers measured in step (c) is measured in the cells provided in step (a) prior to and following exposure to the skin sensitizing agent of predetermined potency, and wherein the difference in expression between the one or more biomarkers prior to and following step (c) is indicative of the potency of the skin sensitizing agent of step (b).

By 'difference in expression' we include that the presence and or amount in a first sample (e.g., a test agent sample) differs from that of a second sample (e.g., a control agent sample). Preferably the presence and/or amount is no more than 40% of that of the comparison sample, for example, no more than 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or 0%.

In an additional or alternative embodiment the one or more biomarker is measured in the cells provided in step (a) prior to and following exposure to the test agent, and wherein the difference in expression between the one or more biomarkers prior to and following exposure to the test agent is indicative of the skin sensitizing potency of the test agent of step (b). Hence, the cells provided in step (a) may provide both the negative control and the test result.

In an additional or alternative embodiment the one or more biomarker is measured in the cells provided in step (a) prior to and following exposure to the test agent, and wherein the difference in expression between the one or more biomarkers prior to and following step (c) is indicative of the skin sensitizing potency of the test agent of step (b). Hence, the cells provided in step (a) may provide both the negative control and the test result.

In an additional or alternative embodiment the method comprises the further steps of:
 (i) providing a further population of dendritic-like cells according to the first or second aspect;
 (j) exposing the cells provided in step (i) to a skin sensitizing agent of predetermined potency;
 (k) measuring in the cells of step (j) the expression of the one or more biomarkers measured in step (c);
 wherein the correspondence in expression between the one or more biomarkers measured in step (c) and the one or more biomarkers measured in step (k) is indicative of the skin sensitizing potency of the test agent.

By 'correspondence in expression' we include that that the presence and or amount in a first sample (e.g., a test agent sample) is similar or identical to the presence and/or amount in a second sample (e.g., a control sample). Preferably the presence and/or amount is at least 60% of that of the control sample, for example, at least 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

In an additional or alternative embodiment the method comprises the further step of:
 (I) identifying the skin sensitizing potency of the test agent.

In an additional or alternative embodiment the skin sensitizing agent of predetermined potency comprises or consist of agents selected from the group consisting of 1-Butanol, 4-Aminobenzoic acid, Benzaldehyde, Chlorobenzene, Diethyl phthalate, Dimethyl formamide, Ethyl vanillin, Glycerol, Isopropanol, Lactic acid, Methyl salicylate, Octanoic acid, Propylene glycol, Phenol, p-hydroxybenzoic acid, Potassium permanganate, Salicylic acid, Sodium dodecyl sulphate, Tween 80, Zinc sulphate, 2,4-Dinitrochlorobenzene, Oxazolone, Potassium dichromate, Kathon CG (MC/MCI), Formaldehyde, 2-Aminophenol, 2-nitro-1,4-Phenylendiamine, p-Phenylendiamine, Hexylcinnamic aldehyde, 2-Hydroxyethyl acrylate, 2-Mercaptobenzothiazole, Glyoxal, Cinnamaldehyde, Isoeugenol, Ethylendiamine, Resorcinol, Cinnamic alcohol, Eugenol, Penicillin G, Geraniol and DMSO.

In a preferred embodiment of the method of any aspect of the invention, step (b), (c), (e), (g) and/or (k) comprises or consists of measuring the expression of a nucleic acid molecule of one or more of the biomarkers. The nucleic acid molecule may be a DNA molecule or a cDNA molecule or an mRNA molecule. Preferably, the nucleic acid molecule is an mRNA molecule. However, the nucleic acid molecule may be a cDNA molecule.

In one embodiment the measurement of the expression of one or more of the biomarkers in step (b), (c), (e), (g) and/or (k) is performed using a method selected from the group consisting of Southern hybridisation, Northern hybridisation, polymerase chain reaction (PCR), reverse transcriptase PCR (RT-PCR), quantitative real-time PCR (qRT-PCR), nanoarray, microarray, macroarray, autoradiography and in situ hybridisation. Preferably, the expression of one or more biomarker(s) is measured using a DNA microarray.

In an additional or alternative embodiment the one or more biomarkers measured in step (b), (c), (e), (g) and/or (k) is measured using an array (e.g., a DNA array). In an additional or alternative embodiment the one or more biomarkers measured in step (b), (c), (e), (g) and/or (k) is measured using a whole genome array (e.g., the Affymetrix Human Gene 1.0 ST array or Affymetrix Human Gene 2.0 ST array). In an alternative or additional embodiment, the Nanostring nCounter system is used (e.g., custom Nanostring nCounter code sets based on selection from a whole genome array (e.g., Affymetrix Human Gene 1.0 ST array or Affymetrix Human Gene 2.0 ST array).

The method may comprise measuring the expression of one or more biomarkers in step (b), (c), (e), (g) and/or (k) using one or more binding moieties, each capable of binding selectively to a nucleic acid molecule encoding one of the biomarkers identified in one or more of Tables A, B, C, D, E. Preferably, the method comprises measuring the expression of two or more biomarkers in step (b), (c), (e), (g) and/or (k) using two or more binding moieties, each capable of binding selectively to a nucleic acid molecule encoding one of the biomarkers identified in one or more of Tables A, B, C, D, E. For example, the expression of any particular combination of biomarkers described above may be measured using an equivalent combination of binding moieties capable of binding selectively to each of those biomarkers.

In one embodiment the one or more binding moieties each comprise or consist of a nucleic acid molecule. In a further embodiment the one or more binding moieties each comprise or consist of DNA, RNA, PNA, LNA, GNA, TNA or PMO. Preferably, the one or more binding moieties each comprise or consist of DNA. In one embodiment, the one or more binding moieties are 5 to 100 nucleotides in length. However, in an alternative embodiment, they are 15 to 35 nucleotides in length.

The one or more binding moieties may comprise or consist of one or more probe from the Human Gene 1.0 ST Array (Affymetrix, Santa Clara, CA, USA). Probe identification numbers are provided in Tables A-E herein.

Suitable binding agents (also referred to as binding molecules or binding moieties) may be selected or screened from a library based on their ability to bind a given nucleic acid, protein or amino acid motif, as discussed below.

In a preferred embodiment, the binding moiety comprises a detectable moiety.

By a "detectable moiety" we include a moiety which permits its presence and/or relative amount and/or location (for example, the location on an array) to be determined, either directly or indirectly.

Suitable detectable moieties are well known in the art.

For example, the detectable moiety may be a fluorescent and/or luminescent and/or chemiluminescent moiety which, when exposed to specific conditions, may be detected. Such a fluorescent moiety may need to be exposed to radiation (i.e. light) at a specific wavelength and intensity to cause excitation of the fluorescent moiety, thereby enabling it to emit detectable fluorescence at a specific wavelength that may be detected.

Alternatively, the detectable moiety may be an enzyme which is capable of converting a (preferably undetectable) substrate into a detectable product that can be visualised and/or detected. Examples of suitable enzymes are discussed in more detail below in relation to, for example, ELISA assays.

The detectable moiety may be a radioactive moiety and comprise or consists of a radioactive atom. The radioactive atom may be selected from the group consisting of technetium-99m, iodine-123, iodine-125, iodine-131, indium-111, fluorine-19, carbon-13, nitrogen-15, oxygen-17, phosphorus-32, sulphur-35, deuterium, tritium, rhenium-186, rhenium-188 and yttrium-90.

Hence, the detectable moiety may be selected from the group consisting of: a fluorescent moiety; a luminescent moiety; a chemiluminescent moiety; a radioactive moiety (for example, a radioactive atom); or an enzymatic moiety.

Clearly, the agent to be detected (such as, for example, the one or more biomarkers in the test sample and/or control sample described herein and/or an antibody molecule for use in detecting a selected protein) must have sufficient of the appropriate atomic isotopes in order for the detectable moiety to be readily detectable.

In an alternative preferred embodiment, the detectable moiety of the binding moiety is a fluorescent moiety.

The radio- or other labels may be incorporated into the biomarkers present in the samples of the methods of the invention and/or the binding moieties of the invention in known ways. For example, if the binding agent is a polypeptide it may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the binding moiety. Yttrium-90 can be attached via a lysine residue. The IODOGEN method (Fraker et al (1978) Biochem. Biophys. Res. Comm. 80, 49-57) can be used to incorporate $^{123}$I. Reference ("Monoclonal Antibodies in Immunoscintigraphy", J-F Chatal, CRC Press, 1989) describes other methods in detail. Methods for conjugating other detectable moieties (such as enzymatic, fluorescent, luminescent, chemiluminescent or radioactive moieties) to proteins are well known in the art.

It will be appreciated by persons skilled in the art that biomarkers in the sample(s) to be tested may be labelled with a moiety which indirectly assists with determining the presence, amount and/or location of said proteins. Thus, the moiety may constitute one component of a multicomponent detectable moiety. For example, the biomarkers in the sample(s) to be tested may be labelled with biotin, which allows their subsequent detection using streptavidin fused or otherwise joined to a detectable label.

The method provided in the first aspect of the present invention may comprise or consist of, in step (b), (c), (e), (g) and/or (k), determining the expression of the protein of one or more biomarker defined in one or more of Tables A-E. The method may comprise measuring the expression of one or more biomarkers in step (b), (c), (e), (g) and/or (k) using one or more binding moieties each capable of binding selectively to one of the biomarkers identified in one or more of Tables A-E. The one or more binding moieties may comprise or consist of an antibody or an antigen-binding fragment thereof such as a monoclonal antibody or fragment thereof.

The term "antibody" includes any synthetic antibodies, recombinant antibodies or antibody hybrids, such as but not limited to, a single-chain antibody molecule produced by phage-display of immunoglobulin light and/or heavy chain variable and/or constant regions, or other immunointeractive molecules capable of binding to an antigen in an immunoassay format that is known to those skilled in the art. We also include the use of antibody-like binding agents, such as affibodies and aptamers.

The one or more protein-binding moieties may comprise a detectable moiety. The detectable moiety may be selected from the group consisting of a fluorescent moiety, a luminescent moiety, a chemiluminescent moiety, a radioactive moiety and an enzymatic moiety.

In a further embodiment of the methods of the invention, step (b), (c), (e), (g) and/or (k) may be performed using an assay comprising a second binding agent capable of binding to the one or more proteins, the second binding agent also comprising a detectable moiety. Suitable second binding agents are described in detail above in relation to the first binding agents.

Thus, the proteins of interest in the sample to be tested may first be isolated and/or immobilised using the first binding agent, after which the presence and/or relative amount of said biomarkers may be determined using a second binding agent.

In one embodiment, the second binding agent is an antibody or antigen-binding fragment thereof; typically a recombinant antibody or fragment thereof. Conveniently, the antibody or fragment thereof is selected from the group consisting of: scFv; Fab; a binding domain of an immunoglobulin molecule. Alternatively, the second binding agent may be an antibody-like binding agent, such as an affibody or aptamer.

Alternatively, where the detectable moiety on the protein in the sample to be tested comprises or consists of a member of a specific binding pair (e.g. biotin), the second binding agent may comprise or consist of the complimentary member of the specific binding pair (e.g. streptavidin).

Where a detection assay is used, it is preferred that the detectable moiety is selected from the group consisting of: a fluorescent moiety; a luminescent moiety; a chemiluminescent moiety; a radioactive moiety; an enzymatic moiety. Examples of suitable detectable moieties for use in the methods of the invention are described above.

Preferred assays for detecting serum or plasma proteins include enzyme linked immunosorbent assays (ELISA), radioimmunoassay (RIA), immunoradiometric assays (IRMA) and immunoenzymatic assays (IEMA), including sandwich assays using monoclonal and/or polyclonal antibodies. Exemplary sandwich assays are described by David et al in U.S. Pat. Nos. 4,376,110 and 4,486,530, hereby incorporated by reference. Antibody staining of cells on slides may be used in methods well known in cytology laboratory diagnostic tests, as well known to those skilled in the art.

Thus, in one embodiment the assay is an ELISA (Enzyme Linked Immunosorbent Assay) which typically involves the use of enzymes which give a coloured reaction product, usually in solid phase assays. Enzymes such as horseradish peroxidase and phosphatase have been widely employed. A way of amplifying the phosphatase reaction is to use NADP as a substrate to generate NAD which now acts as a coenzyme for a second enzyme system. Pyrophosphatase from *Escherichia coli* provides a good conjugate because the enzyme is not present in tissues, is stable and gives a good reaction colour. Chemiluminescent systems based on enzymes such as luciferase can also be used.

Conjugation with the vitamin biotin is frequently used since this can readily be detected by its reaction with enzyme-linked avidin or streptavidin to which it binds with great specificity and affinity.

In an alternative embodiment, the assay used for protein detection is conveniently a fluorometric assay. Thus, the detectable moiety of the second binding agent may be a fluorescent moiety, such as an Alexa fluorophore (for example Alexa-647).

Preferably, steps (b) (c), (e), (g) and/or (k) of the methods are performed using an array. The array may be a bead-based array or a surface-based array. The array may be selected from the group consisting of: macroarray; microarray; nanoarray.

Arrays per se are well known in the art. Typically they are formed of a linear or two-dimensional structure having spaced apart (i.e. discrete) regions ("spots"), each having a finite area, formed on the surface of a solid support. An array can also be a bead structure where each bead can be identified by a molecular code or colour code or identified in a continuous flow. Analysis can also be performed sequentially where the sample is passed over a series of spots each adsorbing the class of molecules from the solution. The solid support is typically glass or a polymer, the most commonly used polymers being cellulose, polyacrylamide, nylon, polystyrene, polyvinyl chloride or polypropylene. The solid supports may be in the form of tubes, beads, discs, silicon chips, microplates, polyvinylidene difluoride (PVDF) membrane, nitrocellulose membrane, nylon membrane, other porous membrane, non-porous membrane (e.g. plastic, polymer, perspex, silicon, amongst others), a plurality of polymeric pins, or a plurality of microtitre wells, or any other surface suitable for immobilising proteins, polynucleotides and other suitable molecules and/or conducting an immunoassay. The binding processes are well known in the art and generally consist of cross-linking covalently binding or physically adsorbing a protein molecule, polynucleotide or the like to the solid support. Alternatively, affinity coupling of the probes via affinity-tags or similar constructs may be employed. By using well-known techniques, such as contact or non-contact printing, masking or photolithography, the location of each spot can be defined. For reviews see Jenkins, R. E., Pennington, S. R. (2001, *Proteomics*, 2, 13-29) and Lal et al (2002, *Drug Discov Today* 15; 7(18 Suppl):S143-9).

Typically the array is a microarray. By "microarray" we include the meaning of an array of regions having a density of discrete regions of at least about 100/cm$^2$, and preferably at least about 1000/cm$^2$. The regions in a microarray have typical dimensions, e.g. diameter, in the range of between about 10-250 μm, and are separated from other regions in the array by about the same distance. The array may alternatively be a macroarray or a nanoarray.

Once suitable binding molecules (discussed above) have been identified and isolated, the skilled person can manufacture an array using methods well known in the art of molecular biology.

In an additional or alternative embodiment one or more biomarker measured in step (b), (c), (e), (g) and/or (k) is a nucleic acid (e.g., DNA, mRNA or cDNA etc). In an additional or alternative embodiment one or more biomarkers measured in step (b), (c), (e), (g) and/or (k) is a protein or polypeptide.

In an additional or alternative embodiment the method is performed in vitro, in vivo, ex vivo or in silico. Preferably, the method is performed in vitro.

In an additional or alternative embodiment, the method comprises one or more of the following steps:
(i) cultivating dendritic-like cells according to the first or second aspect;
(ii) seeding cells of (i) in one or more wells, preferably at steady state growth phase, e.g. wells of one or more multi-well assay plate;
(iii) adding to one or more well(s) of (ii) the agent(s) to be tested;
(iv) adding to one or more separate well(s) of (ii) positive control(s);
(v) adding to one or more separate well(s) of (ii) negative control(s); and/or leaving one or more separate well(s) of (ii) unstimulated to obtain a medium control;
(vi) incubating cells in wells of (iii)-(v), preferably for about 24 hours; and, optionally, harvesting cells from wells of (iii)-(v); and, further optionally, removing supernatant and storing in TRIzol reagent;
(vii) isolating purified total RNA from the cells of (vi) and, optionally, converting mRNA into cDNA;
(viii) quantifying expression levels of individual mRNA transcripts from (vii), e.g. using an array, such as an Affymetrix Human Gene 1.0 ST array;
(ix) exporting and normalizing data from (viii), e.g. using appropriate algorithms;
(x) isolating data from (ix) originating from biomarkers of one or more of Tables A-E);
(xi) applying a prediction model to the data of (x), e.g. a frozen SVM model previously established and trained on historical data to predict the allergenicity or sensitizer status (e.g. classify as allergen/non-allergen and/or sensitizer/non-sensitizer), of tested agents(s) and negative/positive control(s).

By "test protein" we include any protein or proteinaceous entity (or mixture of proteins or proteinaceous entities) for which allergenic or sensitization status is to be determined.

By "allergenic" we include or mean a protein (or mixture of proteins) which is an allergen, and/or which is capable of inducing an allergic response, in a mammal.

In an additional or alternative embodiment the allergenicity comprises a hypersensitivity response (e.g., a cell-mediated hypersensitivity response). In an additional or alternative embodiment the hypersensitivity response is a type I hypersensitivity response. In an additional or alternative embodiment the hypersensitivity response is respiratory allergy.

In an additional or alternative embodiment, the method of the eighth aspect is for identifying the sensitization status of a protein in a mammal. For example, the expression of the one or more biomarkers measured in step (b) or (c) may be indicative of the sensitization status of the test protein. By "sensitization status" we include or mean whether or not a test protein (or mixture of test proteins) is a sensitizer or not (e.g., a skin sensitizer and/or a respiratory sensitizer). In an additional or alternative embodiment, the method is for identifying proteins which are capable of inducing respiratory sensitization in a mammal. For example, the expression of the two or more biomarkers measured in step (c) may be indicative of the respiratory sensitizing effect of the test protein. In one embodiment, the method is for identifying proteins capable of inducing a respiratory hypersensitivity response. Preferably, the hypersensitivity response is a humoral hypersensitivity response, for example, a type I hypersensitivity response. In one embodiment, the method is for identifying agents capable of inducing respiratory allergy.

By "indicative of the respiratory sensitizing effect of the test protein" we include determining whether or not the test protein is a respiratory sensitizer and/or determining the potency of the test protein as a respiratory sensitizer. By proteins "capable of inducing respiratory sensitization" we mean any protein capable of inducing and triggering a Type I immediate hypersensitivity reaction in the respiratory tract of a mammal. Preferably the mammal is a human. Preferably, the Type I immediate hypersensitivity reaction is DC-mediated and/or involves the differentiation of T cells into Th2 cells. Preferably the Type I immediate hypersensitivity reaction results in humoral immunity and/or respiratory allergy.

The conducting zone of the mammalian lung contains the trachea, the bronchi, the bronchioles, and the terminal bronchioles. The respiratory zone contains the respiratory bronchioles, the alveolar ducts, and the alveoli. The conducting zone is made up of airways, has no gas exchange with the blood, and is reinforced with cartilage in order to hold open the airways. The conducting zone humidifies inhaled air and warms it to 37° C. (99° F.). It also cleanses the air by removing particles via cilia located on the walls of all the passageways. The respiratory zone is the site of gas exchange with blood.

In one embodiment, the protein "capable of inducing respiratory sensitization" is a protein capable of inducing and triggering a Type I immediate hypersensitivity reaction at a site of lung epithelium in a mammal. Preferably, the site of lung epithelium is in the respiratory zone of the lung, but may alternatively or additionally be in the conductive zone of the lung.

In an additional or alternative embodiment, the method is for identifying food proteins which are allergenic in a mammal. For example, the expression of the two or more biomarkers measured in step (c) may be indicative of the allergenicity of the food protein. Preferably, the allergenicity of the food protein is due to a Type 1 hypersensitivity response.

The mammal may be any domestic or farm animal. Preferably, the mammal is a rat, mouse, guinea pig, cat, dog, horse or a primate. Most preferably, the mammal is human.

In a further aspect of the invention there is provided the use of a population of dendritic-like cells according to the first or second aspect for determining the sensitizing effect and/or the allergenicity of a test agent.

In a further aspect of the invention there is provided an analytical kit comprising:
  i. an array comprising one or more binding moieties; and
  ii. one or more cell or a cell culture as defined in the first or second aspect; and
  iii. (optionally) one or more control agent; and
  iv. (optionally) instructions for use.

In a further aspect of the invention there is provided an analytical kit for use in a method of the invention comprising:
  i. an array comprising one or more binding moieties as defined herein; and
  ii. one or more cell or a cell culture as defined in the first or second aspects; and
  iii. (optionally) one or more control agent; and
  iv. (optionally) instructions for performing the method of the invention.

The skilled person will appreciate that all non-conflicting embodiments may be used in combination. Hence, embodiments from one aspect of the invention may equally be applied to another aspect of the invention.

The listing or discussion of an apparently prior-published document in the specification should not necessarily be taken as an acknowledgment that the document is part of the state of the art or common general knowledge.

Preferred, non-limiting examples which embody certain aspects of the invention will now be described, with reference to the following figures:

FIG. 1. The expression levels for the different surface markers were used in a hierarchical clustering to compare the cell lines. The numbers in the label represents the experiments. The clustering groups the cells in two separate clusters.

Figure 2:
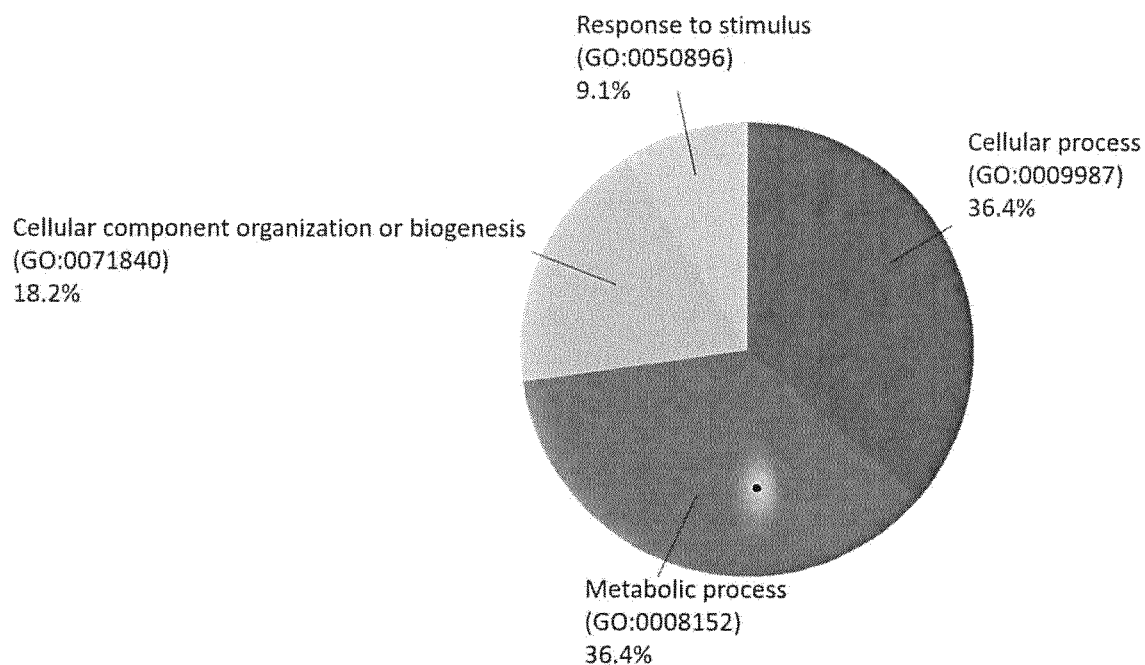

FIG. 2. SenzaCell; Distribution of the biological processes that were associated with the genes predicted to be affected with high or moderate impact by the unique variants.

Figure 3:
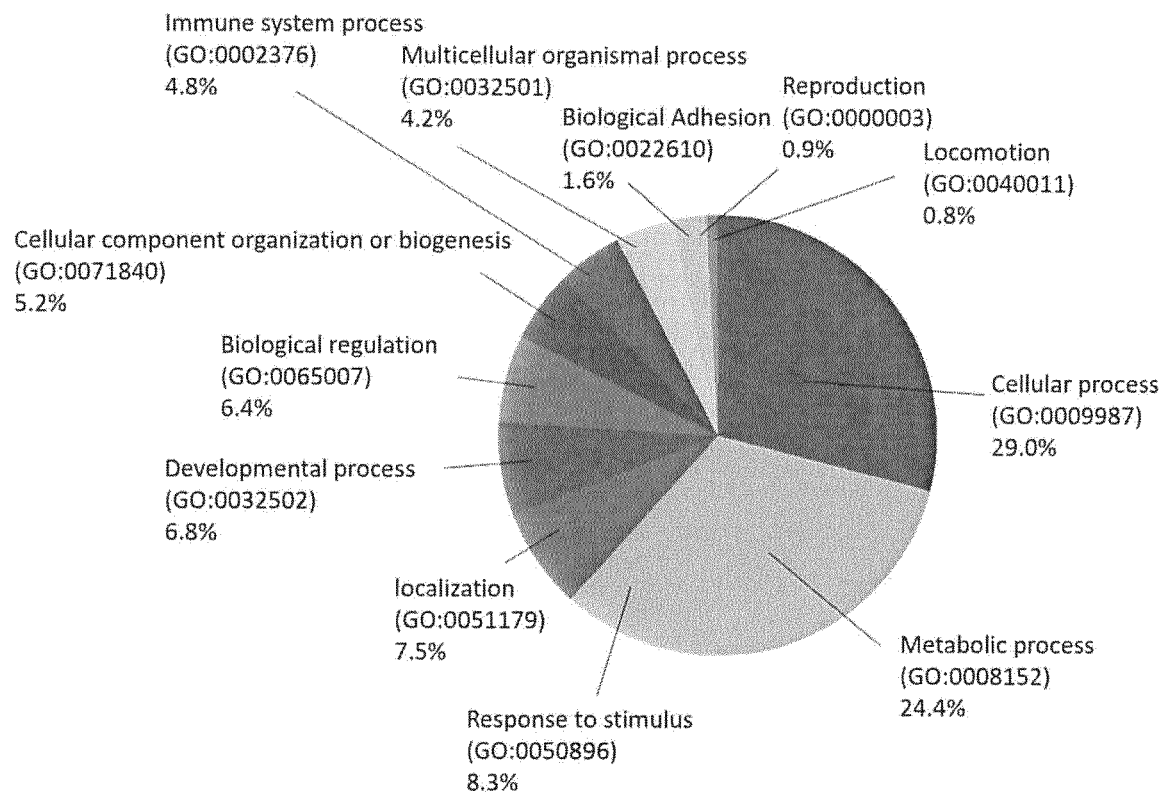

FIG. 3. MUTZ-3; Distribution of the biological processes that were associated with the genes predicted to be affected with high or moderate impact by the identified variants.

Figure 4:
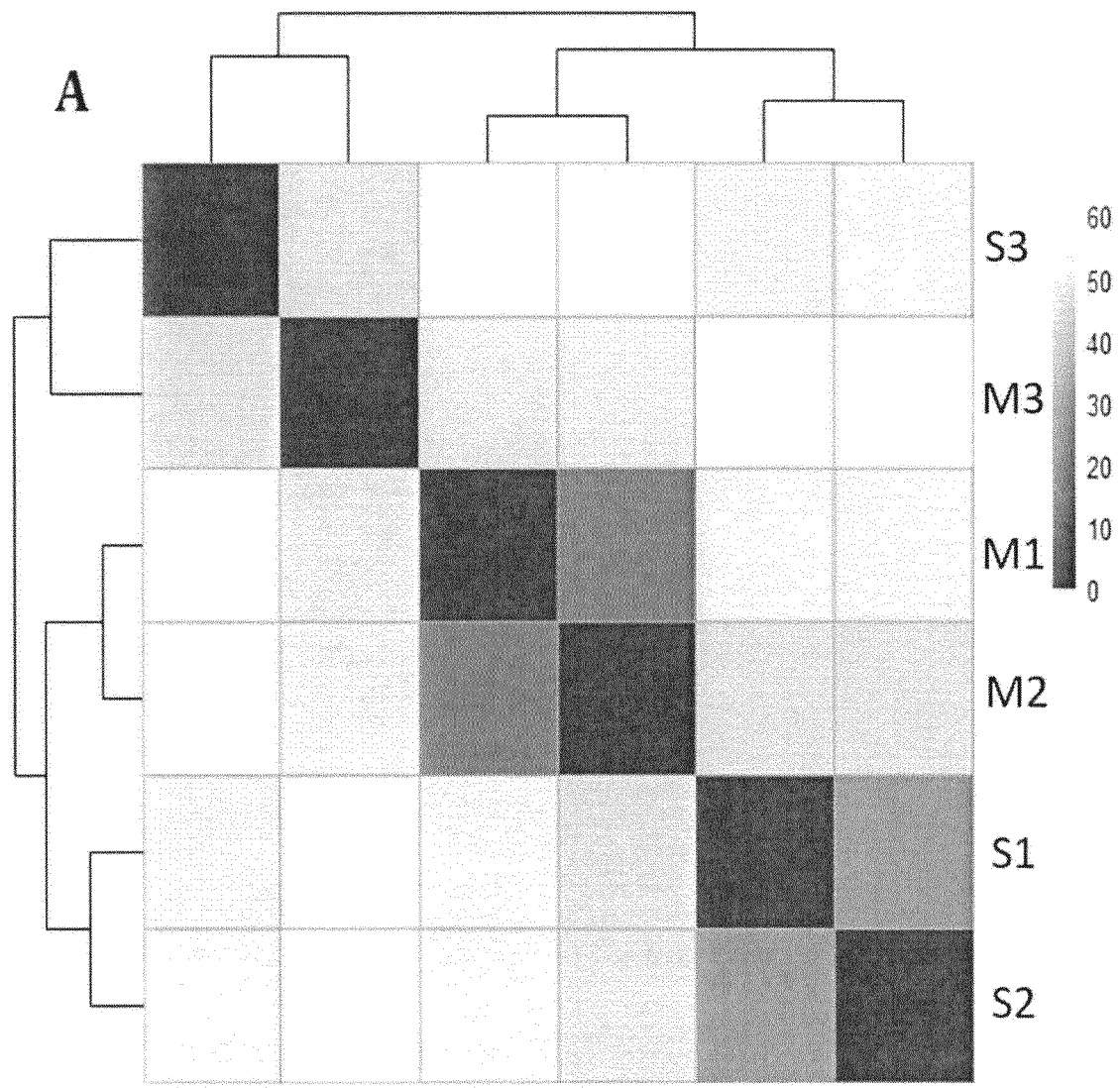
Figure 4:
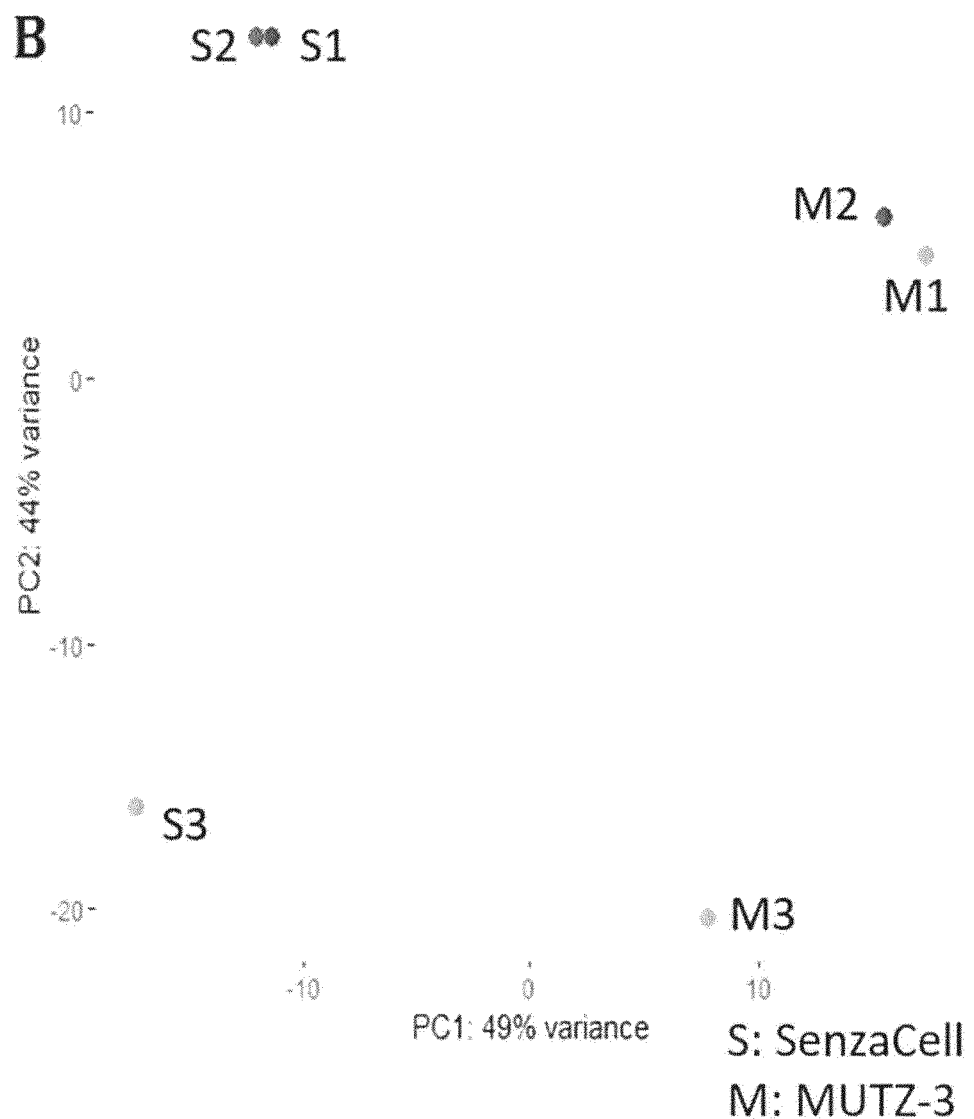

FIG. 4. A) A hierarchical clustering of the RNA-seq data shows a separate cluster for the samples obtained at experiment 3. The cells from experiment 1 and 2 form separate clusters for the cell lines. B) The PCA plot of the samples show that the largest source of variation can be explained by differences between the cell lines. It is also clear that the samples prepared at experiment 3 deviates from the remaining samples.

Figure 5:
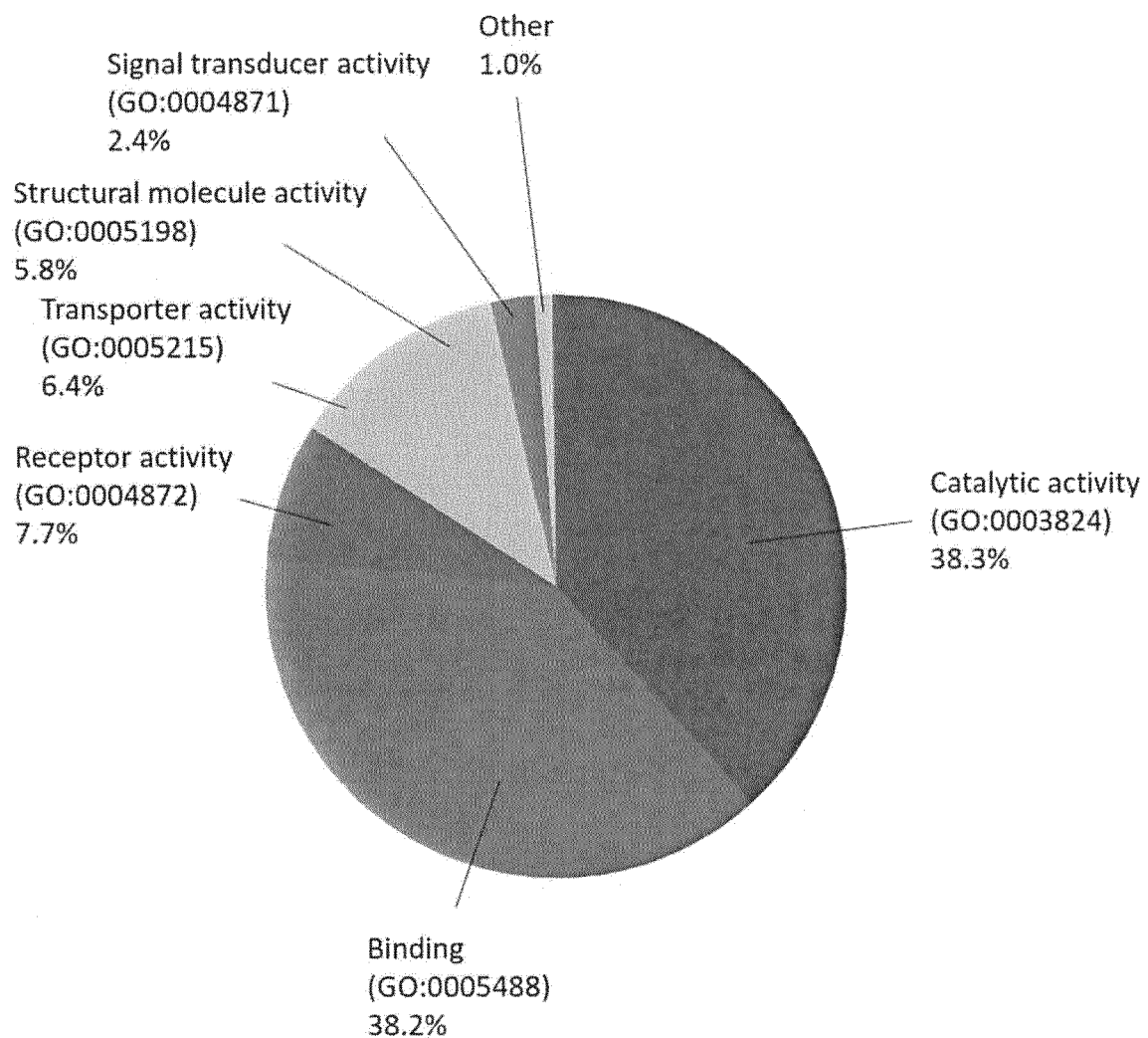

FIG. 5. The pie chart represents the distribution of the molecular functions that the discovered Differentially Expressed Genes (DEGs) were mapped to using PANTHER.

Figure 6:
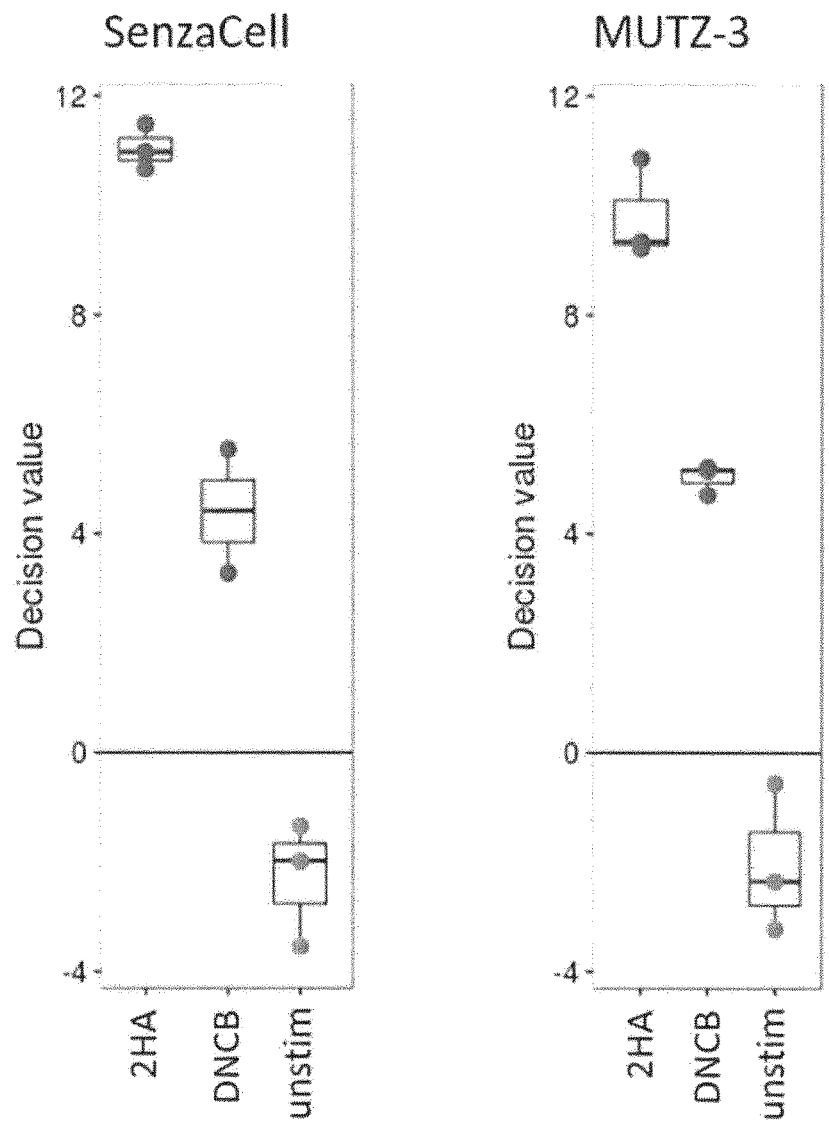

FIG. 6. SVM skin sensitizer predictions when using the expression values obtained from MUTZ-3 and SenzaCell after being stimulated with the test chemicals DNCB and 2-hydroxyethylacrylate. All the predictions correctly correspond to the true class.

EXAMPLE 1

Background

Allergic contact dermatitis (ACD) is an inflammatory skin disease that affects a large proportion of the population. It is caused by the repeated exposure to skin sensitizers and results in symptoms such as eczema. The sensitization phase of ACD requires a skin sensitizer to activate an immune response leading to the production of allergen specific effector and memory T-cells (1). The known mechanisms for sensitization have been well described (1-4). In short, skin sensitizers gain access to the viable dermis where it reacts with proteins to form hapten-protein complexes. These hapten-protein complexes can be recognized by different immune cells or structural cells that exert inflammatory signals. Activated dendritic cells process the hapten-protein complexes and migrate to lymph nodes where they present them to naïve T-cells on MHC-molecules. Subsequently, effector and memory T-cells are produced that upon renewed exposure to the same sensitizer elicits inflammatory functions, giving rise to the symptoms of ACD (3). Conventional methods for assessing chemicals' abilities to induce allergic reactions at skin contact have mainly been conducted using animal models (1). Legislations and trends drive research to come up with better and more ethical in-vitro methods for the evaluation of chemical sensitizers (5-7).

The Genomic Allergen Rapid Detection (GARD) is an in vitro assay developed at Department of Immunotechnology, Lund University, for the assessment of chemical sensitizers. It uses transcriptional profiles from a dendritic cell-like cell line (8), to predict the sensitizing potential of chemicals (9). The transcriptional profiles consist of genes that were identified as having the greatest predicting performance in distinguishing sensitizers from non-sensitizers. The genes were identified using statistical data mining methods on transcription data originating from Affymetrix microarrays. No a priori information of the genes in the GARD Prediction Signature (GPS) were used for their identification, which could have made the signature specific for the cell line (10).

The inventors now provide a non-naturally occurring dendritic-like myeloid leukemia cell line "SenzaCell" (ATCC Patent Deposit Designation PTA-123875; deposited at ATCC on 9 Mar. 2017) which is suitable for use in the GARD assays. SenzaCell has been compared to the MUTZ-3 dendritic-like cell line which may also be used in GARD methods. The comparison included a phenotypic analysis where the expression of a panel of biomarkers were compared, a transcriptional analysis where the transcription levels of the cell lines were compared, a comparison of their DNA sequences and a functional analysis, which revealed many quantifiable differences in the phenotype and transcriptional profiles.

Materials and Methods

Cell Maintenance

MUTZ-3 (DSMZ, Braunschweig, Germany (www.dsmz.de; DSMZ No. ACC 295)) and SenzaCell cells were cultivated in minimum essential medium alpha (α-MEM) (GE Healthcare Life Sciences, Logan, UT) supplemented with 20% (V/V) fetal calf serum (FCS) (Thermo Fisher Scientific, Waltham, MA) and 40 ng/ml granulocyte macrophage colony stimulating factor (GM-CSF) (Miltenyi Biotec, Bergisch Gladbach, Germany). Throughout this report the media is referred to as complete media. Cells were maintained at a concentration of 200 000 cells/ml and the media was renewed every 3-4 days. The cells were maintained at 37° C. and 5% $CO_2$.

Phenotypic Characterization

Growing cells were harvested, counted and seeded at a concentration of 200 000 cells/ml in complete media. To prepare the cells for staining, 1 ml of cell suspension was transferred to FACS tubes. The cells were washed in wash buffer, PBS (GE Healthcare Life Sciences) with 1% BSA (Saveen & Werner, Limhamn, Sweden) (w/V), twice. All washing steps were performed by the addition of 1 ml of wash buffer, centrifugation at 1200 rpm at 4° C. and removal of the supernatant. After the second wash, the cells were resuspended in 50 µl wash buffer. The antibodies; isotype PE/FITC, CD40 FITC, CD54 PE, CD86 FITC (BD Pharmingen, San Diego, CA); CD1a FITC, CD5 FITC, CD14 PE, CD19 PE (DAKO); CD13 PE, CD123 PE, OX40L PE (Pharmingen, San Diego, CA); CD11b PE, CD34 FITC, CD32 FITC, CD80 PE, HLA-DR FITC, CD137 PE, CD16 PE, CD64 PE (BD, Franklin Lakes, NJ); BDCA-3 APC (Miltenyi, Bergisch Gladbach, Germany); CD209 PE (R&D Systems, Minneapolis, MN); BDCA-1 APC (eBioscience, San Diego, CA); OX40 PE (BD Bioscience, San Jose, CA); CD15 FITC (Milteny); TLR2 PE, TLR4 PE (biolegend, San Diego, CA), were added to the resuspended cells and incubated for 15 min at 4° C. in the dark. Following staining, the cells were washed in wash buffer once more and then resuspended in 200 µl of wash buffer. The cells were kept in 4° C. until analyzed with flow cytometry. The flow cytometry was performed on a FACS CANTO II (BD Bioscience) with BD DIVA software (BD Bioscience) as the data acquisition program where 10 000 events were recorded for each sample. The data was analyzed using FACS Express V3 (De Novo Software, Los Angeles, CA). Appropriate gates were set using isotype controls and unstained cells. The measurements were performed at three separate experiments with technical duplicates at each, generating 6 measurements for each marker and cell line.

The expression levels were compared using t-tests where the generated p-values were corrected with the Benjamini Hochberg method to control the false discovery rate. A clustering algorithm was performed to compare the cell lines. The clustering was performed using R (15). A bootstrap algorithm was performed to assess the stability of the discovered clusters using the fpc (16) package. The bootstrap algorithm was run for 5000 iteration and the calculated mean Jaccard coefficients was used as an indication on cluster stability.

DNA—Whole Genome Sequencing

DNA from both MUTZ-3 and SenzaCell cells was isolated using Quick-gDNA™ Miniprep (Zymo Research, Irvine CA). The isolation was performed as follows; $5*10^6$ cells were harvested and centrifuged and the supernatant was removed. The remaining cell pellets were lysed in Quick-gDNA™ genomic lysis buffer and incubated for 10 minutes. The lysed cells were loaded to the supplied spin columns and washed. DNA was eluted in RNAse/DNase free water. DNA concentration and DNA purity were determined using NanoDrop, and the quality was evaluated by gel electrophoresis. The DNA whole genome sequencing was performed by SciLifeLabs (Stockholm, Sweden). The services from SciLifeLabs included library preparation, sequencing and best practice basic analysis. The DNA libraries were prepared with Illumina TruSeq PCR-free, 350 bp and the sequencing were performed with Illumina HiSeq X v2.5, PE 2×150 bp at 30× coverage.

The best practice basic analysis included mapping of the reads to the human assembly build 37 using bwa-mem. The Genome Analysis Toolkit (GATK) workflow (17, 18) for best practice analysis were followed for variant calling and genomic variant call format (gVCF) files were delivered from SciLifeLabs. The obtained gVCF files were merged and genotyped using GATK genotypeGVCFS. The variant were further processed using GATK Variant Quality Score Recalibration (VQSR) as recommended by the GATK workflow. The VQSR calculates new variant quality scores and filters variants that are predicted to be false positive discoveries using machine learning. The recalibrated variant call format (VCF) file was annotated and the variant effects were predicted using snpEff (19) to the human assembly build GRCh37.75. The variants that were unique to either of the cell lines were identified using SnpSift (20) casecontrol and the other variants were filtered using SnpSift filter. The list of unique variants was further filtered by their genotype quality scores were variants with a score <20 was removed (21). Finally variants predicted to have a high or moderate impact were retained for further analysis. PANTHER classification system (22) was used for classification of the molecular function of the genes which were identified to be impacted by the variants.

RNA—RNAseq

Total RNA was isolated from both MUTZ-3 and SenzaCell cell lines in three experiments to generate triplicate RNAseq samples. 200,000 cells were isolated and lysed in TRIzol reagent (Thermo Scientific, Waltham, MA). RNA was isolated using Direct-zol™ RNA Miniprep (Zymo research). The lysed samples were mixed with ethanol and added to the spin columns. The RNA was bound and washed with the supplied wash buffers. RNA was eluted in RNase/DNase free water and quality controlled with Agilent Bioanalyzer 2100 (Agilent Technologies, Santa Clara, CA). The samples were stored at −80° C. until shipped on dry ice to SciLifeLabs for RNA-seq. The libraries were prepared using Illumina TruSeq stranded mRNA, Poly-A selection. The sequencing was performed using Illumina HiSeq Rapid mode v2, SR 1×50 bp. The best practice basic analysis was performed by SciLifeLabs which included mapping of the reads using topHat v2.0.4 (23), sorting of the generated bam files with samtools (24), marking duplicates with piccard-tools and quantifying the counts using HTSeq (25).

The obtained count table were loaded into R and differential expression analysis was performed using edgeR v3.14.0 (26) and DESeq2 v1.12.4 (27), which performs normalization and fitting of negative binomial models to the count data, enabling effective differential expression analysis. The recommended workflows for differential expression (DE) analysis were followed for both packages. The model matrix used for hypothesis testing were designed to incorporate the experiment batch in the model due to batch effects which were discovered when analyzing PCA plots of the samples. A transcript was considered differentially expressed if both edgeR and DESeq called it significantly differentially expressed with a false discovery rate below 0.05. The molecular functions and the biological processes that the identified transcripts were mapped to were analyzed using PANTHER classification system. To identify gene ontology (GO) terms that were over- or underrepresented among the differentially expressed transcripts an overrepresentation test was performed, also using PANTHER. The background reference list was submitted as all the non-zero counts that were obtained in the count table, which is the same list that was entered into the DE analysis. The p-values of the identified GO terms were corrected with the Bonferroni method. GO terms with a corrected p-value below 0.05 were considered significantly over- or underrepresented. Additionally, pathway analysis was performed using Signaling Pathway Impact Analysis v2.24.0 (SPIA) (28) and KEGG pathways (29, 30) release 79.0. The list of significant DE transcripts was entered with accompanying $\log_2$-fold change values and all the non-zero transcripts were entered as background. The $\log_2$-fold change values were calculated using DESeq2 v1.12.4.

Finally a concordance analysis was made for the results of the phenotype analysis and the RNA-seq analysis. The genes corresponding to the measured surface markers were compared to the surface marker expression. The comparison was made similar to an evaluation of a classification with the classes significantly upregulated/expressed, significantly downregulated/expressed or no significant difference between the two cell lines. Therefore, if both the RNA-seq analysis and the phenotype analysis calls the transcript level or surface expression significantly higher, this would be considered a concordant result. Cohens Kappa (31) was calculated as an indication of the concordance between the analysis methods.

Functional Analysis

MUTZ-3 was used in the GARD assay to assess its ability to distinguish skin sensitizers from non-sensitizers using the GARD prediction signature as compared to SenzaCell. The GARD standard operating procedures were followed which has previously been described in detail (9). In short, the cells (MUTZ-3 or SenzaCell) were seeded in 24-well plates at a volume of 1.8 ml and a cell concentration of 222 000 cells/ml. The chemicals used for the stimulation were (2, 4)-dinitrochlorobenzene (DNCB) and 2-hydroxyethylacrylate. An unstimulated sample was also included as a negative control. DNCB was dissolved in DMSO to a concentration of 4 mM and 2-hydroxyethylacrylate in water to a concentration of 100 mM. Both chemicals were then diluted, in α-MEM supplemented with 20% FCS, 100× and finally diluted once more 10× as 200 µl was added to the wells. The in-well concentration for the stimulations was 4 µM and 100 µM for DNCB and 2-hydroxyethylacrylate, respectively. 200 µl of MEM-alpha was added to the unstimulated cells, giving an in-well cell concentration of 200 000 cells/ml for every sample. The cells were incubated with the chemicals for 24 h at 37° C. at 5% $CO_2$. Following incubation, cells were harvested into RNase free Eppendorf tubes and lysed in TRIzol. Cell viability was assessed by flow cytometry using propidium iodide (PI) (Thermo Fisher Scientific) staining. RNA was extracted and purified using Direct-zol RNA kits (Zymo research). RNA was extracted as described and quality controlled using Agilent Bioanalyzer 2100 Samples with an RNA integrity numbers (RIN)≥8 and an RNA concentration ≥20 ng/µl was used for quantification. The genes in the GPS (see Table A below) were quantified using NanoString nCounter systems (NanoString Technologies, Seattle, WA), using protocols and reagents supplied by the manufacturer. The raw counts of the genes were exported from NanoString and normalized by a count per total counts normalization, where each gene's count is divided by the sum of counts for a single sample. The classification was performed by Support vector machine from the R package e1071 (32) with a training set consisting of gene profiles of 40 chemical stimulations in replicates (10). The data was aligned with the training data prior to the classification by calculating the shifts in the first 4 principal components for the unstimulated samples in both data sets. The calculated shifts were then used to adjust every sample from the test samples.

Methodology for distinguishing skin sensitizers from non-sensitizers using the GARD prediction signature is also described in detail in WO 2012/056236; Johansson et al. (2017) Evaluation of the GARD assay in a blind Cosmetics Europe study. ALTEX Online first Feb. 17, 2017; Forreryd et al. (2016) From genome-wide arrays to tailor-made biomarker readout—Progress towards routine analysis of skin sensitizing chemicals with GARD. Toxicolgy In Vitro; Johansson et al. (2014) GARD in-house validation—A proof of concept. Tox Sci; Johansson et al., (2011) A genomic biomarker signature can predict skin sensitizers using a cell-based in vitro alternative to animal tests. BMC Genomics, 2011), each incorporated herein by reference.

TABLE A

| Gene Title | Gene Symbol | NCBI reference sequence |
|---|---|---|
| Table A-A | | |
| fatty acid synthase | FASN | NM_004104 |
| squalene epoxidase | SQLE | NM_003129 |
| taste receptor, type 2, member 5 | TAS2R5 | NM_018980 |
| keratinocyte growth factor-like protein 1/2/hypothetical protein FLJ20444 | KGFLP1/2/FLJ20444 | AF523265 |
| transmembrane anterior posterior transformation 1 | TAPT1 | NM_153365 |
| Sprouty homolog 2 | SPRY2 | NM_005842 |
| B-cell CLL/lymphoma 7A | BCL7A | NM_020993 |
| solute carrier family 25, member 32 | SLC25A32 | NM_030780 |
| ferritin, heavy polypeptide pseudogene 1 | FTHP1 | GENSCAN00000008165 |
| ATPase, H+ transporting, lysosomal 50/57 kDa, V1 subunit H | ATP6V1H | NM_015941 |
| Histone cluster 1, H1e | HIST1H1E | NM_005321 |
| Table A-B | | |
| 4-aminobutyrate aminotransferase | ABAT | NM_020686 |
| abhydrolase domain containing 5 | ABHD5 | NM_016006 |
| alkaline ceramidase 2 | ACER2 | NM_001010887 |
| ATP citrate lyase | ACLY | NM_001096 |
| actin-related protein 10 homolog | ACTR10 | NM_018477 |
| ADAM metallopeptidase domain 20 | ADAM20 | NM_003814 |
| aldehyde dehydrogenase 18 family, member A1 | ALDH18A1 | NM_002860 |
| aldehyde dehydrogenase 1 family, member B1 | ALDH1B1 | NM_000692 |
| alkB, alkylation repair homolog 6 (*E. coli*) | ALKBH6 | NM_032878 |
| anaphase promoting complex subunit 1 | ANAPC1 | NM_022662 |
| anaphase promoting complex subunit 5 | ANAPC5 | NM_016237 |
| ankyrin repeat, family A (RFXANK-like), 2 | ANKRA2 | NM_023039 |
| ADP-ribosylation factor GTPase activating protein 3 | ARFGAP3 | NM_014570 |
| Rho GTPase activating protein 9 | ARHGAP9 | NM_032496 |
| ankyrin repeat and SOCS box-containing 7 | ASB7 | NM_198243 |
| ATPase, H+ transporting, lysosomal 9 kDa, V0 subunit e1 | ATP6V0E1 | NM_003945 |
| bridging integrator 2 | BIN2 | NM_016293 |
| bleomycin hydrolase | BLMH | NM_000386 |
| brix domain containing 1/ribosome production factor 2 homolog | BXDC1/RPF2 | ENST00000368864 |
| chromosome 11 open reading frame 67 | C11orf67 | NM_024684 |
| chromosome 12 open reading frame 57 | C12orf57 | NM_138425 |
| chromosome 15 open reading frame 24 | C15orf24 | NM_020154 |
| chromosome 19 open reading frame 54 | C19orf54 | NM_198476 |
| chromosome 1 open reading frame 174 | C1orf174 | NM_207356 |
| chromosome 1 open reading frame 183 | C1orf183 | NM_019099 |
| chromosome 20 open reading frame 111 | C20orf111 | NM_016470 |
| chromosome 20 open reading frame 24 | C20orf24 | BC004446 |
| chromosome 3 open reading frame 62/ubiquitin specific peptidase 4 (proto-oncogene) | C3orf62/USP4 | BC023586 |
| chromosome 9 open reading frame 89 | C9orf89 | BC038856 |
| coactivator-associated arginine methyltransferase 1 | CARM1 | NM_199141 |
| CD33 molecule | CD33 | NM_001772 |
| CD86 molecule | CD86 | NM_175862 |
| CD93 molecule | CD93 | NM_012072 |
| cytochrome c oxidase subunit VIIa polypeptide 2 like | COX7A2L | NM_004718 |
| corticotropin releasing hormone binding protein | CRHBP | NM_001882 |
| chondroitin sulfate N-acetylgalactosaminyltransferase 2 | CSGALNACT2 | NM_018590 |
| Cytochrome P450 51A1 | CYP51A1 | NM_000786.2 |
| DDRGK domain containing 1 | DDRGK1 | NM_023935 |
| DEAD (Asp-Glu-Ala-Asp) box polypeptide 21 | DDX21 | NM_004728 |
| 24-dehydrocholesterol reductase | DHCR24 | NM_014762 |
| 7-dehydrocholesterol reductase | DHCR7 | NM_001360 |
| DEAH (Asp-Glu-Ala-His) box polypeptide 33 | DHX33 | NM_020162 |
| DnaJ (Hsp40) homolog, subfamily B, member 4 | DNAJB4 | NM_007034 |
| DnaJ (Hsp40) homolog, subfamily B, member 9 | DNAJB9 | NM_012328 |
| DnaJ (Hsp40) homolog, subfamily C, member 5 | DNAJC5 | NM_025219 |
| DnaJ (Hsp40) homolog, subfamily C, member 9 | DNAJC9 | NM_015190 |
| D-tyrosyl-tRNA deacylase 1 homolog | DTD1 | NM_080820 |
| ER degradation enhancer, mannosidase alpha-like 2 | EDEM2 | NM_018217 |
| ecotropic viral integration site 2B | EVI2B | NM_006495 |
| family with sequence similarity 36, member A | FAM36A | NM_198076 |
| family with sequence similarity 86, member A | FAM86A | NM_201400 |
| Fas (TNF receptor superfamily, member 6) | FAS | NM_000043 |
| MGC44478 | FDPSL2A | NR_003262 |
| ferredoxin reductase | FDXR | NM_024417 |
| forkhead box O4 | FOXO4 | NM_005938 |
| FTHL10-001, Transcribed processed pseudogene | FTHL10-001 | NR_002200 |
| fucosidase, alpha-L-2, plasma | FUCA2 | NM_032020 |
| growth arrest-specific 2 like 3 | GAS2L3 | NM_174942 |
| ganglioside induced differentiation associated protein 2 | GDAP2 | NM_017686 |

TABLE A-continued

| Gene Title | Gene Symbol | NCBI reference sequence |
|---|---|---|
| growth differentiation factor 11 | GDF11 | NM_005811 |
| glutaredoxin (thioltransferase) | GLRX | NM_002064 |
| guanine nucleotide binding protein-like 3 | GNL3L | NM_019067 |
| glucosamine-phosphate N-acetyltransferase 1 | GNPNAT1 | NM_198066 |
| glutathione reductase | GSR | NM_000637 |
| general transcription factor IIIC, polypeptide 2 beta | GTF3C2 | NM_001521 |
| HMG-box transcription factor 1 | HBP1 | NM_012257 |
| histone cluster 1, H1c | HIST1H1C | NM_005319 |
| histone cluster 1, H2ae | HIST1H2AE | NM_021052 |
| histone cluster 1, H2be | HIST1H2BE | NM_003523 |
| histone cluster 1, H3g | HIST1H3G | NM_003534 |
| histone cluster 1, H3j | HIST1H3J | NM_003535 |
| histone cluster 1, H4a | HIST1H4A | NM_003538 |
| histone clusters 2, H2aa3/2, H2aa4 | HIST2H2AA3/4 | NM_003516 |
| high-mobility group box 3 | HMGB3 | NM_005342 |
| 3-hydroxy-3-methylglutaryl-Coenzyme A reductase | HMGCR | NM_000859 |
| 3-hydroxy-3-methylglutaryl-Coenzyme A synthase 1 | HMGCS1 | NM_001098272 |
| heme oxygenase (decycling) 1 | HMOX1 | NM_002133 |
| heterogeneous nuclear ribonucleoprotein L | HNRNPL | NM_001533 |
| insulin receptor substrate 2 | IRS2 | NM_003749 |
| iron-sulfur cluster scaffold homolog | ISCU | NM_014301 |
| interferon stimulated exonuclease gene 20 kDa-like 2 | ISG20L2 | NM_030980 |
| potassium voltage-gated channel, Isk-related family, member 3 | KCNE3 | NM_005472 |
| hypothetical protein LOC100132855/ATPase, H+ transporting, lysosomal 38 kDa, V0 subunit d1 | LOC100132855/ ATP6V0D1 | NM_004691 |
| hCG1651476 | LOC284417 | NM_001085488 |
| lysophosphatidic acid receptor 1 | LPAR1 | NM_057159 |
| leucine-rich PPR-motif containing | LRPPRC | NM_133259 |
| lymphocyte antigen 96 | LY96 | NM_015364 |
| mitogen-activated protein kinase kinase 1 | MAP2K1 | NM_002755 |
| mitogen-activated protein kinase 13 | MAPK13 | NM_002754 |
| methyltransferase like 2A | METTL2A | NM_181725 |
| microsomal glutathione S-transferase 3 | MGST3 | NM_004528 |
| mitochondrial ribosomal protein L30 | MRPL30 | NM_145212 |
| mitochondrial ribosomal protein L4 | MRPL4 | NM_146388 |
| mitochondrial ribosomal protein S17 | MRPS17 | NM_015969 |
| 5-methyltetrahydrofolate-homocysteine methyltransferase | MTR | NM_000254 |
| MYB binding protein (P160) 1a | MYBBP1A | NM_014520 |
| neighbor of BRCA1 gene 1 | NBR1 | NM_031858 |
| nuclear import 7 homolog | NIP7 | NM_016101 |
| NLR family, pyrin domain containing 12 | NLRP12 | NM_144687 |
| nucleolar protein family 6 (RNA-associated) | NOL6 | NM_022917 |
| NAD(P)H dehydrogenase, quinone 1 | NQO1 | NM_000903 |
| nuclear receptor binding protein 1 | NRBP1 | NM_013392 |
| nucleotide binding protein-like | NUBPL | NM_025152 |
| nudix (nucleoside diphosphate linked moiety X)-type motif 14 | NUDT14 | NM_177533 |
| nuclear fragile X mental retardation protein interacting protein 1 | NUFIP1 | NM_012345 |
| nucleoporin 153 kDa | NUP153 | NM_005124 |
| olfactory receptor, family 5, subfamily B, member 21 | OR5B21 | NM_001005218 |
| PAS domain containing serine/threonine kinase | PASK | NM_015148 |
| PRKC, apoptosis, WT1, regulator | PAWR | NM_002583 |
| PDGFA associated protein 1 | PDAP1 | NM_014891 |
| phosphodiesterase 1B, calmodulin-dependent | PDE1B | NM_000924 |
| phosphoribosylformylglycinamidine synthase | PFAS | NM_012393 |
| pleckstrin homology-like domain, family A, member 3 | PHLDA3 | NM_012396 |
| phosphoinositide-3-kinase adaptor protein 1 | PIK3AP1 | NM_152309 |
| PTEN induced putative kinase 1 | PINK1 | NM_032409 |
| phosphomannomutase 2 | PMM2 | NM_000303 |
| partner of NOB1 homolog | PNO1 | NM_020143 |
| polymerase (RNA) II (DNA directed) polypeptide E, 25 kDa | POLR2E | NM_002695 |
| polymerase (RNA) III (DNA directed) polypeptide E (80 kD) | POLR3E | NM_018119 |
| protein phosphatase 1D magnesium-dependent, delta isoform | PPM1D | BC042418 |
| phosphatidylinositol-3,4,5-trisphosphate-dependent Rac exchange factor 1 | PREX1 | NM_020820 |
| proline-serine-threonine phosphatase interacting protein 1 | PSTPIP1 | NM_003978 |
| RAB33B, member RAS oncogene family | RAB33B | NM_031296 |
| renin binding protein | RENBP | NM_002910 |
| replication factor C (activator 1) 2, 40 kDa | RFC2 | NM_181471 |
| ribonuclease H1 | RNASEH1 | NM_002936 |
| ring finger protein 146 | RNF146 | NM_030963 |
| ring finger protein 24 | RNF24 | NM_007219 |
| ring finger protein 26 | RNF26 | NM_032015 |
| ribosomal protein SA/small nucleolar RNA, H/ACA box 62 | RPSA/SNORA62 | NM_014570 |
| RNA pseudouridylate synthase domain containing 2 | RPUSD2 | NM_152260 |
| ribosomal RNA processing 12 homolog | RRP12 | NM_015179 |
| retinoid X receptor, alpha | RXRA | NM_002957 |

TABLE A-continued

| Gene Title | Gene Symbol | NCBI reference sequence |
| --- | --- | --- |
| scavenger receptor class B, member 2 | SCARB2 | NM_005506 |
| SERPINE1 mRNA binding protein 1 | SERBP1 | NM_001018067 |
| splicing factor proline/glutamine-rich | SFPQ | NM_005066 |
| solute carrier family 35, member B3 | SLC35B3 | BX538271 |
| solute carrier family 37, member 4 | SLC37A4 | NM_001467 |
| solute carrier family 5, member 6 | SLC5A6 | NM_021095 |
| sphingomyelin phosphodiesterase 4, neutral membrane | SMPD4 | NM_017751 |
| small nucleolar(sn)RNA host gene 1, non-coding/snRNA C/D box 26 | SNHG1/SNORD26 | NM_002032 |
| small nucleolar RNA host gene 12 (non-coding) | SNHG12 | NM_207356 |
| small nucleolar RNA, H/ACA box 45 | SNORA45 | NR_002977 |
| sorting nexin family member 27 | SNX27 | NM_030918 |
| sterol regulatory element binding transcription factor 2 | SREBF2 | NM_004599 |
| ST3 beta-galactoside alpha-2,3-sialyltransferase 6 | ST3GAL6 | NM_006100 |
| serine/threonine kinase 17b | STK17B | NM_004226 |
| tubulin folding cofactor E-like | TBCEL | NM_152715 |
| tectonic family member 2 | TCTN2 | NM_024809 |
| toll-like receptor 6 | TLR6 | NM_006068 |
| toll-like receptor 9/twinfilin homolog 2 | TLR9/TWF2 | NM_007284 |
| transmembrane protein 55A | TMEM55A | NM_018710 |
| transmembrane protein 59 | TMEM59 | NM_004872 |
| transmembrane protein 77 | TMEM77 | BC091509 |
| transmembrane protein 97 | TMEM97 | NM_014573 |
| translocase of outer mitochondrial membrane 34 | TOMM34 | NM_006809 |
| translocase of outer mitochondrial membrane 40 homolog | TOMM40 | BC001779 |
| translocase of outer mitochondrial membrane 5 homolog/ F-box protein 10 | TOMM5/FBXO10 | NM_012166 |
| tumor protein p53 inducible protein 3 | TP53I3 | NM_004881 |
| tumor protein p53 inducible nuclear protein 1 | TP53INP1 | NM_033285 |
| thioredoxin reductase 1 | TXNRD1 | NM_003330 |
| ubiquitin-fold modifier conjugating enzyme 1 | UFC1 | NM_016406 |
| ubiquitin specific peptidase 10 | USP10 | NM_005153 |
| vesicle-associated membrane protein 3 (cellubrevin) | VAMP3 | NM_004781 |
| valyl-tRNA synthetase | VARS | NM_006295 |
| vacuolar protein sorting 37 homolog A | VPS37A | NM_152415 |
| zinc finger protein 211 | ZNF211 | NM_006385 |
| zinc finger protein 223 | ZNF223 | NM_013361 |
| zinc finger protein 561 | ZNF561 | NM_152289 |
| zinc finger protein 79 | ZNF79 | NM_007135 |
| The following gene titles are based on HUGO gene nomenclature | | |
| DDX19A | DDX19A | NM_018332.3 |
| HIST2H2AA3 | HIST2H2AA3 HIST2H2AA4_x2 | BC001629.1 |
| HIST2H2BF | HIST2H2BF | NM_001024599.2 |
| KIAA0226L | KIAA0226L | NM_025113.3 |
| LINC00987 | LOC100499405 RP11-118B22.3 RP11-118B22.2 | NR_036466.1 |
| MSANTD2 | MSANTD2 | NM_024631.2 |
| OTTHUMT00000400136 | RP11-267J23.4 | OTTHUMT00000400136.1 |
| SRP72P2 | SRP72P2 | ENST00000538672.1 |
| TWF2 | TWF2 | NM_007284.3 |
| VARS | VARS_x1 | BC012808.2 |
| YBX1P1 | YBX1P1 | ENST00000445822.1 |
| U4 | 7966223 | ENST00000363404.1 |
| 8133549 | 8133549 | GPS_8133549b.1 |
| 8140170 | 8140170 | GPS_8140170.1 |
| 8145244 | 8145244 | GPS_8145244b.1 |

Table A legend. Genes were annotated, using the NetAffx database from Affymetrix (www.affymetrix.com, Santa Clara USA). When found, the Unigene (www.ncbi.nlm.nih.gov/UniGene/) ID was chosen as the gene identifier. In the cases where no Unigene ID was reported the best alternative ID was given.

Results

Phenotype Analysis

To investigate any indications of phenotypic differences in SenzaCell compared to MUTZ-3, the expression of a panel of surface markers, Table I, were measured in both cell lines. The selected surface markers are associated with dendritic cells, myeloid cells, hematopoietic cells or cell activation. The populations of positive cells were calculated and the population sizes were compared using t-tests. Out of the 26 surface markers that were measured, 12 were significantly differentially expressed between the cell lines when considering a false discovery rate <0.05 significant, see rows shaded in Table I. The differentially expressed surface markers were CD1a, CD11b, CD14, CD34, CD15, CD32, CD40, CD54, HLA-DR, CD64, Toll like receptor (TLR) 4 and TLR-2. The expression of CD54 is however nearly identical in the cell lines and close to the highest obtainable value, and should be interpreted with caution. The expression was also considered as binary, + if the surface marker was detected and—otherwise. The binary expression of the surface markers were very similar between the cell lines. The only surface markers that showed a different binary expression was CD80 and possibly OX40L. A hierarchical clustering algorithm was performed to further compare the cell lines, see FIG. 1. The clustering groups MUTZ-3 and SenzaCell in 2 separate clusters. A bootstrap algorithm with resampling was performed to evaluate the stability of the identified clusters. The mean Jaccard coefficients for SenzaCell and MUTZ-3 were determined to be 0.85 and 0.89 respectively, which is indicative of stable clusters.

lines were identified by finding positions where one cell line had an identified variant and the other cell line were homozygous to the reference genome. Further filtering was performed to remove variants where the certainty of the homozygous calls was low, by filtering on the genotype quality scores. The obtained variant list consisted of 7,977 variants that could only be found in the SenzaCell and 5,672 variants unique to the MUTZ-3 cell line. Though the list of variants had been decreased significantly, further filtering was necessary to identify mutations that could have an

TABLE I

The expression of a panel of biomarkers were measured for both SenzaCell and MUTZ-3. The expression values are given as the mean percent positive cells ± the standard deviation. T-tests were performed to compare the means of the expression values. The p-values were corrected using Benjamini Hochberg correction. Rows shaded in green represent markers with a corrected p-value below 0.05. The calculations are based on 6 measurements in biological triplicates. A binary representation of the surface expression is represented as + if expressed or − if not expressed. The expression of the surface marker's corresponding genes are given, showing the cell line that exhibits the highest expression if significanlty different. HLA-DR is not reported in the RNA expression column due to its complex genetics:

| SURFACE MARKER | SENZACELL MEAN EXPRESSION (%) | | MUTZ-3 MEAN EXPRESSION (%) | | P-VALUE | BINARY EXPRESSION SENZACELL | BINARY EXPRESSION MUTZ3 | RNA EXPRESSION |
|---|---|---|---|---|---|---|---|---|
| CD1A | 23.4 | ±4.8 | 64.7 | ±1.6 | 1.25E−05 | + | + | M |
| CD4 | 25.0 | ±12.1 | 11.8 | ±4.7 | 3.01E−01 | + | + | |
| CD5 | 0.3 | ±0.2 | 0.5 | ±0.3 | 3.21E−01 | − | − | |
| CD11B | 25.6 | ±7.3 | 54.4 | ±7.0 | 3.52E−04 | + | + | M |
| CD14 | 23.5 | ±3.6 | 55.3 | ±11.9 | 2.13E−03 | + | + | M |
| CD34 | 54.5 | ±11.6 | 32.5 | ±3.7 | 1.48E−02 | + | + | S |
| CD13 | 99.5 | ±0.2 | 99.1 | ±0.7 | 3.01E−01 | + | + | M |
| CD15 | 23.1 | ±10.4 | 49.1 | ±17.2 | 2.85E−02 | + | + | M |
| CD19 | 0.2 | ±0.1 | 0.3 | ±0.2 | 3.83E−01 | − | − | |
| CD32 | 6.8 | ±2.2 | 26.9 | ±2.2 | 5.09E−07 | + | + | S |
| CD40 | 5.2 | ±2.0 | 21.5 | ±9.4 | 1.81E−02 | + | + | S |
| CD54 | 99.99 | ±0.01 | 99.96 | ±0.02 | 1.81E−02 | + | + | S |
| CD86 | 10.7 | ±2.0 | 14.4 | ±3.5 | 1.05E−01 | + | + | |
| CD80 | 0.5 | ±0.5 | 3.2 | ±2.2 | 5.32E−02 | − | + | |
| CD123 | 50.1 | ±20.0 | 30.3 | ±7.4 | 1.11E−01 | + | + | |
| HLA-DR | 82.2 | ±9.4 | 50.7 | ±15.2 | 8.80E−03 | + | + | − |
| CD209 | 0.4 | ±0.4 | 0.5 | ±0.4 | 9.24E−01 | − | − | |
| BDCA-3 | 17.9 | ±3.5 | 16.1 | ±3.2 | 4.27E−01 | + | + | |
| BDCA-1 | 13.5 | ±2.0 | 11.5 | ±5.1 | 4.34E−01 | + | + | S |
| OX40L | 0.6 | ±0.3 | 6.1 | ±10.0 | 3.01E−01 | − | −+ | |
| CD16 | 0.08 | ±0.03 | 0.2 | ±0.2 | 1.92E−01 | − | − | |
| CD64 | 13.9 | ±1.6 | 47.6 | ±8.1 | 7.26E−04 | + | + | S |
| TLR4 | 13.9 | ±4.5 | 52.3 | ±11.1 | 7.26E−04 | + | + | S |
| TLR2 | 12.5 | ±3.3 | 40.0 | ±16.6 | 2.25E−02 | + | + | |
| OX40 | 0.1 | ±0.05 | 0.1 | ±0.02 | 8.31E−01 | − | − | S |
| CD137 | 2.5 | ±1.3 | 9.1 | ±6.9 | 2.75E−01 | + | + | S |

Whole Genome Sequencing

Whole genome sequencing was performed to identify indicators of genetic differences between SenzaCell and MUTZ-3. Indicators could be represented by variants only discovered in either of the cell lines. The investigated variants consisted of single nucleotide polymorphisms (SNPs), insertions or deletions. The number of raw variants that were discovered in the cell lines was 5,080,918 and 5,073,307 in SenzaCell and MUTZ-3 respectively. The gVCF files were merged and genotyped and the variant quality scores in the outputted VCF file were recalibrated. Variants with low quality scores were filtered and removed from further analysis. The similarity between the cell line genomes and the reference genome was calculated to 99.86% for both cell lines, resulting in a variant frequency of 1 variant per ~720 bp. Variants unique to either of the cell impact on the cells. Variants were therefore filtered to remove low impact mutations. Mutations that were predicted to have a high or moderate impact in SenzaCell can be seen in Table 2 and the identified variants for MUTZ-3 can be seen in Table 3. 14 variants were discovered in SenzaCell that matched the described criteria and 28 were found in MUTZ-3. The predicted effects ranged from amino acid substitutions to more severe mutations such as gaining a new stop codons or changes in splice sites. The biological processes that the genes that were impacted by the variants could be mapped to were determined using PANTHER, see FIG. 2 and FIG. 3.

Finally, a similar filtering strategy was performed to determine the number of common variants that could be identified in the cell lines, which resulted in the identification of 4,298,116 variants.

TABLE 2

Unique variants that were only found in SenzaCell (S) which were predicted to have a high or moderate effect. Predicted effects were determined using snpEff. .Gene: identified gene to be affected by the variant, CHR: Chromosome where variant was called, POSITION: variant's position on the chromosome, IMPACT: predicted impact of variant, PREDICTED EFFECT: predicted impact by snpEff, X-GQ: Phred based quality score for genotype quality for respective cell line:

| Gene | Chr | Position | Impact | Predicted effect | M-GQ | S-GQ |
|---|---|---|---|---|---|---|
| RP11-522M21.2 | 1 | 245778159 | High | Splice acceptor variant, splice region variant, intron variant and non-coding exon variant | 33 | 99 |
| FIGN | 2 | 164467322, 164467330, 164467333 | Moderate | Missense variant | 21 | 75 |
| BOD1 | 5 | 173035291 | Moderate | Missense variant | 75 | 75 |
| KRTAP5-3 | 11 | 1628956 | Moderate | Disruptive inframe deletion | 75 | 75 |
| KIF18A | 11 | 28106253 | Moderate | Missense variant | 30 | 99 |
| QSER1 | 11 | 32955122 | Moderate | Missense variant | 33 | 99 |
| DEPDC7 | 11 | 33049341 | Moderate | Missense variant | 51 | 99 |
| APIP | 11 | 34916657 | Moderate | Missense variant and splice region variant | 48 | 99 |
| PDHX | 11 | 34969112 | Moderate | Missense variant | 32 | 99 |
| PRB4 | 12 | 11461541 | Moderate | Conservative inframe deletion | 52 | 91 |
| SON | 21 | 34927396 | Moderate | Disruptive inframe deletion | 63 | 99 |
| SLC25A14 | X | 129480633 | High | Frameshift variant | 42 | 99 |

TABLE 3

Unique variants that were only found in MUTZ-3 (M) that were predicted to have a high or moderate effect. Predicted effects were determined using snpEff. .Gene: identified gene to be affected by the variant, CHR: Chromosome where variant was called, POSITION: variant's position on chromosome, IMPACT: predicted impact of variant, PREDICTED EFFECT: predicted impact by snpEff, X-GQ: Phred based quality score for genotype quality for respective cell line:

| Gene | Chr | Position | Impact | Predicted effect | M-GQ | S-GQ |
|---|---|---|---|---|---|---|
| ZCCHC11 | 1 | 52902561 | Moderate | Missense variant | 99 | 37 |
| HAO2 | 1 | 119925549 | Moderate | Missense variant | 99 | 99 |
| AC079354.1 | 2 | 203054919 | High | Frameshift variant | 99 | 73 |
| ABCA12 | 2 | 215851269 | Moderate | Missense variant | 99 | 99 |
| CNTN6 | 3 | 1394079 | Moderate | Missense variant | 99 | 61 |
| FAM170A | 5 | 118968488 | Moderate | Missense variant | 99 | 99 |
| SNAP91 | 6 | 84375184 | Moderate | Missense variant | 99 | 99 |
| MYB | 6 | 135517061 | High | Frameshift variant | 99 | 81 |
| SOSTDC1 | 7 | 16502281 | Moderate | Missense variant | 99 | 99 |
| AOAH | 7 | 36579964 | Moderate | Missense variant | 99 | 99 |
| GS1-259H13.2 | 7 | 99203012 | High | Splice acceptor variant, splice region variant, intron variant and non-coding exon variant | 99 | 93 |
| CEP41 | 7 | 130040006, 130044465 | Moderate | Missense variant | 99, 99 | 71, 87 |
| LRGUK | 7 | 133812130 | Moderate | Missense variant | 99 | 53 |
| TRBV10-2 | 7 | 142206520, 142206551 | Moderate | Missense variant | 99 | 99 |
| CNTNAP2 | 7 | 147335933 | High | Frameshift variant | 99 | 74 |
| WISP1 | 8 | 134232964 | Moderate | Missense variant | 99 | 99 |
| DRD4 | 11 | 640098 | High | Frameshift variant | 36 | 99 |
| TNNT3 | 11 | 1956105 | Moderate | Missense variant | 99 | 84 |
| MS4A2 | 11 | 59857861 | Moderate | Missense variant | 99 | 99 |
| PVRL1 | 11 | 119549125 | Moderate | Missense variant and splice region variant | 85 | 99 |
| AP003062.1 | 11 | 134855495, 134855498 | High | Frameshift variant | 99, 99 | 55, 60 |
| SLC10A2 | 13 | 103698597 | High | Stop gained | 99 | 95 |
| PLA2G4E | 15 | 42302330 | Moderate | Conservative inframe deletion | 99 | 30 |
| SCAMP5 | 15 | 75310783 | Moderate | Missense variant | 99 | 81 |
| PES1 | 22 | 30977586 | Moderate | Missense variant | 99 | 31 |

RNA-Seq Analysis

The transcriptomes of the cell lines were compared to assess the cell states during normal growth and identify any differences between them. An initial analysis of the data was performed by creating a PCA plot of the samples and performing a hierarchical clustering analysis, FIG. 4. The PCA plot indicated the presence of batch effects as the samples from experiment 3 exhibited deviating values in the $2^{nd}$ principal component compared to the samples from the first two experiments. The samples from experiment 3 also formed a separate cluster in the hierarchical clustering which further strengthens the observation that batch effects affected the data. The samples obtained from the first two experiments seemed more similar and samples from the same cell line formed separate groups and clusters. EdgeR and DESeq were used to search for differentially expressed transcripts between the cell lines, where the generalized linear models were designed to account for the observed batch effects. 3644 transcripts were identified as significantly differentially expressed (listed in Supplementary Table 1). The identified transcripts were mapped to molecular functions and biological processes using PANTHER (FIG. 3). The majority of the transcripts were mapped to the molecular functions catalytic activity and binding and the biological processes cellular- and metabolic processes. An overrepresentation test was then performed to investigate if any biological processes were significantly under- or overrepresented among the DE transcripts. 94 GO terms were identified as statistically under- or overrepresented with a Bonferroni corrected p-value below 0.05, see Supplementary Table 2. To gain further insight into the differences between the cell lines a topological pathway analysis was also performed. The pathway analysis discovered 19 activated and 2 inhibited signaling pathways in MUTZ-3 compared to SenzaCell, Table 4.

The regulation of the genes selected in the GPS are important for the identification and separation of sensitizers and non-sensitizers in the GARD assay. The genes in the GPS were therefore compared to the DE transcripts which revealed that 43 transcripts were found in both lists. This demonstrated that almost 22% of the genes in the GPS were differentially expressed between the cell lines.

A comparison between the results in the phenotype and the RNA-seq data was performed to investigate the analysis methods and possibly give more validity to the findings. The panel of biomarkers and their corresponding genes were compared in a concordance analysis. The comparison was performed as an evaluation of a classification task with the groups significantly higher, significantly lower or not different in the MUTZ-3 compared to SenzaCell. The analysis resulted in a Cohens Kappa value of 0.44, suggesting concordance between the two methods, see expression for each marker in Table 1. 8 of the 10 surface markers that showed an increased expression also showed an increased expression in the RNAseq analysis. CD54 shows an increased gene expression in MUTZ-3 which is opposed to the surface marker expression. The gene for TLR2 is not called as differentially expressed. 8 of the 14 surface markers that were not call significant did not have differentially expressed genes either. The gene expression levels for the remaining 6 markers were however found to be differentially expressed. CD34 was the only marker that was found to have significantly lower expression levels in the MUTZ-3 in both transcription levels and surface expression. HLA-DR was left out of this comparison due to its complex genetics.

TABLE 4

Significantly different signaling pathways from SPIA after p-value correction using the Bonferroni method. The global p-values calculated by SPIA considers both the number of genes affected in the pathway and the perturbation of the signaling pathway.

| Signaling Pathway | KEGG ID | $pG_{FWER}$ | Status |
|---|---|---|---|
| Cytokine-cytokine receptor interaction | 4060 | 4.97E−11 | Activated |
| Transcriptional misregulation in cancer | 5202 | 5.08E−11 | Activated |
| NF-kappa B signaling pathway | 4064 | 8.20E−09 | Activated |
| Osteoclast differentiation | 4380 | 5.51E−08 | Activated |
| Rheumatoid arthritis | 5323 | 3.49E−06 | Activated |
| Leishmaniasis | 5140 | 3.86E−06 | Activated |
| Tuberculosis | 5152 | 2.79E−05 | Activated |
| MAPK signaling pathway | 4010 | 0.000138 | Activated |
| Lysosome | 4142 | 0.000413 | Activated |
| Toll-like receptor signaling pathway | 4620 | 0.000705 | Activated |
| Prostate cancer | 5215 | 0.002444 | Activated |
| Chemokine signaling pathway | 4062 | 0.002986 | Activated |
| Type I diabetes mellitus | 4940 | 0.007456 | Activated |
| Toxoplasmosis | 5145 | 0.015427 | Inhibited |
| Natural killer cell mediated cytotoxicity | 4650 | 0.018134 | Activated |
| Legionellosis | 5134 | 0.024336 | Activated |
| Graft-versus-host disease | 5332 | 0.026753 | Activated |
| Salmonella infection | 5132 | 0.029971 | Activated |
| Influenza A | 5164 | 0.037206 | Activated |
| Allograft rejection | 5330 | 0.037554 | Activated |
| B cell receptor signaling pathway | 4662 | 0.044202 | Inhibited |

Functional Analysis

MUTZ-3 and SenzaCell's ability to distinguish skin sensitizers when analyzing the expression of the genes in the GARD prediction signature (GPS) after chemical exposure was assessed by using the cells in the well-established assay workflow. 2-hydroxyethylacrylate and DNCB were used to stimulate the cells and an unstimulated sample was used as negative control. RNA was quantified and the samples were classified using a SVM model trained on genetic profiles from SenzaCell. The chemicals were correctly classified as sensitizers and the unstimulated sample as non-sensitizer using both MUTZ-3 and SenzaCell, FIG. 6. Further on, the prediction pattern, where 2-hydroxyethylacrylate has a higher prediction value than DNCB, is similar for MUTZ-3 as to what is obtained with SenzaCell.

DISCUSSION

Allergic contact dermatitis is a condition with increasing prevalence that causes significant costs for society. Contact with skin sensitizers can trigger an immune response to attack the complexes that are formed between the chemical and biomolecules, resulting in an attack on healthy tissue (1). Assessment of a chemicals' ability to induce ACD is important to reduce the number of people that are affected by ACD. The gold standard for sensitization testing, the local lymph node assay (LLNA) (33), rely on animal testing and is being phased out by more ethical in vitro assays (6, 7, 34). The GARD assay is an in-vitro assay that distinguishes between sensitizers and non-sensitizers by analyzing the gene expression of the genes in the GARD prediction signature. The transcripts are isolated from a dendritic cell-like cell line that has been exposed to test chemicals. The assay relies on the innate decision making of the cell line to recognize sensitizers and adapt its gene expression, making it possible to quantify the changes and learn to recognize sensitizers (9). MUTZ-3 and SenzaCell are suitable cells for this task due their ability to resemble dendritic cells, which are important for recognizing antigens and orchestrate immune responses.

SenzaCell was compared to MUTZ-3 by characterizing their phenotype, genotype and assessing the cell line's ability to distinguish sensitizers from non-sensitizers when used in the assay. The expression levels of a panel of surface markers were determined for both cell lines. The results demonstrated that 12 out of 26 surface markers had a different expression levels in MUTZ-3 compared to Senza-Cell. A hierarchical clustering algorithm with bootstrapping also showed the possibility to group the cell lines into different stable clusters, implying that the cell lines are more similar to themselves than the other cell line over the course of the experiments. The surface markers that had higher expression values in MUTZ-3 were CD1a, CD11b, CD14, CD15, CD32, CD40, CD64, TLR2 and TLR4 while CD34, CD54 and HLA-DR had lower expression values. MUTZ-3 cells can, based on CD14 and CD34 expression, be divided into three subpopulations; $CD34^+$ $CD14^-$, $CD34^-$ $CD14^-$ and $CD34^-$ $CD14^+$. Previous analysis of the populations revealed that the $CD34^+$ $CD14^-$ is the proliferating population which give rise to the other populations (35). Some of the differences between SenzaCell and MUTZ-3 could therefore possibly be explained by the differences between the subpopulations, e.g. the increased amount of $CD14^+$ cells in MUTZ-3 could possibly explain the increased $CD11b^+$ expression (35). However, considering the available data, the different levels in expression cannot be explained solely due to different sizes of the subpopulations. CD1a is expressed in both cell lines, which has preciously not been recorded in undifferentiated MUTZ-3 (8, 35, 36). The expression of CD1a could therefore indicate differentiation of the MUTZ-3 cells towards a more dendritic cell like phenotype. MUTZ-3 displayed a larger population of CD1a positive cells, which could indicate that it is more differentiated than SenzaCell. Evidence that further implies that MUTZ-3 could be more differentiated comes from the increased CD40 expression, which is a marker that increases in expression as cells differentiate towards a DC phenotype (37). Although both CD1a and CD40 are expressed in higher levels in MUTZ-3, the expression of other surface markers show evidence of the contrary. HLA-DR is another marker whose expression has been shown to moderately increase with differentiation which is more expressed in SenzaCell, making it difficult to draw any conclusions regarding unequal levels of differentiation between the cell lines (37). Further on, neither of the cell lines' morphology exhibits the characteristic dendrites that are formed as MUTZ-3 differentiates (data not shown). Considering the roles of the surface markers that are differentially expressed, many are related to myeloid cell differentiation, e.g. the FC-gamma receptors CD32 and CD64 (38), the pathogen recognition receptors (PRR) TLR2 and TLR4 (39-41) or the carbohydrate adhesion molecule CD15 (42). This could indicate that there is some form of differentiation that is responsible for the observed differences; however the nature of the differentiation process is difficult to determine using only the obtained expression values.

The whole genome sequencing was performed to compare the genomes of the cell lines and search for indications of genetic differences. The number of identified variants lie within the expected range as a typical person differs at 4.1 million to 5 million sites compared to the reference genome (43). Variants that were unique to either of the cell lines were identified and their predicted impacts were assessed. In total, 7,977 unique variants were discovered in the SenzaCell and 5,672 in MUTZ-3. Comparing the number of discovered unique variants to the number of common variants makes the observed differences seem small. However when filtering variants with low impact and assessing variants predicted to have a moderate or high impact, the situation was reversed. 14 variants were discovered in SenzaCell and 28 mutations in MUTZ-3. One of the reasons for these results could be due to the insensitivity of the method used to identify variants. Whole genome sequencing is a high throughput method which generates billions of reads. The process of transforming the reads into interpretable results is difficult and an ongoing challenge. However, if assuming that the discovered variants are unique to the cell lines and not the artifacts from detection, they could be the product of other biological processes. Genetic differences can be caused by selective pressure as the cell lines grow. If MUTZ-3 contains subpopulations with different variants in its genome, it is possible that some of them have been lost in SenzaCell. Genetic heterogeneity has previously been shown in cell lines (44). Another possibility is that MUTZ-3 has been expanded in parallel to SenzaCell, which could have generated the discovered variants. A parallel expansion of MUTZ-3 cell line could result in finding unique variants that are absent in the SenzaCell cells, but would require the mutations to be of high or moderate impact with higher frequency. A continued parallel expansion could possibly introduce additional differences between the cell lines. The biological processes that were mapped to the genes predicted to be impacted by the mutations are general terms and difficult to draw functional conclusions from. This is made even harder when considering the impact that a mutation has, e.g. the effect of a missense variant where an amino acid in the resulting protein is changed to another amino acid. However, studying the gene lists reveals interesting variants. The high impact variant found in MUTZ-3 in the MYB gene could be a relevant finding. The MYB is an identified oncogene that normally has important functions in the regulation of stem- and progenitor cells (45). Another interesting observation is the mutation in the WISP1 gene, also in the MUTZ-3. WISP1 functions in the WNT signaling pathways which has important roles in mediating cell-cell interactions and stem cell regulation and control (46-48). Both of these mutations could be important for the function and regulation of the cell lines, and the lack of these variants in SenzaCell could have a functional impact.

Analysis of the cell transcriptomes were performed by quantification of transcription levels using RNA-seq during ordinary cultivation. A comparison of the expression levels revealed that 3644 transcripts were differentially expressed, which is close to 10% of all the transcripts that were analyzed after removing zero count transcripts. The high number of differentially expressed genes suggests that large differences between the cell lines can be observed at molecular level. An overrepresentation test and a topological pathway analysis were performed to get a better understanding of the potential impacts that the identified genes could have on the cells. 94 biological process GO terms were identified as over- or underrepresented amongst the identified transcripts. Due to the comparative analysis of identifying differences between the cell lines, overrepresented terms are of the greatest importance. Underrepresented terms can be interesting in other types of analyses, e.g. to identify key biological processes necessary for cell function. However, most of the identified GO terms were overrepresented. To briefly mention some of the GO terms, myeloid leukocyte activation and leukocyte chemotaxis were identified as the biological processes with largest fold change between the expected and the observed number of transcripts. Both of these terms indicate response to external stimuli (49). Positive regulation of MAP kinase activity was also identified with many related GO terms. The MAP kinases are involved in signaling pathways that control important cellular processes such as cell differentiation, cell proliferation and cell death (50). Different inflammatory responses and immune processes were also identified as overrepresented, which could be of importance due to the functional role of Senza-Cell in the GARD assay. Continuing the analysis of the RNA-seq data, a pathway analysis was performed to gain further knowledge about the differences between the cell lines. The pathway analysis discovered 19 signaling pathways that were significantly activated and 2 that were inhibited in the MUTZ-3 cells compared to SenzaCell. MAP kinase signaling pathway was identified as activated in MUTZ-3. MAP kinase activity was also identified as an overrepresented biological process, giving additional evidence of changes in cellular processes between the cell lines. NF-kappa B signaling is another interesting pathway that was discovered as activated, which is intimately linked to inflammatory responses (51). These observations together with the activated toll-like receptor signaling could be the result of an inflammatory response.

The functional analysis showed that MUTZ-3 was able to produce predictions similar to what is achieved when using SenzaCell in the assay. The sensitizers DNCB and 2-hydroxyethylacrylate were correctly predicted as sensitizers by assessing the transcriptional levels of the genes in the GPS. The predicted decision values also showed a similar pattern between the two cell lines. The ability to separate the chemicals do however not directly give any measure of similarity. It is possible that the cells react similar to stimuli and that the GPS captures these changes well.

To summarize the comparisons, we have completed a phenotypic analysis which revealed that 12 out of 26 surface markers were differentially expressed between MUTZ-3 and SenzaCell. Cluster analysis on the expression values forms two separate clusters which separates the cell lines. Whole genome sequencing identified more unique variants in the SenzaCell cell line when assessing all the discovered variants. When filtering out low impact variants, the MUTZ-3 cell lines contained 28 variants compared to 14 in the SenzaCell cell line. Some of the identified variants could have important impacts in the functions of the cells. The RNA-seq analysis found 3644 transcripts that were differentially expressed. An overrepresentation test and a pathway analysis revealed that many biological processes and signaling pathways were differentially activated. Finally, MUTZ-3 and SenzaCell have been used in the GARD assay to evaluate their ability to recognize sensitizers and produce predictions. The classifications of the samples resulted in correct predictions for all the chemicals, indicating that both cell lines could be used in the assays, despite observed differences.

In conclusion, we have identified numerous differences between SenzaCell and MUTZ-3 in phenotypic and genotypic analyses. Collectively the differences indicate that SenzaCell has unique expression of surface molecules and cellular functions, yet both cell lines can be used in the GARD assays.

SUPPLEMENTARY TABLE 1

List of the identified differentially expressed transcripts after DE analysis using DESeq2 and edgeR-

| ENSEMBL | Symbol | $\text{Log}_2$ Fold Change | False discovery rate |
| --- | --- | --- | --- |
| ENSG00000102962 | CCL22 | 4.123123 | 2.62E−192 |
| ENSG00000211899 |  | −3.45692 | 2.01E−109 |
| ENSG00000115008 | IL1A | 2.520256 | 6.72E−93 |
| ENSG00000197561 | ELANE | 2.709104 | 6.32E−90 |
| ENSG00000115009 | CCL20 | 3.089019 | 5.82E−86 |
| ENSG00000172260 | NEGR1 | −3.31573 | 2.29E−85 |
| ENSG00000171617 | ENC1 | −2.0878 | 1.39E−82 |
| ENSG00000184368 | MAP7D2 | 2.668051 | 9.27E−80 |
| ENSG00000163220 | S100A9 | 1.872061 | 3.74E−75 |
| ENSG00000125538 | IL1B | 2.138323 | 9.85E−72 |
| ENSG00000073910 | FRY | 2.825691 | 3.33E−71 |
| ENSG00000211898 |  | −3.9313 | 3.39E−71 |
| ENSG00000092067 | CEBPE | 2.667064 | 2.19E−67 |
| ENSG00000169385 | RNASE2 | 2.243835 | 1.89E−64 |
| ENSG00000136689 | IL1RN | 1.708561 | 2.52E−64 |
| ENSG00000198521 | ZNF43 | −3.2071 | 5.19E−64 |
| ENSG00000104219 | ZDHHC2 | −2.75589 | 1.77E−61 |
| ENSG00000106789 | CORO2A | 2.099002 | 3.22E−59 |
| ENSG00000128567 | PODXL | −2.66184 | 1.50E−57 |
| ENSG00000164070 | HSPA4L | 2.663608 | 1.50E−57 |
| ENSG00000166025 | AMOTL1 | 3.916451 | 3.68E−56 |
| ENSG00000121966 | CXCR4 | 2.276018 | 4.60E−56 |
| ENSG00000165092 | ALDH1A1 | −3.09609 | 1.07E−55 |
| ENSG00000143546 | S100A8 | 1.752797 | 3.17E−55 |
| ENSG00000214212 | C19orf38 | 2.157473 | 7.43E−55 |
| ENSG00000170017 | ALCAM | 1.745714 | 1.20E−53 |
| ENSG00000196415 | PRTN3 | 2.031909 | 3.79E−53 |
| ENSG00000119042 | SATB2 | 3.086264 | 4.84E−53 |
| ENSG00000067113 | PLPP1 | 2.613582 | 7.64E−51 |
| ENSG00000166446 | CDYL2 | −2.58598 | 5.15E−50 |
| ENSG00000166532 | RIMKLB | −2.07617 | 6.73E−50 |
| ENSG00000128641 | MYO1B | −2.13719 | 5.83E−49 |
| ENSG00000173200 | PARP15 | −2.94694 | 1.17E−48 |
| ENSG00000157570 | TSPAN18 | −2.74536 | 2.76E−48 |
| ENSG00000103528 | SYT17 | −3.23566 | 7.68E−48 |
| ENSG00000143110 | C1orf162 | 1.822263 | 9.61E−48 |
| ENSG00000105205 | CLC | 2.036686 | 9.68E−48 |
| ENSG00000161905 | ALOX15 | 1.912847 | 6.20E−46 |

SUPPLEMENTARY TABLE 1-continued

List of the identified differentially expressed transcripts after DE analysis using DESeq2 and edgeR-

| ENSEMBL | Symbol | Log$_2$ Fold Change | False discovery rate |
|---|---|---|---|
| ENSG00000103942 | HOMER2 | −2.06151 | 1.38E−45 |
| ENSG00000242550 | SERPINB10 | 2.438655 | 7.00E−45 |
| ENSG00000169896 | ITGAM | 1.535044 | 5.26E−44 |
| ENSG00000111344 | RASAL1 | 2.27749 | 8.73E−44 |
| ENSG00000109099 | PMP22 | 2.696206 | 9.04E−44 |
| ENSG00000112394 | SLC16A10 | 2.717125 | 2.64E−43 |
| ENSG00000107968 | MAP3K8 | 1.697925 | 3.41E−42 |
| ENSG00000166920 | C15orf48 | 3.173252 | 6.56E−42 |
| ENSG00000166147 | FBN1 | 2.478197 | 9.50E−42 |
| ENSG00000100473 | COCH | −2.99481 | 1.13E−41 |
| ENSG00000232810 | TNF | 2.364805 | 2.98E−41 |
| ENSG00000145246 | ATP10D | −1.80444 | 8.23E−41 |
| ENSG00000135052 | GOLM1 | 2.300466 | 1.26E−40 |
| ENSG00000139880 | CDH24 | 2.012996 | 3.76E−40 |
| ENSG00000129824 | RPS4Y1 | −4.40067 | 4.46E−40 |
| ENSG00000118503 | TNFAIP3 | 1.691312 | 4.74E−40 |
| ENSG00000115112 | TFCP2L1 | 2.219946 | 1.56E−39 |
| ENSG00000172232 | AZU1 | 1.369037 | 5.37E−38 |
| ENSG00000117090 | SLAMF1 | 2.39219 | 8.32E−38 |
| ENSG00000138623 | SEMA7A | 1.562484 | 1.22E−37 |
| ENSG00000153113 | CAST | −1.88228 | 3.84E−37 |
| ENSG00000101425 | BPI | 1.587417 | 4.05E−37 |
| ENSG00000112303 | VNN2 | −2.39174 | 3.13E−36 |
| ENSG00000106178 | CCL24 | 2.48614 | 5.60E−36 |
| ENSG00000102471 | NDFIP2 | 2.708166 | 2.19E−35 |
| ENSG00000163739 | CXCL1 | 1.779606 | 3.45E−35 |
| ENSG00000144792 | ZNF660 | −3.52959 | 8.16E−35 |
| ENSG00000197043 | ANXA6 | −2.27294 | 1.11E−34 |
| ENSG00000242308 |  | −3.05075 | 1.28E−34 |
| ENSG00000169397 | RNASE3 | 1.89974 | 2.50E−34 |
| ENSG00000005486 | RHBDD2 | 1.319517 | 5.25E−34 |
| ENSG00000158517 | NCF1 | 1.733696 | 1.56E−33 |
| ENSG00000205542 | TMSB4X | 1.292791 | 1.84E−33 |
| ENSG00000169981 | ZNF35 | −2.49419 | 2.61E−33 |
| ENSG00000137642 | SORL1 | −2.44646 | 4.35E−33 |
| ENSG00000113916 | BCL6 | 2.122035 | 6.90E−33 |
| ENSG00000100985 | MMP9 | 2.993912 | 1.02E−32 |
| ENSG00000091972 | CD200 | −2.18297 | 2.95E−32 |
| ENSG00000115339 | GALNT3 | 1.941517 | 8.29E−32 |
| ENSG00000049449 | RCN1 | −1.43462 | 1.65E−31 |
| ENSG00000060749 | QSER1 | −1.43403 | 2.80E−31 |
| ENSG00000205269 | TMEM170B | 1.735782 | 5.02E−31 |
| ENSG00000167281 | RBFOX3 | 3.300351 | 5.48E−31 |
| ENSG00000171223 | JUNB | 1.555901 | 7.89E−31 |
| ENSG00000255587 | RAB44 | 1.504611 | 1.19E−30 |
| ENSG00000154262 | ABCA6 | −2.16223 | 1.44E−30 |
| ENSG00000130529 | TRPM4 | 1.643649 | 1.96E−30 |
| ENSG00000100300 | TSPO | 1.589284 | 5.09E−30 |
| ENSG00000165682 | CLEC1B | −1.96051 | 8.67E−30 |
| ENSG00000226777 | KIAA0125 | −1.34688 | 1.60E−29 |
| ENSG00000158050 | DUSP2 | 1.488983 | 1.79E−29 |
| ENSG00000168546 | GFRA2 | 2.990533 | 1.79E−29 |
| ENSG00000182378 | PLCXD1 | −1.27974 | 2.05E−29 |
| ENSG00000225485 |  | −1.69536 | 2.40E−29 |
| ENSG00000196189 | SEMA4A | 1.61718 | 4.00E−29 |
| ENSG00000124788 | ATXN1 | 2.333093 | 6.14E−29 |
| ENSG00000091622 | PITPNM3 | 1.703609 | 8.93E−29 |
| ENSG00000163993 | S100P | 1.703326 | 9.59E−29 |
| ENSG00000165178 | NCF1C | 1.627538 | 1.05E−28 |
| ENSG00000112299 | VNN1 | −1.72818 | 1.46E−28 |
| ENSG00000168329 | CX3CR1 | −1.66555 | 3.57E−28 |
| ENSG00000012779 | ALOX5 | 1.865681 | 3.86E−28 |
| ENSG00000163563 | MNDA | 1.309734 | 4.34E−28 |
| ENSG00000023445 | BIRC3 | 2.258108 | 6.71E−28 |
| ENSG00000111729 | CLEC4A | 2.69362 | 6.92E−28 |
| ENSG00000154229 | PRKCA | 1.569989 | 6.92E−28 |
| ENSG00000157703 | SVOPL | −1.59437 | 1.26E−27 |
| ENSG00000197937 | ZNF347 | −2.85425 | 1.43E−27 |
| ENSG00000134531 | EMP1 | −1.82285 | 3.90E−27 |
| ENSG00000175471 | MCTP1 | 1.291777 | 4.38E−27 |
| ENSG00000184588 | PDE4B | 1.693027 | 1.08E−26 |
| ENSG00000184371 | CSF1 | 2.042032 | 1.23E−26 |
| ENSG00000177169 | ULK1 | 1.331273 | 1.26E−26 |
| ENSG00000188725 | SMIM15 | −1.35353 | 2.00E−26 |
| ENSG00000157110 | RBPMS | −1.48798 | 2.06E−26 |

SUPPLEMENTARY TABLE 1-continued

List of the identified differentially expressed transcripts after DE analysis using DESeq2 and edgeR-

| ENSEMBL | Symbol | Log$_2$ Fold Change | False discovery rate |
|---|---|---|---|
| ENSG00000120875 | DUSP4 | 1.460099 | 2.11E−26 |
| ENSG00000163956 | LRPAP1 | 1.224615 | 2.25E−26 |
| ENSG00000169442 | CD52 | 1.392453 | 3.73E−26 |
| ENSG00000164929 | BAALC | −2.22524 | 6.26E−26 |
| ENSG00000064989 | CALCRL | −1.19146 | 1.68E−25 |
| ENSG00000137331 | IER3 | 1.64983 | 1.71E−25 |
| ENSG00000138185 | ENTPD1 | 1.46728 | 1.77E−25 |
| ENSG00000250722 | SEPPI | −2.86532 | 1.99E−25 |
| ENSG00000110324 | IL10RA | 1.315974 | 4.22E−25 |
| ENSG00000131355 | ADGRE3 | 1.637766 | 4.49E−25 |
| ENSG00000138449 | SLC40A1 | −1.87137 | 4.52E−25 |
| ENSG00000131669 | NINJ1 | 1.479819 | 5.29E−25 |
| ENSG00000138772 | ANXA3 | 1.327704 | 5.48E−25 |
| ENSG00000169429 | CXCL8 | 1.284099 | 7.05E−25 |
| ENSG00000134463 | ECHDC3 | −3.0198 | 9.60E−25 |
| ENSG00000070018 | LRP6 | −1.67722 | 1.05E−24 |
| ENSG00000186431 | FCAR | 1.604409 | 1.51E−24 |
| ENSG00000138722 | MMRN1 | −2.28656 | 1.69E−24 |
| ENSG00000159496 | RGL4 | 1.521802 | 2.24E−24 |
| ENSG00000198736 | MSRB1 | 1.25494 | 3.07E−24 |
| ENSG00000174059 | CD34 | −1.50709 | 3.16E−24 |
| ENSG00000109576 | AADAT | −1.75206 | 3.39E−24 |
| ENSG00000256771 | ZNF253 | −1.71224 | 5.17E−24 |
| ENSG00000058091 | CDK14 | 1.936302 | 5.89E−24 |
| ENSG00000148468 | FAM171A1 | −2.63414 | 8.70E−24 |
| ENSG00000145335 | SNCA | −1.54258 | 1.19E−23 |
| ENSG00000182557 | SPNS3 | 1.995036 | 1.44E−23 |
| ENSG00000107165 | TYRP1 | −2.01223 | 1.81E−23 |
| ENSG00000146070 | PLA2G7 | 2.906727 | 1.86E−23 |
| ENSG00000149100 | EIF3M | −1.02196 | 2.70E−23 |
| ENSG00000159339 | PADI4 | 1.407783 | 2.70E−23 |
| ENSG00000108947 | EFNB3 | −1.62478 | 2.87E−23 |
| ENSG00000135387 | CAPRIN1 | −1.0511 | 3.10E−23 |
| ENSG00000168497 | SDPR | −1.89261 | 3.10E−23 |
| ENSG00000117461 | PIK3R3 | 1.286659 | 3.18E−23 |
| ENSG00000214063 | TSPAN4 | 1.437514 | 4.45E−23 |
| ENSG00000113389 | NPR3 | −1.4573 | 6.93E−23 |
| ENSG00000163736 | PPBP | −1.84886 | 1.12E−22 |
| ENSG00000198848 | CES1 | 1.867213 | 1.13E−22 |
| ENSG00000127824 | TUBA4A | 1.224405 | 1.25E−22 |
| ENSG00000160161 | CILP2 | 2.302167 | 1.80E−22 |
| ENSG00000121691 | CAT | −1.09421 | 3.32E−22 |
| ENSG00000073737 | DHRS9 | 1.423372 | 3.37E−22 |
| ENSG00000122694 | GLIPR2 | 1.130655 | 4.83E−22 |
| ENSG00000113273 | ARSB | 1.102375 | 1.04E−21 |
| ENSG00000140379 | BCL2A1 | 1.082409 | 1.08E−21 |
| ENSG00000085265 | FCN1 | 2.075745 | 1.21E−21 |
| ENSG00000039560 | RAI14 | −1.31817 | 1.57E−21 |
| ENSG00000060982 | BCAT1 | −1.21679 | 1.78E−21 |
| ENSG00000135372 | NAT10 | −1.08879 | 2.00E−21 |
| ENSG00000166401 | SERPINB8 | 1.362048 | 2.43E−21 |
| ENSG00000178538 | CA8 | 1.650778 | 2.48E−21 |
| ENSG00000055118 | KCNH2 | 2.110973 | 3.11E−21 |
| ENSG00000144802 | NFKBIZ | 1.740977 | 3.63E−21 |
| ENSG00000136315 |  | 1.612605 | 5.66E−21 |
| ENSG00000087245 | MMP2 | −1.50687 | 6.10E−21 |
| ENSG00000184307 | ZDHHC23 | −1.47084 | 9.60E−21 |
| ENSG00000112297 | AIM1 | 2.169093 | 1.34E−20 |
| ENSG00000152932 | RAB3C | 1.95027 | 1.66E−20 |
| ENSG00000134489 | HRH4 | 2.434787 | 1.88E−20 |
| ENSG00000110422 | HIPK3 | −1.30744 | 2.20E−20 |
| ENSG00000173391 | OLR1 | 1.664069 | 2.24E−20 |
| ENSG00000143167 | GPA33 | −1.32673 | 2.57E−20 |
| ENSG00000100906 | NFKBIA | 1.219965 | 2.85E−20 |
| ENSG00000170873 | MTSS1 | −1.89491 | 3.60E−20 |
| ENSG00000204257 | HLA-DMA | −1.45249 | 6.59E−20 |
| ENSG00000120256 | LRP11 | −2.69974 | 7.62E−20 |
| ENSG00000100448 | CTSG | 1.162552 | 8.84E−20 |
| ENSG00000115604 | IL18R1 | 1.366065 | 9.52E−20 |
| ENSG00000159388 | BTG2 | 1.253231 | 1.09E−19 |
| ENSG00000101307 | SIRPB1 | 1.194443 | 1.28E−19 |
| ENSG00000155926 | SLA | 1.187957 | 1.37E−19 |
| ENSG00000026508 | CD44 | −0.9481 | 1.58E−19 |
| ENSG00000178623 | GPR35 | 1.546849 | 1.62E−19 |
| ENSG00000168916 | ZNF608 | −1.53335 | 2.01E−19 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000121552 | CSTA | 1.29929 | 2.33E−19 |
| ENSG00000182885 | ADGRG3 | 1.022942 | 2.33E−19 |
| ENSG00000197046 | SIGLEC15 | −1.36513 | 2.56E−19 |
| ENSG00000139278 | GLIPR1 | −0.97146 | 2.76E−19 |
| ENSG00000145819 | ARHGAP26 | 1.146262 | 3.21E−19 |
| ENSG00000046889 | PREX2 | −2.08654 | 3.33E−19 |
| ENSG00000185275 |  | 1.691109 | 3.64E−19 |
| ENSG00000126016 | AMOT | −2.94732 | 3.96E−19 |
| ENSG00000115607 | IL18RAP | 1.396531 | 4.53E−19 |
| ENSG00000162433 | AK4 | 1.447695 | 5.26E−19 |
| ENSG00000000938 | FGR | 1.161581 | 5.70E−19 |
| ENSG00000121310 | ECHDC2 | −3.05665 | 6.15E−19 |
| ENSG00000164100 | NDST3 | −1.31812 | 6.83E−19 |
| ENSG00000182010 | RTKN2 | 1.961911 | 8.71E−19 |
| ENSG00000088305 | DNMT3B | −1.15917 | 9.19E−19 |
| ENSG00000005381 | MPO | 1.246629 | 1.28E−18 |
| ENSG00000076662 | ICAM3 | 0.961891 | 1.59E−18 |
| ENSG00000100097 | LGALS1 | 1.095567 | 1.62E−18 |
| ENSG00000163874 | ZC3H12A | 1.38201 | 2.14E−18 |
| ENSG00000197928 | ZNF677 | −2.56131 | 2.14E−18 |
| ENSG00000041353 | RAB27B | −1.0001 | 2.15E−18 |
| ENSG00000135363 | LMO2 | −1.21791 | 2.20E−18 |
| ENSG00000260833 |  | −2.2377 | 2.83E−18 |
| ENSG00000099860 | GADD45B | 1.186935 | 3.65E−18 |
| ENSG00000127948 | POR | 1.00795 | 3.87E−18 |
| ENSG00000163421 | PROK2 | 2.364393 | 4.43E−18 |
| ENSG00000106780 | MEGF9 | 1.215229 | 4.65E−18 |
| ENSG00000171798 | KNDC1 | 1.40671 | 9.13E−18 |
| ENSG00000123358 | NR4A1 | 1.314283 | 9.43E−18 |
| ENSG00000109929 | SC5D | −1.35376 | 9.90E−18 |
| ENSG00000198589 | LRBA | −0.94474 | 1.12E−17 |
| ENSG00000032444 | PNPLA6 | 1.18285 | 1.30E−17 |
| ENSG00000110047 | EHD1 | 1.075667 | 1.55E−17 |
| ENSG00000198355 | PIM3 | 1.392739 | 1.75E−17 |
| ENSG00000186074 | CD300LF | 1.218858 | 1.76E−17 |
| ENSG00000122862 | SRGN | 0.945867 | 1.92E−17 |
| ENSG00000171236 | LRG1 | 1.099099 | 1.95E−17 |
| ENSG00000184937 | WT1 | −1.20817 | 2.27E−17 |
| ENSG00000125726 | CD70 | 1.628283 | 2.48E−17 |
| ENSG00000103037 | SETD6 | −2.98225 | 2.76E−17 |
| ENSG00000139626 | ITGB7 | 1.342262 | 3.27E−17 |
| ENSG00000127920 | GNG11 | −1.29355 | 3.97E−17 |
| ENSG00000167680 | SEMA6B | 1.153629 | 4.01E−17 |
| ENSG00000049089 | COL9A2 | 1.066559 | 4.79E−17 |
| ENSG00000214455 |  | −1.69767 | 4.83E−17 |
| ENSG00000151012 | SLC7A11 | 1.234853 | 5.65E−17 |
| ENSG00000125430 | HS3ST3B1 | 2.223313 | 6.96E−17 |
| ENSG00000147443 | DOK2 | 0.929769 | 7.04E−17 |
| ENSG00000166326 | TRIM44 | −1.2524 | 8.10E−17 |
| ENSG00000257743 | MGAM2 | 1.734896 | 9.90E−17 |
| ENSG00000174837 | ADGRE1 | 1.013873 | 1.51E−16 |
| ENSG00000167775 | CD320 | 1.276526 | 1.72E−16 |
| ENSG00000224940 | PRRT4 | 2.13921 | 1.75E−16 |
| ENSG00000089177 | KIF16B | −2.16086 | 1.77E−16 |
| ENSG00000052126 | PLEKHA5 | −1.07754 | 2.18E−16 |
| ENSG00000164512 | ANKRD55 | 1.848602 | 2.47E−16 |
| ENSG00000234493 | RHOXF1P1 | 1.894632 | 2.53E−16 |
| ENSG00000197249 | SERPINA1 | 1.21653 | 2.77E−16 |
| ENSG00000119686 | FLVCR2 | 1.472465 | 3.20E−16 |
| ENSG00000187049 | TMEM216 | −1.99899 | 3.26E−16 |
| ENSG00000123095 | BHLHE41 | 1.87136 | 3.37E−16 |
| ENSG00000186652 | PRG2 | 1.791934 | 3.49E−16 |
| ENSG00000135838 | NPL | 1.723577 | 3.49E−16 |
| ENSG00000130300 | PLVAP | −1.5462 | 3.49E−16 |
| ENSG00000114439 | BBX | −1.15627 | 4.24E−16 |
| ENSG00000140678 | ITGAX | 0.978735 | 4.28E−16 |
| ENSG00000105088 | OLFM2 | 2.097081 | 4.93E−16 |
| ENSG00000197608 | ZNF841 | −1.24994 | 5.10E−16 |
| ENSG00000169247 | SH3TC2 | −1.66832 | 5.66E−16 |
| ENSG00000154188 | ANGPT1 | −1.11781 | 5.71E−16 |
| ENSG00000148943 | LIN7C | −1.01614 | 6.30E−16 |
| ENSG00000174944 | P2RY14 | 1.140986 | 6.74E−16 |
| ENSG00000081189 | MEF2C | −0.93383 | 7.36E−16 |
| ENSG00000178053 | MLF1 | −2.94468 | 9.46E−16 |
| ENSG00000234147 |  | 1.27994 | 1.17E−15 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000186827 | TNFRSF4 | 1.587586 | 1.29E−15 |
| ENSG00000157404 | KIT | −1.25057 | 1.50E−15 |
| ENSG00000140030 | GPR65 | 1.393958 | 1.55E−15 |
| ENSG00000090674 | MCOLN1 | 1.124467 | 1.73E−15 |
| ENSG00000198842 | DUSP27 | −1.70887 | 1.73E−15 |
| ENSG00000189190 | ZNF600 | −1.55929 | 1.87E−15 |
| ENSG00000121053 | EPX | 2.719348 | 2.55E−15 |
| ENSG00000179776 | CDH5 | −2.02669 | 2.55E−15 |
| ENSG00000164111 | ANXA5 | 0.842223 | 2.67E−15 |
| ENSG00000171049 | FPR2 | 1.494454 | 3.04E−15 |
| ENSG00000086548 | CEACAM6 | 1.90978 | 3.14E−15 |
| ENSG00000133195 | SLC39A11 | 0.894129 | 3.35E−15 |
| ENSG00000023330 | ALAS1 | 1.06202 | 4.43E−15 |
| ENSG00000143515 | ATP8B2 | −0.99973 | 4.52E−15 |
| ENSG00000160307 | S100B | 1.382946 | 4.55E−15 |
| ENSG00000078081 | LAMP3 | 2.86482 | 4.87E−15 |
| ENSG00000100342 | APOL1 | −1.88248 | 6.18E−15 |
| ENSG00000114013 | CD86 | 1.651351 | 8.23E−15 |
| ENSG00000100368 | CSF2RB | 0.887203 | 9.52E−15 |
| ENSG00000102554 | KLF5 | 1.480746 | 9.58E−15 |
| ENSG00000101197 | BIRC7 | 1.103902 | 1.02E−14 |
| ENSG00000268758 | ADGRE4P | 1.138616 | 1.04E−14 |
| ENSG00000184221 | OLIG1 | 1.304906 | 1.36E−14 |
| ENSG00000182487 | NCF1B | 1.474133 | 2.77E−14 |
| ENSG00000223865 | HLA-DPB1 | −1.29641 | 3.21E−14 |
| ENSG00000176788 | BASP1 | 1.030939 | 3.24E−14 |
| ENSG00000171159 | C9orf16 | 1.038514 | 3.34E−14 |
| ENSG00000174403 | | −1.82945 | 3.39E−14 |
| ENSG00000115170 | ACVR1 | 1.477417 | 3.41E−14 |
| ENSG00000176340 | COX8A | 0.873816 | 3.48E−14 |
| ENSG00000115286 | NDUFS7 | 1.17336 | 3.48E−14 |
| ENSG00000163565 | IFI16 | −0.97578 | 3.83E−14 |
| ENSG00000145287 | PLAC8 | 0.943553 | 3.96E−14 |
| ENSG00000182986 | ZNF320 | −1.13022 | 4.03E−14 |
| ENSG00000113140 | SPARC | −1.06506 | 4.06E−14 |
| ENSG00000106976 | DNM1 | −1.06998 | 4.35E−14 |
| ENSG00000197256 | KANK2 | −1.00487 | 4.87E−14 |
| ENSG00000127955 | GNAI1 | −1.14996 | 5.06E−14 |
| ENSG00000151693 | ASAP2 | −2.70513 | 5.17E−14 |
| ENSG00000163661 | PTX3 | 1.289043 | 7.81E−14 |
| ENSG00000102265 | TIMP1 | 0.889532 | 7.92E−14 |
| ENSG00000132819 | RBM38 | 1.100501 | 8.03E−14 |
| ENSG00000146278 | PNRC1 | 1.000352 | 8.07E−14 |
| ENSG00000103811 | CTSH | 1.037916 | 8.60E−14 |
| ENSG00000186529 | CYP4F3 | 2.070624 | 8.79E−14 |
| ENSG00000110435 | PDHX | −0.94796 | 9.87E−14 |
| ENSG00000100292 | HMOX1 | 1.156909 | 1.03E−13 |
| ENSG00000108691 | CCL2 | 1.285276 | 1.10E−13 |
| ENSG00000124942 | AHNAK | −0.9651 | 1.11E−13 |
| ENSG00000156535 | CD109 | −1.03038 | 1.15E−13 |
| ENSG00000197632 | SERPINB2 | 2.358363 | 1.43E−13 |
| ENSG00000198825 | INPP5F | −0.9648 | 1.58E−13 |
| ENSG00000107742 | SPOCK2 | −1.7638 | 1.70E−13 |
| ENSG00000134369 | NAV1 | −1.51327 | 2.06E−13 |
| ENSG00000105669 | COPE | 0.924119 | 2.18E−13 |
| ENSG00000084731 | KIF3C | −1.14016 | 2.32E−13 |
| ENSG00000110429 | FBXO3 | −1.00915 | 2.32E−13 |
| ENSG00000223547 | ZNF844 | −1.52031 | 2.32E−13 |
| ENSG00000182287 | AP1S2 | 1.066371 | 2.34E−13 |
| ENSG00000243244 | STON1 | 1.217477 | 2.39E−13 |
| ENSG00000027075 | PRKCH | −1.55444 | 2.52E−13 |
| ENSG00000175104 | TRAF6 | −1.11852 | 2.68E−13 |
| ENSG00000148926 | ADM | 1.195769 | 2.79E−13 |
| ENSG00000135636 | DYSF | 1.811885 | 2.86E−13 |
| ENSG00000110442 | COMMD9 | −0.85147 | 3.14E−13 |
| ENSG00000134256 | CD101 | 1.40696 | 3.24E−13 |
| ENSG00000107796 | ACTA2 | −1.47665 | 3.50E−13 |
| ENSG00000182578 | CSF1R | −1.21106 | 4.01E−13 |
| ENSG00000131127 | ZNF141 | −1.49911 | 4.08E−13 |
| ENSG00000109911 | ELP4 | −1.1467 | 4.32E−13 |
| ENSG00000211829 | | 1.341914 | 4.38E−13 |
| ENSG00000109736 | MFSD10 | 0.974795 | 4.78E−13 |
| ENSG00000142583 | SLC2A5 | −0.8059 | 5.43E−13 |
| ENSG00000104419 | NDRG1 | 0.981239 | 5.81E−13 |
| ENSG00000105290 | APLP1 | 1.933475 | 6.69E−13 |

SUPPLEMENTARY TABLE 1-continued

List of the identified differentially expressed transcripts after DE analysis using DESeq2 and edgeR-

| ENSEMBL | Symbol | Log$_2$ Fold Change | False discovery rate |
| --- | --- | --- | --- |
| ENSG00000119943 | PYROXD2 | 1.177352 | 7.42E-13 |
| ENSG00000064687 | ABCA7 | 1.182353 | 9.08E-13 |
| ENSG00000117525 | F3 | 1.377249 | 9.08E-13 |
| ENSG00000135525 | MAP7 | -0.96695 | 9.45E-13 |
| ENSG00000152219 | ARL14EP | -1.06339 | 1.00E-12 |
| ENSG00000186710 | CFAP73 | 2.287932 | 1.02E-12 |
| ENSG00000203710 | CR1 | 1.234258 | 1.02E-12 |
| ENSG00000177700 | POLR2L | 0.922973 | 1.07E-12 |
| ENSG00000140443 | IGF1R | 0.956037 | 1.14E-12 |
| ENSG00000167613 | LAIR1 | 0.838263 | 1.26E-12 |
| ENSG00000133636 | NTS | -2.15828 | 1.54E-12 |
| ENSG00000147408 | CSGALNACT1 | 1.398341 | 1.54E-12 |
| ENSG00000130818 | ZNF426 | -1.23788 | 1.60E-12 |
| ENSG00000151135 | TMEM263 | -1.2275 | 1.78E-12 |
| ENSG00000239998 | LILRA2 | 1.141153 | 1.80E-12 |
| ENSG00000095739 | BAMBI | 1.407313 | 1.80E-12 |
| ENSG00000138395 | CDK15 | 1.876828 | 2.10E-12 |
| ENSG00000179104 | TMTC2 | -1.29874 | 2.12E-12 |
| ENSG00000172270 | BSG | 0.75884 | 2.32E-12 |
| ENSG00000163606 | CD200R1 | 2.046589 | 2.56E-12 |
| ENSG00000121933 | ADORA3 | 1.109796 | 2.86E-12 |
| ENSG00000131979 | GCH1 | 0.941214 | 2.91E-12 |
| ENSG00000143195 | ILDR2 | -1.81541 | 3.06E-12 |
| ENSG00000151320 | AKAP6 | -2.2415 | 3.25E-12 |
| ENSG00000171649 | ZIK1 | -1.36067 | 3.54E-12 |
| ENSG00000141526 | SLC16A3 | 0.742233 | 3.85E-12 |
| ENSG00000108176 | DNAJC12 | -2.42404 | 4.00E-12 |
| ENSG00000087303 | NID2 | -2.40631 | 4.06E-12 |
| ENSG00000163734 | CXCL3 | 1.124028 | 4.15E-12 |
| ENSG00000171502 | COL24A1 | -2.12533 | 4.15E-12 |
| ENSG00000105810 | CDK6 | -0.77731 | 4.50E-12 |
| ENSG00000125910 | S1PR4 | 1.057041 | 4.50E-12 |
| ENSG00000155659 | VSIG4 | 0.783741 | 4.52E-12 |
| ENSG00000078902 | TOLLIP | 0.84835 | 4.71E-12 |
| ENSG00000165029 | ABCA1 | 1.477978 | 5.19E-12 |
| ENSG00000133805 | AMPD3 | 0.908407 | 5.73E-12 |
| ENSG00000226742 | HSBP1L1 | -2.59081 | 6.08E-12 |
| ENSG00000112294 | ALDH5A1 | -0.79982 | 6.63E-12 |
| ENSG00000251442 | | 1.047537 | 7.00E-12 |
| ENSG00000177606 | JUN | 1.564343 | 7.04E-12 |
| ENSG00000188580 | NKAIN2 | -1.7336 | 7.06E-12 |
| ENSG00000152082 | MZT2B | 1.169163 | 7.43E-12 |
| ENSG00000175899 | A2M | 1.822085 | 7.56E-12 |
| ENSG00000149131 | SERPING1 | -0.96159 | 7.63E-12 |
| ENSG00000164904 | ALDH7A1 | -1.71845 | 8.96E-12 |
| ENSG00000233452 | | 1.112907 | 9.09E-12 |
| ENSG00000166897 | ELFN2 | -1.82216 | 9.13E-12 |
| ENSG00000181409 | AATK | 1.837932 | 9.19E-12 |
| ENSG00000196533 | | 1.122125 | 1.09E-11 |
| ENSG00000130702 | LAMA5 | 1.585422 | 1.19E-11 |
| ENSG00000197208 | SLC22A4 | 1.222311 | 1.20E-11 |
| ENSG00000251400 | | -1.94592 | 1.38E-11 |
| ENSG00000160211 | G6PD | 0.792996 | 1.45E-11 |
| ENSG00000161921 | CXCL16 | 1.378373 | 1.58E-11 |
| ENSG00000171403 | KRT9 | 1.284098 | 1.62E-11 |
| ENSG00000103569 | AQP9 | 1.933102 | 1.82E-11 |
| ENSG00000078804 | TP53INP2 | 1.005663 | 1.91E-11 |
| ENSG00000198018 | ENTPD7 | 0.928567 | 1.96E-11 |
| ENSG00000121807 | CCR2 | -1.25195 | 1.97E-11 |
| ENSG00000188822 | CNR2 | 1.210094 | 1.97E-11 |
| ENSG00000104825 | NFKBIB | 0.965019 | 1.99E-11 |
| ENSG00000167996 | FTH1 | 0.972512 | 2.17E-11 |
| ENSG00000006534 | ALDH3B1 | 1.157444 | 2.19E-11 |
| ENSG00000168685 | IL7R | -1.0326 | 2.37E-11 |
| ENSG00000110002 | VWA5A | -1.00959 | 2.43E-11 |
| ENSG00000145916 | RMND5B | 0.961704 | 2.51E-11 |
| ENSG00000175806 | MSRA | 0.926555 | 2.55E-11 |
| ENSG00000051523 | CYBA | 0.846223 | 2.56E-11 |
| ENSG00000117115 | PADI2 | 1.11432 | 3.01E-11 |
| ENSG00000134569 | LRP4 | 2.197876 | 3.05E-11 |
| ENSG00000188404 | SELL | -1.83763 | 3.12E-11 |
| ENSG00000066468 | FGFR2 | 2.337813 | 3.43E-11 |
| ENSG00000143226 | FCGR2A | 1.026362 | 3.95E-11 |
| ENSG00000136193 | SCRN1 | -0.75755 | 4.24E-11 |
| ENSG00000066294 | CD84 | 1.194909 | 4.45E-11 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
| --- | --- | --- | --- |
| ENSG00000145390 | USP53 | −0.89497 | 4.69E−11 |
| ENSG00000182179 | UBA7 | −1.01387 | 4.86E−11 |
| ENSG00000104904 | OAZ1 | 0.738116 | 4.87E−11 |
| ENSG00000204161 | C10orf128 | 0.795656 | 5.01E−11 |
| ENSG00000134460 | IL2RA | 1.297269 | 5.22E−11 |
| ENSG00000110697 | PITPNM1 | 0.829531 | 5.76E−11 |
| ENSG00000122861 | PLAU | 0.859094 | 5.76E−11 |
| ENSG00000138670 | RASGEF1B | 1.560963 | 5.79E−11 |
| ENSG00000185624 | P4HB | 0.742683 | 5.87E−11 |
| ENSG00000176102 | CSTF3 | −0.80194 | 5.92E−11 |
| ENSG00000160446 | ZDHHC12 | 1.017044 | 6.33E−11 |
| ENSG00000179163 | FUCA1 | 0.874401 | 6.33E−11 |
| ENSG00000085719 | CPNE3 | −0.82544 | 6.58E−11 |
| ENSG00000136068 | FLNB | −0.81077 | 6.98E−11 |
| ENSG00000022567 | SLC45A4 | 1.046936 | 7.43E−11 |
| ENSG00000166925 | TSC22D4 | 0.851932 | 7.68E−11 |
| ENSG00000118729 | CASQ2 | 2.028469 | 7.76E−11 |
| ENSG00000152642 | GPD1L | 0.840004 | 9.00E−11 |
| ENSG00000150722 | PPP1R1C | −2.03236 | 9.12E−11 |
| ENSG00000179855 | GIPC3 | −0.99041 | 9.26E−11 |
| ENSG00000168779 | SHOX2 | 1.495878 | 9.61E−11 |
| ENSG00000197555 | SIPA1L1 | 0.874909 | 9.68E−11 |
| ENSG00000062282 | DGAT2 | 1.153281 | 9.73E−11 |
| ENSG00000131981 | LGALS3 | 2.146264 | 9.83E−11 |
| ENSG00000160179 | ABCG1 | 1.561886 | 1.05E−10 |
| ENSG00000103187 | COTL1 | 0.733312 | 1.08E−10 |
| ENSG00000064932 | SBNO2 | 0.819581 | 1.13E−10 |
| ENSG00000136848 | DAB2IP | −1.11132 | 1.22E−10 |
| ENSG00000034053 | APBA2 | −2.32067 | 1.23E−10 |
| ENSG00000142512 | SIGLEC10 | 1.090716 | 1.27E−10 |
| ENSG00000171222 | SCAND1 | 1.05435 | 1.36E−10 |
| ENSG00000170458 | CD14 | 2.178732 | 1.39E−10 |
| ENSG00000169313 | P2RY12 | −1.62342 | 1.40E−10 |
| ENSG00000158715 | SLC45A3 | 1.104343 | 1.45E−10 |
| ENSG00000197635 | DPP4 | −2.18505 | 1.51E−10 |
| ENSG00000168672 | FAM84B | −1.32253 | 1.52E−10 |
| ENSG00000165300 | SLITRK5 | 2.102202 | 1.54E−10 |
| ENSG00000174083 |  | 0.911639 | 1.68E−10 |
| ENSG00000163554 | SPTA1 | −2.07309 | 1.68E−10 |
| ENSG00000136878 | USP20 | 0.754552 | 1.70E−10 |
| ENSG00000164211 | STARD4 | 0.884969 | 1.72E−10 |
| ENSG00000179218 | CALR | 0.763751 | 1.80E−10 |
| ENSG00000240065 | PSMB9 | −1.2973 | 2.03E−10 |
| ENSG00000066336 | SPI1 | 0.742796 | 2.21E−10 |
| ENSG00000079393 | DUSP13 | 2.194285 | 2.25E−10 |
| ENSG00000167208 | SNX20 | 1.086183 | 2.42E−10 |
| ENSG00000112541 | PDE10A | −0.91957 | 2.47E−10 |
| ENSG00000136295 | TTYH3 | 0.729159 | 2.50E−10 |
| ENSG00000140368 | PSTPIP1 | 0.810961 | 2.76E−10 |
| ENSG00000196371 | FUT4 | 0.881633 | 2.98E−10 |
| ENSG00000091073 | DTX2 | 1.080507 | 3.17E−10 |
| ENSG00000138316 | ADAMTS14 | 1.152859 | 3.19E−10 |
| ENSG00000005379 | BZRAP1 | −0.87884 | 3.27E−10 |
| ENSG00000105520 | PLPPR2 | 1.013332 | 3.35E−10 |
| ENSG00000186891 | TNFRSF18 | 1.411961 | 3.43E−10 |
| ENSG00000134324 | LPIN1 | −0.9501 | 3.63E−10 |
| ENSG00000146409 | SLC18B1 | −1.3506 | 3.63E−10 |
| ENSG00000164983 | TMEM65 | −0.88348 | 3.82E−10 |
| ENSG00000133101 | CCNA1 | 0.980613 | 3.91E−10 |
| ENSG00000106852 | LHX6 | −2.06741 | 3.95E−10 |
| ENSG00000118985 | ELL2 | 0.815896 | 4.01E−10 |
| ENSG00000166527 | CLEC4D | −1.23207 | 4.36E−10 |
| ENSG00000174516 | PELI3 | 1.2112 | 4.51E−10 |
| ENSG00000198794 | SCAMP5 | −0.85329 | 4.51E−10 |
| ENSG00000126259 | KIRREL2 | 1.228709 | 4.62E−10 |
| ENSG00000117984 | CTSD | 0.826183 | 4.82E−10 |
| ENSG00000067798 | NAV3 | 2.223469 | 4.94E−10 |
| ENSG00000108846 | ABCC3 | −1.69006 | 5.04E−10 |
| ENSG00000013725 | CD6 | −1.51278 | 5.04E−10 |
| ENSG00000143382 | ADAMTSL4 | 1.119137 | 5.15E−10 |
| ENSG00000051128 | HOMER3 | 0.93552 | 5.16E−10 |
| ENSG00000228695 | CES1P1 | 2.064601 | 5.16E−10 |
| ENSG00000134107 | BHLHE40 | 0.695459 | 5.20E−10 |
| ENSG00000110841 | PPFIBP1 | −1.00958 | 5.53E−10 |
| ENSG00000187051 | RPS19BP1 | 0.830272 | 5.81E−10 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000134070 | IRAK2 | 1.213933 | 5.88E−10 |
| ENSG00000183242 | WT1-AS | −1.71233 | 5.88E−10 |
| ENSG00000125503 | PPP1R12C | 0.764484 | 5.92E−10 |
| ENSG00000104879 | CKM | 1.095863 | 6.44E−10 |
| ENSG00000040531 | CTNS | 0.756944 | 6.73E−10 |
| ENSG00000150907 | FOXO1 | −1.26312 | 7.14E−10 |
| ENSG00000106123 | EPHB6 | −1.792 | 7.43E−10 |
| ENSG00000135476 | ESPL1 | 0.938668 | 7.87E−10 |
| ENSG00000084234 | APLP2 | 0.658316 | 8.60E−10 |
| ENSG00000151651 | ADAM8 | 1.031656 | 1.04E−09 |
| ENSG00000021645 | NRXN3 | 2.135821 | 1.08E−09 |
| ENSG00000055163 | CYFIP2 | 0.780586 | 1.11E−09 |
| ENSG00000146232 | NFKBIE | 0.757965 | 1.16E−09 |
| ENSG00000122025 | FLT3 | −1.75886 | 1.18E−09 |
| ENSG00000112715 | VEGFA | 0.82666 | 1.21E−09 |
| ENSG00000126947 | ARMCX1 | −1.01414 | 1.24E−09 |
| ENSG00000156587 | UBE2L6 | −0.79123 | 1.26E−09 |
| ENSG00000182718 | ANXA2 | 0.982043 | 1.28E−09 |
| ENSG00000196914 | ARHGEF12 | −1.0235 | 1.49E−09 |
| ENSG00000125170 | DOK4 | −0.91406 | 1.56E−09 |
| ENSG00000157350 | ST3GAL2 | 0.754134 | 1.57E−09 |
| ENSG00000187653 |  | 1.154484 | 1.68E−09 |
| ENSG00000104093 | DMXL2 | 0.871262 | 1.75E−09 |
| ENSG00000166123 | GPT2 | −1.12206 | 1.90E−09 |
| ENSG00000008394 | MGST1 | −0.70294 | 1.95E−09 |
| ENSG00000182087 | TMEM259 | 0.728522 | 2.07E−09 |
| ENSG00000170946 | DNAJC24 | −0.90698 | 2.13E−09 |
| ENSG00000138443 | ABI2 | −0.77737 | 2.17E−09 |
| ENSG00000175130 | MARCKSL1 | 0.667422 | 2.20E−09 |
| ENSG00000079215 | SLC1A3 | 1.963955 | 2.31E−09 |
| ENSG00000103363 | TCEB2 | 0.727518 | 2.34E−09 |
| ENSG00000187147 | RNF220 | −0.94472 | 2.35E−09 |
| ENSG00000161671 | EMC10 | −2.28295 | 2.37E−09 |
| ENSG00000183049 | CAMK1D | 0.899499 | 2.46E−09 |
| ENSG00000134184 | GSTM1 | −0.94809 | 2.65E−09 |
| ENSG00000091181 | IL5RA | 1.90425 | 2.94E−09 |
| ENSG00000224397 |  | 1.338518 | 2.94E−09 |
| ENSG00000183048 | SLC25A10 | 1.097202 | 3.05E−09 |
| ENSG00000099624 | ATP5D | 0.795493 | 3.11E−09 |
| ENSG00000141577 | CEP131 | 1.078366 | 3.38E−09 |
| ENSG00000165659 |  | −1.4416 | 3.80E−09 |
| ENSG00000169519 | METTL15 | −1.14667 | 3.88E−09 |
| ENSG00000046604 | DSG2 | −0.67359 | 3.98E−09 |
| ENSG00000162174 | ASRGL1 | 1.735424 | 4.13E−09 |
| ENSG00000115738 | ID2 | 0.66026 | 4.18E−09 |
| ENSG00000125780 | TGM3 | 2.150465 | 4.38E−09 |
| ENSG00000136630 | HLX | 1.305935 | 4.40E−09 |
| ENSG00000148411 | NACC2 | 0.881732 | 4.40E−09 |
| ENSG00000184164 | CRELD2 | 0.8474 | 4.56E−09 |
| ENSG00000116991 | SIPA1L2 | 1.021288 | 4.62E−09 |
| ENSG00000077238 | IL4R | 0.682532 | 4.92E−09 |
| ENSG00000173221 | GLRX | 0.727319 | 5.07E−09 |
| ENSG00000189120 | SP6 | −1.06394 | 5.07E−09 |
| ENSG00000139832 | RAB20 | 1.080902 | 5.08E−09 |
| ENSG00000173542 | MOB1B | −0.79318 | 5.20E−09 |
| ENSG00000116670 | MAD2L2 | 0.720264 | 5.45E−09 |
| ENSG00000147955 | SIGMAR1 | −2.22512 | 5.53E−09 |
| ENSG00000135842 | FAM129A | 0.909156 | 5.71E−09 |
| ENSG00000258573 | LOC254028 | 1.249683 | 5.71E−09 |
| ENSG00000196968 | FUT11 | −0.96879 | 6.16E−09 |
| ENSG00000198055 | GRK6 | 0.694266 | 6.18E−09 |
| ENSG00000156575 | PRG3 | 2.03733 | 6.38E−09 |
| ENSG00000109854 | HTATIP2 | −2.20322 | 6.39E−09 |
| ENSG00000134138 | MEIS2 | 0.796773 | 6.53E−09 |
| ENSG00000146373 | RNF217 | −0.86196 | 7.10E−09 |
| ENSG00000125089 | SH3TC1 | 0.74578 | 7.17E−09 |
| ENSG00000161091 | MFSD12 | 0.705096 | 7.81E−09 |
| ENSG00000099364 | FBXL19 | 0.728086 | 7.92E−09 |
| ENSG00000127951 | FGL2 | 1.678797 | 8.06E−09 |
| ENSG00000011523 | CEP68 | −0.87708 | 8.18E−09 |
| ENSG00000197982 | C1orf122 | 0.963059 | 8.36E−09 |
| ENSG00000164237 | CMBL | −0.79327 | 8.42E−09 |
| ENSG00000145901 | TNIP1 | 1.016378 | 8.45E−09 |
| ENSG00000114626 | ABTB1 | 0.879817 | 8.55E−09 |
| ENSG00000187796 | CARD9 | 1.036579 | 8.85E−09 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000180530 | NRIP1 | −0.94102 | 9.18E−09 |
| ENSG00000127564 | PKMYT1 | 0.953262 | 9.57E−09 |
| ENSG00000178773 | CPNE7 | −2.10424 | 9.76E−09 |
| ENSG00000078177 | N4BP2 | −0.88902 | 9.82E−09 |
| ENSG00000131591 | C1orf159 | 1.000939 | 1.01E−08 |
| ENSG00000125912 | NCLN | 0.77824 | 1.05E−08 |
| ENSG00000180815 | MAP3K15 | 1.653179 | 1.06E−08 |
| ENSG00000085276 | MECOM | −0.74395 | 1.08E−08 |
| ENSG00000131242 | RAB11FIP4 | 0.771799 | 1.17E−08 |
| ENSG00000156858 | PRR14 | 0.804773 | 1.20E−08 |
| ENSG00000143995 | MEIS1 | −0.85028 | 1.20E−08 |
| ENSG00000088992 | TESC | 0.819297 | 1.23E−08 |
| ENSG00000158887 | MPZ | 0.907861 | 1.23E−08 |
| ENSG00000155760 | FZD7 | 1.417614 | 1.27E−08 |
| ENSG00000113296 | THBS4 | 1.981552 | 1.29E−08 |
| ENSG00000172602 | RND1 | 1.676185 | 1.31E−08 |
| ENSG00000185669 | SNAI3 | 0.849852 | 1.35E−08 |
| ENSG00000188157 | AGRN | 0.852897 | 1.41E−08 |
| ENSG00000171488 | LRRC8C | −0.64215 | 1.46E−08 |
| ENSG00000184635 | ZNF93 | −1.19861 | 1.49E−08 |
| ENSG00000132879 | FBXO44 | −1.78685 | 1.50E−08 |
| ENSG00000139112 | GABARAPL1 | 1.034369 | 1.63E−08 |
| ENSG00000160570 | DEDD2 | 0.866394 | 1.78E−08 |
| ENSG00000100065 | CARD10 | −1.58327 | 1.79E−08 |
| ENSG00000158477 | CD1A | 2.085673 | 1.81E−08 |
| ENSG00000130396 | MLLT4 | 0.788646 | 1.82E−08 |
| ENSG00000161618 | ALDH16A1 | 0.884262 | 1.84E−08 |
| ENSG00000164251 | F2RL1 | −0.88578 | 1.88E−08 |
| ENSG00000175832 | ETV4 | 1.431785 | 1.91E−08 |
| ENSG00000142657 | PGD | 0.611752 | 1.95E−08 |
| ENSG00000112773 | FAM46A | 0.812949 | 1.97E−08 |
| ENSG00000163453 | IGFBP7 | 0.702139 | 1.97E−08 |
| ENSG00000020633 | RUNX3 | −0.66332 | 2.03E−08 |
| ENSG00000197183 | NOL4L | −0.80478 | 2.23E−08 |
| ENSG00000197548 | ATG7 | 0.699327 | 2.24E−08 |
| ENSG00000151229 | SLC2A13 | 0.883008 | 2.26E−08 |
| ENSG00000128228 | SDF2L1 | 0.995988 | 2.27E−08 |
| ENSG00000154654 | NCAM2 | −1.5459 | 2.31E−08 |
| ENSG00000187773 | FAM69C | −1.6243 | 2.31E−08 |
| ENSG00000129195 | FAM64A | 1.220863 | 2.32E−08 |
| ENSG00000204852 | TCTN1 | −1.13464 | 2.32E−08 |
| ENSG00000109944 | C11orf63 | −2.03045 | 2.33E−08 |
| ENSG00000142634 | EFHD2 | 0.676071 | 2.39E−08 |
| ENSG00000172216 | CEBPB | 0.92701 | 2.58E−08 |
| ENSG00000007062 | PROM1 | −2.07315 | 2.65E−08 |
| ENSG00000055332 | EIF2AK2 | −0.7539 | 2.66E−08 |
| ENSG00000105404 | RABAC1 | 0.970328 | 2.78E−08 |
| ENSG00000117266 | CDK18 | −1.27602 | 3.05E−08 |
| ENSG00000166352 | C11orf74 | −0.91663 | 3.08E−08 |
| ENSG00000081059 | TCF7 | 1.827126 | 3.22E−08 |
| ENSG00000178860 | MSC | 0.790043 | 3.30E−08 |
| ENSG00000127507 | ADGRE2 | 0.671737 | 3.34E−08 |
| ENSG00000166432 | ZMAT1 | −1.54456 | 3.34E−08 |
| ENSG00000149798 | CDC42EP2 | 1.712342 | 3.36E−08 |
| ENSG00000018280 | SLC11A1 | 1.853447 | 3.48E−08 |
| ENSG00000133246 | PRAM1 | 0.663462 | 3.56E−08 |
| ENSG00000131634 | TMEM204 | −1.88043 | 3.68E−08 |
| ENSG00000143333 | RGS16 | 1.076041 | 3.69E−08 |
| ENSG00000230400 | LOC105372566 | −1.24423 | 3.71E−08 |
| ENSG00000092929 | UNC13D | 0.67647 | 4.09E−08 |
| ENSG00000071655 | MBD3 | 0.752242 | 4.16E−08 |
| ENSG00000133466 | C1QTNF6 | −1.22831 | 4.66E−08 |
| ENSG00000237440 | ZNF737 | −1.0715 | 4.67E−08 |
| ENSG00000155629 | PIK3AP1 | 0.773809 | 4.86E−08 |
| ENSG00000146094 | DOK3 | 0.67849 | 5.07E−08 |
| ENSG00000168528 | SERINC2 | 1.226275 | 5.09E−08 |
| ENSG00000160255 | ITGB2 | 0.811241 | 5.20E−08 |
| ENSG00000115641 | FHL2 | −1.47765 | 5.50E−08 |
| ENSG00000254726 | MEX3A | −1.39153 | 5.66E−08 |
| ENSG00000167671 | UBXN6 | 0.660037 | 5.71E−08 |
| ENSG00000173402 | DAG1 | 0.81646 | 5.74E−08 |
| ENSG00000173868 | PHOSPHO1 | 1.243181 | 5.87E−08 |
| ENSG00000101188 | NTSR1 | −1.25224 | 6.06E−08 |
| ENSG00000110717 | NDUFS8 | 0.750138 | 6.10E−08 |
| ENSG00000129925 | TMEM8A | 0.798238 | 6.20E−08 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000144218 | AFF3 | 1.370444 | 6.46E−08 |
| ENSG00000122970 | IFT81 | −1.1841 | 6.94E−08 |
| ENSG00000205730 | ITPRIPL2 | −0.67899 | 6.94E−08 |
| ENSG00000152582 | SPEF2 | −1.18855 | 6.98E−08 |
| ENSG00000154479 | CCDC173 | −1.07731 | 7.22E−08 |
| ENSG00000059728 | MXD1 | 0.754029 | 7.33E−08 |
| ENSG00000100417 | PMM1 | 1.015706 | 7.41E−08 |
| ENSG00000042753 | AP2S1 | 0.607581 | 7.77E−08 |
| ENSG00000138758 | 42624 | −0.5967 | 7.94E−08 |
| ENSG00000099804 | CDC34 | 0.777768 | 7.99E−08 |
| ENSG00000169641 | LUZP1 | −0.64199 | 8.02E−08 |
| ENSG00000124334 | IL9R | 1.286308 | 8.12E−08 |
| ENSG00000196950 | SLC39A10 | −0.67639 | 8.17E−08 |
| ENSG00000106034 | CPED1 | −1.95559 | 8.26E−08 |
| ENSG00000168843 | FSTL5 | −1.82321 | 8.28E−08 |
| ENSG00000180257 | ZNF816 | −0.81335 | 8.28E−08 |
| ENSG00000154447 | SH3RF1 | −0.86192 | 8.57E−08 |
| ENSG00000154930 | ACSS1 | −0.68449 | 8.66E−08 |
| ENSG00000076944 | STXBP2 | 0.689494 | 8.92E−08 |
| ENSG00000160883 | HK3 | 0.802249 | 9.29E−08 |
| ENSG00000213347 | MXD3 | 1.325643 | 9.54E−08 |
| ENSG00000129235 | TXNDC17 | 0.647322 | 1.05E−07 |
| ENSG00000183621 | ZNF438 | 0.772469 | 1.07E−07 |
| ENSG00000119865 | CNRIP1 | −1.02429 | 1.07E−07 |
| ENSG00000204482 | LST1 | 0.816169 | 1.08E−07 |
| ENSG00000120156 | TEK | −1.86197 | 1.08E−07 |
| ENSG00000166557 | TMED3 | 0.629074 | 1.08E−07 |
| ENSG00000167851 | CD300A | −0.80424 | 1.08E−07 |
| ENSG00000256660 | CLEC12B | 0.956101 | 1.09E−07 |
| ENSG00000135631 | RAB11FIP5 | 1.177441 | 1.11E−07 |
| ENSG00000011132 | APBA3 | 0.900283 | 1.11E−07 |
| ENSG00000137135 | ARHGEF39 | 0.966284 | 1.16E−07 |
| ENSG00000272825 |  | 1.34735 | 1.17E−07 |
| ENSG00000073169 | SELO | 0.768382 | 1.17E−07 |
| ENSG00000159069 | FBXW5 | 0.697845 | 1.17E−07 |
| ENSG00000172380 | GNG12 | −0.81467 | 1.20E−07 |
| ENSG00000157554 | ERG | −0.95548 | 1.27E−07 |
| ENSG00000164087 | POC1A | 0.766508 | 1.31E−07 |
| ENSG00000131650 | KREMEN2 | 1.148435 | 1.34E−07 |
| ENSG00000169744 | LDB2 | −1.61812 | 1.34E−07 |
| ENSG00000162722 | TRIM58 | −1.1009 | 1.40E−07 |
| ENSG00000100284 | TOM1 | 0.825963 | 1.40E−07 |
| ENSG00000130429 | ARPC1B | 0.660219 | 1.41E−07 |
| ENSG00000081041 | CXCL2 | 0.901795 | 1.45E−07 |
| ENSG00000164484 | TMEM200A | −1.03562 | 1.45E−07 |
| ENSG00000108091 | CCDC6 | −0.61793 | 1.45E−07 |
| ENSG00000197562 | RAB40C | 0.79755 | 1.52E−07 |
| ENSG00000011422 | PLAUR | 0.768379 | 1.52E−07 |
| ENSG00000130775 | THEMIS2 | 0.718886 | 1.53E−07 |
| ENSG00000152818 | UTRN | −0.76068 | 1.58E−07 |
| ENSG00000243477 | NAT6 | 0.837498 | 1.58E−07 |
| ENSG00000100242 | SUN2 | 0.701911 | 1.60E−07 |
| ENSG00000162522 | KIAA1522 | −0.85202 | 1.60E−07 |
| ENSG00000173272 | MZT2A | 0.816388 | 1.62E−07 |
| ENSG00000137834 | SMAD6 | −0.81355 | 1.64E−07 |
| ENSG00000205978 | NYNRIN | −0.83996 | 1.65E−07 |
| ENSG00000153993 | SEMA3D | 1.004467 | 1.68E−07 |
| ENSG00000087448 | KLHL42 | −0.67194 | 1.69E−07 |
| ENSG00000149970 | CNKSR2 | 1.942516 | 1.78E−07 |
| ENSG00000171045 | TSNARE1 | 1.023097 | 1.79E−07 |
| ENSG00000091129 | NRCAM | 1.367825 | 1.84E−07 |
| ENSG00000106701 | FSD1L | −0.81322 | 1.86E−07 |
| ENSG00000074706 | IPCEF1 | 0.771771 | 1.91E−07 |
| ENSG00000123989 | CHPF | 1.324982 | 1.95E−07 |
| ENSG00000227507 | LTB | 1.020814 | 1.95E−07 |
| ENSG00000076555 | ACACB | 1.24664 | 1.95E−07 |
| ENSG00000128973 | CLN6 | 0.653747 | 2.21E−07 |
| ENSG00000110046 | ATG2A | 0.846574 | 2.22E−07 |
| ENSG00000144451 | SPAG16 | −1.06831 | 2.22E−07 |
| ENSG00000163959 | SLC51A | 1.917389 | 2.23E−07 |
| ENSG00000183134 | PTGDR2 | 1.118398 | 2.24E−07 |
| ENSG00000115306 | SPTBN1 | −0.89926 | 2.26E−07 |
| ENSG00000116641 | DOCK7 | −0.66692 | 2.33E−07 |
| ENSG00000197329 | PELI1 | 0.671373 | 2.63E−07 |
| ENSG00000001561 | ENPP4 | 0.944282 | 2.64E−07 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000163694 | RBM47 | 1.175887 | 2.68E−07 |
| ENSG00000185803 | SLC52A2 | 0.720374 | 2.76E−07 |
| ENSG00000170293 | CMTM8 | −1.45942 | 2.79E−07 |
| ENSG00000172575 | RASGRP1 | 1.569079 | 2.85E−07 |
| ENSG00000231991 |  | 0.897965 | 2.86E−07 |
| ENSG00000122417 | ODF2L | −0.77896 | 2.89E−07 |
| ENSG00000130312 | MRPL34 | 0.820916 | 2.89E−07 |
| ENSG00000180448 | HMHA1 | 0.707138 | 2.91E−07 |
| ENSG00000064961 | HMG20B | 0.637654 | 2.96E−07 |
| ENSG00000088053 | GP6 | −1.56716 | 3.00E−07 |
| ENSG00000010327 | STAB1 | 0.901465 | 3.01E−07 |
| ENSG00000184990 | SIVA1 | 0.768433 | 3.02E−07 |
| ENSG00000188486 | H2AFX | 0.760588 | 3.09E−07 |
| ENSG00000127533 | F2RL3 | −1.25821 | 3.12E−07 |
| ENSG00000135940 | COX5B | 0.621568 | 3.12E−07 |
| ENSG00000167601 | AXL | −1.47516 | 3.14E−07 |
| ENSG00000138119 | MYOF | 1.626182 | 3.21E−07 |
| ENSG00000174886 | NDUFA11 | 0.889145 | 3.22E−07 |
| ENSG00000155307 | SAMSN1 | 0.660224 | 3.28E−07 |
| ENSG00000183019 | MCEMP1 | 0.734523 | 3.41E−07 |
| ENSG00000019582 | CD74 | −0.85428 | 3.49E−07 |
| ENSG00000140836 | ZFHX3 | −0.85631 | 3.55E−07 |
| ENSG00000111679 | PTPN6 | 0.717076 | 3.58E−07 |
| ENSG00000135766 | EGLN1 | 0.925058 | 3.62E−07 |
| ENSG00000131446 | MGAT1 | 0.708452 | 3.64E−07 |
| ENSG00000100258 | LMF2 | 0.828102 | 3.79E−07 |
| ENSG00000108001 | EBF3 | −0.98063 | 3.79E−07 |
| ENSG00000171811 | CFAP46 | 1.762816 | 3.83E−07 |
| ENSG00000187699 | C2orf88 | −0.88613 | 3.83E−07 |
| ENSG00000135549 | PKIB | −0.71289 | 3.89E−07 |
| ENSG00000105963 | ADAP1 | 1.072983 | 3.99E−07 |
| ENSG00000040487 | PQLC2 | 0.699456 | 4.01E−07 |
| ENSG00000071242 | RPS6KA2 | −1.4098 | 4.04E−07 |
| ENSG00000167552 | TUBA1A | −0.70669 | 4.04E−07 |
| ENSG00000116663 | FBXO6 | 0.835172 | 4.18E−07 |
| ENSG00000131409 | LRRC4B | 0.693306 | 4.26E−07 |
| ENSG00000070882 | OSBPL3 | −0.67238 | 4.27E−07 |
| ENSG00000164308 | ERAP2 | −0.64352 | 4.27E−07 |
| ENSG00000130881 | LRP3 | 0.924758 | 4.38E−07 |
| ENSG00000091409 | ITGA6 | −0.85349 | 4.54E−07 |
| ENSG00000160949 | TONSL | 0.793889 | 4.59E−07 |
| ENSG00000167580 | AQP2 | −1.68782 | 4.61E−07 |
| ENSG00000166341 | DCHS1 | −1.19523 | 4.65E−07 |
| ENSG00000196526 | AFAP1 | 0.954973 | 4.66E−07 |
| ENSG00000162437 | RAVER2 | −0.70834 | 4.75E−07 |
| ENSG00000095906 | NUBP2 | 0.849386 | 4.98E−07 |
| ENSG00000125657 | TNFSF9 | 0.813432 | 4.99E−07 |
| ENSG00000011600 | TYROBP | 0.78425 | 5.06E−07 |
| ENSG00000133612 | AGAP3 | 0.822727 | 5.09E−07 |
| ENSG00000224051 | CPTP | 0.849856 | 5.09E−07 |
| ENSG00000198171 | DDRGK1 | 0.648055 | 5.26E−07 |
| ENSG00000167232 | ZNF91 | −0.742 | 5.27E−07 |
| ENSG00000103326 | CAPN15 | 0.770461 | 5.48E−07 |
| ENSG00000166793 | YPEL4 | 1.130472 | 5.51E−07 |
| ENSG00000121621 | KIF18A | −0.84832 | 5.54E−07 |
| ENSG00000023191 | RNH1 | 0.65674 | 5.77E−07 |
| ENSG00000147459 | DOCK5 | −0.60628 | 5.95E−07 |
| ENSG00000105327 | BBC3 | 0.859583 | 6.04E−07 |
| ENSG00000187800 | PEAR1 | −0.95926 | 6.23E−07 |
| ENSG00000182541 | LIMK2 | 0.641583 | 6.32E−07 |
| ENSG00000197016 | ZNF470 | −1.23045 | 6.38E−07 |
| ENSG00000078900 | TP73 | 1.19705 | 6.72E−07 |
| ENSG00000214655 | ZSWIM8 | 0.667465 | 6.85E−07 |
| ENSG00000112992 | NNT | −0.56853 | 7.03E−07 |
| ENSG00000188921 | HACD4 | −0.60463 | 7.03E−07 |
| ENSG00000149639 | SOGA1 | −0.72411 | 7.10E−07 |
| ENSG00000121413 | ZSCAN18 | −1.10588 | 7.10E−07 |
| ENSG00000109436 | TBC1D9 | −0.66539 | 7.22E−07 |
| ENSG00000198133 | TMEM229B | −1.76046 | 7.28E−07 |
| ENSG00000114654 | EFCC1 | −1.58082 | 7.38E−07 |
| ENSG00000169991 | IFFO2 | −0.7706 | 7.38E−07 |
| ENSG00000099795 | NDUFB7 | 0.779297 | 7.61E−07 |
| ENSG00000077454 | LRCH4 | 0.59053 | 7.68E−07 |
| ENSG00000078399 | HOXA9 | −0.66529 | 8.02E−07 |
| ENSG00000175756 | AURKAIP1 | 0.675622 | 8.17E−07 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000160326 | SLC2A6 | 1.834033 | 8.42E−07 |
| ENSG00000102096 | PIM2 | 0.98834 | 8.67E−07 |
| ENSG00000205336 | ADGRG1 | −1.04267 | 8.80E−07 |
| ENSG00000257176 | LOC100506606 | −0.95784 | 8.80E−07 |
| ENSG00000134575 | ACP2 | 0.753907 | 8.90E−07 |
| ENSG00000102780 | DGKH | −0.69491 | 9.04E−07 |
| ENSG00000185565 | LSAMP | −0.79358 | 9.04E−07 |
| ENSG00000184117 | NIPSNAP1 | −0.61704 | 9.05E−07 |
| ENSG00000171988 | JMJD1C | −0.66702 | 9.10E−07 |
| ENSG00000112077 | RHAG | −1.69649 | 9.12E−07 |
| ENSG00000130066 | SAT1 | 0.78536 | 1.02E−06 |
| ENSG00000178163 | ZNF518B | −0.9379 | 1.04E−06 |
| ENSG00000141506 | PIK3R5 | 0.695559 | 1.04E−06 |
| ENSG00000180900 | SCRIB | 0.814221 | 1.06E−06 |
| ENSG00000134955 | SLC37A2 | 0.993017 | 1.06E−06 |
| ENSG00000117289 |  | 0.598214 | 1.09E−06 |
| ENSG00000156026 | MCU | 0.601103 | 1.09E−06 |
| ENSG00000177191 | B3GNT8 | 1.125331 | 1.11E−06 |
| ENSG00000143774 | GUK1 | 0.737841 | 1.13E−06 |
| ENSG00000007080 | CCDC124 | 0.752978 | 1.14E−06 |
| ENSG00000152492 | CCDC50 | −0.67992 | 1.14E−06 |
| ENSG00000168071 | CCDC88B | 0.803277 | 1.15E−06 |
| ENSG00000104885 | DOT1L | 0.640849 | 1.15E−06 |
| EN5G00000064545 | TMEM161A | 0.691537 | 1.16E−06 |
| ENSG00000137871 | ZNF280D | −0.74122 | 1.17E−06 |
| ENSG00000131408 | NR1H2 | 0.708825 | 1.18E−06 |
| ENSG00000161677 | JOSD2 | 1.074698 | 1.19E−06 |
| ENSG00000198400 | NTRK1 | 0.846919 | 1.21E−06 |
| ENSG00000165915 | SLC39A13 | 0.723723 | 1.24E−06 |
| ENSG00000168280 | KIF5C | 1.670436 | 1.24E−06 |
| ENSG00000235609 |  | −0.99608 | 1.26E−06 |
| ENSG00000143771 | CNIH4 | 0.611428 | 1.27E−06 |
| ENSG00000069974 | RAB27A | 0.606059 | 1.28E−06 |
| ENSG00000127329 | PTPRB | −0.58998 | 1.30E−06 |
| ENSG00000003436 | TFPI | −0.8345 | 1.31E−06 |
| ENSG00000035403 | VCL | −0.53703 | 1.31E−06 |
| ENSG00000197019 | SERTAD1 | 0.770913 | 1.35E−06 |
| ENSG00000211445 | GPX3 | 1.581994 | 1.37E−06 |
| ENSG00000078808 | SDF4 | 0.600326 | 1.41E−06 |
| ENSG00000104870 | FCGRT | 0.709885 | 1.42E−06 |
| ENSG00000119139 | TJP2 | 0.565264 | 1.46E−06 |
| ENSG00000196588 | MKL1 | 0.58518 | 1.49E−06 |
| ENSG00000165168 | CYBB | 0.650769 | 1.49E−06 |
| ENSG00000161835 | GRASP | 1.507466 | 1.51E−06 |
| ENSG00000005187 | ACSM3 | 0.635143 | 1.52E−06 |
| ENSG00000143889 | HNRNPLL | 0.646476 | 1.52E−06 |
| ENSG00000105397 | TYK2 | 0.567088 | 1.56E−06 |
| ENSG00000168502 | MTCL1 | 1.873915 | 1.57E−06 |
| ENSG00000175505 | CLCF1 | 1.399845 | 1.61E−06 |
| ENSG00000183696 | UPP1 | 0.673995 | 1.61E−06 |
| ENSG00000185236 | RAB11B | 0.628339 | 1.67E−06 |
| ENSG00000104918 | RETN | 0.911944 | 1.70E−06 |
| ENSG00000163191 | S100A11 | 0.563603 | 1.77E−06 |
| ENSG00000176978 | DPP7 | 0.640101 | 1.77E−06 |
| ENSG00000196126 | HLA-DRB1 | −0.84201 | 1.79E−06 |
| ENSG00000108219 | TSPAN14 | 0.552881 | 1.80E−06 |
| ENSG00000125995 | ROMO1 | 0.698154 | 1.82E−06 |
| ENSG00000111666 | CHPT1 | 0.741369 | 1.83E−06 |
| ENSG00000100083 | GGA1 | 0.602745 | 1.85E−06 |
| ENSG00000136960 | ENPP2 | 0.760236 | 1.85E−06 |
| ENSG00000108854 | SMURF2 | −0.61602 | 1.95E−06 |
| ENSG00000177600 | RPLP2 | 0.527011 | 1.95E−06 |
| ENSG00000074370 | ATP2A3 | 0.593379 | 1.98E−06 |
| ENSG00000165757 | KIAA1462 | −1.57259 | 1.98E−06 |
| ENSG00000173890 | GPR160 | 0.602471 | 1.98E−06 |
| ENSG00000015475 | BID | 0.769542 | 2.01E−06 |
| ENSG00000148488 | ST8SIA6 | −1.04955 | 2.02E−06 |
| ENSG00000266709 | MGC12916 | 1.687222 | 2.02E−06 |
| ENSG00000172366 | FAM195A | 0.784739 | 2.02E−06 |
| ENSG00000104774 | MAN2B1 | 0.708106 | 2.03E−06 |
| ENSG00000152926 | ZNF117 | −0.63501 | 2.06E−06 |
| ENSG00000173546 | CSPG4 | −1.56365 | 2.07E−06 |
| ENSG00000178950 | GAK | 0.572793 | 2.08E−06 |
| ENSG00000111145 | ELK3 | −0.71538 | 2.10E−06 |
| ENSG00000226979 | LTA | 1.536465 | 2.11E−06 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000146535 | GNA12 | −0.65414 | 2.11E−06 |
| ENSG00000120885 | CLU | 0.971778 | 2.11E−06 |
| ENSG00000149761 | NUDT22 | 0.786299 | 2.14E−06 |
| ENSG00000171631 | P2RY6 | 1.479139 | 2.17E−06 |
| ENSG00000008516 | MMP25 | 0.992629 | 2.18E−06 |
| ENSG00000100365 | NCF4 | 0.579321 | 2.19E−06 |
| ENSG00000186152 |  | 1.396854 | 2.19E−06 |
| ENSG00000105373 | GLTSCR2 | 0.630947 | 2.21E−06 |
| ENSG00000165685 | TMEM52B | 1.535667 | 2.22E−06 |
| ENSG00000130706 | ADRM1 | 0.662362 | 2.26E−06 |
| ENSG00000121594 | CD80 | 1.853457 | 2.27E−06 |
| ENSG00000242802 | AP5Z1 | 0.663183 | 2.29E−06 |
| ENSG00000165434 | PGM2L1 | 0.597847 | 2.30E−06 |
| ENSG00000133275 | CSNK1G2 | 0.638882 | 2.35E−06 |
| ENSG00000179388 | EGR3 | 0.809618 | 2.35E−06 |
| ENSG00000138061 | CYP1B1 | −1.81856 | 2.38E−06 |
| ENSG00000163131 | CTSS | 0.590127 | 2.38E−06 |
| ENSG00000160685 | ZBTB7B | 0.650985 | 2.39E−06 |
| ENSG00000118432 | CNR1 | 1.629899 | 2.41E−06 |
| ENSG00000063241 | ISOC2 | 0.650005 | 2.50E−06 |
| ENSG00000104886 | PLEKHJ1 | 0.608317 | 2.53E−06 |
| ENSG00000057252 | SOAT1 | −0.65467 | 2.53E−06 |
| ENSG00000184232 | OAF | −0.77934 | 2.54E−06 |
| ENSG00000155252 | PI4K2A | 0.699903 | 2.59E−06 |
| ENSG00000162367 | TAL1 | −0.63564 | 2.61E−06 |
| ENSG00000113721 | PDGFRB | −1.45417 | 2.63E−06 |
| ENSG00000121104 | FAM117A | 0.82145 | 2.65E−06 |
| ENSG00000158825 | CDA | 1.08697 | 2.68E−06 |
| ENSG00000118965 | WDR35 | −0.80228 | 2.68E−06 |
| ENSG00000158869 | FCER1G | 0.691345 | 2.75E−06 |
| ENSG00000185112 | FAM43A | 0.78456 | 2.75E−06 |
| ENSG00000163840 | DTX3L | −0.74081 | 2.79E−06 |
| ENSG00000140564 | FURIN | 0.553879 | 2.80E−06 |
| ENSG00000120129 | DUSP1 | 1.203565 | 2.81E−06 |
| ENSG00000169223 | LMAN2 | 0.57829 | 2.84E−06 |
| ENSG00000104368 | PLAT | 1.661803 | 2.85E−06 |
| ENSG00000197497 | ZNF665 | −1.77168 | 2.86E−06 |
| ENSG00000130733 | YIPF2 | 0.657911 | 2.95E−06 |
| ENSG00000167460 | TPM4 | −0.62827 | 2.95E−06 |
| ENSG00000114480 | GBE1 | 0.58396 | 2.98E−06 |
| ENSG00000164889 | SLC4A2 | 0.587251 | 3.02E−06 |
| ENSG00000142875 | PRKACB | −0.53518 | 3.05E−06 |
| ENSG00000149823 | VPS51 | 0.623445 | 3.09E−06 |
| ENSG00000135916 | ITM2C | 0.555132 | 3.09E−06 |
| ENSG00000167994 | RAB3IL1 | −1.05377 | 3.16E−06 |
| ENSG00000151746 | BICD1 | −0.83978 | 3.21E−06 |
| ENSG00000233762 |  | 0.673281 | 3.29E−06 |
| ENSG00000042980 | ADAM28 | −0.79401 | 3.32E−06 |
| ENSG00000188343 | FAM92A1 | −0.78213 | 3.35E−06 |
| ENSG00000008517 | IL32 | 1.396014 | 3.36E−06 |
| ENSG00000163931 | TKT | 0.53882 | 3.43E−06 |
| ENSG00000180316 | PNPLA1 | 1.422926 | 3.49E−06 |
| ENSG00000204389 | HSPA1A | −1.63443 | 3.57E−06 |
| ENSG00000197766 | CFD | 0.691056 | 3.57E−06 |
| ENSG00000121039 | RDH10 | 0.709679 | 3.59E−06 |
| ENSG00000139793 | MBNL2 | −1.29339 | 3.60E−06 |
| ENSG00000179750 | APOBEC3B | 0.698806 | 3.61E−06 |
| ENSG00000257335 | MGAM | 0.597385 | 3.65E−06 |
| ENSG00000142185 | TRPM2 | 0.932535 | 3.68E−06 |
| ENSG00000185198 | PRSS57 | 1.081696 | 3.78E−06 |
| ENSG00000154146 | NRGN | 0.708687 | 3.86E−06 |
| ENSG00000145779 | TNFAIP8 | 0.527117 | 3.93E−06 |
| ENSG00000110881 | ASIC1 | 0.647613 | 3.93E−06 |
| ENSG00000204252 | HLA-DOA | −1.42195 | 3.93E−06 |
| ENSG00000069399 | BCL3 | 0.74496 | 3.97E−06 |
| ENSG00000262814 | MRPL12 | 0.879836 | 4.06E−06 |
| ENSG00000142556 | ZNF614 | −0.60962 | 4.14E−06 |
| ENSG00000077463 | SIRT6 | 0.687268 | 4.17E−06 |
| ENSG00000090316 | MAEA | 0.637074 | 4.32E−06 |
| ENSG00000221866 | PLXNA4 | 1.395107 | 4.38E−06 |
| ENSG00000115602 | IL1RL1 | 0.739964 | 4.39E−06 |
| ENSG00000159128 | IFNGR2 | 0.802349 | 4.46E−06 |
| ENSG00000104888 | SLC17A7 | −1.26831 | 4.48E−06 |
| ENSG00000203326 | ZNF525 | −0.67886 | 4.54E−06 |
| ENSG00000100298 | APOBEC3H | −0.88813 | 4.63E−06 |

SUPPLEMENTARY TABLE 1-continued

List of the identified differentially expressed transcripts after DE analysis using DESeq2 and edgeR-

| ENSEMBL | Symbol | Log$_2$ Fold Change | False discovery rate |
| --- | --- | --- | --- |
| ENSG00000140983 | RHOT2 | 0.608402 | 4.70E-06 |
| ENSG00000204237 | OXLD1 | 0.715125 | 4.71E-06 |
| ENSG00000056558 | TRAF1 | 1.710966 | 4.73E-06 |
| ENSG00000140682 | TGFB1I1 | -1.623 | 4.73E-06 |
| ENSG00000000971 | CFH | -1.24425 | 4.76E-06 |
| ENSG00000167645 | YIF1B | 0.670479 | 4.79E-06 |
| ENSG00000198520 | C1orf228 | 0.772538 | 4.93E-06 |
| ENSG00000110719 | TCIRG1 | 0.607516 | 4.99E-06 |
| ENSG00000235605 |  | 0.749361 | 5.01E-06 |
| ENSG00000182154 | MRPL41 | 0.874727 | 5.04E-06 |
| ENSG00000070423 | RNF126 | 0.761157 | 5.13E-06 |
| ENSG00000112473 | SLC39A7 | 0.538266 | 5.13E-06 |
| ENSG00000114107 | CEP70 | -0.91301 | 5.14E-06 |
| ENSG00000116809 | ZBTB17 | 0.66948 | 5.17E-06 |
| ENSG00000119711 | ALDH6A1 | -0.58814 | 5.18E-06 |
| ENSG00000128626 | MRPS12 | 0.641982 | 5.23E-06 |
| ENSG00000159399 | HK2 | 0.627342 | 5.24E-06 |
| ENSG00000204217 | BMPR2 | -0.5869 | 5.26E-06 |
| ENSG00000153214 | TMEM87B | -0.58944 | 5.34E-06 |
| ENSG00000261005 |  | 1.007292 | 5.45E-06 |
| ENSG00000160593 | JAML | 0.79125 | 5.51E-06 |
| ENSG00000126934 | MAP2K2 | 0.575486 | 5.60E-06 |
| ENSG00000147650 | LRP12 | 0.628228 | 5.61E-06 |
| ENSG00000106484 | MEST | 0.818759 | 5.62E-06 |
| ENSG00000166974 | MAPRE2 | -0.62303 | 5.62E-06 |
| ENSG00000129932 | DOHH | 0.949883 | 5.62E-06 |
| ENSG00000153094 | BCL2L11 | 0.777148 | 5.66E-06 |
| ENSG00000186193 | SAPCD2 | 0.665656 | 5.66E-06 |
| ENSG00000154258 | ABCA9 | -1.32331 | 5.71E-06 |
| ENSG00000188389 | PDCD1 | 1.48654 | 5.79E-06 |
| ENSG00000007376 | RPUSD1 | 0.676225 | 5.87E-06 |
| ENSG00000099385 | BCL7C | 0.612882 | 5.87E-06 |
| ENSG00000116691 | MIIP | 0.808073 | 5.91E-06 |
| ENSG00000008277 | ADAM22 | 0.787443 | 6.04E-06 |
| ENSG00000165322 | ARHGAP12 | -0.92895 | 6.10E-06 |
| ENSG00000117410 | ATP6V0B | 0.541924 | 6.27E-06 |
| ENSG00000143702 | CEP170 | -0.66843 | 6.30E-06 |
| ENSG00000127124 | HIVEP3 | -0.73893 | 6.34E-06 |
| ENSG00000101160 | CTSZ | 0.58164 | 6.48E-06 |
| ENSG00000130635 | COL5A1 | -1.06914 | 6.67E-06 |
| ENSG00000124107 | SLPI | 1.634011 | 6.73E-06 |
| ENSG00000115268 | RPS15 | 0.53159 | 6.74E-06 |
| ENSG00000205592 |  | -1.75602 | 6.77E-06 |
| ENSG00000072818 | ACAP1 | 0.552696 | 6.78E-06 |
| ENSG00000099219 | ERMP1 | -0.52488 | 6.79E-06 |
| ENSG00000162999 | DUSP19 | -1.44611 | 6.79E-06 |
| ENSG00000235568 | NFAM1 | 0.932045 | 6.81E-06 |
| ENSG00000060069 | CTDP1 | 0.63313 | 7.04E-06 |
| ENSG00000079739 | PGM1 | 1.343214 | 7.12E-06 |
| ENSG00000112149 | CD83 | 1.654499 | 7.18E-06 |
| ENSG00000104951 | IL4I1 | 1.754339 | 7.21E-06 |
| ENSG00000133065 | SLC41A1 | -0.7693 | 7.22E-06 |
| ENSG00000160867 | FGFR4 | 0.659231 | 7.53E-06 |
| ENSG00000132510 | KDM6B | 0.67017 | 7.53E-06 |
| ENSG00000027697 | IFNGR1 | 0.65129 | 7.55E-06 |
| ENSG00000135046 | ANXA1 | -0.70511 | 7.69E-06 |
| ENSG00000153317 | ASAP1 | 0.535222 | 7.71E-06 |
| ENSG00000146858 | ZC3HAV1L | -0.97525 | 7.88E-06 |
| ENSG00000130600 | H19 | -1.54122 | 7.94E-06 |
| ENSG00000144040 | SFXN5 | 0.720056 | 7.96E-06 |
| ENSG00000152104 | PTPN14 | -0.88 | 8.04E-06 |
| ENSG00000177674 | AGTRAP | 0.574167 | 8.06E-06 |
| ENSG00000156011 | PSD3 | 0.846146 | 8.10E-06 |
| ENSG00000237604 |  | 1.023956 | 8.13E-06 |
| ENSG00000146066 | HIGD2A | 0.543526 | 8.23E-06 |
| ENSG00000198075 | SULT1C4 | -1.23969 | 8.33E-06 |
| ENSG00000127586 | CHTF18 | 0.881386 | 8.38E-06 |
| ENSG00000160957 | RECQL4 | 0.825233 | 8.43E-06 |
| ENSG00000130844 | ZNF331 | -0.98689 | 8.47E-06 |
| ENSG00000074842 | MYDGF | 0.560164 | 8.47E-06 |
| ENSG00000133027 | PEMT | 0.65733 | 8.47E-06 |
| ENSG00000232368 |  | 0.610687 | 8.77E-06 |
| ENSG00000102145 | GATA1 | 0.761869 | 8.81E-06 |
| ENSG00000137801 | THBS1 | 0.798825 | 8.83E-06 |
| ENSG00000149089 | APIP | -0.7281 | 8.85E-06 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000117245 | KIF17 | −1.09371 | 8.88E−06 |
| ENSG00000226976 |  | 0.646203 | 8.88E−06 |
| ENSG00000176783 | RUFY1 | −0.73725 | 8.89E−06 |
| ENSG00000126264 | HCST | 0.669474 | 9.03E−06 |
| ENSG00000215417 | MIR17HG | −0.76339 | 9.03E−06 |
| ENSG00000164120 | HPGD | 0.571594 | 9.12E−06 |
| ENSG00000137968 | SLC44A5 | −1.22548 | 9.27E−06 |
| ENSG00000124593 | PRICKLE4 | −0.78944 | 9.28E−06 |
| ENSG00000232203 |  | 1.0306 | 9.41E−06 |
| ENSG00000109320 | NFKB1 | 0.811778 | 9.74E−06 |
| ENSG00000163322 | FAM175A | −0.56597 | 9.74E−06 |
| ENSG00000168081 | PNOC | 1.492102 | 9.86E−06 |
| ENSG00000107819 | SFXN3 | −0.54815 | 1.00E−05 |
| ENSG00000099849 | RASSF7 | 0.796668 | 1.03E−05 |
| ENSG00000175701 |  | 0.967692 | 1.05E−05 |
| ENSG00000204287 | HLA-DRA | −0.81839 | 1.05E−05 |
| ENSG00000077984 | CST7 | 0.706267 | 1.09E−05 |
| ENSG00000126249 | PDCD2L | −1.00196 | 1.14E−05 |
| ENSG00000089351 | GRAMD1A | 0.837231 | 1.16E−05 |
| ENSG00000151474 | FRMD4A | −0.60205 | 1.17E−05 |
| ENSG00000099800 | TIMM13 | 0.609545 | 1.18E−05 |
| ENSG00000110446 | SLC15A3 | 1.373008 | 1.18E−05 |
| ENSG00000160191 | PDE9A | −0.86177 | 1.18E−05 |
| ENSG00000161847 | RAVER1 | 0.717388 | 1.18E−05 |
| ENSG00000175463 | TBC1D10C | 0.599589 | 1.19E−05 |
| ENSG00000165028 | NIPSNAP3B | −0.8809 | 1.20E−05 |
| ENSG00000171051 | FPR1 | 1.36443 | 1.20E−05 |
| ENSG00000186047 | DLEU7 | 1.093422 | 1.24E−05 |
| ENSG00000229671 |  | −0.85435 | 1.25E−05 |
| ENSG00000131018 | SYNE1 | 1.36425 | 1.26E−05 |
| ENSG00000166927 | MS4A7 | −0.66549 | 1.26E−05 |
| ENSG00000130332 | LSM7 | 0.569014 | 1.27E−05 |
| ENSG00000203306 |  | 1.336411 | 1.27E−05 |
| ENSG00000163683 | SMIM14 | 1.157575 | 1.28E−05 |
| ENSG00000188566 | NDOR1 | 0.725985 | 1.28E−05 |
| ENSG00000251322 | SHANK3 | −0.71354 | 1.32E−05 |
| ENSG00000112667 | DNPH1 | 0.693869 | 1.33E−05 |
| ENSG00000180263 | FGD6 | −0.81932 | 1.34E−05 |
| ENSG00000180871 | CXCR2 | 0.871767 | 1.34E−05 |
| ENSG00000186318 | BACE1 | −0.64574 | 1.35E−05 |
| ENSG00000102362 | SYTL4 | −0.66302 | 1.35E−05 |
| ENSG00000204604 | ZNF468 | −0.58134 | 1.35E−05 |
| ENSG00000163870 | TPRA1 | 0.615314 | 1.41E−05 |
| ENSG00000123643 | SLC36A1 | 0.622685 | 1.41E−05 |
| ENSG00000161011 | SQSTM1 | 0.804597 | 1.43E−05 |
| ENSG00000164323 | CFAP97 | −0.56945 | 1.44E−05 |
| ENSG00000107521 | HPS1 | 0.544429 | 1.45E−05 |
| ENSG00000156642 | NPTN | 0.500792 | 1.49E−05 |
| ENSG00000136869 | TLR4 | 0.791318 | 1.54E−05 |
| ENSG00000145569 | FAM105A | 0.883044 | 1.57E−05 |
| ENSG00000176108 | CHMP6 | 0.72476 | 1.61E−05 |
| ENSG00000155363 | MOV10 | −0.57468 | 1.62E−05 |
| ENSG00000147206 | NXF3 | 0.54415 | 1.63E−05 |
| ENSG00000089693 | MLF2 | 0.508934 | 1.64E−05 |
| ENSG00000139174 | PRICKLE1 | −1.53659 | 1.64E−05 |
| ENSG00000117091 | CD48 | 0.660172 | 1.64E−05 |
| ENSG00000109861 | CTSC | 0.533139 | 1.65E−05 |
| ENSG00000132142 |  | −0.52366 | 1.67E−05 |
| ENSG00000100299 | ARSA | 0.742688 | 1.67E−05 |
| ENSG00000042493 | CAPG | 0.628364 | 1.68E−05 |
| ENSG00000034152 | MAP2K3 | 0.570915 | 1.71E−05 |
| ENSG00000139572 | GPR84 | 1.058139 | 1.71E−05 |
| ENSG00000142089 | IFITM3 | −0.80584 | 1.73E−05 |
| ENSG00000204386 | NEU1 | 0.625283 | 1.76E−05 |
| ENSG00000079156 | OSBPL6 | −0.63973 | 1.76E−05 |
| ENSG00000197381 | ADARB1 | 0.752805 | 1.77E−05 |
| ENSG00000126246 | IGFLR1 | 1.223056 | 1.80E−05 |
| ENSG00000168993 | CPLX1 | 1.108348 | 1.81E−05 |
| ENSG00000174804 | FZD4 | −1.61854 | 1.83E−05 |
| ENSG00000070371 | CLTCL1 | 0.824427 | 1.85E−05 |
| ENSG00000211450 | C11orf31 | 0.684084 | 1.85E−05 |
| ENSG00000119138 | KLF9 | 0.679608 | 1.87E−05 |
| ENSG00000090612 | ZNF268 | −0.57165 | 1.88E−05 |
| ENSG00000106153 | CHCHD2 | 0.52037 | 1.88E−05 |
| ENSG00000131323 | TRAF3 | 0.580253 | 1.88E−05 |

SUPPLEMENTARY TABLE 1-continued

List of the identified differentially expressed transcripts after DE analysis using DESeq2 and edgeR-

| ENSEMBL | Symbol | Log$_2$ Fold Change | False discovery rate |
| --- | --- | --- | --- |
| ENSG00000175567 | UCP2 | 0.488792 | 1.89E−05 |
| ENSG00000109103 | UNC119 | 0.600254 | 1.96E−05 |
| ENSG00000196693 | ZNF33B | −0.58917 | 1.98E−05 |
| ENSG00000137177 | KIF13A | −0.66409 | 2.00E−05 |
| ENSG00000136840 | ST6GALNAC4 | 0.739593 | 2.01E−05 |
| ENSG00000162910 | MRPL55 | 0.727342 | 2.02E−05 |
| ENSG00000259020 | | 0.680466 | 2.05E−05 |
| ENSG00000271975 | | −0.91736 | 2.10E−05 |
| ENSG00000130675 | MNX1 | 0.908674 | 2.11E−05 |
| ENSG00000148343 | FAM73B | 0.620398 | 2.12E−05 |
| ENSG00000227205 | | 0.936053 | 2.13E−05 |
| ENSG00000002587 | HS3ST1 | −1.37011 | 2.16E−05 |
| ENSG00000133317 | LGALS12 | 0.874859 | 2.18E−05 |
| ENSG00000165646 | SLC18A2 | −0.63478 | 2.22E−05 |
| ENSG00000180044 | C3orf80 | −0.72053 | 2.25E−05 |
| ENSG00000100401 | RANGAP1 | 0.52374 | 2.29E−05 |
| ENSG00000138821 | SLC39A8 | 0.62848 | 2.30E−05 |
| ENSG00000105472 | CLEC11A | 0.651568 | 2.31E−05 |
| ENSG00000167535 | CACNB3 | −0.77752 | 2.31E−05 |
| ENSG00000162783 | IER5 | 0.628289 | 2.35E−05 |
| ENSG00000134318 | ROCK2 | −0.51339 | 2.36E−05 |
| ENSG00000110218 | PANX1 | −0.67842 | 2.37E−05 |
| ENSG00000132359 | RAP1GAP2 | −0.7299 | 2.37E−05 |
| ENSG00000124766 | SOX4 | −0.67184 | 2.37E−05 |
| ENSG00000188636 | LDOC1L | −0.5971 | 2.39E−05 |
| ENSG00000164733 | CTSB | 0.53478 | 2.40E−05 |
| ENSG00000198399 | ITSN2 | −0.50327 | 2.40E−05 |
| ENSG00000198643 | FAM3D | −1.48797 | 2.43E−05 |
| ENSG00000160791 | CCR5 | 1.024096 | 2.46E−05 |
| ENSG00000128524 | ATP6V1F | 0.542137 | 2.52E−05 |
| ENSG00000164897 | TMUB1 | 0.89267 | 2.55E−05 |
| ENSG00000141504 | SAT2 | 0.716065 | 2.55E−05 |
| ENSG00000196865 | NHLRC2 | −0.57136 | 2.55E−05 |
| ENSG00000185420 | SMYD3 | −0.53766 | 2.56E−05 |
| ENSG00000104880 | ARHGEF18 | 0.617396 | 2.61E−05 |
| ENSG00000247774 | PCED1B-AS1 | 1.041996 | 2.66E−05 |
| ENSG00000105374 | NKG7 | 0.655033 | 2.68E−05 |
| ENSG00000166794 | PPIB | 0.515567 | 2.77E−05 |
| ENSG00000175414 | ARL10 | −1.64145 | 2.77E−05 |
| ENSG00000006451 | RALA | −0.53846 | 2.81E−05 |
| ENSG00000128268 | MGAT3 | 0.915313 | 2.81E−05 |
| ENSG00000197858 | GPAA1 | 0.659863 | 2.81E−05 |
| ENSG00000256234 | | 1.633152 | 2.84E−05 |
| ENSG00000062822 | POLD1 | 0.687233 | 2.85E−05 |
| ENSG00000140284 | SLC27A2 | 0.780945 | 2.85E−05 |
| ENSG00000073008 | PVR | 0.701404 | 2.86E−05 |
| ENSG00000178217 | SH2D4B | 1.37417 | 2.90E−05 |
| ENSG00000168350 | DEGS2 | −1.1947 | 2.94E−05 |
| ENSG00000230195 | | −0.98485 | 2.96E−05 |
| ENSG00000244331 | | 0.725641 | 2.97E−05 |
| ENSG00000133030 | MPRIP | −0.60835 | 2.99E−05 |
| ENSG00000149212 | SESN3 | 0.803936 | 3.03E−05 |
| ENSG00000122515 | ZMIZ2 | 0.602262 | 3.04E−05 |
| ENSG00000099992 | TBC1D10A | 1.039586 | 3.06E−05 |
| ENSG00000164088 | PPM1M | 0.677662 | 3.06E−05 |
| ENSG00000196247 | ZNF107 | −0.67754 | 3.06E−05 |
| ENSG00000113303 | BTNL8 | 1.489582 | 3.06E−05 |
| ENSG00000063176 | SPHK2 | 0.728562 | 3.07E−05 |
| ENSG00000111912 | NCOA7 | −0.59186 | 3.08E−05 |
| ENSG00000169738 | DCXR | 0.547218 | 3.09E−05 |
| ENSG00000186010 | NDUFA13 | 0.753459 | 3.10E−05 |
| ENSG00000167646 | DNAAF3 | 0.72244 | 3.12E−05 |
| ENSG00000197442 | MAP3K5 | −0.58705 | 3.13E−05 |
| ENSG00000137509 | PRCP | 0.49777 | 3.15E−05 |
| ENSG00000197312 | DDI2 | −0.51298 | 3.16E−05 |
| ENSG00000184465 | WDR27 | −0.6776 | 3.19E−05 |
| ENSG00000064225 | ST3GAL6 | 0.570774 | 3.19E−05 |
| ENSG00000179348 | GATA2 | 0.583271 | 3.19E−05 |
| ENSG00000120262 | CCDC170 | −1.39913 | 3.22E−05 |
| ENSG00000185862 | EVI2B | 0.50731 | 3.25E−05 |
| ENSG00000178802 | MPI | −0.55868 | 3.36E−05 |
| ENSG00000127334 | DYRK2 | −0.53801 | 3.62E−05 |
| ENSG00000136231 | IGF2BP3 | 0.513755 | 3.65E−05 |
| ENSG00000183166 | CALN1 | −1.01932 | 3.69E−05 |
| ENSG00000178605 | GTPBP6 | 0.749561 | 3.71E−05 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000178719 | GRINA | 0.649232 | 3.71E−05 |
| ENSG00000079432 | CIC | 0.622897 | 3.85E−05 |
| ENSG00000108106 | UBE2S | 1.112414 | 3.90E−05 |
| ENSG00000138639 | ARHGAP24 | 1.069599 | 3.91E−05 |
| ENSG00000166575 | TMEM135 | −0.63597 | 3.91E−05 |
| ENSG00000197506 | SLC28A3 | 0.794783 | 3.94E−05 |
| ENSG00000211689 | TARP | 0.676758 | 3.99E−05 |
| ENSG00000118046 | STK11 | 0.526271 | 3.99E−05 |
| ENSG00000169242 | EFNA1 | −1.32565 | 4.01E−05 |
| ENSG00000189013 | KIR2DL4 | 1.266654 | 4.01E−05 |
| ENSG00000169100 | SLC25A6 | 0.474919 | 4.08E−05 |
| ENSG00000105701 | FKBP8 | 0.552166 | 4.09E−05 |
| ENSG00000198795 | ZNF521 | −0.93115 | 4.10E−05 |
| ENSG00000040933 | INPP4A | 0.60308 | 4.10E−05 |
| ENSG00000164684 | ZNF704 | 1.511661 | 4.13E−05 |
| ENSG00000079277 | MKNK1 | 0.58402 | 4.14E−05 |
| ENSG00000176973 | FAM89B | 0.800335 | 4.14E−05 |
| ENSG00000065308 | TRAM2 | −0.54762 | 4.15E−05 |
| ENSG00000169136 | ATF5 | 0.649429 | 4.19E−05 |
| ENSG00000126005 |  | 0.533586 | 4.25E−05 |
| ENSG00000166091 | CMTM5 | −1.44426 | 4.25E−05 |
| ENSG00000150337 | FCGR1A | 1.039571 | 4.28E−05 |
| ENSG00000122490 | PQLC1 | 0.584723 | 4.29E−05 |
| ENSG00000183741 | CBX6 | 0.56015 | 4.30E−05 |
| ENSG00000101474 | APMAP | 0.485705 | 4.30E−05 |
| ENSG00000157881 | PANK4 | 0.677743 | 4.38E−05 |
| ENSG00000180574 |  | −0.52105 | 4.42E−05 |
| ENSG00000080298 | RFX3 | −0.94968 | 4.45E−05 |
| ENSG00000123933 | MXD4 | 0.517144 | 4.47E−05 |
| ENSG00000162032 | SPSB3 | 0.685119 | 4.49E−05 |
| ENSG00000257017 | HP | 1.140175 | 4.50E−05 |
| ENSG00000079313 | REXO1 | 0.60587 | 4.52E−05 |
| ENSG00000166106 | ADAMTS15 | 1.281952 | 4.54E−05 |
| ENSG00000158292 | GPR153 | 0.958735 | 4.61E−05 |
| ENSG00000135899 | SP110 | −0.69205 | 4.64E−05 |
| ENSG00000168334 | XIRP1 | −1.22694 | 4.64E−05 |
| ENSG00000196961 | AP2A1 | 0.546074 | 4.66E−05 |
| ENSG00000109680 | TBC1D19 | −1.15776 | 4.68E−05 |
| ENSG00000116106 | EPHA4 | −1.55652 | 4.69E−05 |
| ENSG00000198346 | ZNF813 | −0.6291 | 4.72E−05 |
| ENSG00000071282 | LMCD1 | −0.92408 | 4.76E−05 |
| ENSG00000156860 | FBRS | 0.535141 | 4.78E−05 |
| ENSG00000181751 | C5orf30 | −0.58269 | 4.83E−05 |
| ENSG00000173193 | PARP14 | −0.75064 | 4.86E−05 |
| ENSG00000159788 | RGS12 | 0.602227 | 4.88E−05 |
| ENSG00000067225 | PKM | 0.445392 | 4.90E−05 |
| ENSG00000018189 | RUFY3 | −0.67541 | 4.96E−05 |
| ENSG00000175416 | CLTB | 0.592996 | 5.18E−05 |
| ENSG00000136213 | CHST12 | 0.866774 | 5.22E−05 |
| ENSG00000196867 | ZFP28 | −1.11689 | 5.24E−05 |
| ENSG00000165512 | ZNF22 | −0.55599 | 5.32E−05 |
| ENSG00000197070 | ARRDC1 | 0.578062 | 5.32E−05 |
| ENSG00000100628 | ASB2 | 1.236625 | 5.33E−05 |
| ENSG00000239809 |  | 0.620555 | 5.36E−05 |
| ENSG00000137496 | IL18BP | 0.690293 | 5.36E−05 |
| ENSG00000249550 | LINC01234 | −1.27392 | 5.38E−05 |
| ENSG00000107404 | DVL1 | 0.684147 | 5.42E−05 |
| ENSG00000085832 | EPS15 | −0.47256 | 5.43E−05 |
| ENSG00000162929 | KIAA1841 | −0.7427 | 5.45E−05 |
| ENSG00000167508 | MVD | 0.663406 | 5.46E−05 |
| ENSG00000070081 | NUCB2 | 0.538003 | 5.65E−05 |
| ENSG00000196628 | TCF4 | −0.61592 | 5.67E−05 |
| ENSG00000120306 | CYSTM1 | 0.661474 | 5.73E−05 |
| ENSG00000166002 | SMCO4 | 0.860847 | 5.73E−05 |
| ENSG00000205476 | CCDC85C | 0.836118 | 5.75E−05 |
| ENSG00000131116 | ZNF428 | 0.610412 | 5.76E−05 |
| ENSG00000186469 | GNG2 | −1.07584 | 5.85E−05 |
| ENSG00000164953 | TMEM67 | −1.03093 | 5.87E−05 |
| ENSG00000233328 |  | 0.494941 | 5.89E−05 |
| ENSG00000115350 | POLE4 | 0.629516 | 5.91E−05 |
| ENSG00000105483 | CARD8 | −0.48211 | 6.20E−05 |
| ENSG00000140961 | OSGIN1 | 1.00531 | 6.24E−05 |
| ENSG00000076924 | XAB2 | 0.522499 | 6.26E−05 |
| ENSG00000265273 |  | 0.537621 | 6.35E−05 |
| ENSG00000205138 | SDHAF1 | 0.676309 | 6.37E−05 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
| --- | --- | --- | --- |
| ENSG00000173218 | VANGL1 | −0.57197 | 6.42E−05 |
| ENSG00000151882 | CCL28 | −0.65743 | 6.48E−05 |
| ENSG00000172164 | SNTB1 | 0.487476 | 6.48E−05 |
| ENSG00000225674 | | −0.56325 | 6.48E−05 |
| ENSG00000147324 | MFHAS1 | −0.60146 | 6.53E−05 |
| ENSG00000169231 | THBS3 | −0.69409 | 6.59E−05 |
| ENSG00000105518 | TMEM205 | 0.603499 | 6.61E−05 |
| ENSG00000138764 | CCNG2 | 0.643214 | 6.62E−05 |
| ENSG00000100162 | CENPM | 0.713866 | 6.71E−05 |
| ENSG00000131797 | CLUHP3 | −1.38346 | 6.74E−05 |
| ENSG00000167468 | GPX4 | 0.477497 | 6.82E−05 |
| ENSG00000108639 | SYNGR2 | 0.486426 | 6.85E−05 |
| ENSG00000104903 | LYL1 | 0.523094 | 6.88E−05 |
| ENSG00000030582 | GRN | 0.650924 | 6.95E−05 |
| ENSG00000116741 | RGS2 | 0.911476 | 6.95E−05 |
| ENSG00000026950 | BTN3A1 | −0.73557 | 7.02E−05 |
| ENSG00000106258 | CYP3A5 | 1.500546 | 7.06E−05 |
| ENSG00000198677 | TTC37 | −0.47883 | 7.12E−05 |
| ENSG00000148335 | NTMT1 | 0.56768 | 7.15E−05 |
| ENSG00000253159 | PCDHGA12 | −1.22918 | 7.21E−05 |
| ENSG00000120756 | PLS1 | 1.302973 | 7.23E−05 |
| ENSG00000166896 | ATP23 | 0.62096 | 7.23E−05 |
| ENSG00000169184 | MN1 | −0.49585 | 7.33E−05 |
| ENSG00000107872 | FBXL15 | 0.95857 | 7.33E−05 |
| ENSG00000105726 | ATP13A1 | 0.540112 | 7.34E−05 |
| ENSG00000198721 | ECI2 | −0.67502 | 7.34E−05 |
| ENSG00000163235 | TGFA | 1.065857 | 7.41E−05 |
| ENSG00000198053 | SIRPA | 0.571393 | 7.43E−05 |
| ENSG00000174099 | MSRB3 | 1.185439 | 7.51E−05 |
| ENSG00000147168 | IL2RG | 0.634018 | 7.53E−05 |
| ENSG00000138078 | PREPL | −0.48568 | 7.60E−05 |
| ENSG00000167513 | CDT1 | 0.691377 | 7.60E−05 |
| ENSG00000103249 | CLCN7 | 0.546952 | 7.64E−05 |
| ENSG00000176533 | GNG7 | −0.5781 | 7.66E−05 |
| ENSG00000175183 | CSRP2 | −1.05882 | 7.75E−05 |
| ENSG00000196458 | ZNF605 | −0.60546 | 7.89E−05 |
| ENSG00000227191 | | 0.702837 | 7.92E−05 |
| ENSG00000070718 | AP3M2 | −0.67097 | 7.98E−05 |
| ENSG00000166165 | CKB | 0.678893 | 8.04E−05 |
| ENSG00000184897 | H1FX | 0.671421 | 8.07E−05 |
| ENSG00000132613 | MTSS1L | 0.673854 | 8.16E−05 |
| ENSG00000268734 | | 1.347743 | 8.16E−05 |
| ENSG00000141524 | TMC6 | 0.547438 | 8.25E−05 |
| ENSG00000174469 | CNTNAP2 | −0.96357 | 8.27E−05 |
| ENSG00000245648 | LOC101928100 | 1.561093 | 8.57E−05 |
| ENSG00000154099 | DNAAF1 | 1.577755 | 8.77E−05 |
| ENSG00000102445 | KIAA0226L | 1.369751 | 8.83E−05 |
| ENSG00000189089 | | −1.52592 | 8.83E−05 |
| ENSG00000127863 | TNFRSF19 | −1.48607 | 8.87E−05 |
| ENSG00000090581 | GNPTG | 0.568088 | 9.07E−05 |
| ENSG00000119522 | DENND1A | 0.515137 | 9.26E−05 |
| ENSG00000179085 | DPM3 | 0.908285 | 9.31E−05 |
| ENSG00000261211 | | 1.426066 | 9.31E−05 |
| ENSG00000132334 | PTPRE | 0.582226 | 9.43E−05 |
| ENSG00000108294 | | 0.458921 | 9.43E−05 |
| ENSG00000083799 | CYLD | 0.564817 | 9.44E−05 |
| ENSG00000102879 | CORO1A | 0.573127 | 9.58E−05 |
| ENSG00000174233 | ADCY6 | −0.62678 | 9.58E−05 |
| ENSG00000123384 | LRP1 | 1.220295 | 9.62E−05 |
| ENSG00000108984 | MAP2K6 | −1.46491 | 9.72E−05 |
| ENSG00000138399 | FASTKD1 | −0.49788 | 9.77E−05 |
| ENSG00000122359 | ANXA11 | 0.461851 | 9.78E−05 |
| ENSG00000141552 | ANAPC11 | 0.621909 | 9.78E−05 |
| ENSG00000099203 | TMED1 | 0.611044 | 1.00E−04 |
| ENSG00000181631 | P2RY13 | 0.906771 | 1.00E−04 |
| ENSG00000115255 | REEP6 | 0.738307 | 0.0001 |
| ENSG00000091879 | ANGPT2 | −1.26248 | 0.000101 |
| ENSG00000167797 | CDK2AP2 | 0.570809 | 0.000101 |
| ENSG00000237649 | KIFC1 | 0.508432 | 0.000101 |
| ENSG00000204681 | GABBR1 | −0.93439 | 0.000104 |
| ENSG00000134780 | DAGLA | 1.06719 | 0.000105 |
| ENSG00000149927 | DOC2A | −1.04553 | 0.000105 |
| ENSG00000172922 | RNASEH2C | 0.597996 | 0.000105 |
| ENSG00000204498 | NFKBIL1 | 0.755858 | 0.000106 |
| ENSG00000172932 | ANKRD13D | 0.490257 | 0.000107 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000189068 | VSTM1 | 0.777405 | 0.000108 |
| ENSG00000183309 | ZNF623 | −0.59613 | 0.000108 |
| ENSG00000107537 | PHYH | −0.74001 | 0.000108 |
| ENSG00000077420 | APBB1IP | −0.52113 | 0.000108 |
| ENSG00000128000 | ZNF780B | −0.58372 | 0.000108 |
| ENSG00000119559 | C19orf25 | 0.55608 | 0.000109 |
| ENSG00000102048 | ASB9 | −0.76982 | 0.00011 |
| ENSG00000171700 | RGS19 | 0.492829 | 0.00011 |
| ENSG00000100726 | TELO2 | 0.65902 | 0.000111 |
| ENSG00000177105 | RHOG | 0.497779 | 0.000113 |
| ENSG00000124762 | CDKN1A | 0.46046 | 0.000114 |
| ENSG00000076984 | MAP2K7 | 0.524319 | 0.000116 |
| ENSG00000105402 | NAPA | 0.52981 | 0.000116 |
| ENSG00000105750 | ZNF85 | −0.66537 | 0.000117 |
| ENSG00000138172 | CALHM2 | −0.64272 | 0.000118 |
| ENSG00000121481 | RNF2 | −0.48131 | 0.000119 |
| ENSG00000127952 | STYXL1 | −0.53907 | 0.000121 |
| ENSG00000105642 | KCNN1 | −0.58045 | 0.000121 |
| ENSG00000112062 | MAPK14 | 0.44798 | 0.000121 |
| ENSG00000126432 | PRDX5 | 0.455182 | 0.000121 |
| ENSG00000206557 | TRIM71 | −0.62279 | 0.000123 |
| ENSG00000167962 | ZNF598 | 0.621218 | 0.000124 |
| ENSG00000125534 | PPDPF | 0.579431 | 0.000125 |
| ENSG00000128059 | PPAT | −0.56192 | 0.000125 |
| ENSG00000137802 | MAPKBP1 | −0.61827 | 0.000126 |
| ENSG00000123064 | DDX54 | 0.509124 | 0.000126 |
| ENSG00000124920 | MYRF | 0.847488 | 0.000127 |
| ENSG00000122642 | FKBP9 | −0.68746 | 0.000129 |
| ENSG00000233968 | LOC101928834 | −1.3292 | 0.000132 |
| ENSG00000140859 | KIFC3 | 0.800731 | 0.000134 |
| ENSG00000110400 | NECTIN1 | 1.108315 | 0.000135 |
| ENSG00000127445 | PIN1 | 0.561054 | 0.000136 |
| ENSG00000155465 | SLC7A7 | 1.011231 | 0.000136 |
| ENSG00000070413 | DGCR2 | 0.545089 | 0.000136 |
| ENSG00000132024 | CC2D1A | 0.58398 | 0.00014 |
| ENSG00000253981 |  | 1.421516 | 0.00014 |
| ENSG00000175602 | CCDC85B | 1.027114 | 0.000141 |
| ENSG00000197321 | SVIL | 0.5705 | 0.000141 |
| ENSG00000125835 | SNRPB | 0.481389 | 0.000141 |
| ENSG00000103485 | QPRT | −0.55054 | 0.000141 |
| ENSG00000137713 | PPP2R1B | −0.47722 | 0.000143 |
| ENSG00000140990 | NDUFB10 | 0.478178 | 0.000146 |
| ENSG00000221963 | APOL6 | −0.67449 | 0.000147 |
| ENSG00000099817 | POLR2E | 0.521823 | 0.000147 |
| ENSG00000130305 | NSUN5 | 0.663921 | 0.000148 |
| ENSG00000169764 | UGP2 | 0.452835 | 0.00015 |
| ENSG00000069020 | MAST4 | −0.89745 | 0.00015 |
| ENSG00000127419 | TMEM175 | 0.749343 | 0.00015 |
| ENSG00000198363 | ASPH | −0.48054 | 0.000151 |
| ENSG00000112033 | PPARD | 0.790925 | 0.000152 |
| ENSG00000173269 | MMRN2 | −0.78373 | 0.000153 |
| ENSG00000197956 | S100A6 | −0.91491 | 0.000157 |
| ENSG00000163221 | S100A12 | 1.452638 | 0.000158 |
| ENSG00000126790 | L3HYPDH | −0.86954 | 0.000159 |
| ENSG00000116127 | ALMS1 | −0.53676 | 0.00016 |
| ENSG00000004059 | ARF5 | 0.48212 | 0.00016 |
| ENSG00000047365 | ARAP2 | 0.644225 | 0.000161 |
| ENSG00000125798 | FOXA2 | −1.46113 | 0.000161 |
| ENSG00000268518 |  | 0.917333 | 0.000162 |
| ENSG00000152556 | PFKM | −0.6627 | 0.000164 |
| ENSG00000182326 | C1S | −0.79393 | 0.000165 |
| ENSG00000028277 | POU2F2 | 0.863364 | 0.000165 |
| ENSG00000094916 | CBX5 | −0.4305 | 0.000165 |
| ENSG00000145494 | NDUFS6 | 0.557326 | 0.000166 |
| ENSG00000102575 | ACP5 | 1.369974 | 0.000166 |
| ENSG00000132846 | ZBED3 | −0.5064 | 0.000167 |
| ENSG00000020181 | ADGRA2 | −0.91048 | 0.000167 |
| ENSG00000163393 | SLC22A15 | 0.673426 | 0.000168 |
| ENSG00000167723 | TRPV3 | 1.264817 | 0.000168 |
| ENSG00000187116 | LILRA5 | 1.121746 | 0.000171 |
| ENSG00000105298 | CACTIN | 0.568822 | 0.000172 |
| ENSG00000138801 | PAPSS1 | 0.607751 | 0.000172 |
| ENSG00000125648 | SLC25A23 | −0.54686 | 0.000175 |
| ENSG00000218175 |  | 0.468903 | 0.000175 |
| ENSG00000167210 | LOXHD1 | −0.56777 | 0.000176 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000165983 | PTER | −0.48057 | 0.000178 |
| ENSG00000160404 | TOR2A | 0.519308 | 0.000185 |
| ENSG00000145391 | SETD7 | −0.58311 | 0.000186 |
| ENSG00000162144 | CYB561A3 | 0.484682 | 0.000188 |
| ENSG00000120949 | TNFRSF8 | 0.783945 | 0.000189 |
| ENSG00000065268 | WDR18 | 0.549038 | 0.00019 |
| ENSG00000160213 | CSTB | 0.501861 | 0.000192 |
| ENSG00000124496 | TRERF1 | 0.514726 | 0.000193 |
| ENSG00000168476 | REEP4 | 0.608636 | 0.000194 |
| ENSG00000106009 | BRAT1 | 0.543251 | 0.000194 |
| ENSG00000122741 | DCAF10 | −0.49358 | 0.000195 |
| ENSG00000112759 | SLC29A1 | 0.546862 | 0.000196 |
| ENSG00000233355 | CHRM3-AS2 | 1.165979 | 0.0002 |
| ENSG00000079616 | KIF22 | 0.466913 | 0.000205 |
| ENSG00000181619 | GPR135 | −0.88344 | 0.000206 |
| ENSG00000106537 | TSPAN13 | −0.72556 | 0.000207 |
| ENSG00000239713 | APOBEC3G | −0.76249 | 0.000208 |
| ENSG00000105366 | SIGLEC8 | 1.068339 | 0.000208 |
| ENSG00000144485 | HES6 | 0.802821 | 0.000212 |
| ENSG00000170638 | TRABD | 0.555254 | 0.000215 |
| ENSG00000124785 | NRN1 | 0.476534 | 0.000217 |
| ENSG00000182568 | SATB1 | −0.43865 | 0.000217 |
| ENSG00000152689 | RASGRP3 | −0.56673 | 0.000218 |
| ENSG00000166851 | PLK1 | 0.469851 | 0.000219 |
| ENSG00000100154 | TTC28 | −1.03308 | 0.00022 |
| ENSG00000115825 | PRKD3 | −0.50332 | 0.000221 |
| ENSG00000229425 |  | −1.45242 | 0.000221 |
| ENSG00000100311 | PDGFB | 1.475228 | 0.000224 |
| ENSG00000167578 | RAB4B | 0.782874 | 0.000225 |
| ENSG00000169692 | AGPAT2 | 0.594086 | 0.000225 |
| ENSG00000100003 | SEC14L2 | 1.110019 | 0.000227 |
| ENSG00000198130 | HIBCH | −0.57235 | 0.000227 |
| ENSG00000173327 | MAP3K11 | 0.55772 | 0.000232 |
| ENSG00000197785 | ATAD3A | 0.608867 | 0.000233 |
| ENSG00000113448 | PDE4D | −0.63378 | 0.000233 |
| ENSG00000002822 | MAD1L1 | 0.561865 | 0.000236 |
| ENSG00000126254 | RBM42 | 0.54281 | 0.000237 |
| ENSG00000238243 | OR2W3 | −0.92475 | 0.000238 |
| ENSG00000130560 | UBAC1 | 0.490115 | 0.000239 |
| ENSG00000144647 | POMGNT2 | 0.899715 | 0.000242 |
| ENSG00000163497 | FEV | −1.40401 | 0.000242 |
| ENSG00000136653 |  | 0.495147 | 0.000244 |
| ENSG00000204406 | MBD5 | −0.56365 | 0.000244 |
| ENSG00000168386 | FILIP1L | 0.563293 | 0.000245 |
| ENSG00000177200 | CHD9 | −0.45883 | 0.000245 |
| ENSG00000171161 | ZNF672 | 0.541072 | 0.000246 |
| ENSG00000236081 | ELFN1-AS1 | 0.79783 | 0.000248 |
| ENSG00000186111 | PIP5K1C | 0.48726 | 0.000251 |
| ENSG00000185386 | MAPK11 | −0.66694 | 0.000252 |
| ENSG00000082438 | COBLL1 | −0.55954 | 0.000254 |
| ENSG00000064195 | DLX3 | −1.0758 | 0.000255 |
| ENSG00000242013 |  | −0.89473 | 0.000256 |
| ENSG00000123836 | PFKFB2 | −0.82761 | 0.000257 |
| ENSG00000124098 | FAM210B | −0.65455 | 0.000257 |
| ENSG00000174307 | PHLDA3 | 0.603662 | 0.000259 |
| ENSG00000157021 |  | −0.88467 | 0.000259 |
| ENSG00000226608 |  | 0.506789 | 0.000259 |
| ENSG00000227097 |  | 0.442066 | 0.000266 |
| ENSG00000153933 | DGKE | −0.64583 | 0.000267 |
| ENSG00000185168 |  | 1.03852 | 0.000267 |
| ENSG00000100908 | EMC9 | 0.707632 | 0.000268 |
| ENSG00000213563 | C8orf82 | 0.690007 | 0.000268 |
| ENSG00000160991 | ORAI2 | 0.526026 | 0.000269 |
| ENSG00000136147 | PHF11 | −0.51766 | 0.000271 |
| ENSG00000254415 | SIGLEC14 | 0.568649 | 0.000272 |
| ENSG00000015413 | DPEP1 | 0.634544 | 0.000272 |
| ENSG00000149503 | INCENP | 0.564919 | 0.000273 |
| ENSG00000136436 | CALCOCO2 | −0.46793 | 0.000274 |
| ENSG00000186635 | ARAP1 | 0.583946 | 0.000277 |
| ENSG00000124406 | ATP8A1 | −0.54356 | 0.000278 |
| ENSG00000198538 | ZNF28 | −0.58072 | 0.000279 |
| ENSG00000116833 | NR5A2 | −1.44632 | 0.000281 |
| ENSG00000167969 | ECU | 0.646621 | 0.000281 |
| ENSG00000104047 | DTWD1 | −0.58161 | 0.000283 |
| ENSG00000127666 | TICAM1 | 0.632663 | 0.000283 |

SUPPLEMENTARY TABLE 1-continued

List of the identified differentially expressed transcripts after DE analysis using DESeq2 and edgeR-

| ENSEMBL | Symbol | Log$_2$ Fold Change | False discovery rate |
|---|---|---|---|
| ENSG00000107438 | PDLIM1 | −0.48287 | 0.000286 |
| ENSG00000051009 | FAM160A2 | 0.568221 | 0.000286 |
| ENSG00000133142 | TCEAL4 | −0.49098 | 0.000287 |
| ENSG00000162076 | FLYWCH2 | 0.718206 | 0.000292 |
| ENSG00000182240 | BACE2 | 0.943716 | 0.000293 |
| ENSG00000187688 | TRPV2 | −0.63588 | 0.000296 |
| ENSG00000162585 | FAAP20 | 0.704097 | 0.000298 |
| ENSG00000244486 | SCARF2 | 1.333805 | 0.000298 |
| ENSG00000136404 | TM6SF1 | 0.655498 | 0.000307 |
| ENSG00000104897 | SF3A2 | 0.503912 | 0.000308 |
| ENSG00000262370 | | 0.603079 | 0.000309 |
| ENSG00000161179 | YDJC | 0.553317 | 0.000312 |
| ENSG00000068001 | HYAL2 | 0.547502 | 0.000313 |
| ENSG00000008130 | NADK | 0.451339 | 0.000313 |
| ENSG00000228203 | RNF144A-AS1 | 0.65372 | 0.000313 |
| ENSG00000171101 | SIGLEC17P | 0.915321 | 0.000317 |
| ENSG00000263753 | LINC00667 | −0.65749 | 0.000321 |
| ENSG00000234444 | ZNF736 | −0.54617 | 0.000324 |
| ENSG00000260273 | | −1.20762 | 0.000325 |
| ENSG00000131584 | ACAP3 | 0.611879 | 0.000327 |
| ENSG00000135919 | SERPINE2 | 1.224518 | 0.000328 |
| ENSG00000177706 | FAM20C | 0.535706 | 0.000328 |
| ENSG00000235297 | | 0.472837 | 0.000328 |
| ENSG00000130340 | SNX9 | 0.533746 | 0.000329 |
| ENSG00000181104 | F2R | −0.55051 | 0.000332 |
| ENSG00000116786 | PLEKHM2 | 0.471645 | 0.000333 |
| ENSG00000185278 | ZBTB37 | −0.5311 | 0.000334 |
| ENSG00000240972 | MIF | 0.631524 | 0.000336 |
| ENSG00000047932 | GOPC | −0.47954 | 0.000337 |
| ENSG00000147813 | NAPRT | 0.577225 | 0.000339 |
| ENSG00000180992 | MRPL14 | 0.502982 | 0.00034 |
| ENSG00000167772 | ANGPTL4 | 1.381012 | 0.000344 |
| ENSG00000100271 | TTLL1 | −0.77187 | 0.000346 |
| ENSG00000122778 | KIAA1549 | −0.5406 | 0.000347 |
| ENSG00000135341 | MAP3K7 | −0.4365 | 0.000351 |
| ENSG00000110880 | CORO1C | −0.44355 | 0.000352 |
| ENSG00000139132 | FGD4 | 0.708359 | 0.000355 |
| ENSG00000132005 | RFX1 | 0.717412 | 0.000355 |
| ENSG00000113749 | HRH2 | 0.688071 | 0.000356 |
| ENSG00000105135 | ILVBL | 0.554801 | 0.000357 |
| ENSG00000156030 | ELMSAN1 | −0.44864 | 0.000358 |
| ENSG00000250337 | LINC01021 | −0.61142 | 0.000358 |
| ENSG00000165804 | ZNF219 | 1.168595 | 0.000358 |
| ENSG00000184281 | TSSC4 | 0.606634 | 0.000358 |
| ENSG00000204160 | ZDHHC18 | 0.630693 | 0.00036 |
| ENSG00000234985 | | 0.751918 | 0.000363 |
| ENSG00000070190 | DAPP1 | 0.721823 | 0.000365 |
| ENSG00000137628 | DDX60 | −0.73641 | 0.000366 |
| ENSG00000214688 | C10orf105 | −1.27288 | 0.000366 |
| ENSG00000214530 | STARD10 | 0.95832 | 0.000367 |
| ENSG00000103496 | STX4 | 0.516925 | 0.000369 |
| ENSG00000151883 | PARP8 | −0.48077 | 0.000373 |
| ENSG00000120784 | ZFP30 | −0.72832 | 0.000373 |
| ENSG00000133256 | PDE6B | −1.23146 | 0.000373 |
| ENSG00000121680 | PEX16 | 0.54961 | 0.000375 |
| ENSG00000126461 | SCAF1 | 0.504205 | 0.000376 |
| ENSG00000196268 | ZNF493 | −0.5917 | 0.000377 |
| ENSG00000196924 | FLNA | 0.499115 | 0.000382 |
| ENSG00000103335 | PIEZO1 | 0.486609 | 0.000383 |
| ENSG00000145734 | BDP1 | −0.53892 | 0.000383 |
| ENSG00000122482 | ZNF644 | −0.42572 | 0.000383 |
| ENSG00000003393 | ALS2 | 0.531151 | 0.000387 |
| ENSG00000182220 | ATP6AP2 | 0.459258 | 0.000387 |
| ENSG00000005059 | CCDC109B | −1.09325 | 0.000396 |
| ENSG00000010310 | GIPR | 1.015362 | 0.000396 |
| ENSG00000236480 | | 0.559287 | 0.000396 |
| ENSG00000181381 | DDX60L | −0.47928 | 0.000396 |
| ENSG00000001084 | GCLC | −0.51147 | 0.000404 |
| ENSG00000131016 | AKAP12 | −0.61368 | 0.000405 |
| ENSG00000244879 | | −0.5996 | 0.000405 |
| ENSG00000104852 | SNRNP70 | 0.420676 | 0.000408 |
| ENSG00000132182 | NUP210 | 0.473831 | 0.000419 |
| ENSG00000103266 | STUB1 | 0.508948 | 0.000419 |
| ENSG00000104805 | NUCB1 | 0.450245 | 0.000419 |
| ENSG00000160226 | C21orf2 | 0.762972 | 0.000419 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000099250 | NRP1 | −0.63872 | 0.000425 |
| ENSG00000196172 | ZNF681 | −0.64629 | 0.000426 |
| ENSG00000124613 | ZNF391 | −0.94058 | 0.000427 |
| ENSG00000179241 | LDLRAD3 | −0.99107 | 0.00043 |
| ENSG00000164442 | CITED2 | 0.463656 | 0.00043 |
| ENSG00000166311 | SMPD1 | 0.63345 | 0.00043 |
| ENSG00000147123 | NDUFB11 | 0.458988 | 0.000437 |
| ENSG00000130726 | TRIM28 | 0.411242 | 0.000437 |
| ENSG00000163823 | CCR1 | 0.598944 | 0.000441 |
| ENSG00000165633 | VSTM4 | 1.328238 | 0.000442 |
| ENSG00000172530 | BANP | 0.864042 | 0.000445 |
| ENSG00000144026 | ZNF514 | −0.65456 | 0.000448 |
| ENSG00000097033 | SH3GLB1 | −0.42863 | 0.000448 |
| ENSG00000100241 | SBF1 | 0.522513 | 0.00045 |
| ENSG00000135535 | CD164 | −0.47103 | 0.000458 |
| ENSG00000110367 | DDX6 | −0.45527 | 0.000458 |
| ENSG00000013288 | MAN2B2 | 0.539162 | 0.00046 |
| ENSG00000142945 | KIF2C | 0.475702 | 0.00046 |
| ENSG00000159200 | RCAN1 | 0.663092 | 0.00046 |
| ENSG00000110057 | UNC93B1 | 0.598065 | 0.000465 |
| ENSG00000153774 | CFDP1 | −0.47373 | 0.000465 |
| ENSG00000134030 | CTIF | 0.608667 | 0.000471 |
| ENSG00000054277 | OPN3 | 0.504096 | 0.000475 |
| ENSG00000116574 | RHOU | 0.560702 | 0.000476 |
| ENSG00000138798 | EGF | −0.82808 | 0.000477 |
| ENSG00000167792 | NDUFV1 | 0.447105 | 0.000478 |
| ENSG00000137818 | RPLP1 | 0.400168 | 0.00048 |
| ENSG00000188971 | | 0.506609 | 0.000482 |
| ENSG00000166825 | ANPEP | 0.456041 | 0.000483 |
| ENSG00000173930 | SLCO4C1 | 0.512207 | 0.000483 |
| ENSG00000100522 | GNPNAT1 | −0.48697 | 0.000484 |
| ENSG00000162944 | RFTN2 | −0.97868 | 0.000484 |
| ENSG00000186088 | GSAP | −1.08397 | 0.000484 |
| ENSG00000184083 | FAM120C | −0.64454 | 0.000488 |
| ENSG00000138434 | SSFA2 | −0.55753 | 0.00049 |
| ENSG00000167992 | VWCE | 1.215177 | 0.000491 |
| ENSG00000113739 | STC2 | −0.97543 | 0.000493 |
| ENSG00000150347 | ARID5B | −0.57116 | 0.000494 |
| ENSG00000162702 | ZNF281 | −0.44997 | 0.000496 |
| ENSG00000102781 | KATNAL1 | −0.69351 | 0.0005 |
| ENSG00000175550 | DRAP1 | 0.507697 | 0.0005 |
| ENSG00000126759 | CFP | 0.579756 | 0.000503 |
| ENSG00000172466 | ZNF24 | −0.41101 | 0.000503 |
| ENSG00000141959 | PFKL | 0.480769 | 0.000504 |
| ENSG00000177425 | PAWR | −0.473 | 0.000504 |
| ENSG00000125454 | SLC25A19 | 0.527979 | 0.000507 |
| ENSG00000160410 | SHKBP1 | 0.462101 | 0.000507 |
| ENSG00000106560 | GIMAP2 | −0.62701 | 0.000512 |
| ENSG00000178852 | EFCAB13 | −0.89069 | 0.000515 |
| ENSG00000256804 | | 0.74139 | 0.000516 |
| ENSG00000126453 | BCL2L12 | 0.546373 | 0.000516 |
| ENSG00000236365 | | −1.04559 | 0.000516 |
| ENSG00000105501 | SIGLEC5 | 0.724087 | 0.00052 |
| ENSG00000198648 | STK39 | −0.61228 | 0.00052 |
| ENSG00000087086 | FTL | 0.471882 | 0.000523 |
| ENSG00000123595 | RAB9A | 0.559127 | 0.000523 |
| ENSG00000132965 | ALOX5AP | 0.578147 | 0.000523 |
| ENSG00000142330 | CAPN10 | 0.60237 | 0.000523 |
| ENSG00000005961 | ITGA2B | 0.413336 | 0.000525 |
| ENSG00000256087 | ZNF432 | −0.57464 | 0.000533 |
| ENSG00000171443 | ZNF524 | 0.771148 | 0.000534 |
| ENSG00000130741 | EIF2S3 | −0.39995 | 0.000536 |
| ENSG00000108021 | FAM208B | −0.47803 | 0.000536 |
| ENSG00000178896 | EXOSC4 | 0.623069 | 0.000538 |
| ENSG00000120586 | | −0.57378 | 0.000539 |
| ENSG00000123609 | NMI | −0.43859 | 0.000539 |
| ENSG00000167703 | SLC43A2 | 1.208569 | 0.000539 |
| ENSG00000068137 | PLEKHH3 | 0.965864 | 0.000541 |
| ENSG00000198829 | SUCNR1 | 0.441758 | 0.000541 |
| ENSG00000019144 | PHLDB1 | 0.630382 | 0.000549 |
| ENSG00000035115 | SH3YL1 | −0.5485 | 0.000551 |
| ENSG00000108100 | CCNY | −0.4216 | 0.000551 |
| ENSG00000037280 | FLT4 | 0.580153 | 0.000551 |
| ENSG00000214456 | PLIN5 | 1.132891 | 0.000551 |
| ENSG00000131023 | LATS1 | −0.44523 | 0.000554 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000125354 | 42619 | −0.41851 | 0.000555 |
| ENSG00000076770 | MBNL3 | −0.49255 | 0.000565 |
| ENSG00000185869 | ZNF829 | −1.10346 | 0.000569 |
| ENSG00000204130 | RUFY2 | −0.58009 | 0.000572 |
| ENSG00000043462 | LCP2 | 0.430626 | 0.000579 |
| ENSG00000183690 | EFHC2 | −0.74787 | 0.000586 |
| ENSG00000147862 | NFIB | −0.87586 | 0.000593 |
| ENSG00000244482 | LILRB3 | 1.404449 | 0.000598 |
| ENSG00000254470 | AP5B1 | 0.566816 | 0.000602 |
| ENSG00000099814 | CEP170B | 0.732245 | 0.000604 |
| ENSG00000163412 | EIF4E3 | 1.209182 | 0.000604 |
| ENSG00000228300 | C19orf24 | 0.674854 | 0.000604 |
| ENSG00000198482 | ZNF808 | −0.58618 | 0.000608 |
| ENSG00000189283 | FHIT | −1.25251 | 0.000609 |
| ENSG00000148400 | NOTCH1 | 0.47124 | 0.000611 |
| ENSG00000183011 | NAA38 | 0.550217 | 0.000611 |
| ENSG00000163132 | MSX1 | 1.288461 | 0.000617 |
| ENSG00000184967 | NOC4L | 0.55577 | 0.00062 |
| ENSG00000122223 | CD244 | 0.414801 | 0.000621 |
| ENSG00000117480 | FAAH | 0.902992 | 0.000622 |
| ENSG00000075702 | WDR62 | 0.54384 | 0.000625 |
| ENSG00000116017 | ARID3A | 0.589403 | 0.000628 |
| ENSG00000126705 | AHDC1 | 0.604974 | 0.000629 |
| ENSG00000100290 | BIK | −1.25071 | 0.000633 |
| ENSG00000253352 |  | −0.40937 | 0.000644 |
| ENSG00000163701 | IL17RE | −0.64863 | 0.000648 |
| ENSG00000165806 | CASP7 | −0.47505 | 0.000648 |
| ENSG00000168906 | MAT2A | −0.47917 | 0.000649 |
| ENSG00000150681 | RGS18 | −0.43646 | 0.000651 |
| ENSG00000144369 | FAM171B | −0.60348 | 0.000655 |
| ENSG00000121741 | ZMYM2 | −0.41695 | 0.000656 |
| ENSG00000135272 | MDFIC | 0.644442 | 0.000658 |
| ENSG00000263264 |  | 0.990104 | 0.000663 |
| ENSG00000007944 | MYLIP | 0.634059 | 0.000667 |
| ENSG00000176148 | TCP11L1 | −0.75039 | 0.000671 |
| ENSG00000151835 | SACS | −0.64052 | 0.000674 |
| ENSG00000171451 | DSEL | −1.16818 | 0.000675 |
| ENSG00000125652 | ALKBH7 | 0.594963 | 0.000687 |
| ENSG00000084093 | REST | −0.41867 | 0.000696 |
| ENSG00000130592 | LSP1 | 0.454146 | 0.000697 |
| ENSG00000136205 | TNS3 | −0.69524 | 0.000697 |
| ENSG00000159267 | HLCS | −0.60202 | 0.000705 |
| ENSG00000107863 | ARHGAP21 | −0.55451 | 0.000706 |
| ENSG00000169398 | PTK2 | −0.63438 | 0.000707 |
| ENSG00000106266 | SNX8 | 0.455695 | 0.000707 |
| ENSG00000117450 | PRDX1 | −0.42383 | 0.000714 |
| ENSG00000204519 | ZNF551 | −0.5088 | 0.00072 |
| ENSG00000171476 | HOPX | 0.640409 | 0.000724 |
| ENSG00000050767 | COL23A1 | 0.727012 | 0.000725 |
| ENSG00000140287 | HDC | 0.698419 | 0.000727 |
| ENSG00000144589 | STK11IP | 0.457473 | 0.000727 |
| ENSG00000101290 | CDS2 | −0.43254 | 0.000731 |
| ENSG00000167657 | DAPK3 | 0.528153 | 0.000731 |
| ENSG00000225892 |  | 1.024993 | 0.000743 |
| ENSG00000116260 | QSOX1 | 0.575369 | 0.00075 |
| ENSG00000141873 | SLC39A3 | 0.509593 | 0.000754 |
| ENSG00000075240 | GRAMD4 | 0.48276 | 0.000761 |
| ENSG00000089639 | GMIP | 0.473537 | 0.000763 |
| ENSG00000105364 | MRPL4 | 0.482827 | 0.000771 |
| ENSG00000157637 | SLC38A10 | 0.519398 | 0.000773 |
| ENSG00000101916 | TLR8 | 1.383468 | 0.000773 |
| ENSG00000133250 | ZNF414 | 0.819986 | 0.00078 |
| ENSG00000135480 | KRT7 | 1.352729 | 0.000791 |
| ENSG00000111331 | OAS3 | −0.61463 | 0.000796 |
| ENSG00000110852 | CLEC2B | −0.46644 | 0.000806 |
| ENSG00000106804 | C5 | −0.75186 | 0.00081 |
| ENSG00000148248 | SURF4 | 0.398762 | 0.000811 |
| ENSG00000135250 | SRPK2 | −0.42573 | 0.000812 |
| ENSG00000105325 | FZR1 | 0.491387 | 0.000813 |
| ENSG00000141720 |  | −0.43686 | 0.000816 |
| ENSG00000101336 | HCK | 0.563036 | 0.000819 |
| ENSG00000198780 | FAM169A | −0.69418 | 0.000823 |
| ENSG00000136044 | APPL2 | −0.51677 | 0.000825 |
| ENSG00000142694 | EVA1B | 0.91429 | 0.000826 |
| ENSG00000148950 | IMMP1L | −0.71426 | 0.000833 |

SUPPLEMENTARY TABLE 1-continued

List of the identified differentially expressed transcripts
after DE analysis using DESeq2 and edgeR-

| ENSEMBL | Symbol | Log₂ Fold Change | False discovery rate |
|---|---|---|---|
| ENSG00000130165 | ELOF1 | 0.448993 | 0.000833 |
| ENSG00000106785 | TRIM14 | 0.44435 | 0.00084 |
| ENSG00000012983 | MAP4K5 | −0.45786 | 0.000844 |
| ENSG00000106268 | NUDT1 | 0.577287 | 0.000844 |
| ENSG00000198223 | CSF2RA | 0.447538 | 0.000847 |
| ENSG00000132854 | KANK4 | −1.02185 | 0.000851 |
| ENSG00000132205 | EMILIN2 | 0.448409 | 0.000854 |
| ENSG00000108582 | CPD | 0.464265 | 0.000858 |
| ENSG00000219738 | | 1.348254 | 0.00086 |
| ENSG00000196782 | MAML3 | −0.61758 | 0.00087 |
| ENSG00000198131 | ZNF544 | −0.51328 | 0.00087 |
| ENSG00000138794 | CASP6 | −0.50421 | 0.000872 |
| ENSG00000164405 | UQCRQ | 0.445166 | 0.000876 |
| ENSG00000161513 | FDXR | 0.53231 | 0.000878 |
| ENSG00000148334 | PTGES2 | 0.497969 | 0.000885 |
| ENSG00000102893 | PHKB | −0.41278 | 0.000896 |
| ENSG00000109881 | CCDC34 | −0.60723 | 0.0009 |
| ENSG00000101199 | ARFGAP1 | 0.455006 | 0.000914 |
| ENSG00000164880 | INTS1 | 0.485775 | 0.000914 |
| ENSG00000142920 | AZIN2 | 1.246343 | 0.000921 |
| ENSG00000104450 | SPAG1 | 0.683714 | 0.000925 |
| ENSG00000121406 | ZNF549 | −0.5285 | 0.000931 |
| ENSG00000117174 | ZNHIT6 | −0.41796 | 0.000932 |
| ENSG00000187189 | TSPYL4 | −0.46202 | 0.000933 |
| ENSG00000035862 | TIMP2 | 0.475982 | 0.000936 |
| ENSG00000205021 | | 1.197927 | 0.000937 |
| ENSG00000169224 | GCSAML | −0.44261 | 0.000938 |
| ENSG00000125148 | MT2A | 0.610147 | 0.000943 |
| ENSG00000170089 | LOC728554 | −0.82192 | 0.000949 |
| ENSG00000153721 | CNKSR3 | 0.943662 | 0.000957 |
| ENSG00000184293 | CLECL1 | −0.52535 | 0.000957 |
| ENSG00000178761 | FAM219B | −0.43464 | 0.000966 |
| ENSG00000154122 | ANKH | 0.704263 | 0.00097 |
| ENSG00000152990 | ADGRA3 | −0.46578 | 0.000974 |
| ENSG00000064601 | CTSA | 0.42457 | 0.000978 |
| ENSG00000142546 | NOSIP | 0.475453 | 0.000979 |
| ENSG00000142765 | SYTL1 | 0.516391 | 0.000979 |
| ENSG00000166971 | AKTIP | 0.895524 | 0.000979 |
| ENSG00000198093 | ZNF649 | −0.51807 | 0.000991 |
| ENSG00000134830 | C5AR2 | 1.016659 | 0.000993 |
| ENSG00000267041 | ZNF850 | −0.69391 | 0.000993 |
| ENSG00000130734 | ATG4D | 0.595993 | 0.000998 |
| ENSG00000262246 | CORO7 | 0.52176 | 0.000998 |
| ENSG00000215105 | | −0.49121 | 0.001008 |
| ENSG00000176101 | SSNA1 | 0.506812 | 0.001017 |
| ENSG00000196352 | CD55 | 0.497816 | 0.001018 |
| ENSG00000169696 | ASPSCR1 | 0.589909 | 0.001024 |
| ENSG00000184840 | TMED9 | 0.430041 | 0.001025 |
| ENSG00000103490 | PYCARD | 0.480226 | 0.001032 |
| ENSG00000125753 | VASP | 0.41356 | 0.001035 |
| ENSG00000166289 | PLEKHF1 | 0.73445 | 0.001039 |
| ENSG00000110274 | CEP164 | 0.474099 | 0.001046 |
| ENSG00000069849 | ATP1B3 | 0.426498 | 0.001049 |
| ENSG00000141503 | MINK1 | 0.486492 | 0.001051 |
| ENSG00000053918 | KCNQ1 | 0.649667 | 0.001063 |
| ENSG00000085644 | ZNF213 | 0.563649 | 0.001066 |
| ENSG00000107140 | TESK1 | 0.568618 | 0.001072 |
| ENSG00000149781 | FERMT3 | 0.4275 | 0.001074 |
| ENSG00000101421 | CHMP4B | 0.406289 | 0.001084 |
| ENSG00000111077 | TNS2 | −0.70649 | 0.001094 |
| ENSG00000119986 | AVPI1 | 0.897517 | 0.001096 |
| ENSG00000117226 | GBP3 | −0.77455 | 0.001097 |
| ENSG00000093010 | COMT | 0.478363 | 0.001102 |
| ENSG00000144681 | STAC | 1.109719 | 0.001102 |
| ENSG00000168884 | TNIP2 | 0.489117 | 0.001102 |
| ENSG00000123131 | PRDX4 | 0.424827 | 0.001117 |
| ENSG00000233846 | | 0.552042 | 0.001117 |
| ENSG00000213753 | CENPBD1P1 | 0.474587 | 0.001118 |
| ENSG00000003402 | CFLAR | 0.559216 | 0.001126 |
| ENSG00000002330 | BAD | 0.693174 | 0.00113 |
| ENSG00000162976 | PQLC3 | −0.52572 | 0.001143 |
| ENSG00000131759 | RARA | 0.449251 | 0.001151 |
| ENSG00000145431 | PDGFC | −0.49647 | 0.001159 |
| ENSG00000124588 | NQO2 | 0.534324 | 0.00116 |
| ENSG00000121797 | CCRL2 | 0.621939 | 0.001164 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000138336 | TET1 | −0.59771 | 0.001166 |
| ENSG00000027869 | SH2D2A | 0.718002 | 0.001171 |
| ENSG00000164292 | RHOBTB3 | −0.77482 | 0.001178 |
| ENSG00000234420 | ZNF37BP | −0.49364 | 0.001178 |
| ENSG00000090776 | EFNB1 | −0.47825 | 0.001179 |
| ENSG00000197535 | MYO5A | 0.600822 | 0.001189 |
| ENSG00000120217 | CD274 | 1.331007 | 0.001195 |
| ENSG00000077585 | GPR137B | 0.647973 | 0.001201 |
| ENSG00000218418 |  | −0.7172 | 0.001202 |
| ENSG00000146192 | FGD2 | 1.028052 | 0.001209 |
| ENSG00000105401 | CDC37 | 0.388875 | 0.001215 |
| ENSG00000133639 | BTG1 | 1.188902 | 0.001215 |
| ENSG00000112787 | FBRSL1 | 0.460934 | 0.00123 |
| ENSG00000135241 | PNPLA8 | 0.472153 | 0.001231 |
| ENSG00000105464 | GRIN2D | 0.549313 | 0.001241 |
| ENSG00000163513 | TGFBR2 | 0.510914 | 0.001247 |
| ENSG00000101220 | C20orf27 | 0.469093 | 0.001265 |
| ENSG00000186017 | ZNF566 | −0.54973 | 0.001265 |
| ENSG00000139405 | RITA1 | 0.437172 | 0.001267 |
| ENSG00000079950 | STX7 | −0.4922 | 0.001291 |
| ENSG00000106624 | AEBP1 | −1.19543 | 0.001291 |
| ENSG00000111885 | MAN1A1 | −1.09269 | 0.001291 |
| ENSG00000147804 | SLC39A4 | 0.649216 | 0.001294 |
| ENSG00000087301 | TXNDC16 | −0.51265 | 0.001307 |
| ENSG00000100263 | RHBDD3 | 0.532254 | 0.00132 |
| ENSG00000128487 | SPECC1 | −0.46484 | 0.001322 |
| ENSG00000141522 | ARHGDIA | 0.492126 | 0.001322 |
| ENSG00000183508 | FAM46C | 0.729799 | 0.001322 |
| ENSG00000066933 | MYO9A | −0.49511 | 0.001323 |
| ENSG00000174004 | NRROS | 0.473844 | 0.001323 |
| ENSG00000068323 | TFE3 | 0.445912 | 0.001325 |
| ENSG00000144677 | CTDSPL | 0.772086 | 0.00133 |
| ENSG00000139318 | DUSP6 | −0.42918 | 0.001331 |
| ENSG00000259207 | ITGB3 | −1.1127 | 0.001333 |
| ENSG00000162636 | FAM102B | −0.63152 | 0.001335 |
| ENSG00000069712 | KIAA1107 | −1.07716 | 0.001345 |
| ENSG00000103494 | RPGRIP1L | −0.67656 | 0.001355 |
| ENSG00000148154 | UGCG | 0.910148 | 0.001355 |
| ENSG00000143537 | ADAM15 | 0.451583 | 0.001357 |
| ENSG00000187266 | EPOR | 1.046103 | 0.001364 |
| ENSG00000136490 | LIMD2 | 0.42271 | 0.001368 |
| ENSG00000087586 | AURKA | 0.430469 | 0.00137 |
| ENSG00000243679 |  | 0.837772 | 0.00137 |
| ENSG00000140995 | DEF8 | 0.468991 | 0.001381 |
| ENSG00000182500 |  | 0.459565 | 0.001391 |
| ENSG00000186862 | PDZD7 | −0.9651 | 0.001409 |
| ENSG00000127540 | UQCR11 | 0.440704 | 0.001414 |
| ENSG00000162244 | RPL29 | 0.400347 | 0.001414 |
| ENSG00000128185 | DGCR6L | 0.620174 | 0.001434 |
| ENSG00000111665 | CDCA3 | 0.529643 | 0.001435 |
| ENSG00000267287 |  | 1.307994 | 0.001452 |
| ENSG00000148841 | ITPRIP | 0.466982 | 0.001453 |
| ENSG00000100239 | PPP6R2 | 0.40958 | 0.00146 |
| ENSG00000131374 | TBC1D5 | −0.43525 | 0.001466 |
| ENSG00000243449 | C4orf48 | 1.074502 | 0.001467 |
| ENSG00000163113 |  | 0.722564 | 0.001477 |
| ENSG00000183751 | TBL3 | 0.539213 | 0.00148 |
| ENSG00000167967 | E4F1 | 0.548778 | 0.001484 |
| ENSG00000244485 |  | 0.664347 | 0.00149 |
| ENSG00000118276 | B4GALT6 | −0.4517 | 0.001491 |
| ENSG00000198931 | APRT | 0.433441 | 0.001494 |
| ENSG00000257698 |  | 0.515736 | 0.001495 |
| ENSG00000128016 | ZFP36 | 0.527007 | 0.001499 |
| ENSG00000142794 | NBPF3 | 0.546864 | 0.001499 |
| ENSG00000166225 | FRS2 | −0.44595 | 0.00151 |
| ENSG00000182162 | P2RY8 | 0.426175 | 0.00153 |
| ENSG00000160256 | FAM207A | 0.749261 | 0.001531 |
| ENSG00000167995 | BEST1 | 1.053017 | 0.001532 |
| ENSG00000115275 | MOGS | 0.443968 | 0.001536 |
| ENSG00000198464 | ZNF480 | −0.43077 | 0.001541 |
| ENSG00000070669 | ASNS | −0.58397 | 0.001545 |
| ENSG00000174080 | CTSF | −0.79641 | 0.001545 |
| ENSG00000159692 | CTBP1 | 0.436915 | 0.001546 |
| ENSG00000166503 | HDGFRP3 | −0.46396 | 0.001548 |
| ENSG00000165156 | ZHX1 | −0.4236 | 0.001551 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000007264 | MATK | 0.411961 | 0.001557 |
| ENSG00000070404 | FSTL3 | 0.892739 | 0.001563 |
| ENSG00000171298 | GAA | 0.547148 | 0.001567 |
| ENSG00000174938 | SEZ6L2 | −0.76436 | 0.001585 |
| ENSG00000157483 | MYO1E | −1.26734 | 0.001597 |
| ENSG00000164284 | GRPEL2 | −0.46179 | 0.001597 |
| ENSG00000164896 | FASTK | 0.545006 | 0.001597 |
| ENSG00000169972 | PUSH | 0.641817 | 0.001597 |
| ENSG00000235084 | | 0.816711 | 0.001597 |
| ENSG00000072274 | TFRC | −0.41963 | 0.001604 |
| ENSG00000101439 | CST3 | 0.610802 | 0.001604 |
| ENSG00000184470 | TXNRD2 | 0.46498 | 0.001612 |
| ENSG00000094975 | SUCO | 0.463365 | 0.001615 |
| ENSG00000158156 | XKR8 | 0.503409 | 0.001617 |
| ENSG00000119535 | CSF3R | 0.405857 | 0.00162 |
| ENSG00000163536 | SERPINI1 | 0.927068 | 0.001624 |
| ENSG00000084444 | FAM234B | −0.52569 | 0.001625 |
| ENSG00000188994 | ZNF292 | −0.43654 | 0.001629 |
| ENSG00000103642 | LACTB | 0.444779 | 0.00163 |
| ENSG00000167394 | ZNF668 | 0.70209 | 0.00163 |
| ENSG00000095303 | PTGS1 | 0.383662 | 0.001635 |
| ENSG00000141994 | DUS3L | 0.501476 | 0.001635 |
| ENSG00000169733 | RFNG | 0.591348 | 0.001636 |
| ENSG00000143578 | CREB3L4 | −0.56782 | 0.001653 |
| ENSG00000171314 | PGAM1 | 0.440922 | 0.001653 |
| ENSG00000085563 | ABCB1 | −1.0076 | 0.001658 |
| ENSG00000178947 | | −1.19352 | 0.001665 |
| ENSG00000102221 | JADE3 | −0.46754 | 0.001669 |
| ENSG00000143067 | ZNF697 | −0.48655 | 0.00167 |
| ENSG00000106003 | LFNG | 0.432563 | 0.001675 |
| ENSG00000170191 | NANP | −0.46575 | 0.001675 |
| ENSG00000187792 | ZNF70 | −0.67333 | 0.001675 |
| ENSG00000110237 | ARHGEF17 | −0.63343 | 0.001677 |
| ENSG00000134986 | NREP | −0.46537 | 0.001683 |
| ENSG00000103152 | MPG | 0.508739 | 0.001697 |
| ENSG00000119979 | FAM45A | 0.560723 | 0.001702 |
| ENSG00000132561 | MATN2 | −0.74133 | 0.001703 |
| ENSG00000147416 | ATP6V1B2 | 0.495106 | 0.001704 |
| ENSG00000144036 | EXOC6B | −0.64151 | 0.001711 |
| ENSG00000132356 | PRKAA1 | −0.43811 | 0.001724 |
| ENSG00000154263 | ABCA10 | −1.25811 | 0.001741 |
| ENSG00000071794 | HLTF | −0.41873 | 0.001742 |
| ENSG00000142669 | SH3BGRL3 | 0.371202 | 0.001747 |
| ENSG00000187231 | SESTD1 | −0.45259 | 0.00175 |
| ENSG00000129355 | CDKN2D | 0.647067 | 0.001758 |
| ENSG00000100024 | UPB1 | 1.217796 | 0.001762 |
| ENSG00000196843 | ARID5A | 0.490474 | 0.001776 |
| ENSG00000162413 | KLHL21 | 0.459932 | 0.001782 |
| ENSG00000100031 | GGT1 | 0.9162 | 0.001782 |
| ENSG00000103245 | NARFL | 0.501732 | 0.001783 |
| ENSG00000171055 | FEZ2 | −0.4308 | 0.001783 |
| ENSG00000164506 | STXBP5 | 0.473859 | 0.001785 |
| ENSG00000197961 | ZNF121 | −0.4389 | 0.001786 |
| ENSG00000068305 | MEF2A | −0.39408 | 0.001794 |
| ENSG00000107957 | SH3PXD2A | −0.52537 | 0.001804 |
| ENSG00000229953 | | 1.063159 | 0.001807 |
| ENSG00000184922 | FMNL1 | 0.390287 | 0.001821 |
| ENSG00000165716 | FAM69B | 1.006361 | 0.001832 |
| ENSG00000111817 | DSE | −0.48668 | 0.001835 |
| ENSG00000159335 | PTMS | 0.537725 | 0.001844 |
| ENSG00000213799 | ZNF845 | −0.48015 | 0.001845 |
| ENSG00000145491 | ROPN1L | 0.81377 | 0.001848 |
| ENSG00000148339 | SLC25A25 | 0.567318 | 0.001852 |
| ENSG00000272405 | | 0.59835 | 0.001853 |
| ENSG00000138468 | SENP7 | −0.46763 | 0.001855 |
| ENSG00000155660 | PDIA4 | 0.406081 | 0.00186 |
| ENSG00000105656 | ELL | 0.504716 | 0.001864 |
| ENSG00000095932 | SMIM24 | −0.70371 | 0.001867 |
| ENSG00000107223 | EDF1 | 0.381557 | 0.001876 |
| ENSG00000071859 | FAM50A | 0.481143 | 0.001882 |
| ENSG00000078401 | EDN1 | 1.27269 | 0.001882 |
| ENSG00000175137 | SH3BP5L | 0.472745 | 0.001882 |
| ENSG00000130303 | BST2 | −0.51949 | 0.001889 |
| ENSG00000107890 | ANKRD26 | −0.59153 | 0.00189 |
| ENSG00000114902 | SPCS1 | 0.429703 | 0.001891 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
| --- | --- | --- | --- |
| ENSG00000157538 | DSCR3 | −0.39222 | 0.001891 |
| ENSG00000186432 | KPNA4 | −0.42758 | 0.001891 |
| ENSG00000111670 | GNPTAB | −0.40939 | 0.001902 |
| ENSG00000168421 | RHOH | 0.628219 | 0.001903 |
| ENSG00000182903 | ZNF721 | −0.49468 | 0.001904 |
| ENSG00000184205 | TSPYL2 | 0.486891 | 0.001904 |
| ENSG00000176871 | WSB2 | 0.400678 | 0.001905 |
| ENSG00000233755 | | 1.221536 | 0.00191 |
| ENSG00000213463 | SYNJ2BP | −0.59091 | 0.001914 |
| ENSG00000137274 | BPHL | −0.64369 | 0.001935 |
| ENSG00000145911 | N4BP3 | 1.187798 | 0.001943 |
| ENSG00000181019 | NQO1 | −0.46569 | 0.001943 |
| ENSG00000247746 | USP51 | −0.77536 | 0.001945 |
| ENSG00000166501 | PRKCB | −0.39789 | 0.001949 |
| ENSG00000156017 | CARNMT1 | −0.49516 | 0.001951 |
| ENSG00000214022 | REPIN1 | 0.432621 | 0.002018 |
| ENSG00000174502 | SLC26A9 | −1.20252 | 0.00202 |
| ENSG00000063245 | EPN1 | 0.471347 | 0.002031 |
| ENSG00000157540 | DYRK1A | −0.38129 | 0.002036 |
| ENSG00000181790 | ADGRB1 | −0.60697 | 0.002052 |
| ENSG00000213846 | | −0.6208 | 0.002057 |
| ENSG00000176055 | MBLAC2 | −0.5165 | 0.00206 |
| ENSG00000184436 | THAP7 | 0.506716 | 0.00206 |
| ENSG00000174989 | FBXW8 | −0.60719 | 0.002063 |
| ENSG00000166166 | TRMT61A | 0.504471 | 0.002074 |
| ENSG00000123080 | CDKN2C | 0.436183 | 0.002078 |
| ENSG00000163930 | BAP1 | 0.378224 | 0.002088 |
| ENSG00000071246 | VASH1 | −0.51699 | 0.002117 |
| ENSG00000133739 | LRRCC1 | −0.60889 | 0.002119 |
| ENSG00000231389 | HLA-DPA1 | −1.03732 | 0.002132 |
| ENSG00000116761 | CTH | −0.74263 | 0.002132 |
| ENSG00000251194 | | −0.96829 | 0.00215 |
| ENSG00000118412 | CASP8AP2 | −0.42337 | 0.00215 |
| ENSG00000165272 | AQP3 | 0.618427 | 0.00215 |
| ENSG00000108256 | NUFIP2 | −0.36561 | 0.002151 |
| ENSG00000114120 | SLC25A36 | −0.41307 | 0.002159 |
| ENSG00000148180 | GSN | −0.53878 | 0.002189 |
| ENSG00000198466 | ZNF587 | −0.4321 | 0.002192 |
| ENSG00000174718 | KIAA1551 | −0.52468 | 0.002203 |
| ENSG00000142409 | ZNF787 | 0.48247 | 0.002207 |
| ENSG00000227295 | | 0.835231 | 0.002213 |
| ENSG00000120725 | SIL1 | 0.425416 | 0.002225 |
| ENSG00000086619 | ERO1B | −0.80631 | 0.002239 |
| ENSG00000196417 | ZNF765 | −0.46276 | 0.00225 |
| ENSG00000182544 | MFSD5 | 0.464822 | 0.002254 |
| ENSG00000182208 | MOB2 | 0.530406 | 0.002258 |
| ENSG00000247596 | TWF2 | 0.449871 | 0.002258 |
| ENSG00000167302 | ENTHD2 | 0.503129 | 0.002263 |
| ENSG00000126262 | FFAR2 | 1.219805 | 0.002265 |
| ENSG00000142065 | ZFP14 | −0.76316 | 0.002267 |
| ENSG00000164535 | DAGLB | 0.470432 | 0.002275 |
| ENSG00000172757 | CFL1 | 0.356184 | 0.002276 |
| ENSG00000265485 | LOC729950 | −1.02993 | 0.002279 |
| ENSG00000135503 | ACVR1B | 0.467067 | 0.002292 |
| ENSG00000099899 | TRMT2A | 0.427479 | 0.002306 |
| ENSG00000001036 | FUCA2 | 0.424446 | 0.002307 |
| ENSG00000130203 | APOE | 1.107503 | 0.002308 |
| ENSG00000147155 | EBP | 0.422425 | 0.002308 |
| ENSG00000073792 | IGF2BP2 | −0.39565 | 0.002323 |
| ENSG00000063587 | ZNF275 | −0.44047 | 0.002329 |
| ENSG00000153944 | MSI2 | −0.426 | 0.002329 |
| ENSG00000164327 | RICTOR | −0.41602 | 0.002329 |
| ENSG00000173611 | SCAI | −0.56081 | 0.002329 |
| ENSG00000136908 | DPM2 | 0.41939 | 0.002374 |
| ENSG00000164076 | CAMKV | −1.17735 | 0.002374 |
| ENSG00000213096 | ZNF254 | −0.45907 | 0.002378 |
| ENSG00000170619 | COMMD5 | 0.492662 | 0.002397 |
| ENSG00000185404 | SP140L | −0.49738 | 0.00241 |
| ENSG00000171148 | TADA3 | 0.384394 | 0.002414 |
| ENSG00000117298 | ECE1 | 0.518243 | 0.002425 |
| ENSG00000100427 | MLC1 | 0.40209 | 0.002426 |
| ENSG00000103126 | AXIN1 | 0.431309 | 0.002451 |
| ENSG00000107731 | UNC5B | −0.6273 | 0.002455 |
| ENSG00000133019 | CHRM3 | −0.51767 | 0.002455 |
| ENSG00000172465 | TCEAL1 | −0.5337 | 0.002456 |

SUPPLEMENTARY TABLE 1-continued

List of the identified differentially expressed transcripts
after DE analysis using DESeq2 and edgeR-

| ENSEMBL | Symbol | Log₂ Fold Change | False discovery rate |
|---|---|---|---|
| ENSG00000173638 | SLC19A1 | 0.474215 | 0.002456 |
| ENSG00000146376 | ARHGAP18 | −0.44376 | 0.002466 |
| ENSG00000131389 | SLC6A6 | 0.436364 | 0.002514 |
| ENSG00000131652 | THOC6 | 0.432011 | 0.002522 |
| ENSG00000118508 | RAB32 | 0.471332 | 0.002536 |
| ENSG00000233280 | | −0.73385 | 0.002537 |
| ENSG00000152484 | USP12 | 0.387857 | 0.002538 |
| ENSG00000182308 | DCAF4L1 | 0.582162 | 0.002568 |
| ENSG00000059915 | PSD | 1.230722 | 0.00258 |
| ENSG00000170876 | TMEM43 | −0.39523 | 0.002585 |
| ENSG00000011304 | PTBP1 | 0.377195 | 0.002602 |
| ENSG00000101974 | ATP11C | −0.40853 | 0.002602 |
| ENSG00000139289 | PHLDA1 | 1.115592 | 0.002602 |
| ENSG00000150048 | CLEC1A | 0.940559 | 0.002602 |
| ENSG00000175048 | ZDHHC14 | 0.470248 | 0.002602 |
| ENSG00000198420 | TCAF1 | −0.54719 | 0.002602 |
| ENSG00000123870 | | −0.7894 | 0.002602 |
| ENSG00000143847 | PPFIA4 | 0.771445 | 0.002604 |
| ENSG00000033327 | GAB2 | −0.49755 | 0.002616 |
| ENSG00000205045 | SLFN12L | −1.21987 | 0.002616 |
| ENSG00000185262 | UBALD2 | 0.630437 | 0.002625 |
| ENSG00000149269 | PAK1 | 0.407866 | 0.002637 |
| ENSG00000180336 | MEIOC | −0.83575 | 0.00265 |
| ENSG00000125656 | CLPP | 0.472181 | 0.002668 |
| ENSG00000104055 | TGM5 | 0.904708 | 0.002673 |
| ENSG00000173153 | ESRRA | 0.425843 | 0.002673 |
| ENSG00000161981 | SNRNP25 | 0.415558 | 0.002674 |
| ENSG00000059588 | TARBP1 | −0.4269 | 0.002705 |
| ENSG00000165312 | OTUD1 | 0.905239 | 0.002705 |
| ENSG00000167600 | CYP2S1 | −0.59648 | 0.002705 |
| ENSG00000180667 | YOD1 | −0.51842 | 0.002706 |
| ENSG00000138380 | CARF | −0.57928 | 0.002709 |
| ENSG00000177595 | PIDD1 | 0.541929 | 0.002709 |
| ENSG00000128872 | TMOD2 | 0.604495 | 0.002711 |
| ENSG00000164828 | SUN1 | 0.514172 | 0.002713 |
| ENSG00000014919 | COX15 | −0.38484 | 0.002727 |
| ENSG00000221926 | TRIM16 | 0.716056 | 0.002727 |
| ENSG00000100321 | SYNGR1 | 0.467367 | 0.002731 |
| ENSG00000134444 | KIAA1468 | −0.40718 | 0.00274 |
| ENSG00000184903 | IMMP2L | −0.53109 | 0.002745 |
| ENSG00000170340 | B3GNT2 | −0.40144 | 0.002751 |
| ENSG00000133574 | GIMAP4 | 1.204888 | 0.002757 |
| ENSG00000090006 | LTBP4 | 0.507249 | 0.002771 |
| ENSG00000168393 | DTYMK | 0.501508 | 0.002782 |
| ENSG00000107175 | CREB3 | 0.462832 | 0.002783 |
| ENSG00000261221 | ZNF865 | 0.589788 | 0.002783 |
| ENSG00000139323 | POC1B | −0.44538 | 0.002795 |
| ENSG00000217128 | FNIP1 | −0.42126 | 0.002798 |
| ENSG00000144136 | SLC20A1 | −0.39632 | 0.002799 |
| ENSG00000147475 | ERLIN2 | −0.42656 | 0.002808 |
| ENSG00000269640 | | −0.68557 | 0.002811 |
| ENSG00000179630 | LACC1 | 0.405304 | 0.002817 |
| ENSG00000205339 | IPO7 | −0.38194 | 0.002817 |
| ENSG00000023171 | GRAMD1B | 0.45473 | 0.002825 |
| ENSG00000267416 | LOC105371849 | 1.160554 | 0.002837 |
| ENSG00000196365 | LONP1 | 0.442824 | 0.00287 |
| ENSG00000104635 | SLC39A14 | −0.401 | 0.002889 |
| ENSG00000155254 | MARVELD1 | −0.45123 | 0.002891 |
| ENSG00000254004 | ZNF260 | −0.41576 | 0.002896 |
| ENSG00000173041 | ZNF680 | −0.47925 | 0.00291 |
| ENSG00000162511 | LAPTM5 | 0.365856 | 0.002919 |
| ENSG00000162430 | SEPN1 | 0.390227 | 0.002925 |
| ENSG00000171466 | ZNF562 | −0.40367 | 0.002936 |
| ENSG00000007541 | PIGQ | 0.478566 | 0.002941 |
| ENSG00000079691 | LRRC16A | −0.55296 | 0.002948 |
| ENSG00000112159 | MDN1 | −0.44654 | 0.002948 |
| ENSG00000112972 | HMGCS1 | −0.48268 | 0.00296 |
| ENSG00000162062 | C16orf59 | 0.71242 | 0.002966 |
| ENSG00000104856 | RELB | 1.131975 | 0.002968 |
| ENSG00000106803 | SEC61B | 0.399549 | 0.002984 |
| ENSG00000146463 | ZMYM4 | −0.36034 | 0.002987 |
| ENSG00000154945 | ANKRD40 | −0.38998 | 0.003006 |
| ENSG00000012124 | CD22 | −1.17525 | 0.003033 |
| ENSG00000221869 | CEBPD | 0.574886 | 0.003033 |
| ENSG00000267121 | | 0.780028 | 0.003037 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
| --- | --- | --- | --- |
| ENSG00000123505 | AMD1 | −0.35986 | 0.003038 |
| ENSG00000099256 | PRTFDC1 | −0.6475 | 0.003047 |
| ENSG00000197020 | ZNF100 | −0.42864 | 0.003047 |
| ENSG00000165832 | TRUB1 | −0.41701 | 0.003059 |
| ENSG00000177426 | TGIF1 | 0.506166 | 0.003059 |
| ENSG00000085721 | RRN3 | −0.37174 | 0.003085 |
| ENSG00000180773 | SLC36A4 | 0.427546 | 0.003101 |
| ENSG00000104872 | PIH1D1 | 0.392164 | 0.003109 |
| ENSG00000135441 | BLOC1S1 | 0.507942 | 0.003111 |
| ENSG00000167637 | ZNF283 | −0.63398 | 0.003118 |
| ENSG00000151422 | FER | −0.4724 | 0.00314 |
| ENSG00000179933 | C14orf119 | 0.390098 | 0.003144 |
| ENSG00000125505 | MBOAT7 | 0.376097 | 0.003151 |
| ENSG00000243335 | KCTD7 | 0.674415 | 0.003157 |
| ENSG00000197253 | TPSB2 | 0.620274 | 0.003165 |
| ENSG00000104967 | NOVA2 | −0.77949 | 0.003201 |
| ENSG00000119655 | NPC2 | 0.403954 | 0.003209 |
| ENSG00000272620 | AFAP1-AS1 | 0.496734 | 0.003212 |
| ENSG00000183307 | CECR6 | −0.61431 | 0.003213 |
| ENSG00000116791 | CRYZ | −0.56324 | 0.003219 |
| ENSG00000087253 | LPCAT2 | 0.349445 | 0.003227 |
| ENSG00000139998 | RAB15 | 0.72542 | 0.003232 |
| ENSG00000146540 | C7orf50 | 0.589122 | 0.003232 |
| ENSG00000059122 | FLYWCH1 | 0.455388 | 0.003237 |
| ENSG00000079337 | RAPGEF3 | −0.80832 | 0.003242 |
| ENSG00000130052 | STARD8 | −0.44888 | 0.003253 |
| ENSG00000106853 | PTGR1 | −0.53119 | 0.003257 |
| ENSG00000085433 | WDR47 | −0.4814 | 0.003257 |
| ENSG00000125967 | NECAB3 | 0.561192 | 0.003262 |
| ENSG00000100201 | DDX17 | −0.34913 | 0.003264 |
| ENSG00000122952 | ZWINT | 0.463894 | 0.003264 |
| ENSG00000086504 | MRPL28 | 0.431267 | 0.003269 |
| ENSG00000171791 | BCL2 | −0.45492 | 0.003271 |
| ENSG00000250508 | LOC105369364 | −0.66987 | 0.003275 |
| ENSG00000132017 | DCAF15 | 0.429588 | 0.003276 |
| ENSG00000174738 | NR1D2 | −0.55226 | 0.003284 |
| ENSG00000021762 | OSBPL5 | −0.59782 | 0.003299 |
| ENSG00000122435 | TRMT13 | −0.43531 | 0.003309 |
| ENSG00000060762 | MPC1 | 0.45461 | 0.003332 |
| ENSG00000165996 | HACD1 | −0.56734 | 0.003357 |
| ENSG00000196358 | NTNG2 | 0.645603 | 0.003365 |
| ENSG00000175470 | PPP2R2D | 0.424472 | 0.00337 |
| ENSG00000197863 | ZNF790 | −0.65976 | 0.00337 |
| ENSG00000188807 | TMEM201 | 0.452682 | 0.003391 |
| ENSG00000104973 | MED25 | 0.422398 | 0.003392 |
| ENSG00000148362 | C9orf142 | 0.529451 | 0.003392 |
| ENSG00000146433 | TMEM181 | −0.4244 | 0.003409 |
| ENSG00000163818 | LZTFL1 | −0.48334 | 0.003409 |
| ENSG00000177383 | MAGEF1 | 0.506845 | 0.003409 |
| ENSG00000242372 | EIF6 | 0.385204 | 0.003409 |
| ENSG00000112218 | GPR63 | 0.759225 | 0.003414 |
| ENSG00000229162 | | −1.18224 | 0.003414 |
| ENSG00000175221 | MED16 | 0.490814 | 0.003418 |
| ENSG00000014164 | ZC3H3 | 0.492534 | 0.003424 |
| ENSG00000089060 | SLC8B1 | 0.438788 | 0.003424 |
| ENSG00000162078 | ZG16B | 0.534053 | 0.003445 |
| ENSG00000180867 | | 0.362893 | 0.003445 |
| ENSG00000122068 | FYTTD1 | −0.37292 | 0.003449 |
| ENSG00000176595 | KBTBD11 | 0.84457 | 0.003453 |
| ENSG00000007312 | CD79B | 0.636356 | 0.003467 |
| ENSG00000182095 | TNRC18 | 0.464366 | 0.003484 |
| ENSG00000065243 | PKN2 | −0.4011 | 0.003486 |
| ENSG00000164713 | BRI3 | 0.468196 | 0.003516 |
| ENSG00000105835 | NAMPT | 0.543207 | 0.003531 |
| ENSG00000171522 | PTGER4 | 0.667935 | 0.003532 |
| ENSG00000149218 | ENDOD1 | −1.00695 | 0.003535 |
| ENSG00000171634 | BPTF | −0.38617 | 0.003535 |
| ENSG00000197558 | SSPO | −1.03117 | 0.003535 |
| ENSG00000168116 | KIAA1586 | −0.41093 | 0.003536 |
| ENSG00000169891 | REPS2 | −0.96338 | 0.003536 |
| ENSG00000132718 | SYT11 | −0.57876 | 0.003567 |
| ENSG00000176058 | TPRN | 0.503192 | 0.003591 |
| ENSG00000109265 | KIAA1211 | −0.58805 | 0.003612 |
| ENSG00000134247 | PTGFRN | 0.759068 | 0.003633 |
| ENSG00000175155 | YPEL2 | 0.718821 | 0.003638 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000005075 | POLR2J | 0.471605 | 0.003655 |
| ENSG00000043591 | ADRB1 | −0.81666 | 0.00367 |
| ENSG00000108961 | RANGRF | 0.429045 | 0.003672 |
| ENSG00000123607 | TTC21B | −0.45786 | 0.003672 |
| ENSG00000172322 | CLEC12A | 0.376667 | 0.003685 |
| ENSG00000072310 | SREBF1 | 0.455056 | 0.003702 |
| ENSG00000141540 | TTYH2 | −0.60421 | 0.003717 |
| ENSG00000151458 | ANKRD50 | −0.43752 | 0.003717 |
| ENSG00000109586 | GALNT7 | −0.35955 | 0.003731 |
| ENSG00000172243 | CLEC7A | 1.028779 | 0.00376 |
| ENSG00000197582 |  | 0.445395 | 0.003765 |
| ENSG00000154743 | TSEN2 | −0.48276 | 0.003776 |
| ENSG00000169718 | DUS1L | 0.423514 | 0.003788 |
| ENSG00000070540 | WIPI1 | 0.751538 | 0.003789 |
| ENSG00000224116 | INHBA-AS1 | −1.058 | 0.0038 |
| ENSG00000123136 | DDX39A | 0.394988 | 0.003808 |
| ENSG00000152454 | ZNF256 | −0.55424 | 0.003813 |
| ENSG00000176853 | FAM91A1 | −0.37305 | 0.003818 |
| ENSG00000134028 | ADAMDEC1 | −0.75446 | 0.003821 |
| ENSG00000116704 | SLC35D1 | −0.38518 | 0.003823 |
| ENSG00000250510 | GPR162 | 0.688322 | 0.00383 |
| ENSG00000171757 | LRRC34 | −0.84773 | 0.003836 |
| ENSG00000198718 | FAM179B | −0.48576 | 0.003836 |
| ENSG00000088727 | KIF9 | −0.56738 | 0.003846 |
| ENSG00000172375 | C2CD2L | 0.537696 | 0.003846 |
| ENSG00000198252 | STYX | −0.38412 | 0.003846 |
| ENSG00000174851 | YIF1A | 0.501363 | 0.003846 |
| ENSG00000180879 | SSR4 | 0.382752 | 0.003858 |
| ENSG00000127603 | MACF1 | −0.44527 | 0.003871 |
| ENSG00000100599 | RIN3 | 0.41168 | 0.003894 |
| ENSG00000126391 | FRMD8 | 0.39925 | 0.003894 |
| ENSG00000143079 | CTTNBP2NL | −0.64611 | 0.003899 |
| ENSG00000196233 | LCOR | −0.40996 | 0.003904 |
| ENSG00000180573 | HIST1H2AC | −0.75363 | 0.003907 |
| ENSG00000157106 | SMG1 | −0.37986 | 0.003907 |
| ENSG00000272068 |  | 0.812571 | 0.003908 |
| ENSG00000106689 | LHX2 | 1.205152 | 0.003913 |
| ENSG00000115155 | OTOF | 1.148901 | 0.003919 |
| ENSG00000244462 | RBM12 | −0.4354 | 0.003929 |
| ENSG00000005020 | SKAP2 | −0.40992 | 0.003956 |
| ENSG00000169245 | CXCL10 | 1.126076 | 0.003956 |
| ENSG00000197603 | C5orf42 | −0.51506 | 0.003956 |
| ENSG00000272502 |  | 1.044695 | 0.003956 |
| ENSG00000011028 | MRC2 | 0.434753 | 0.003976 |
| ENSG00000155100 | OTUD6B | −0.45276 | 0.003991 |
| ENSG00000172428 | MYEOV2 | 0.495141 | 0.003995 |
| ENSG00000101384 | JAG1 | 0.40956 | 0.004001 |
| ENSG00000185973 | TMLHE | −0.54345 | 0.004001 |
| ENSG00000161036 | LRWD1 | 0.501277 | 0.004026 |
| ENSG00000212123 | PRR22 | 0.867307 | 0.004031 |
| ENSG00000112290 | WASF1 | −0.38061 | 0.004036 |
| ENSG00000124299 | PEPD | 0.410977 | 0.004041 |
| ENSG00000102804 | TSC22D1 | −0.48478 | 0.004051 |
| ENSG00000123154 | WDR83 | 0.577471 | 0.004051 |
| ENSG00000172037 | LAMB2 | −0.51922 | 0.004052 |
| ENSG00000100280 | AP1B1 | 0.401453 | 0.004086 |
| ENSG00000137411 | VARS2 | 0.43698 | 0.004105 |
| ENSG00000146830 | GIGYF1 | 0.409861 | 0.004106 |
| ENSG00000267337 | LINC01478 | −1.1796 | 0.004106 |
| ENSG00000185885 | IFITM1 | −0.63293 | 0.004107 |
| ENSG00000105248 | CCDC94 | 0.457975 | 0.004121 |
| ENSG00000116096 | SPR | −0.45892 | 0.004121 |
| ENSG00000164086 | DUSP7 | −0.37351 | 0.004121 |
| ENSG00000185896 | LAMP1 | 0.340925 | 0.004136 |
| ENSG00000172354 | GNB2 | 0.38165 | 0.004143 |
| ENSG00000237513 |  | −1.06996 | 0.004145 |
| ENSG00000165025 | SYK | 0.402928 | 0.004146 |
| ENSG00000100077 | ADRBK2 | 0.577748 | 0.004179 |
| ENSG00000146414 | SHPRH | −0.51624 | 0.004185 |
| ENSG00000100243 | CYB5R3 | 0.374902 | 0.004196 |
| ENSG00000182150 | ERCC6L2 | −0.48052 | 0.004208 |
| ENSG00000142227 | EMP3 | 0.377784 | 0.004211 |
| ENSG00000014138 | POLA2 | 0.414611 | 0.004244 |
| ENSG00000005889 | ZFX | −0.39329 | 0.004261 |
| ENSG00000213468 | FIRRE | −0.7851 | 0.004261 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000072401 | UBE2D1 | 0.454864 | 0.004287 |
| ENSG00000161638 | ITGA5 | −0.38264 | 0.004294 |
| ENSG00000227942 | FRMD8P1 | 0.989822 | 0.004311 |
| ENSG00000137216 | TMEM63B | 0.637344 | 0.004316 |
| ENSG00000119638 | NEK9 | −0.35289 | 0.004322 |
| ENSG00000141655 | TNFRSF11A | −0.88824 | 0.004345 |
| ENSG00000263013 |  | −0.74742 | 0.004348 |
| ENSG00000169860 | P2RY1 | −0.88651 | 0.004353 |
| ENSG00000105708 | ZNF14 | −0.52688 | 0.004362 |
| ENSG00000189007 | ADAT2 | −0.38552 | 0.004403 |
| ENSG00000057019 | DCBLD2 | −0.54746 | 0.004405 |
| ENSG00000101265 | RASSF2 | 0.348217 | 0.004413 |
| ENSG00000198498 | TMA16 | −0.39654 | 0.004421 |
| ENSG00000216490 | IFI30 | 0.993179 | 0.004422 |
| ENSG00000197128 | ZNF772 | −0.50703 | 0.004438 |
| ENSG00000126062 | TMEM115 | 0.495931 | 0.004457 |
| ENSG00000153234 | NR4A2 | 0.58396 | 0.004458 |
| ENSG00000231870 |  | 1.093922 | 0.004486 |
| ENSG00000056277 | ZNF280C | −0.49564 | 0.004496 |
| ENSG00000096092 | TMEM14A | −0.63348 | 0.00451 |
| ENSG00000135124 | P2RX4 | 0.542266 | 0.004513 |
| ENSG00000164603 | C7orf60 | 0.674444 | 0.004544 |
| ENSG00000021826 | CPS1 | −0.3895 | 0.004555 |
| ENSG00000197150 | ABCB8 | 0.519749 | 0.004566 |
| ENSG00000063169 | GLTSCR1 | 0.685631 | 0.004575 |
| ENSG00000153147 | SMARCA5 | −0.35136 | 0.004591 |
| ENSG00000261596 |  | 0.995713 | 0.004608 |
| ENSG00000164305 | CASP3 | 0.420369 | 0.004608 |
| ENSG00000237632 |  | 0.915496 | 0.004617 |
| ENSG00000149115 | TNKS1BP1 | 0.42473 | 0.004638 |
| ENSG00000198818 | SFT2D1 | 0.365424 | 0.004638 |
| ENSG00000182866 | LCK | −0.81872 | 0.00464 |
| ENSG00000138496 | PARP9 | −0.54316 | 0.004698 |
| ENSG00000138834 | MAPK8IP3 | 0.399273 | 0.00471 |
| ENSG00000130255 | RPL36 | 0.344848 | 0.004726 |
| ENSG00000160972 | PPP1R16A | 0.561456 | 0.004746 |
| ENSG00000164050 | PLXNB1 | 0.526972 | 0.004765 |
| ENSG00000167004 | PDIA3 | 0.353173 | 0.004765 |
| ENSG00000135604 | STX11 | 1.142932 | 0.004767 |
| ENSG00000100364 | KIAA0930 | 0.43995 | 0.00477 |
| ENSG00000164066 | INTU | −0.58387 | 0.004774 |
| ENSG00000183688 | FAM101B | 0.377511 | 0.004783 |
| ENSG00000142798 | HSPG2 | −0.51204 | 0.004819 |
| ENSG00000232499 |  | −0.3921 | 0.004819 |
| ENSG00000172878 | METAP1D | −0.47294 | 0.00483 |
| ENSG00000080345 | RIF1 | −0.39747 | 0.004847 |
| ENSG00000138760 | SCARB2 | −0.36633 | 0.004902 |
| ENSG00000196209 | SIRPB2 | 0.611693 | 0.004913 |
| ENSG00000177548 | RABEP2 | 0.49431 | 0.004925 |
| ENSG00000107614 | TRDMT1 | −0.50689 | 0.00494 |
| ENSG00000123329 | ARHGAP9 | 0.383112 | 0.004943 |
| ENSG00000066422 | ZBTB11 | −0.3693 | 0.004969 |
| ENSG00000188641 | DPYD | 0.373681 | 0.005006 |
| ENSG00000158286 | RNF207 | −0.7317 | 0.005012 |
| ENSG00000175634 | RPS6KB2 | 0.373631 | 0.005014 |
| ENSG00000198502 | HLA-DRB5 | −0.57251 | 0.005014 |
| ENSG00000025770 | NCAPH2 | 0.433977 | 0.005019 |
| ENSG00000101079 | NDRG3 | −0.40722 | 0.005019 |
| ENSG00000148175 | STOM | −0.3866 | 0.005028 |
| ENSG00000011009 | LYPLA2 | 0.394894 | 0.005057 |
| ENSG00000123472 | ATPAF1 | −0.41656 | 0.005058 |
| ENSG00000153071 | DAB2 | −0.47672 | 0.00506 |
| ENSG00000086289 | EPDR1 | −0.38922 | 0.005067 |
| ENSG00000185359 | HGS | 0.364348 | 0.005071 |
| ENSG00000004777 | ARHGAP33 | 0.675103 | 0.005076 |
| ENSG00000136250 | AOAH | 0.702224 | 0.005087 |
| ENSG00000108107 | RPL28 | 0.352477 | 0.00509 |
| ENSG00000122042 | UBL3 | −0.39609 | 0.005099 |
| ENSG00000244620 |  | −1.09612 | 0.005125 |
| ENSG00000138688 | KIAA1109 | −0.43566 | 0.005127 |
| ENSG00000150760 | DOCK1 | −0.3663 | 0.005128 |
| ENSG00000158104 | HPD | 0.749071 | 0.005128 |
| ENSG00000067836 | ROGDI | 0.460594 | 0.005137 |
| ENSG00000253710 | ALG11 | −0.55356 | 0.005144 |
| ENSG00000166086 | JAM3 | −0.50003 | 0.005198 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
| --- | --- | --- | --- |
| ENSG00000114737 | CISH | 0.408251 | 0.005201 |
| ENSG00000170545 | SMAGP | −0.54037 | 0.005268 |
| ENSG00000154134 | ROBO3 | −1.04951 | 0.005271 |
| ENSG00000125843 | AP5S1 | 0.467034 | 0.005276 |
| ENSG00000173486 | FKBP2 | 0.479205 | 0.005327 |
| ENSG00000097021 | ACOT7 | 0.442379 | 0.005376 |
| ENSG00000135506 | OS9 | 0.373692 | 0.005376 |
| ENSG00000126814 | TRMT5 | −0.38539 | 0.005431 |
| ENSG00000188002 |  | −0.86526 | 0.005434 |
| ENSG00000143479 | DYRK3 | −0.61886 | 0.00545 |
| ENSG00000198707 | CEP290 | −0.45876 | 0.005464 |
| ENSG00000025039 | RRAGD | 0.813253 | 0.005476 |
| ENSG00000101096 | NFATC2 | −0.48202 | 0.005476 |
| ENSG00000149930 | TAOK2 | 0.374696 | 0.005502 |
| ENSG00000162946 | DISC1 | −0.5698 | 0.005552 |
| ENSG00000154589 | LY96 | 1.071592 | 0.005561 |
| ENSG00000185269 | NOTUM | 0.827645 | 0.005561 |
| ENSG00000196911 | KPNA5 | −0.45915 | 0.005573 |
| ENSG00000100084 | HIRA | 0.461645 | 0.005574 |
| ENSG00000163399 | ATP1A1 | 0.332953 | 0.005574 |
| ENSG00000166579 | NDEL1 | 0.379448 | 0.005575 |
| ENSG00000197461 | PDGFA | 0.644469 | 0.005597 |
| ENSG00000100034 | PPM1F | −0.34097 | 0.005617 |
| ENSG00000099308 | MAST3 | 0.56429 | 0.005619 |
| ENSG00000157500 | APPL1 | −0.38002 | 0.005631 |
| ENSG00000196214 | ZNF766 | −0.43174 | 0.005633 |
| ENSG00000168995 | SIGLEC7 | 0.813363 | 0.005647 |
| ENSG00000166128 | RAB8B | 0.398334 | 0.005649 |
| ENSG00000130449 | ZSWIM6 | −0.45424 | 0.005656 |
| ENSG00000167378 | IRGQ | 0.479185 | 0.00566 |
| ENSG00000119661 | DNAL1 | −0.50801 | 0.005676 |
| ENSG00000197324 | LRP10 | 0.387559 | 0.005693 |
| ENSG00000244026 | FAM86DP | −0.60754 | 0.005735 |
| ENSG00000145247 | OCIAD2 | −0.48349 | 0.005739 |
| ENSG00000099917 | MED15 | 0.358539 | 0.005797 |
| ENSG00000116251 | RPL22 | −0.36196 | 0.005805 |
| ENSG00000211455 | STK38L | 0.373858 | 0.005809 |
| ENSG00000240342 |  | 0.356364 | 0.00581 |
| ENSG00000217027 |  | 0.391357 | 0.005827 |
| ENSG00000111252 | SH2B3 | −0.34963 | 0.00583 |
| ENSG00000136636 | KCTD3 | −0.3628 | 0.00583 |
| ENSG00000161642 | ZNF385A | 0.419444 | 0.005848 |
| ENSG00000251002 |  | 0.889229 | 0.005853 |
| ENSG00000180346 | TIGD2 | −0.47086 | 0.005861 |
| ENSG00000015479 | MATR3 | −0.35055 | 0.005868 |
| ENSG00000179115 | FARSA | 0.406508 | 0.005873 |
| ENSG00000183207 | RUVBL2 | 0.368159 | 0.005877 |
| ENSG00000109189 | USP46 | −0.39739 | 0.005878 |
| ENSG00000078589 | P2RY10 | 0.825296 | 0.0059 |
| ENSG00000109452 | INPP4B | −0.40287 | 0.005904 |
| ENSG00000186814 | ZSCAN30 | −0.42495 | 0.005919 |
| ENSG00000198453 | ZNF568 | −0.90961 | 0.005921 |
| ENSG00000169288 | MRPL1 | −0.37518 | 0.005966 |
| ENSG00000258590 |  | 1.027025 | 0.005966 |
| ENSG00000117620 | SLC35A3 | −0.42139 | 0.005982 |
| ENSG00000078140 | UBE2K | −0.35741 | 0.006011 |
| ENSG00000125898 | FAM110A | 0.534762 | 0.006017 |
| ENSG00000147548 | WHSC1L1 | −0.34735 | 0.006055 |
| ENSG00000105258 | POLR2I | 0.481967 | 0.006069 |
| ENSG00000233016 | SNHG7 | 0.396022 | 0.006147 |
| ENSG00000134250 | NOTCH2 | 0.646973 | 0.006158 |
| ENSG00000181827 | RFX7 | −0.3825 | 0.00616 |
| ENSG00000197852 | FAM212B | −0.5519 | 0.006165 |
| ENSG00000058335 | RASGRF1 | 0.878174 | 0.006167 |
| ENSG00000133740 | E2F5 | −0.65102 | 0.006167 |
| ENSG00000174197 | MGA | −0.45204 | 0.006231 |
| ENSG00000171310 | CHST11 | 0.334086 | 0.00624 |
| ENSG00000119681 | LTBP2 | 0.941051 | 0.006258 |
| ENSG00000186185 | KIF18B | 0.428503 | 0.006266 |
| ENSG00000160877 | NACC1 | 0.348822 | 0.006281 |
| ENSG00000054967 | RELT | 0.383693 | 0.006288 |
| ENSG00000099377 | HSD3B7 | 0.609184 | 0.006292 |
| ENSG00000105369 | CD79A | 0.497354 | 0.006292 |
| ENSG00000165506 | DNAAF2 | −0.44169 | 0.006292 |
| ENSG00000111300 | NAA25 | −0.40023 | 0.006304 |

SUPPLEMENTARY TABLE 1-continued

List of the identified differentially expressed transcripts after DE analysis using DESeq2 and edgeR-

| ENSEMBL | Symbol | Log$_2$ Fold Change | False discovery rate |
|---|---|---|---|
| ENSG00000028137 | TNFRSF1B | 0.356918 | 0.006328 |
| ENSG00000105492 | SIGLEC6 | 0.658139 | 0.006391 |
| ENSG00000160408 | ST6GALNAC6 | 0.405332 | 0.006398 |
| ENSG00000163714 | U2SURP | −0.36799 | 0.006429 |
| ENSG00000112096 | SOD2 | 1.110839 | 0.006447 |
| ENSG00000143158 | MPC2 | 0.419195 | 0.006447 |
| ENSG00000255262 |  | 0.778286 | 0.00645 |
| ENSG00000082516 | GEMIN5 | −0.39235 | 0.006451 |
| ENSG00000122971 | ACADS | 0.436337 | 0.006451 |
| ENSG00000131462 | TUBG1 | 0.404273 | 0.006452 |
| ENSG00000072210 | ALDH3A2 | 0.726886 | 0.00646 |
| ENSG00000185164 | NOMO2 | 0.405484 | 0.006485 |
| ENSG00000140365 | COMMD4 | 0.436528 | 0.006496 |
| ENSG00000164307 | ERAP1 | −0.36384 | 0.006501 |
| ENSG00000198168 | SVIP | 0.528213 | 0.006521 |
| ENSG00000032742 | IFT88 | −0.44813 | 0.006546 |
| ENSG00000006712 | PAF1 | 0.376987 | 0.006548 |
| ENSG00000135451 | TROAP | 0.459673 | 0.006565 |
| ENSG00000162300 | ZFPL1 | 0.439011 | 0.0066 |
| ENSG00000110315 | RNF141 | −0.41888 | 0.006603 |
| ENSG00000185347 | C14orf80 | 0.646991 | 0.006621 |
| ENSG00000160209 | PDXK | 0.37386 | 0.006631 |
| ENSG00000117000 | RLF | −0.37893 | 0.006672 |
| ENSG00000171843 | MLLT3 | −0.464 | 0.006675 |
| ENSG00000188313 | PLSCR1 | 0.345971 | 0.006675 |
| ENSG00000197136 | PCNX3 | 0.44753 | 0.006675 |
| ENSG00000154358 | OBSCN | −0.93762 | 0.00669 |
| ENSG00000173801 | JUP | −0.37253 | 0.006701 |
| ENSG00000181045 | SLC26A11 | 0.936496 | 0.006709 |
| ENSG00000085117 | CD82 | 0.544896 | 0.006725 |
| ENSG00000161267 | BDH1 | 0.366011 | 0.006725 |
| ENSG00000196437 | ZNF569 | −0.48831 | 0.006725 |
| ENSG00000101665 | SMAD7 | 0.422227 | 0.00673 |
| ENSG00000142186 | SCYL1 | 0.37023 | 0.006739 |
| ENSG00000169083 | AR | 0.955327 | 0.00674 |
| ENSG00000100056 | DGCR14 | 0.415493 | 0.006762 |
| ENSG00000135821 | GLUL | 0.371143 | 0.006762 |
| ENSG00000145050 | MANF | 0.369923 | 0.006762 |
| ENSG00000205302 | SNX2 | −0.33596 | 0.006781 |
| ENSG00000233461 |  | 0.772664 | 0.006854 |
| ENSG00000259758 |  | −0.40204 | 0.006879 |
| ENSG00000155545 | MIER3 | −0.3668 | 0.006911 |
| ENSG00000167562 | ZNF701 | −0.51557 | 0.006911 |
| ENSG00000070731 | ST6GALNAC2 | 1.014964 | 0.006919 |
| ENSG00000030419 | IKZF2 | 0.402913 | 0.006931 |
| ENSG00000231344 |  | 0.539784 | 0.006965 |
| ENSG00000155438 | NIFK | −0.34997 | 0.006975 |
| ENSG00000154217 | PITPNC1 | 0.596727 | 0.006992 |
| ENSG00000187912 | CLEC17A | 0.783968 | 0.006995 |
| ENSG00000160336 | ZNF761 | −0.38956 | 0.007016 |
| ENSG00000132688 | NES | −0.8807 | 0.007066 |
| ENSG00000136169 | SETDB2 | −0.43501 | 0.007074 |
| ENSG00000160087 | UBE2J2 | 0.389948 | 0.007128 |
| ENSG00000153560 | UBP1 | −0.33707 | 0.007128 |
| ENSG00000055609 | KMT2C | −0.43483 | 0.007175 |
| ENSG00000156136 | DCK | −0.36714 | 0.007215 |
| ENSG00000198858 | R3HDM4 | 0.363846 | 0.007293 |
| ENSG00000168813 | ZNF507 | −0.42929 | 0.007306 |
| ENSG00000136813 | KIAA0368 | −0.33751 | 0.007317 |
| ENSG00000114383 | TUSC2 | 0.397108 | 0.007354 |
| ENSG00000140264 | SERF2 | 0.343191 | 0.007393 |
| ENSG00000173465 | SSSCA1 | 0.505981 | 0.007399 |
| ENSG00000105516 | DBP | 0.8405 | 0.007419 |
| ENSG00000059145 | UNKL | 0.493161 | 0.007445 |
| ENSG00000187325 | TAF9B | −0.45034 | 0.00747 |
| ENSG00000182957 | SPATA13 | 0.430397 | 0.007529 |
| ENSG00000163935 | SFMBT1 | 0.503087 | 0.007534 |
| ENSG00000064393 | HIPK2 | −0.52802 | 0.007551 |
| ENSG00000134982 | APC | −0.38578 | 0.007706 |
| ENSG00000154803 | FLCN | 0.49417 | 0.007727 |
| ENSG00000068366 | ACSL4 | 0.330828 | 0.007782 |
| ENSG00000133313 | CNDP2 | −0.34136 | 0.007782 |
| ENSG00000228612 |  | 0.521723 | 0.007782 |
| ENSG00000117399 | CDC20 | 0.367505 | 0.007797 |
| ENSG00000101935 | AMMECR1 | −0.40263 | 0.007811 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000136144 | RCBTB1 | −0.43794 | 0.007866 |
| ENSG00000182670 | TTC3 | −0.33078 | 0.007892 |
| ENSG00000101057 | MYBL2 | 0.437343 | 0.007915 |
| ENSG00000124145 | SDC4 | 1.005467 | 0.007926 |
| ENSG00000166562 | SEC11C | 0.440412 | 0.007941 |
| ENSG00000065809 | FAM107B | 0.478152 | 0.007963 |
| ENSG00000178715 | | 0.361753 | 0.007983 |
| ENSG00000148803 | FUOM | 0.435948 | 0.008009 |
| ENSG00000223960 | LOC101927027 | −0.46331 | 0.008009 |
| ENSG00000105514 | RAB3D | 0.393756 | 0.008011 |
| ENSG00000171862 | PTEN | −0.36891 | 0.008011 |
| ENSG00000099810 | MTAP | −0.35834 | 0.008012 |
| ENSG00000169504 | CLIC4 | −0.35635 | 0.008036 |
| ENSG00000170315 | UBB | −0.32533 | 0.008048 |
| ENSG00000058056 | USP13 | −0.3941 | 0.008052 |
| ENSG00000077157 | PPP1R12B | −0.42806 | 0.008066 |
| ENSG00000108518 | PFN1 | 0.328559 | 0.008066 |
| ENSG00000153936 | HS2ST1 | −0.41933 | 0.008066 |
| ENSG00000105552 | BCAT2 | 0.401595 | 0.00807 |
| ENSG00000006757 | PNPLA4 | −0.7027 | 0.008077 |
| ENSG00000165724 | ZMYND19 | 0.393181 | 0.008094 |
| ENSG00000215039 | CD27-AS1 | −0.58751 | 0.008097 |
| ENSG00000160352 | ZNF714 | −0.43511 | 0.008103 |
| ENSG00000172345 | STARD5 | 0.753656 | 0.008103 |
| ENSG00000204099 | NEU4 | 1.081393 | 0.008157 |
| ENSG00000186020 | ZNF529 | −0.39225 | 0.008197 |
| ENSG00000159348 | CYB5R1 | 0.541345 | 0.00821 |
| ENSG00000196976 | LAGE3 | 0.457539 | 0.008216 |
| ENSG00000116586 | LAMTOR2 | 0.373879 | 0.008269 |
| ENSG00000261801 | LOXL1-AS1 | −0.46788 | 0.008269 |
| ENSG00000108262 | GIT1 | 0.366857 | 0.008285 |
| ENSG00000121858 | TNFSF10 | 0.996111 | 0.008297 |
| ENSG00000054148 | PHPT1 | 0.364508 | 0.008305 |
| ENSG00000128311 | TST | 0.47279 | 0.008305 |
| ENSG00000205593 | DENND6B | −0.54354 | 0.00831 |
| ENSG00000146676 | PURB | −0.33749 | 0.008354 |
| ENSG00000157077 | ZFYVE9 | 0.909646 | 0.008354 |
| ENSG00000187164 | SHTN1 | −1.07694 | 0.008375 |
| ENSG00000265982 | | 1.061417 | 0.008498 |
| ENSG00000131653 | TRAF7 | 0.355871 | 0.008523 |
| ENSG00000090661 | CERS4 | 0.395969 | 0.008572 |
| ENSG00000100596 | SPTLC2 | −0.32409 | 0.008572 |
| ENSG00000125630 | POLR1B | −0.35063 | 0.008572 |
| ENSG00000143641 | GALNT2 | 0.330482 | 0.008572 |
| ENSG00000080503 | SMARCA2 | −0.34182 | 0.008575 |
| ENSG00000134809 | TIMM10 | 0.411212 | 0.008575 |
| ENSG00000214026 | MRPL23 | 0.364397 | 0.008581 |
| ENSG00000242358 | | 0.379331 | 0.008593 |
| ENSG00000138944 | KIAA1644 | −0.53101 | 0.008654 |
| ENSG00000006576 | PHTF2 | 0.386519 | 0.008677 |
| ENSG00000083312 | TNPO1 | −0.42069 | 0.008692 |
| ENSG00000137760 | ALKBH8 | −0.42404 | 0.008693 |
| ENSG00000234311 | | 0.816682 | 0.008736 |
| ENSG00000006075 | | 1.123173 | 0.008739 |
| ENSG00000113119 | TMCO6 | −0.5193 | 0.008763 |
| ENSG00000270532 | | 0.511176 | 0.008763 |
| ENSG00000139192 | TAPBPL | 0.471907 | 0.008841 |
| ENSG00000178904 | DPY19L3 | −0.41281 | 0.00887 |
| ENSG00000083844 | ZNF264 | −0.61547 | 0.008873 |
| ENSG00000184730 | APOBR | 0.423291 | 0.008873 |
| ENSG00000151553 | FAM160B1 | −0.37091 | 0.008886 |
| ENSG00000133706 | LARS | −0.33379 | 0.008907 |
| ENSG00000172572 | PDE3A | 0.960391 | 0.008913 |
| ENSG00000183092 | BEGAIN | 0.67433 | 0.008924 |
| ENSG00000228974 | | 0.839781 | 0.008946 |
| ENSG00000128578 | STRIP2 | −0.66217 | 0.008989 |
| ENSG00000101464 | PIGU | 0.377786 | 0.009007 |
| ENSG00000136100 | VPS36 | −0.35743 | 0.009047 |
| ENSG00000048471 | SNX29 | −0.39904 | 0.00907 |
| ENSG00000100629 | CEP128 | −0.45793 | 0.00907 |
| ENSG00000187994 | RINL | 0.459394 | 0.00907 |
| ENSG00000213293 | | 0.373109 | 0.00907 |
| ENSG00000235162 | C12orf75 | −0.62282 | 0.009082 |
| ENSG00000081913 | PHLPP1 | −0.41204 | 0.009082 |
| ENSG00000112078 | KCTD20 | −0.34609 | 0.009108 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000133265 | HSPBP1 | 0.4156 | 0.009108 |
| ENSG00000080189 | SLC35C2 | 0.37849 | 0.009111 |
| ENSG00000140854 | KATNB1 | 0.369253 | 0.009111 |
| ENSG00000177311 | ZBTB38 | 0.526589 | 0.009111 |
| ENSG00000144579 | CTDSP1 | 0.321019 | 0.009124 |
| ENSG00000092621 | PHGDH | −0.47121 | 0.009144 |
| ENSG00000105993 | DNAJB6 | 0.407469 | 0.00916 |
| ENSG00000196712 | NF1 | −0.38083 | 0.00916 |
| ENSG00000142684 | ZNF593 | 0.454248 | 0.009198 |
| ENSG00000260065 |  | −0.44473 | 0.009202 |
| ENSG00000138036 | DYNC2LI1 | −0.50567 | 0.009245 |
| ENSG00000198846 | TOX | −0.38409 | 0.009252 |
| ENSG00000136560 | TANK | 0.494285 | 0.009297 |
| ENSG00000226137 | BAIAP2-AS1 | −0.34164 | 0.009297 |
| ENSG00000132471 | WBP2 | 0.371579 | 0.009301 |
| ENSG00000138600 | SPPL2A | 0.38398 | 0.009317 |
| ENSG00000166900 | STX3 | 0.349508 | 0.009375 |
| ENSG00000130402 | ACTN4 | 0.385924 | 0.009434 |
| ENSG00000091039 | OSBPL8 | −0.3884 | 0.009438 |
| ENSG00000136381 | IREB2 | −0.3789 | 0.009438 |
| ENSG00000229186 |  | −0.53387 | 0.009438 |
| ENSG00000183340 | JRKL | −0.41599 | 0.009452 |
| ENSG00000109756 | RAPGEF2 | −0.46547 | 0.009456 |
| ENSG00000111801 | BTN3A3 | −0.82854 | 0.009462 |
| ENSG00000135902 | CHRND | 1.086544 | 0.009462 |
| ENSG00000187193 | MT1X | 0.634429 | 0.009472 |
| ENSG00000088854 | C20orf194 | −0.36678 | 0.009481 |
| ENSG00000116871 | MAP7D1 | 0.358713 | 0.009481 |
| ENSG00000090339 | ICAM1 | 0.980124 | 0.009521 |
| ENSG00000139266 | 42438 | 0.947134 | 0.009526 |
| ENSG00000102763 | VWA8 | −0.3986 | 0.009562 |
| ENSG00000105671 | DDX49 | 0.400937 | 0.00958 |
| ENSG00000105875 | WDR91 | 0.550172 | 0.00958 |
| ENSG00000144455 | SUMF1 | 0.406835 | 0.00958 |
| ENSG00000198265 | HELZ | −0.35541 | 0.00958 |
| ENSG00000060138 | YBX3 | −0.32174 | 0.0096 |
| ENSG00000154783 | FGD5 | −0.94527 | 0.0096 |
| ENSG00000197258 |  | −0.37284 | 0.0096 |
| ENSG00000141985 | SH3GL1 | 0.389673 | 0.009612 |
| ENSG00000182048 | TRPC2 | −0.51862 | 0.009657 |
| ENSG00000213160 | KLHL23 | −0.42458 | 0.009663 |
| ENSG00000198146 | ZNF770 | −0.35213 | 0.009692 |
| ENSG00000051382 | PIK3CB | 0.343412 | 0.009704 |
| ENSG00000185504 | FAAP100 | 0.429295 | 0.009717 |
| ENSG00000100814 | CCNB1IP1 | −0.32803 | 0.009729 |
| ENSG00000166598 | HSP90B1 | 0.319462 | 0.009835 |
| ENSG00000111452 | ADGRD1 | 0.970904 | 0.009892 |
| ENSG00000267533 |  | 0.450122 | 0.009906 |
| ENSG00000198324 | FAM109A | 0.431903 | 0.009912 |
| ENSG00000167900 | TK1 | 0.415937 | 0.009929 |
| ENSG00000068796 | KIF2A | −0.36037 | 0.009949 |
| ENSG00000135048 | TMEM2 | −0.47332 | 0.009953 |
| ENSG00000127837 | AAMP | 0.357332 | 0.009986 |
| ENSG00000109390 | NDUFC1 | 0.3924 | 0.01001 |
| ENSG00000131378 | RFTN1 | −0.41428 | 0.010014 |
| ENSG00000197119 | SLC25A29 | 0.601981 | 0.010052 |
| ENSG00000168237 | GLYCTK | 0.452537 | 0.010067 |
| ENSG00000133703 | KRAS | −0.346 | 0.01007 |
| ENSG00000163795 | ZNF513 | 0.472306 | 0.010172 |
| ENSG00000205744 | DENND1C | 0.386714 | 0.010176 |
| ENSG00000101152 | DNAJC5 | 0.379029 | 0.010205 |
| ENSG00000106333 | PCOLCE | 0.675631 | 0.010205 |
| ENSG00000137992 | DBT | −0.3985 | 0.010205 |
| ENSG00000171953 | ATPAF2 | 0.388478 | 0.010205 |
| ENSG00000091490 | SEL1L3 | −0.34914 | 0.010248 |
| ENSG00000158470 | B4GALT5 | 0.337242 | 0.010302 |
| ENSG00000079385 | CEACAM1 | 0.768796 | 0.010342 |
| ENSG00000171657 | GPR82 | 0.753863 | 0.010342 |
| ENSG00000114738 | MAPKAPK3 | 0.321634 | 0.010371 |
| ENSG00000218902 |  | 0.612011 | 0.010371 |
| ENSG00000011426 | ANLN | 0.374663 | 0.010409 |
| ENSG00000198799 | LRIG2 | −0.40015 | 0.010409 |
| ENSG00000163346 | PBXIP1 | 0.366554 | 0.010412 |
| ENSG00000197629 | MPEG1 | 1.049603 | 0.010423 |
| ENSG00000224781 |  | −0.40571 | 0.010424 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000133812 | SBF2 | −0.41489 | 0.010424 |
| ENSG00000109458 | GAB1 | −0.45849 | 0.010426 |
| ENSG00000123405 | NFE2 | 0.505441 | 0.010426 |
| ENSG00000170571 | EMB | −0.42231 | 0.010437 |
| ENSG00000259820 |  | −0.43299 | 0.010455 |
| ENSG00000129353 | SLC44A2 | −0.42384 | 0.010464 |
| ENSG00000119927 | GPAM | −0.38664 | 0.010475 |
| ENSG00000136827 | TOR1A | 0.340841 | 0.010475 |
| ENSG00000260260 | SNHG19 | 0.610091 | 0.010475 |
| ENSG00000063854 | HAGH | 0.464887 | 0.010493 |
| ENSG00000113732 | ATP6V0E1 | 0.327908 | 0.010515 |
| ENSG00000213988 | ZNF90 | −1.03416 | 0.010515 |
| ENSG00000198042 | MAK16 | −0.3464 | 0.010533 |
| ENSG00000131495 | NDUFA2 | 0.36482 | 0.010541 |
| ENSG00000129245 | FXR2 | 0.374511 | 0.010545 |
| ENSG00000158402 | CDC25C | 0.600687 | 0.010549 |
| ENSG00000229056 | LOC101927482 | −1.08033 | 0.010605 |
| ENSG00000144668 | ITGA9 | 0.41247 | 0.010619 |
| ENSG00000245526 | LINC00461 | 0.994123 | 0.010629 |
| ENSG00000130590 | SAMD10 | 0.475069 | 0.01065 |
| ENSG00000148516 | ZEB1 | −0.45753 | 0.010665 |
| ENSG00000169684 | CHRNA5 | −0.63776 | 0.010665 |
| ENSG00000260521 | LOC440311 | 0.37223 | 0.010674 |
| ENSG00000119285 | HEATR1 | −0.32925 | 0.010735 |
| ENSG00000216775 | LOC730101 | −0.75981 | 0.010785 |
| ENSG00000197782 | ZNF780A | −0.43515 | 0.010804 |
| ENSG00000169689 | STRA13 | 0.413726 | 0.010834 |
| ENSG00000227124 | ZNF717 | −0.57191 | 0.010834 |
| ENSG00000167981 | ZNF597 | −0.52944 | 0.010839 |
| ENSG00000128923 | FAM63B | −0.40709 | 0.010856 |
| ENSG00000164933 | SLC25A32 | −0.38659 | 0.010869 |
| ENSG00000115760 | BIRC6 | −0.39026 | 0.010877 |
| ENSG00000225614 | ZNF469 | −0.45115 | 0.010877 |
| ENSG00000130309 | COLGALT1 | 0.350123 | 0.010881 |
| ENSG00000170604 | IRF2BP1 | 0.544559 | 0.01093 |
| ENSG00000026652 | AGPAT4 | 0.615482 | 0.010933 |
| ENSG00000138756 | BMP2K | −0.35758 | 0.010933 |
| ENSG00000021355 | SERPINB1 | 0.366267 | 0.010979 |
| ENSG00000115271 | GCA | 0.349492 | 0.010979 |
| ENSG00000169131 | ZNF354A | −0.46837 | 0.010982 |
| ENSG00000227039 | ITGB2-AS1 | 0.958726 | 0.010982 |
| ENSG00000132603 | NIP7 | −0.38594 | 0.011004 |
| ENSG00000173214 | MFSD4B | −0.44772 | 0.011004 |
| ENSG00000141854 | LOC113230 | 0.983144 | 0.01107 |
| ENSG00000169750 | RAC3 | 0.565388 | 0.01107 |
| ENSG00000181656 | GPR88 | 0.773466 | 0.011101 |
| ENSG00000166886 | NAB2 | 0.367282 | 0.011108 |
| ENSG00000090857 | PDPR | −0.33572 | 0.011145 |
| ENSG00000145348 | TBCK | −0.43475 | 0.011149 |
| ENSG00000197045 | GMFB | −0.38338 | 0.011149 |
| ENSG00000112365 | ZBTB24 | −0.44299 | 0.011178 |
| ENSG00000163947 | ARHGEF3 | −0.40291 | 0.011208 |
| ENSG00000159210 | SNF8 | 0.349008 | 0.011232 |
| ENSG00000184924 | PTRHD1 | 0.402211 | 0.011271 |
| ENSG00000181284 | TMEM102 | 0.459757 | 0.011303 |
| ENSG00000196544 | BORCS6 | 0.523666 | 0.011308 |
| ENSG00000224668 |  | −0.39703 | 0.011326 |
| ENSG00000253797 | UTP14C | −0.3591 | 0.011326 |
| ENSG00000160999 | SH2B2 | 0.754382 | 0.011529 |
| ENSG00000175467 | SART1 | 0.364396 | 0.011573 |
| ENSG00000126464 | PRR12 | 0.419259 | 0.011623 |
| ENSG00000151702 | FLI1 | −0.343 | 0.011667 |
| ENSG00000005238 | FAM214B | 0.501137 | 0.011703 |
| ENSG00000182141 | ZNF708 | −0.50464 | 0.011703 |
| ENSG00000125901 | MRPS26 | 0.418479 | 0.011746 |
| ENSG00000161551 | ZNF577 | −0.48536 | 0.011746 |
| ENSG00000117425 | PTCH2 | 0.792648 | 0.011754 |
| ENSG00000260174 |  | 0.659377 | 0.011755 |
| ENSG00000105246 | EBI3 | 1.053745 | 0.011757 |
| ENSG00000115956 | PLEK | 0.465426 | 0.011757 |
| ENSG00000171316 | CHD7 | −0.50519 | 0.011757 |
| ENSG00000198113 | TOR4A | 0.361903 | 0.011757 |
| ENSG00000184216 | IRAK1 | 0.38948 | 0.011765 |
| ENSG00000163644 | PPM1K | −0.70711 | 0.011767 |
| ENSG00000179899 |  | −0.7408 | 0.011802 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000013275 | PSMC4 | 0.324979 | 0.011818 |
| ENSG00000224557 | HLA-DPB2 | 0.709314 | 0.011818 |
| ENSG00000178150 | ZNF114 | −0.44284 | 0.011824 |
| ENSG00000132640 | BTBD3 | −0.36937 | 0.011838 |
| ENSG00000148429 | USP6NL | −0.37703 | 0.011838 |
| ENSG00000167635 | ZNF146 | −0.31248 | 0.011842 |
| ENSG00000104529 | EEF1D | 0.336321 | 0.011883 |
| ENSG00000205885 | C1RL-AS1 | −0.45411 | 0.011883 |
| ENSG00000106992 | AK1 | 0.704702 | 0.011925 |
| ENSG00000135763 | URB2 | −0.38384 | 0.011981 |
| ENSG00000214425 | | −0.4896 | 0.011994 |
| ENSG00000015171 | ZMYND11 | −0.33651 | 0.012005 |
| ENSG00000221968 | FADS3 | −0.45157 | 0.012006 |
| ENSG00000142002 | DPP9 | 0.389368 | 0.012076 |
| ENSG00000124181 | PLCG1 | −0.50186 | 0.012079 |
| ENSG00000196642 | RABL6 | 0.397775 | 0.012079 |
| ENSG00000187535 | IFT140 | −0.48125 | 0.012123 |
| ENSG00000225031 | | −0.39482 | 0.012123 |
| ENSG00000132286 | TIMM10B | −0.34457 | 0.012128 |
| ENSG00000110076 | NRXN2 | −0.93775 | 0.012139 |
| ENSG00000163635 | ATXN7 | −0.35225 | 0.012183 |
| ENSG00000157557 | ETS2 | −0.41834 | 0.012193 |
| ENSG00000119685 | TTLL5 | −0.35916 | 0.012206 |
| ENSG00000216740 | | 0.745344 | 0.012206 |
| ENSG00000151576 | QTRT2 | −0.34707 | 0.012227 |
| ENSG00000176248 | ANAPC2 | 0.38828 | 0.012227 |
| ENSG00000230067 | | −0.80936 | 0.012227 |
| ENSG00000005206 | SPPL2B | 0.409726 | 0.01227 |
| ENSG00000067369 | TP53BP1 | −0.34488 | 0.01227 |
| ENSG00000130520 | LSM4 | 0.333674 | 0.012317 |
| ENSG00000119508 | NR4A3 | 1.022915 | 0.012326 |
| ENSG00000104408 | EIF3E | −0.32958 | 0.012395 |
| ENSG00000125445 | MRPS7 | 0.327378 | 0.012395 |
| ENSG00000135269 | TES | −0.41072 | 0.012395 |
| ENSG00000166780 | C16orf45 | 0.870814 | 0.012395 |
| ENSG00000184076 | UQCR10 | 0.321872 | 0.012402 |
| ENSG00000105677 | TMEM147 | 0.373009 | 0.012445 |
| ENSG00000169908 | TM4SF1 | −0.4805 | 0.012445 |
| ENSG00000174917 | C19orf70 | 0.426187 | 0.012518 |
| ENSG00000173456 | RNF26 | 0.345089 | 0.012526 |
| ENSG00000181744 | C3orf58 | −0.35189 | 0.012557 |
| ENSG00000259706 | HSP90B2P | 0.334604 | 0.012557 |
| ENSG00000151461 | UPF2 | −0.34156 | 0.012586 |
| ENSG00000186815 | TPCN1 | 0.468129 | 0.012589 |
| ENSG00000124279 | FASTKD3 | −0.37092 | 0.012596 |
| ENSG00000122591 | FAM126A | −0.42285 | 0.012612 |
| ENSG00000026751 | SLAMF7 | 1.07919 | 0.012622 |
| ENSG00000067900 | ROCK1 | −0.36692 | 0.012622 |
| ENSG00000105793 | GTPBP10 | −0.38413 | 0.012622 |
| ENSG00000107560 | RAB11FIP2 | −0.44531 | 0.012622 |
| ENSG00000233859 | | −0.38753 | 0.01276 |
| ENSG00000014257 | ACPP | 0.426131 | 0.01276 |
| ENSG00000232952 | | −0.39394 | 0.012824 |
| ENSG00000116514 | RNF19B | 0.380027 | 0.012852 |
| ENSG00000122035 | RASL11A | 0.618188 | 0.012852 |
| ENSG00000115652 | UXS1 | 0.36139 | 0.012897 |
| ENSG00000049246 | PER3 | −0.72737 | 0.012903 |
| ENSG00000135956 | TMEM127 | 0.355413 | 0.012914 |
| ENSG00000128915 | ICE2 | −0.32405 | 0.012929 |
| ENSG00000240950 | | 0.353149 | 0.012946 |
| ENSG00000240849 | TMEM189 | 0.389936 | 0.01297 |
| ENSG00000106772 | PRUNE2 | 0.417699 | 0.012977 |
| ENSG00000188986 | NELFB | 0.360876 | 0.012977 |
| ENSG00000118507 | AKAP7 | −0.50664 | 0.012981 |
| ENSG00000136235 | GPNMB | 1.034689 | 0.012981 |
| ENSG00000155792 | DEPTOR | −0.48515 | 0.012987 |
| ENSG00000158483 | FAM86C1 | −0.68446 | 0.012994 |
| ENSG00000114541 | FRMD4B | −0.42536 | 0.013 |
| ENSG00000162191 | UBXN1 | 0.323255 | 0.013022 |
| ENSG00000131848 | ZSCAN5A | 0.467439 | 0.013027 |
| ENSG00000151062 | CACNA2D4 | 0.353888 | 0.013027 |
| ENSG00000183808 | RBM12B | −0.41428 | 0.013042 |
| ENSG00000197818 | SLC9A8 | 0.377601 | 0.01309 |
| ENSG00000156206 | CFAP161 | −0.61974 | 0.013096 |
| ENSG00000197894 | ADH5 | −0.33344 | 0.013096 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000080200 | CRYBG3 | −0.37086 | 0.013098 |
| ENSG00000044574 | HSPA5 | 0.335193 | 0.013117 |
| ENSG00000104361 | NIPAL2 | −0.40419 | 0.013117 |
| ENSG00000196208 | GREB1 | 0.981319 | 0.013117 |
| ENSG00000134243 | SORT1 | 0.308811 | 0.013141 |
| ENSG00000149428 | HYOU1 | 0.368029 | 0.013176 |
| ENSG00000163803 | PLB1 | 0.31724 | 0.013176 |
| ENSG00000114395 | CYB561D2 | 0.452081 | 0.0132 |
| ENSG00000143543 | JTB | 0.326948 | 0.013201 |
| ENSG00000104979 | C19orf53 | 0.326483 | 0.013244 |
| ENSG00000172725 | CORO1B | 0.422568 | 0.013263 |
| ENSG00000264736 | | −0.97639 | 0.013263 |
| ENSG00000114450 | GNB4 | −0.42255 | 0.013274 |
| ENSG00000129003 | VPS13C | −0.42506 | 0.01329 |
| ENSG00000132589 | FLOT2 | 0.345753 | 0.013295 |
| ENSG00000185100 | ADSSL1 | −0.98152 | 0.013334 |
| ENSG00000135404 | CD63 | 0.316073 | 0.013404 |
| ENSG00000101997 | CCDC22 | 0.387021 | 0.013404 |
| ENSG00000112685 | EXOC2 | −0.34561 | 0.013404 |
| ENSG00000049130 | KITLG | −0.37122 | 0.013408 |
| ENSG00000160392 | C19orf47 | 0.460958 | 0.013435 |
| ENSG00000170365 | SMAD1 | −0.50504 | 0.013435 |
| ENSG00000197245 | FAM110D | −1.04983 | 0.013501 |
| ENSG00000229124 | VIM-AS1 | −0.53921 | 0.013501 |
| ENSG00000234389 | | 0.896711 | 0.013529 |
| ENSG00000112514 | CUTA | 0.348171 | 0.013535 |
| ENSG00000185640 | KRT79 | 0.913288 | 0.01354 |
| ENSG00000070047 | PHRF1 | 0.451426 | 0.013575 |
| ENSG00000130856 | ZNF236 | −0.40032 | 0.013577 |
| ENSG00000092439 | TRPM7 | −0.33353 | 0.013581 |
| ENSG00000123213 | NLN | −0.32466 | 0.013603 |
| ENSG00000204560 | DHX16 | 0.353114 | 0.013603 |
| ENSG00000177380 | PPFIA3 | 0.55311 | 0.01361 |
| ENSG00000198040 | ZNF84 | −0.31735 | 0.013634 |
| ENSG00000186792 | HYAL3 | 0.388726 | 0.013659 |
| ENSG00000152778 | IFIT5 | −0.7009 | 0.013659 |
| ENSG00000167261 | DPEP2 | −0.55786 | 0.013659 |
| ENSG00000136877 | FPGS | 0.349661 | 0.013662 |
| ENSG00000172336 | POP7 | 0.455015 | 0.013677 |
| ENSG00000088808 | PPP1R13B | −0.36649 | 0.013685 |
| ENSG00000144591 | GMPPA | 0.390666 | 0.013693 |
| ENSG00000117597 | DIEXF | −0.36365 | 0.013759 |
| ENSG00000225101 | | 0.528354 | 0.01376 |
| ENSG00000104231 | ZFAND1 | −0.34705 | 0.01376 |
| ENSG00000081386 | ZNF510 | −0.3915 | 0.013788 |
| ENSG00000124151 | NCOA3 | −0.3311 | 0.013788 |
| ENSG00000163344 | PMVK | 0.44441 | 0.013788 |
| ENSG00000182580 | EPHB3 | −0.59382 | 0.013797 |
| ENSG00000163050 | ADCK3 | 0.406695 | 0.013817 |
| ENSG00000146733 | PSPH | −0.49692 | 0.013858 |
| ENSG00000167695 | FAM57A | 0.502993 | 0.013858 |
| ENSG00000141349 | G6PC3 | 0.345848 | 0.013943 |
| ENSG00000198315 | ZKSCAN8 | −0.33439 | 0.014023 |
| ENSG00000140262 | TCF12 | −0.33117 | 0.014033 |
| ENSG00000213281 | NRAS | −0.34727 | 0.014034 |
| ENSG00000013810 | TACC3 | 0.323835 | 0.014052 |
| ENSG00000091106 | NLRC4 | 0.648623 | 0.014084 |
| ENSG00000167384 | ZNF180 | −0.43404 | 0.014086 |
| ENSG00000141456 | PELP1 | 0.359821 | 0.014086 |
| ENSG00000182481 | KPNA2 | 0.309044 | 0.014104 |
| ENSG00000165813 | CCDC186 | −0.36348 | 0.014179 |
| ENSG00000197976 | AKAP17A | 0.390163 | 0.014179 |
| ENSG00000166595 | FAM96B | 0.355671 | 0.014226 |
| ENSG00000185022 | MAFF | 0.706915 | 0.014226 |
| ENSG00000177666 | PNPLA2 | 0.385427 | 0.01424 |
| ENSG00000264868 | | 0.804432 | 0.014252 |
| ENSG00000204623 | ZNRD1ASP | −0.5246 | 0.014277 |
| ENSG00000103254 | FAM173A | 0.718589 | 0.014319 |
| ENSG00000262879 | | −0.5212 | 0.014319 |
| ENSG00000152193 | RNF219 | −0.34463 | 0.014429 |
| ENSG00000171681 | ATF7IP | −0.39436 | 0.014444 |
| ENSG00000118515 | SGK1 | 0.984024 | 0.01445 |
| ENSG00000166484 | MAPK7 | 0.484286 | 0.014551 |
| ENSG00000074071 | MRPS34 | 0.426035 | 0.014553 |
| ENSG00000181555 | SETD2 | −0.31194 | 0.014619 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000104142 | VPS18 | 0.39174 | 0.014646 |
| ENSG00000234883 | MIR155HG | 0.494612 | 0.014669 |
| ENSG00000100612 | DHRS7 | 0.313222 | 0.014689 |
| ENSG00000225339 |  | −0.80118 | 0.014707 |
| ENSG00000115827 | DCAF17 | −0.35159 | 0.014711 |
| ENSG00000175489 | LRRC25 | 0.652731 | 0.014727 |
| ENSG00000105321 | CCDC9 | 0.438556 | 0.014819 |
| ENSG00000064763 | FAR2 | −0.34699 | 0.014843 |
| ENSG00000186174 | BCL9L | 0.441401 | 0.014873 |
| ENSG00000077150 | NFKB2 | 1.057873 | 0.014895 |
| ENSG00000122729 | ACO1 | −0.37633 | 0.014945 |
| ENSG00000138286 | FAM149B1 | −0.42645 | 0.014966 |
| ENSG00000077713 | SLC25A43 | −0.46184 | 0.015101 |
| ENSG00000198182 | ZNF607 | −0.54784 | 0.015103 |
| ENSG00000085224 | ATRX | −0.38218 | 0.015267 |
| ENSG00000198258 | UBL5 | 0.328192 | 0.015267 |
| ENSG00000150776 | C11orf57 | −0.33093 | 0.015275 |
| ENSG00000185800 | DMWD | 0.850885 | 0.015275 |
| ENSG00000228782 |  | −0.65604 | 0.01528 |
| ENSG00000105220 | GPI | 0.2952 | 0.015303 |
| ENSG00000123600 | METTL8 | −0.36302 | 0.015338 |
| ENSG00000137166 | FOXP4 | 0.357265 | 0.015391 |
| ENSG00000173581 | CCDC106 | 0.412999 | 0.015394 |
| ENSG00000170801 | HTRA3 | −0.36635 | 0.015397 |
| ENSG00000173276 | ZBTB21 | −0.40078 | 0.015403 |
| ENSG00000235008 |  | 0.616643 | 0.015505 |
| ENSG00000111348 | ARHGDIB | 0.297669 | 0.015513 |
| ENSG00000113811 | SELK | 0.409979 | 0.015513 |
| ENSG00000176170 | SPHK1 | 0.491069 | 0.015513 |
| ENSG00000068394 | GPKOW | 0.36159 | 0.015534 |
| ENSG00000170759 | KIF5B | −0.31418 | 0.015575 |
| ENSG00000149948 | HMGA2 | −0.57885 | 0.015594 |
| ENSG00000184675 | AMER1 | −0.48263 | 0.01563 |
| ENSG00000092148 | HECTD1 | −0.3224 | 0.015766 |
| ENSG00000047849 | MAP4 | −0.31357 | 0.015779 |
| ENSG00000162591 | MEGF6 | −0.4735 | 0.015862 |
| ENSG00000125611 | CHCHD5 | 0.553941 | 0.015863 |
| ENSG00000165494 | PCF11 | −0.33591 | 0.015896 |
| ENSG00000125746 | EML2 | 0.420953 | 0.015956 |
| ENSG00000114812 | VIPR1 | −0.9793 | 0.016056 |
| ENSG00000137310 | TCF19 | 0.41455 | 0.016115 |
| ENSG00000119714 | GPR68 | 0.552781 | 0.016126 |
| ENSG00000198945 | L3MBTL3 | −0.46468 | 0.016159 |
| ENSG00000084207 | GSTP1 | 0.324333 | 0.01616 |
| ENSG00000078061 | ARAF | 0.323925 | 0.016191 |
| ENSG00000254023 |  | 0.687628 | 0.01625 |
| ENSG00000168487 | BMP1 | 0.357279 | 0.016258 |
| ENSG00000119599 | DCAF4 | −0.39886 | 0.016277 |
| ENSG00000186260 | MKL2 | −0.40909 | 0.016303 |
| ENSG00000187244 | BCAM | −0.90047 | 0.016304 |
| ENSG00000167716 | WDR81 | 0.397568 | 0.016335 |
| ENSG00000165046 | LETM2 | −0.67729 | 0.016366 |
| ENSG00000149806 | FAU | 0.334272 | 0.01637 |
| ENSG00000265798 |  | −0.96604 | 0.016385 |
| ENSG00000185989 | RASA3 | 0.391244 | 0.016401 |
| ENSG00000168209 | DDIT4 | 0.436722 | 0.01641 |
| ENSG00000125744 | RTN2 | 0.427787 | 0.016495 |
| ENSG00000180509 | KCNE1 | 0.889413 | 0.01654 |
| ENSG00000059378 | PARP12 | −0.43934 | 0.01658 |
| ENSG00000104964 | AES | 0.321062 | 0.016599 |
| ENSG00000133121 | STARD13 | −0.40945 | 0.016622 |
| ENSG00000164970 | FAM219A | −0.46035 | 0.016668 |
| ENSG00000114670 | NEK11 | −0.74338 | 0.016706 |
| ENSG00000156515 | HK1 | 0.449485 | 0.016706 |
| ENSG00000198026 | ZNF335 | 0.334518 | 0.016706 |
| ENSG00000139508 | SLC46A3 | −0.897 | 0.016732 |
| ENSG00000204394 | VARS | 0.331075 | 0.016736 |
| ENSG00000214021 | TTLL3 | 0.42308 | 0.016789 |
| ENSG00000116521 | SCAMP3 | 0.323788 | 0.01682 |
| ENSG00000130311 | DDA1 | 0.355065 | 0.016832 |
| ENSG00000089048 | ESF1 | −0.36032 | 0.01684 |
| ENSG00000158006 | PAFAH2 | 0.472176 | 0.016859 |
| ENSG00000160229 |  | −0.84871 | 0.016898 |
| ENSG00000235106 | LINC00094 | −0.46357 | 0.016898 |
| ENSG00000085491 | SLC25A24 | −0.38545 | 0.016914 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000271533 |  | −0.51986 | 0.016923 |
| ENSG00000100591 | AHSA1 | 0.305284 | 0.017015 |
| ENSG00000145907 | G3BP1 | −0.32549 | 0.017052 |
| ENSG00000115165 | CYTIP | 0.417046 | 0.01708 |
| ENSG00000151304 | SRFBP1 | −0.3707 | 0.01708 |
| ENSG00000225774 |  | 0.572657 | 0.017131 |
| ENSG00000103966 | EHD4 | −0.36864 | 0.017146 |
| ENSG00000102226 | USP11 | −0.36111 | 0.017172 |
| ENSG00000126602 | TRAP1 | 0.316072 | 0.017185 |
| ENSG00000188906 | LRRK2 | 1.038937 | 0.017185 |
| ENSG00000119333 | WDR34 | 0.461458 | 0.017244 |
| ENSG00000107745 | MICU1 | 0.304142 | 0.017428 |
| ENSG00000114026 | OGG1 | 0.416631 | 0.017502 |
| ENSG00000163558 | PRKCI | −0.36599 | 0.017502 |
| ENSG00000166171 | DPCD | −0.49396 | 0.017502 |
| ENSG00000119471 | HSDL2 | −0.38966 | 0.017512 |
| ENSG00000143624 | INTS3 | −0.34154 | 0.017552 |
| ENSG00000125730 | C3 | 1.002051 | 0.017601 |
| ENSG00000145332 | KLHL8 | −0.38485 | 0.017631 |
| ENSG00000197372 | ZNF675 | −0.38573 | 0.017631 |
| ENSG00000128309 | MPST | 0.349323 | 0.017643 |
| ENSG00000186567 | CEACAM19 | 0.74644 | 0.017793 |
| ENSG00000104133 | SPG11 | −0.32743 | 0.017795 |
| ENSG00000162129 | CLPB | 0.345385 | 0.017847 |
| ENSG00000169251 | NMD3 | −0.3379 | 0.01787 |
| ENSG00000154328 | NEIL2 | −0.52585 | 0.017872 |
| ENSG00000106723 | SPIN1 | −0.31268 | 0.01796 |
| ENSG00000148200 | NR6A1 | −0.36579 | 0.018058 |
| ENSG00000133816 | MICAL2 | −0.40467 | 0.018061 |
| ENSG00000135164 | DMTF1 | −0.31832 | 0.018066 |
| ENSG00000135845 | PIGC | 0.344742 | 0.018104 |
| ENSG00000166170 | BAG5 | −0.3107 | 0.018145 |
| ENSG00000129277 |  | 1.033495 | 0.018233 |
| ENSG00000124155 | PIGT | 0.321837 | 0.018415 |
| ENSG00000255521 | LOC100507144 | −0.9308 | 0.018418 |
| ENSG00000087053 | MTMR2 | −0.32896 | 0.018442 |
| ENSG00000145545 | SRD5A1 | −0.40165 | 0.01846 |
| ENSG00000164220 | F2RL2 | −0.85055 | 0.018481 |
| ENSG00000096717 | SIRT1 | −0.35613 | 0.018484 |
| ENSG00000176043 |  | 0.329105 | 0.018484 |
| ENSG00000114062 | UBE3A | −0.30877 | 0.018699 |
| ENSG00000059377 | TBXAS1 | −0.35526 | 0.018723 |
| ENSG00000152229 | PSTPIP2 | 0.385048 | 0.018723 |
| ENSG00000175348 | TMEM9B | 0.3542 | 0.018784 |
| ENSG00000229676 | ZNF492 | −0.95522 | 0.018784 |
| ENSG00000163320 | CGGBP1 | −0.29617 | 0.018804 |
| ENSG00000126217 | MCF2L | −0.59629 | 0.01882 |
| ENSG00000146757 | ZNF92 | −0.35791 | 0.018841 |
| ENSG00000105849 | TWISTNB | −0.31091 | 0.018919 |
| ENSG00000010404 | IDS | −0.29113 | 0.01892 |
| ENSG00000260997 |  | −0.39195 | 0.018922 |
| ENSG00000049249 | TNFRSF9 | 1.002059 | 0.018935 |
| ENSG00000057704 | TMCC3 | 0.695944 | 0.018935 |
| ENSG00000138642 | HERC6 | −0.43882 | 0.019021 |
| ENSG00000213024 | NUP62 | 0.311966 | 0.019038 |
| ENSG00000102572 | STK24 | −0.43657 | 0.019043 |
| ENSG00000169727 | GPS1 | 0.356225 | 0.019043 |
| ENSG00000247556 |  | −0.29948 | 0.019043 |
| ENSG00000210195 |  | 0.397185 | 0.019101 |
| ENSG00000125485 | DDX31 | −0.34593 | 0.019129 |
| ENSG00000101751 | POLI | −0.38303 | 0.019137 |
| ENSG00000072506 | HSD17B10 | 0.350219 | 0.019165 |
| ENSG00000168874 | ATOH8 | 0.868057 | 0.019165 |
| ENSG00000071553 | ATP6AP1 | 0.340705 | 0.019174 |
| ENSG00000101181 | MTG2 | 0.360927 | 0.019222 |
| ENSG00000162994 | CLHC1 | −0.49184 | 0.019268 |
| ENSG00000179833 | SERTAD2 | 0.354807 | 0.019268 |
| ENSG00000213762 | ZNF134 | −0.36046 | 0.019274 |
| ENSG00000215030 |  | 0.31134 | 0.019342 |
| ENSG00000130038 | CRACR2A | −0.4027 | 0.0194 |
| ENSG00000227028 | SLC8A1-AS1 | −0.66748 | 0.019445 |
| ENSG00000114648 | KLHL18 | −0.34559 | 0.019458 |
| ENSG00000115828 | QPCT | −0.82479 | 0.019512 |
| ENSG00000008283 | CYB561 | −0.42764 | 0.019525 |
| ENSG00000140451 | PIF1 | 0.526924 | 0.019607 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000143387 | CTSK | 0.646784 | 0.019669 |
| ENSG00000163482 | STK36 | −0.36939 | 0.019669 |
| ENSG00000197933 | ZNF823 | −0.59564 | 0.019669 |
| ENSG00000187961 | KLHL17 | 0.601641 | 0.019694 |
| ENSG00000187240 | DYNC2H1 | −0.35826 | 0.019733 |
| ENSG00000165802 | NSMF | 0.369289 | 0.019785 |
| ENSG00000145476 | CYP4V2 | −0.46962 | 0.019879 |
| ENSG00000108679 | LGALS3BP | −0.89556 | 0.019936 |
| ENSG00000167984 | NLRC3 | −0.46599 | 0.019973 |
| ENSG00000171729 | TMEM51 | 0.456752 | 0.019981 |
| ENSG00000105379 | ETFB | 0.389602 | 0.020002 |
| ENSG00000171608 | PIK3CD | 0.313072 | 0.02001 |
| ENSG00000099998 | GGT5 | 0.359615 | 0.02003 |
| ENSG00000129315 | CCNT1 | −0.32833 | 0.02003 |
| ENSG00000150782 | IL18 | −0.31711 | 0.02003 |
| ENSG00000125877 | ITPA | 0.363379 | 0.020107 |
| ENSG00000170909 | OSCAR | 0.520238 | 0.020119 |
| ENSG00000133943 | C14orf159 | −0.3214 | 0.020135 |
| ENSG00000170234 | PWWP2A | −0.33327 | 0.020136 |
| ENSG00000203667 | COX20 | −0.38024 | 0.020144 |
| ENSG00000069966 | GNB5 | 0.387871 | 0.020152 |
| ENSG00000104324 | CPQ | 0.581175 | 0.020183 |
| ENSG00000112984 | KIF20A | 0.371093 | 0.020183 |
| ENSG00000152223 | EPG5 | 0.457698 | 0.020183 |
| ENSG00000244313 |  | 0.311551 | 0.020183 |
| ENSG00000261040 | WFDC21P | 0.87474 | 0.020267 |
| ENSG00000125844 | RRBP1 | 0.335253 | 0.020274 |
| ENSG00000250746 |  | 0.399875 | 0.020274 |
| ENSG00000198791 | CNOT7 | −0.31186 | 0.020323 |
| ENSG00000077782 | FGFR1 | −0.62953 | 0.020332 |
| ENSG00000100319 | ZMAT5 | 0.462102 | 0.020332 |
| ENSG00000204673 | AKT1S1 | 0.377648 | 0.020332 |
| ENSG00000196605 | ZNF846 | −0.66797 | 0.020375 |
| ENSG00000080546 | SESN1 | −0.37361 | 0.020396 |
| ENSG00000116044 | NFE2L2 | 0.397413 | 0.020448 |
| ENSG00000103351 | CLUAP1 | −0.44507 | 0.020488 |
| ENSG00000179271 | GADD45GIP1 | 0.386041 | 0.020541 |
| ENSG00000229325 |  | −0.93666 | 0.02055 |
| ENSG00000196705 | ZNF431 | −0.3761 | 0.020557 |
| ENSG00000127954 | STEAP4 | 0.940207 | 0.02056 |
| ENSG00000140396 | NCOA2 | −0.38219 | 0.020562 |
| ENSG00000146670 | CDCA5 | 0.343328 | 0.020562 |
| ENSG00000141219 | C17orf80 | −0.36262 | 0.02062 |
| ENSG00000186687 | LYRM7 | −0.31958 | 0.020744 |
| ENSG00000054523 | KIF1B | −0.33297 | 0.020757 |
| ENSG00000113648 | H2AFY | −0.29217 | 0.020785 |
| ENSG00000196646 | ZNF136 | −0.39925 | 0.020827 |
| ENSG00000144043 | TEX261 | 0.301679 | 0.020856 |
| ENSG00000176619 | LMNB2 | 0.331476 | 0.020856 |
| ENSG00000110711 | AIP | 0.35025 | 0.0209 |
| ENSG00000095951 | HIVEP1 | 0.470705 | 0.02093 |
| ENSG00000188305 | C19orf35 | 0.788209 | 0.020944 |
| ENSG00000143669 | LYST | 0.416344 | 0.021069 |
| ENSG00000064666 | CNN2 | −0.30943 | 0.021103 |
| ENSG00000185052 | SLC24A3 | 0.430846 | 0.021113 |
| ENSG00000078246 | TULP3 | −0.48125 | 0.02118 |
| ENSG00000106261 | ZKSCAN1 | −0.35684 | 0.021188 |
| ENSG00000225531 |  | −0.58712 | 0.021188 |
| ENSG00000140006 | WDR89 | −0.35806 | 0.02124 |
| ENSG00000127580 | WDR24 | 0.506236 | 0.021323 |
| ENSG00000155099 | TMEM55A | 0.398765 | 0.021393 |
| ENSG00000122376 | FAM35A | −0.35618 | 0.021415 |
| ENSG00000226745 |  | 0.530568 | 0.021587 |
| ENSG00000126878 | AIF1L | 0.848325 | 0.021619 |
| ENSG00000272216 |  | −0.83117 | 0.021619 |
| ENSG00000119537 | KDSR | −0.34862 | 0.021659 |
| ENSG00000095383 | TBC1D2 | 0.566466 | 0.021787 |
| ENSG00000104490 | NCALD | −0.43529 | 0.021787 |
| ENSG00000074621 | SLC24A1 | −0.474 | 0.021853 |
| ENSG00000163939 | PBRM1 | −0.34291 | 0.021853 |
| ENSG00000105618 | PRPF31 | 0.36142 | 0.021887 |
| ENSG00000144893 | MED12L | 0.562771 | 0.021927 |
| ENSG00000107719 | PALD1 | 0.386769 | 0.021962 |
| ENSG00000007968 | E2F2 | 0.448596 | 0.021997 |
| ENSG00000104218 | CSPP1 | −0.36482 | 0.02202 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000090266 | NDUFB2 | 0.320259 | 0.022084 |
| ENSG00000120832 | MTERF2 | −0.64221 | 0.022181 |
| ENSG00000154928 | EPHB1 | 0.833119 | 0.022282 |
| ENSG00000124789 | NUP153 | −0.28915 | 0.02236 |
| ENSG00000009413 | REV3L | −0.37217 | 0.02237 |
| ENSG00000164902 | PHAX | −0.32807 | 0.022439 |
| ENSG00000036549 | ZZZ3 | −0.30296 | 0.022518 |
| ENSG00000152061 | RABGAP1L | −0.32232 | 0.022558 |
| ENSG00000139687 | RB1 | −0.31137 | 0.022612 |
| ENSG00000137563 | GGH | 0.388416 | 0.022623 |
| ENSG00000183020 | AP2A2 | 0.318087 | 0.022651 |
| ENSG00000133136 | | 0.47206 | 0.022769 |
| ENSG00000271122 | | −0.55625 | 0.022781 |
| ENSG00000198298 | ZNF485 | −0.51783 | 0.022937 |
| ENSG00000085982 | USP40 | −0.33656 | 0.022974 |
| ENSG00000159110 | IFNAR2 | 0.405426 | 0.022974 |
| ENSG00000145777 | TSLP | 0.922049 | 0.023001 |
| ENSG00000228234 | | 0.732532 | 0.023001 |
| ENSG00000085063 | CD59 | −0.29931 | 0.023117 |
| ENSG00000168283 | BMI1 | −0.37924 | 0.023172 |
| ENSG00000153443 | UBALD1 | 0.453341 | 0.02321 |
| ENSG00000118058 | KMT2A | −0.36373 | 0.02328 |
| ENSG00000117877 | CD3EAP | −0.4014 | 0.023327 |
| ENSG00000137494 | ANKRD42 | −0.39567 | 0.02343 |
| ENSG00000089820 | ARHGAP4 | 0.359507 | 0.023441 |
| ENSG00000163464 | CXCR1 | 0.848976 | 0.023451 |
| ENSG00000168701 | TMEM208 | 0.363526 | 0.023455 |
| ENSG00000188868 | ZNF563 | −0.80716 | 0.023455 |
| ENSG00000136874 | STX17 | −0.36515 | 0.023476 |
| ENSG00000156795 | WDYHV1 | −0.42776 | 0.023476 |
| ENSG00000102189 | EEA1 | −0.40215 | 0.023545 |
| ENSG00000186834 | HEXIM1 | 0.30345 | 0.023545 |
| ENSG00000075407 | ZNF37A | −0.33278 | 0.023567 |
| ENSG00000197771 | MCMBP | −0.3037 | 0.023595 |
| ENSG00000163577 | EIF5A2 | 0.531702 | 0.023696 |
| ENSG00000057935 | MTA3 | −0.34644 | 0.023708 |
| ENSG00000165912 | PACSIN3 | 0.591926 | 0.023708 |
| ENSG00000249212 | | 0.953121 | 0.023708 |
| ENSG00000154174 | TOMM70 | −0.28936 | 0.023762 |
| ENSG00000136158 | SPRY2 | 0.459084 | 0.023785 |
| ENSG00000149557 | FEZ1 | −0.88327 | 0.023793 |
| ENSG00000005007 | UPF1 | 0.306402 | 0.023849 |
| ENSG00000162852 | CNST | −0.32011 | 0.023889 |
| ENSG00000102996 | MMP15 | −0.42341 | 0.023905 |
| ENSG00000184898 | RBM43 | −0.43736 | 0.023905 |
| ENSG00000187808 | SOWAHD | 0.744901 | 0.023905 |
| ENSG00000135709 | KIAA0513 | 0.4604 | 0.023917 |
| ENSG00000258469 | | 0.465711 | 0.023926 |
| ENSG00000005801 | ZNF195 | −0.31268 | 0.023933 |
| ENSG00000139597 | N4BP2L1 | 0.574835 | 0.023933 |
| ENSG00000179632 | MAF1 | 0.299893 | 0.023933 |
| ENSG00000205189 | ZBTB10 | −0.40126 | 0.023933 |
| ENSG00000241732 | | −0.73095 | 0.023933 |
| ENSG00000167766 | ZNF83 | −0.34359 | 0.023945 |
| ENSG00000112701 | SENP6 | −0.29093 | 0.023959 |
| ENSG00000197746 | PSAP | 0.349872 | 0.023964 |
| ENSG00000163564 | PYHIN1 | −0.63785 | 0.023974 |
| ENSG00000168778 | TCTN2 | −0.52485 | 0.023974 |
| ENSG00000110721 | CHKA | 0.351772 | 0.024094 |
| ENSG00000117318 | ID3 | 0.558227 | 0.024179 |
| ENSG00000138385 | SSB | −0.32147 | 0.024179 |
| ENSG00000138768 | USO1 | −0.29221 | 0.024179 |
| ENSG00000173621 | LRFN4 | 0.442872 | 0.024179 |
| ENSG00000222041 | LINC00152 | −0.50437 | 0.024179 |
| ENSG00000130684 | ZNF337 | −0.37767 | 0.024238 |
| ENSG00000197969 | VPS13A | −0.36939 | 0.024238 |
| ENSG00000196411 | EPHB4 | −0.41322 | 0.024274 |
| ENSG00000196923 | PDLIM7 | 0.365292 | 0.024331 |
| ENSG00000150779 | TIMM8B | 0.35747 | 0.024394 |
| ENSG00000137145 | DENND4C | −0.32295 | 0.024449 |
| ENSG00000198517 | MAFK | 0.399834 | 0.024501 |
| ENSG00000049883 | PTCD2 | −0.4439 | 0.024624 |
| ENSG00000173137 | ADCK5 | 0.553303 | 0.024624 |
| ENSG00000105245 | NUMBL | 0.463165 | 0.024639 |
| ENSG00000237940 | LOC102723927 | −0.81826 | 0.024639 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
| --- | --- | --- | --- |
| ENSG00000138398 | PPIG | −0.31634 | 0.024644 |
| ENSG00000056586 | RC3H2 | −0.3211 | 0.024678 |
| ENSG00000063046 | EIF4B | −0.28297 | 0.024678 |
| ENSG00000143815 | LBR | 0.387129 | 0.024684 |
| ENSG00000117748 | RPA2 | 0.327339 | 0.024688 |
| ENSG00000106605 | BLVRA | −0.50804 | 0.024788 |
| ENSG00000119446 | RBM18 | −0.31131 | 0.024788 |
| ENSG00000196850 | PPTC7 | −0.29547 | 0.024788 |
| ENSG00000254986 | DPP3 | 0.34047 | 0.024788 |
| ENSG00000107263 | RAPGEF1 | 0.360296 | 0.024817 |
| ENSG00000244300 | | 0.517129 | 0.024845 |
| ENSG00000117394 | SLC2A1 | 0.374094 | 0.024867 |
| ENSG00000147124 | ZNF41 | −0.35725 | 0.024867 |
| ENSG00000103342 | GSPT1 | −0.28353 | 0.024962 |
| ENSG00000181418 | DDN | 0.779313 | 0.025036 |
| ENSG00000116685 | KIAA2013 | 0.323737 | 0.025065 |
| ENSG00000146243 | IRAK1BP1 | −0.57508 | 0.025065 |
| ENSG00000197165 | SULT1A2 | 0.954527 | 0.025131 |
| ENSG00000260686 | | −0.7628 | 0.025218 |
| ENSG00000174600 | CMKLR1 | −0.51721 | 0.025236 |
| ENSG00000197563 | PIGN | −0.32631 | 0.025333 |
| ENSG00000206560 | ANKRD28 | −0.36899 | 0.025577 |
| ENSG00000163596 | ICA1L | −0.46809 | 0.025632 |
| ENSG00000154025 | SLC5A10 | 0.905291 | 0.025898 |
| ENSG00000169230 | PRELID1 | 0.299176 | 0.025898 |
| ENSG00000039650 | PNKP | 0.40822 | 0.025926 |
| ENSG00000108509 | CAMTA2 | 0.340211 | 0.025926 |
| ENSG00000237984 | PTENP1 | −0.3686 | 0.026077 |
| ENSG00000122644 | ARL4A | 0.316265 | 0.026166 |
| ENSG00000100647 | SUSD6 | 0.367085 | 0.026204 |
| ENSG00000260742 | | −0.62793 | 0.026379 |
| ENSG00000204165 | CXorf65 | 0.929109 | 0.02639 |
| ENSG00000128040 | SPINK2 | −0.44294 | 0.026499 |
| ENSG00000175203 | DCTN2 | 0.29003 | 0.026516 |
| ENSG00000164611 | PTTG1 | 0.400525 | 0.026597 |
| ENSG00000087299 | L2HGDH | 0.374687 | 0.026604 |
| ENSG00000002726 | AOC1 | 0.884236 | 0.026646 |
| ENSG00000132953 | XPO4 | −0.36519 | 0.026668 |
| ENSG00000170296 | GABARAP | 0.593572 | 0.02667 |
| ENSG00000178980 | SEPW1 | 0.311717 | 0.026681 |
| ENSG00000144362 | PHOSPHO2 | −0.65653 | 0.026734 |
| ENSG00000106400 | ZNHIT1 | 0.33501 | 0.026754 |
| ENSG00000182185 | RAD51B | −0.53524 | 0.026904 |
| ENSG00000173166 | RAPH1 | 0.800682 | 0.026959 |
| ENSG00000113758 | DBN1 | 0.398196 | 0.027143 |
| ENSG00000150712 | MTMR12 | −0.32156 | 0.027143 |
| ENSG00000198839 | ZNF277 | −0.33829 | 0.027216 |
| ENSG00000219626 | FAM228B | −0.58354 | 0.027256 |
| ENSG00000011478 | QPCTL | 0.451354 | 0.027275 |
| ENSG00000153879 | CEBPG | −0.29905 | 0.027287 |
| ENSG00000166689 | PLEKHA7 | 0.471087 | 0.027287 |
| ENSG00000130812 | ANGPTL6 | 0.457456 | 0.027315 |
| ENSG00000110651 | CD81 | 0.339445 | 0.027332 |
| ENSG00000149485 | FADS1 | −0.36693 | 0.027373 |
| ENSG00000089091 | DZANK1 | −0.61829 | 0.027424 |
| ENSG00000105879 | CBLL1 | −0.30116 | 0.027425 |
| ENSG00000163811 | WDR43 | −0.33914 | 0.02755 |
| ENSG00000170144 | HNRNPA3 | −0.33744 | 0.027553 |
| ENSG00000173020 | ADRBK1 | 0.29623 | 0.027553 |
| ENSG00000188747 | NOXA1 | 0.617365 | 0.027575 |
| ENSG00000196562 | SULF2 | −0.82624 | 0.027575 |
| ENSG00000149541 | B3GAT3 | 0.450824 | 0.027632 |
| ENSG00000166068 | SPRED1 | −0.41663 | 0.027649 |
| ENSG00000140718 | FTO | −0.34405 | 0.027654 |
| ENSG00000215301 | DDX3X | −0.30433 | 0.027667 |
| ENSG00000158792 | SPATA2L | 0.519296 | 0.027719 |
| ENSG00000175387 | SMAD2 | −0.30655 | 0.027719 |
| ENSG00000244682 | | 0.947384 | 0.027719 |
| ENSG00000183963 | SMTN | 0.389893 | 0.027743 |
| ENSG00000197483 | ZNF628 | 0.698839 | 0.027743 |
| ENSG00000185000 | DGAT1 | 0.329762 | 0.027845 |
| ENSG00000184481 | FOXO4 | 0.505257 | 0.02791 |
| ENSG00000100442 | FKBP3 | −0.3485 | 0.027921 |
| ENSG00000128159 | TUBGCP6 | 0.328568 | 0.027934 |
| ENSG00000049239 | H6PD | −0.35294 | 0.027969 |

SUPPLEMENTARY TABLE 1-continued

List of the identified differentially expressed transcripts after DE analysis using DESeq2 and edgeR-

| ENSEMBL | Symbol | Log$_2$ Fold Change | False discovery rate |
|---|---|---|---|
| ENSG00000128581 | IFT22 | −0.47934 | 0.027969 |
| ENSG00000163104 | SMARCAD1 | −0.30162 | 0.027969 |
| ENSG00000165283 | STOML2 | 0.311615 | 0.028019 |
| ENSG00000214160 | ALG3 | 0.319024 | 0.028077 |
| ENSG00000136930 | PSMB7 | 0.29736 | 0.02808 |
| ENSG00000110911 | SLC11A2 | 0.382491 | 0.028093 |
| ENSG00000107854 | TNKS2 | −0.29414 | 0.028181 |
| ENSG00000145012 | LPP | −0.33129 | 0.028181 |
| ENSG00000226535 |  | 0.380353 | 0.028181 |
| ENSG00000169592 | INO80E | 0.331217 | 0.028182 |
| ENSG00000013583 | HEBP1 | −0.34755 | 0.028203 |
| ENSG00000050344 | NFE2L3 | 0.512603 | 0.028218 |
| ENSG00000158481 | CD1C | 0.925001 | 0.028221 |
| ENSG00000079308 | TNS1 | 0.368817 | 0.028267 |
| ENSG00000186448 | ZNF197 | −0.31257 | 0.028328 |
| ENSG00000131013 | PPIL4 | −0.33804 | 0.028331 |
| ENSG00000133794 | ARNTL | 0.423379 | 0.028331 |
| ENSG00000183742 | MACC1 | 0.438106 | 0.028331 |
| ENSG00000092068 | SLC7A8 | 0.623359 | 0.028331 |
| ENSG00000091009 | RBM27 | −0.32286 | 0.028367 |
| ENSG00000104853 | CLPTM1 | 0.314041 | 0.028387 |
| ENSG00000110063 | DCPS | 0.336695 | 0.028533 |
| ENSG00000137574 | TGS1 | −0.30443 | 0.028533 |
| ENSG00000180771 |  | −0.40431 | 0.028546 |
| ENSG00000186470 | BTN3A2 | −0.44468 | 0.028573 |
| ENSG00000213079 | SCAF8 | −0.29291 | 0.028575 |
| ENSG00000259985 |  | −0.60376 | 0.028575 |
| ENSG00000127980 | PEX1 | −0.3771 | 0.028578 |
| ENSG00000180304 | OAZ2 | 0.316203 | 0.028596 |
| ENSG00000074219 | TEAD2 | −0.75243 | 0.028725 |
| ENSG00000167005 | NUDT21 | −0.31693 | 0.028797 |
| ENSG00000085840 | ORC1 | 0.322102 | 0.028798 |
| ENSG00000113328 | CCNG1 | −0.29773 | 0.028798 |
| ENSG00000234130 |  | −0.38615 | 0.028889 |
| ENSG00000213516 | RBMXL1 | −0.31033 | 0.028915 |
| ENSG00000181904 | C5orf24 | −0.29326 | 0.028928 |
| ENSG00000197021 | CXorf40B | 0.366028 | 0.028928 |
| ENSG00000072163 | LIMS2 | −0.70671 | 0.028958 |
| ENSG00000182858 | ALG12 | 0.373935 | 0.028958 |
| ENSG00000213462 | ERV3-1 | −0.37946 | 0.029015 |
| ENSG00000100815 | TRIP11 | −0.32467 | 0.029028 |
| ENSG00000174100 |  | −0.30252 | 0.029028 |
| ENSG00000105229 | PIAS4 | 0.371897 | 0.02908 |
| ENSG00000187634 | SAMD11 | −0.59373 | 0.029122 |
| ENSG00000197147 | LRRC8B | −0.32476 | 0.029274 |
| ENSG00000267002 |  | −0.57749 | 0.029274 |
| ENSG00000117009 | KMO | 0.919167 | 0.029307 |
| ENSG00000166508 | MCM7 | 0.323116 | 0.029331 |
| ENSG00000065970 | FOXJ2 | 0.463358 | 0.029594 |
| ENSG00000273151 |  | 0.66487 | 0.029594 |
| ENSG00000105771 | SMG9 | 0.329576 | 0.029599 |
| ENSG00000168675 | LDLRAD4 | −0.39528 | 0.029616 |
| ENSG00000198455 | ZXDB | −0.42742 | 0.02981 |
| ENSG00000205755 | CRLF2 | 0.879343 | 0.029879 |
| ENSG00000272505 |  | 0.885555 | 0.02996 |
| ENSG00000130748 | TMEM160 | 0.740945 | 0.029998 |
| ENSG00000235438 |  | 0.823886 | 0.030017 |
| ENSG00000168938 | PPIC | −0.87125 | 0.030055 |
| ENSG00000065150 | IPO5 | −0.29414 | 0.030085 |
| ENSG00000245849 | RAD51-AS1 | −0.75536 | 0.030141 |
| ENSG00000263327 | TAPT1-AS1 | −0.61552 | 0.030195 |
| ENSG00000163975 | MELTF | 0.419286 | 0.030222 |
| ENSG00000118705 | RPN2 | 0.284049 | 0.030237 |
| ENSG00000164151 | ICE1 | −0.29305 | 0.030237 |
| ENSG00000167264 | DUS2 | 0.364037 | 0.030237 |
| ENSG00000237161 |  | −0.38978 | 0.030237 |
| ENSG00000181894 | ZNF329 | −0.45354 | 0.030267 |
| ENSG00000065183 | WDR3 | −0.31717 | 0.030287 |
| ENSG00000120137 | PANK3 | −0.30984 | 0.030349 |
| ENSG00000078124 | ACER3 | 0.420996 | 0.030355 |
| ENSG00000083168 | KAT6A | −0.32245 | 0.030424 |
| ENSG00000110066 | KMT5B | −0.29024 | 0.030424 |
| ENSG00000174744 | BRMS1 | 0.368008 | 0.030476 |
| ENSG00000180488 | FAM73A | −0.40588 | 0.030476 |
| ENSG00000196659 | TTC30B | −0.54917 | 0.030506 |

SUPPLEMENTARY TABLE 1-continued

List of the identified differentially expressed transcripts after DE analysis using DESeq2 and edgeR-

| ENSEMBL | Symbol | Log$_2$ Fold Change | False discovery rate |
|---|---|---|---|
| ENSG00000142459 | EVI5L | 0.448094 | 0.030556 |
| ENSG00000204592 | HLA-E | 0.286317 | 0.030692 |
| ENSG00000172009 | THOP1 | 0.313926 | 0.030747 |
| ENSG00000130669 | PAK4 | 0.382129 | 0.03078 |
| ENSG00000116337 | AMPD2 | 0.340953 | 0.030804 |
| ENSG00000116497 | S100PBP | −0.33473 | 0.030866 |
| ENSG00000136628 | EPRS | −0.31548 | 0.030954 |
| ENSG00000111752 | PHC1 | −0.74152 | 0.030979 |
| ENSG00000235437 | LINC01278 | −0.39621 | 0.031027 |
| ENSG00000039123 | SKIV2L2 | −0.28796 | 0.031078 |
| ENSG00000143751 | SDE2 | −0.31529 | 0.031078 |
| ENSG00000111859 | NEDD9 | 0.340948 | 0.031082 |
| ENSG00000103174 | NAGPA | 0.374278 | 0.031088 |
| ENSG00000243445 |  | 0.520097 | 0.031088 |
| ENSG00000126267 | COX6B1 | 0.338242 | 0.031103 |
| ENSG00000213107 |  | 0.875174 | 0.031244 |
| ENSG00000226986 |  | 0.436808 | 0.031382 |
| ENSG00000182809 | CRIP2 | −0.54655 | 0.031566 |
| ENSG00000111731 | C2CD5 | −0.31234 | 0.031574 |
| ENSG00000107551 | RASSF4 | 0.819833 | 0.03162 |
| ENSG00000107902 | LHPP | −0.39798 | 0.031688 |
| ENSG00000241781 |  | 0.762712 | 0.031763 |
| ENSG00000198909 | MAP3K3 | 0.378166 | 0.031763 |
| ENSG00000171858 | RPS21 | 0.26898 | 0.031816 |
| ENSG00000164338 | UTP15 | −0.32461 | 0.031817 |
| ENSG00000228305 |  | 0.396302 | 0.031855 |
| ENSG00000161813 | LARP4 | −0.30495 | 0.031857 |
| ENSG00000137522 | RNF121 | 0.383089 | 0.031873 |
| ENSG00000067533 | RRP15 | −0.34856 | 0.031875 |
| ENSG00000173275 | ZNF449 | −0.42403 | 0.031875 |
| ENSG00000165959 | CLMN | −0.79295 | 0.031882 |
| ENSG00000100075 | SLC25A1 | 0.330826 | 0.032019 |
| ENSG00000104946 | TBC1D17 | 0.561834 | 0.032045 |
| ENSG00000156976 | EIF4A2 | −0.27432 | 0.032045 |
| ENSG00000129515 | SNX6 | −0.28839 | 0.032069 |
| ENSG00000124164 | VAPB | −0.31993 | 0.032368 |
| ENSG00000099194 | SCD | −0.34186 | 0.03237 |
| ENSG00000267796 | LIN37 | 0.691438 | 0.032376 |
| ENSG00000188976 | NOC2L | 0.315468 | 0.032595 |
| ENSG00000111775 | COX6A1 | 0.34457 | 0.032612 |
| ENSG00000085514 | PILRA | 0.920088 | 0.03265 |
| ENSG00000082074 | FYB | −0.31139 | 0.032662 |
| ENSG00000136643 | RPS6KC1 | −0.32265 | 0.032714 |
| ENSG00000198642 | KLHL9 | −0.29631 | 0.032714 |
| ENSG00000029725 | RABEP1 | −0.27732 | 0.032756 |
| ENSG00000129317 | PUS7L | −0.41455 | 0.032814 |
| ENSG00000076928 | ARHGEF1 | 0.357442 | 0.032867 |
| ENSG00000104131 | EIF3J | −0.29419 | 0.032936 |
| ENSG00000141582 | CBX4 | 0.436496 | 0.032954 |
| ENSG00000124813 | RUNX2 | 0.672625 | 0.033101 |
| ENSG00000125970 | RALY | 0.303775 | 0.033128 |
| ENSG00000103994 | ZNF106 | −0.29326 | 0.033193 |
| ENSG00000172840 | PDP2 | −0.44534 | 0.033231 |
| ENSG00000169221 | TBC1D10B | 0.289223 | 0.033232 |
| ENSG00000213820 |  | 0.784087 | 0.033326 |
| ENSG00000175455 | CCDC14 | −0.29867 | 0.033334 |
| ENSG00000085449 | WDFY1 | −0.29306 | 0.033355 |
| ENSG00000102743 | SLC25A15 | −0.40501 | 0.033355 |
| ENSG00000197903 | HIST1H2BK | −0.39326 | 0.033355 |
| ENSG00000138442 | WDR12 | −0.28101 | 0.033368 |
| ENSG00000065883 | CDK13 | −0.30784 | 0.033394 |
| ENSG00000164626 | KCNK5 | 0.400576 | 0.033395 |
| ENSG00000257564 |  | −0.52638 | 0.033442 |
| ENSG00000164944 | KIAA1429 | −0.28654 | 0.033479 |
| ENSG00000120162 | MOB3B | −0.44426 | 0.033524 |
| ENSG00000137100 | DCTN3 | 0.302951 | 0.033524 |
| ENSG00000088247 | KHSRP | 0.283885 | 0.03363 |
| ENSG00000172292 | CERS6 | −0.2835 | 0.033676 |
| ENSG00000141002 | TCF25 | 0.30507 | 0.033725 |
| ENSG00000108292 |  | 0.369741 | 0.033769 |
| ENSG00000060656 | PTPRU | 0.742097 | 0.034036 |
| ENSG00000104960 | PTOV1 | 0.321545 | 0.034036 |
| ENSG00000251369 | ZNF550 | −0.37399 | 0.034036 |
| ENSG00000204775 |  | 0.829919 | 0.034097 |
| ENSG00000198894 | CIPC | −0.414 | 0.03422 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000157353 | FUK | 0.404385 | 0.034239 |
| ENSG00000130511 | SSBP4 | 0.378562 | 0.034283 |
| ENSG00000070495 | JMJD6 | 0.334273 | 0.034358 |
| ENSG00000173960 | UBXN2A | −0.36764 | 0.034358 |
| ENSG00000083750 | RRAGB | −0.44735 | 0.034565 |
| ENSG00000196715 | VKORC1L1 | −0.31331 | 0.034704 |
| ENSG00000157514 | TSC22D3 | −0.86917 | 0.034705 |
| ENSG00000111676 | ATN1 | 0.387468 | 0.034726 |
| ENSG00000138796 | HADH | −0.31456 | 0.0349 |
| ENSG00000140577 | CRTC3 | −0.35737 | 0.0349 |
| ENSG00000198440 | ZNF583 | −0.45661 | 0.0349 |
| ENSG00000174021 | GNG5 | 0.331292 | 0.034963 |
| ENSG00000163629 | PTPN13 | −0.37694 | 0.034968 |
| ENSG00000170906 | NDUFA3 | 0.334657 | 0.034976 |
| ENSG00000083720 | OXCT1 | −0.34231 | 0.035019 |
| ENSG00000104976 | SNAPC2 | 0.375666 | 0.035019 |
| ENSG00000136153 | LMO7 | −0.44708 | 0.035019 |
| ENSG00000111678 | C12orf57 | 0.402918 | 0.035033 |
| ENSG00000138641 | HERC3 | −0.34293 | 0.035181 |
| ENSG00000161800 | RACGAP1 | 0.30854 | 0.035181 |
| ENSG00000234494 | SP2-AS1 | −0.83065 | 0.035211 |
| ENSG00000177084 | POLE | −0.26981 | 0.035247 |
| ENSG00000123395 | ATG101 | 0.328557 | 0.035251 |
| ENSG00000092531 | SNAP23 | −0.27042 | 0.035406 |
| ENSG00000180626 | ZNF594 | −0.5731 | 0.035593 |
| ENSG00000100092 | SH3BP1 | 0.281762 | 0.035607 |
| ENSG00000159433 | STARD9 | −0.41877 | 0.03562 |
| ENSG00000204634 | TBC1D8 | 0.414243 | 0.03562 |
| ENSG00000160741 | CRTC2 | 0.330604 | 0.0357 |
| ENSG00000079805 | DNM2 | 0.335292 | 0.035768 |
| ENSG00000213742 | ZNF337-AS1 | −0.78459 | 0.03577 |
| ENSG00000180479 | ZNF571 | −0.51957 | 0.035838 |
| ENSG00000221829 | FANCG | 0.33546 | 0.035838 |
| ENSG00000116675 | DNAJC6 | −0.86089 | 0.035898 |
| ENSG00000124357 | NAGK | 0.450223 | 0.035965 |
| ENSG00000135617 | PRADC1 | 0.410585 | 0.036001 |
| ENSG00000228797 |  | 0.804013 | 0.036039 |
| ENSG00000105723 | GSK3A | 0.317855 | 0.036084 |
| ENSG00000010278 | CD9 | −0.88652 | 0.036087 |
| ENSG00000117054 | ACADM | −0.28196 | 0.03609 |
| ENSG00000271856 | LINC01215 | 0.425156 | 0.03609 |
| ENSG00000105855 | ITGB8 | −0.48764 | 0.036269 |
| ENSG00000049656 | CLPTM1L | 0.281684 | 0.03631 |
| ENSG00000157693 | C9orf91 | −0.37167 | 0.036365 |
| ENSG00000113407 | TARS | −0.28671 | 0.036433 |
| ENSG00000140105 | WARS | 0.319 | 0.036559 |
| ENSG00000162441 | LZIC | −0.31633 | 0.036564 |
| ENSG00000171241 | SHCBP1 | 0.338409 | 0.03657 |
| ENSG00000226721 |  | 0.480475 | 0.036688 |
| ENSG00000130338 | TULP4 | −0.39392 | 0.036833 |
| ENSG00000137965 | IFI44 | −0.86485 | 0.036836 |
| ENSG00000166439 | RNF169 | −0.29334 | 0.036847 |
| ENSG00000171291 | ZNF439 | −0.392 | 0.036847 |
| ENSG00000188647 | PTAR1 | −0.33109 | 0.036847 |
| ENSG00000075945 | KIFAP3 | −0.3458 | 0.036849 |
| ENSG00000213402 | PTPRCAP | 0.360824 | 0.036849 |
| ENSG00000266282 |  | 0.332567 | 0.036915 |
| ENSG00000147679 | UTP23 | −0.34784 | 0.036998 |
| ENSG00000171940 | ZNF217 | −0.33458 | 0.036998 |
| ENSG00000174903 | RAB1B | 0.290818 | 0.03711 |
| ENSG00000109466 | KLHL2 | 0.346891 | 0.03717 |
| ENSG00000103226 | NOMO3 | 0.763012 | 0.037201 |
| ENSG00000260336 |  | −0.3857 | 0.037227 |
| ENSG00000204525 | HLA-C | 0.342961 | 0.037296 |
| ENSG00000164604 | GPR85 | 0.345021 | 0.037467 |
| ENSG00000233137 |  | −0.28999 | 0.037608 |
| ENSG00000178149 | DALRD3 | −0.35871 | 0.037647 |
| ENSG00000244038 | DDOST | 0.28964 | 0.037677 |
| ENSG00000164631 | ZNF12 | −0.29345 | 0.03775 |
| ENSG00000203880 | PCMTD2 | −0.33809 | 0.037861 |
| ENSG00000137275 | RIPK1 | −0.2949 | 0.037982 |
| ENSG00000138757 | G3BP2 | −0.26941 | 0.038024 |
| ENSG00000265206 |  | 0.441956 | 0.038027 |
| ENSG00000133561 | GIMAP6 | −0.37308 | 0.038081 |
| ENSG00000136270 | TBRG4 | 0.294276 | 0.038153 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000146410 | MTFR2 | 0.386215 | 0.038153 |
| ENSG00000052795 | FNIP2 | −0.362 | 0.03825 |
| ENSG00000102317 | RBM3 | 0.290395 | 0.03831 |
| ENSG00000139637 | C12orf10 | 0.336396 | 0.03832 |
| ENSG00000128050 | PAICS | −0.28793 | 0.03841 |
| ENSG00000115216 | NRBP1 | 0.273082 | 0.038415 |
| ENSG00000088298 | EDEM2 | 0.310185 | 0.038434 |
| ENSG00000167987 | VPS37C | 0.361879 | 0.038434 |
| ENSG00000167536 | DHRS13 | 0.493797 | 0.038462 |
| ENSG00000116984 | MTR | −0.29159 | 0.038545 |
| ENSG00000181135 | ZNF707 | 0.426152 | 0.038565 |
| ENSG00000113658 | SMAD5 | −0.30145 | 0.038681 |
| ENSG00000105011 | ASF1B | 0.331346 | 0.038729 |
| ENSG00000186283 | TOR3A | 0.291333 | 0.038782 |
| ENSG00000167658 | EEF2 | 0.268495 | 0.038787 |
| ENSG00000086200 | IPO11 | −0.33522 | 0.038862 |
| ENSG00000117602 | RCAN3 | −0.32445 | 0.038908 |
| ENSG00000273142 | | 0.472199 | 0.038908 |
| ENSG00000131748 | STARD3 | 0.328155 | 0.038949 |
| ENSG00000168061 | SAC3D1 | 0.568004 | 0.038949 |
| ENSG00000169018 | FEM1B | −0.28967 | 0.038949 |
| ENSG00000096746 | HNRNPH3 | −0.30885 | 0.039095 |
| ENSG00000198373 | WWP2 | 0.293489 | 0.039114 |
| ENSG00000248866 | USP46-AS1 | −0.67122 | 0.039154 |
| ENSG00000118482 | PHF3 | −0.27539 | 0.039262 |
| ENSG00000113070 | HBEGF | 0.40574 | 0.03936 |
| ENSG00000126903 | SLC10A3 | 0.32776 | 0.039477 |
| ENSG00000080823 | MOK | −0.63506 | 0.039551 |
| ENSG00000248530 | | 0.610436 | 0.03959 |
| ENSG00000083535 | PIBF1 | −0.35756 | 0.039606 |
| ENSG00000141068 | KSR1 | 0.380968 | 0.039646 |
| ENSG00000258289 | CHURC1 | −0.30165 | 0.039682 |
| ENSG00000103522 | IL21R | 0.91582 | 0.039724 |
| ENSG00000132635 | PCED1A | −0.36109 | 0.039799 |
| ENSG00000231925 | TAPBP | 0.327328 | 0.039799 |
| ENSG00000065675 | PRKCQ | −0.34375 | 0.039809 |
| ENSG00000185043 | CIB1 | 0.331271 | 0.039826 |
| ENSG00000123739 | PLA2G12A | −0.34345 | 0.039862 |
| ENSG00000158290 | CUL4B | −0.31211 | 0.039943 |
| ENSG00000005175 | RPAP3 | −0.29366 | 0.039949 |
| ENSG00000048707 | VPS13D | −0.31022 | 0.039949 |
| ENSG00000159618 | ADGRG5 | 0.31125 | 0.039949 |
| ENSG00000103253 | HAGHL | 0.606761 | 0.039981 |
| ENSG00000158488 | CD1E | 0.802822 | 0.039999 |
| ENSG00000259000 | | −0.37779 | 0.040284 |
| ENSG00000206530 | CFAP44 | −0.40738 | 0.04045 |
| ENSG00000171992 | SYNPO | −0.84728 | 0.040501 |
| ENSG00000079999 | KEAP1 | 0.290542 | 0.040557 |
| ENSG00000128791 | TWSG1 | −0.3047 | 0.040761 |
| ENSG00000099977 | DDT | 0.384817 | 0.040769 |
| ENSG00000166266 | CUL5 | −0.29456 | 0.040769 |
| ENSG00000171823 | FBXL14 | 0.441765 | 0.040769 |
| ENSG00000246596 | | −0.78315 | 0.040769 |
| ENSG00000091527 | CDV3 | −0.26197 | 0.04087 |
| ENSG00000100297 | MCM5 | 0.330124 | 0.04087 |
| ENSG00000242612 | DECR2 | 0.403091 | 0.04087 |
| ENSG00000189350 | FAM179A | 0.664839 | 0.040934 |
| ENSG00000149516 | MS4A3 | 0.550959 | 0.040978 |
| ENSG00000153107 | ANAPC1 | −0.32429 | 0.040978 |
| ENSG00000087884 | AAMDC | −0.45293 | 0.041083 |
| ENSG00000132485 | ZRANB2 | −0.27824 | 0.041083 |
| ENSG00000167136 | ENDOG | 0.419689 | 0.041083 |
| ENSG00000130649 | CYP2E1 | −0.76679 | 0.041113 |
| ENSG00000189043 | NDUFA4 | 0.28242 | 0.041152 |
| ENSG00000082397 | EPB41L3 | 0.662187 | 0.041326 |
| ENSG00000146072 | TNFRSF21 | 0.432055 | 0.041384 |
| ENSG00000119041 | GTF3C3 | −0.27341 | 0.041386 |
| ENSG00000203485 | INF2 | 0.29506 | 0.041425 |
| ENSG00000162980 | ARL5A | −0.28518 | 0.041443 |
| ENSG00000249353 | | −0.26944 | 0.041443 |
| ENSG00000173480 | ZNF417 | −0.42215 | 0.041457 |
| ENSG00000164620 | RELL2 | 0.46452 | 0.041746 |
| ENSG00000263002 | ZNF234 | −0.38255 | 0.041852 |
| ENSG00000102100 | SLC35A2 | 0.342606 | 0.041922 |
| ENSG00000271707 | | 0.369207 | 0.04199 |

SUPPLEMENTARY TABLE 1-continued

List of the identified differentially expressed transcripts
after DE analysis using DESeq2 and edgeR-

| ENSEMBL | Symbol | Log₂ Fold Change | False discovery rate |
|---|---|---|---|
| ENSG00000234284 | ZNF879 | −0.55273 | 0.042015 |
| ENSG00000248092 | | −0.42288 | 0.042017 |
| ENSG00000091127 | PUS7 | −0.31394 | 0.042023 |
| ENSG00000048649 | RSF1 | −0.29471 | 0.042045 |
| ENSG00000233347 | | 0.395566 | 0.042071 |
| ENSG00000023516 | AKAP11 | −0.35608 | 0.042094 |
| ENSG00000171813 | PWWP2B | 0.407158 | 0.042094 |
| ENSG00000141425 | RPRD1A | −0.29124 | 0.042222 |
| ENSG00000205609 | EIF3CL | −0.33808 | 0.042223 |
| ENSG00000124743 | KLHL31 | −0.75469 | 0.04239 |
| ENSG00000148288 | GBGT1 | 0.339303 | 0.042567 |
| ENSG00000112419 | PHACTR2 | 0.316047 | 0.042693 |
| ENSG00000100030 | MAPK1 | −0.32634 | 0.042748 |
| ENSG00000227671 | | −0.30052 | 0.042798 |
| ENSG00000237861 | | 0.469991 | 0.042801 |
| ENSG00000056998 | GYG2 | −0.56062 | 0.042821 |
| ENSG00000068120 | COASY | 0.287873 | 0.042821 |
| ENSG00000213020 | ZNF611 | −0.40371 | 0.042821 |
| ENSG00000213904 | LIPE-AS1 | 0.658215 | 0.042837 |
| ENSG00000187954 | CYHR1 | 0.345741 | 0.042896 |
| ENSG00000167565 | SERTAD3 | 0.41154 | 0.042898 |
| ENSG00000125484 | GTF3C4 | −0.29894 | 0.043016 |
| ENSG00000170266 | GLB1 | 0.293928 | 0.043047 |
| ENSG00000183484 | GPR132 | 0.389797 | 0.043047 |
| ENSG00000176018 | LYSMD3 | −0.30548 | 0.043166 |
| ENSG00000100330 | MTMR3 | 0.300731 | 0.043212 |
| ENSG00000197779 | ZNF81 | −0.44587 | 0.043218 |
| ENSG00000204131 | NHSL2 | −0.40728 | 0.043321 |
| ENSG00000156873 | PHKG2 | 0.324099 | 0.043348 |
| ENSG00000246985 | SOCS2-AS1 | −0.46305 | 0.043435 |
| ENSG00000145725 | PPIP5K2 | −0.3464 | 0.043479 |
| ENSG00000167850 | CD300C | 0.425908 | 0.043513 |
| ENSG00000096872 | IFT74 | −0.378 | 0.043537 |
| ENSG00000214181 | | −0.49113 | 0.043537 |
| ENSG00000146425 | DYNLT1 | −0.37398 | 0.043561 |
| ENSG00000118454 | ANKRD13C | −0.31732 | 0.043592 |
| ENSG00000170396 | ZNF804A | 0.48413 | 0.043659 |
| ENSG00000217835 | | −0.44297 | 0.043673 |
| ENSG00000107290 | SETX | −0.31164 | 0.043687 |
| ENSG00000101216 | GMEB2 | 0.329707 | 0.043713 |
| ENSG00000136261 | BZW2 | −0.25874 | 0.043769 |
| ENSG00000137700 | SLC37A4 | 0.299175 | 0.043839 |
| ENSG00000160813 | PPP1R35 | 0.469291 | 0.043839 |
| ENSG00000013523 | ANGEL1 | −0.32895 | 0.043917 |
| ENSG00000184545 | DUSP8 | 0.897719 | 0.043917 |
| ENSG00000138594 | TMOD3 | −0.27008 | 0.044031 |
| ENSG00000062725 | APPBP2 | −0.30757 | 0.044062 |
| ENSG00000072958 | AP1M1 | 0.30944 | 0.044073 |
| ENSG00000169032 | MAP2K1 | 0.299435 | 0.044154 |
| ENSG00000132274 | TRIM22 | −0.28434 | 0.044178 |
| ENSG00000104689 | TNFRSF10A | 0.446534 | 0.04426 |
| ENSG00000237181 | | 0.674406 | 0.044273 |
| ENSG00000185261 | KIAA0825 | −0.68565 | 0.044315 |
| ENSG00000251667 | | −0.63653 | 0.044315 |
| ENSG00000167114 | SLC27A4 | 0.35555 | 0.044351 |
| ENSG00000110799 | VWF | −0.82899 | 0.044439 |
| ENSG00000126777 | KTN1 | −0.26828 | 0.044439 |
| ENSG00000221930 | | 0.496731 | 0.044581 |
| ENSG00000173653 | RCE1 | 0.346792 | 0.044589 |
| ENSG00000128590 | DNAJB9 | 0.349466 | 0.044623 |
| ENSG00000168038 | ULK4 | −0.44815 | 0.044623 |
| ENSG00000123552 | USP45 | −0.32603 | 0.044654 |
| ENSG00000166963 | MAP1A | 0.496368 | 0.044736 |
| ENSG00000073111 | MCM2 | 0.311371 | 0.044825 |
| ENSG00000170006 | TMEM154 | 0.308232 | 0.044898 |
| ENSG00000172339 | ALG14 | 0.482923 | 0.044995 |
| ENSG00000196954 | CASP4 | −0.27853 | 0.045032 |
| ENSG00000121289 | CEP89 | −0.40322 | 0.04512 |
| ENSG00000163634 | THOC7 | −0.2888 | 0.045458 |
| ENSG00000108510 | MED13 | −0.28099 | 0.045467 |
| ENSG00000074935 | TUBE1 | −0.32509 | 0.045555 |
| ENSG00000181826 | RELL1 | 0.54915 | 0.045555 |
| ENSG00000043514 | TRIT1 | −0.33115 | 0.04559 |
| ENSG00000086730 | LAT2 | −0.28347 | 0.04559 |
| ENSG00000103591 | AAGAB | 0.284062 | 0.045783 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000134824 | FADS2 | −0.26877 | 0.045801 |
| ENSG00000213523 | SRA1 | 0.36825 | 0.045801 |
| ENSG00000105486 | LIG1 | 0.324822 | 0.046013 |
| ENSG00000158711 | ELK4 | −0.27072 | 0.046041 |
| ENSG00000163156 | SCNM1 | 0.29876 | 0.04608 |
| ENSG00000142156 | COL6A1 | 0.903154 | 0.046242 |
| ENSG00000139624 | CERS5 | 0.283352 | 0.04628 |
| ENSG00000231007 | | 0.349273 | 0.046371 |
| ENSG00000177888 | ZBTB41 | −0.42454 | 0.046415 |
| ENSG00000187742 | SECISBP2 | −0.27391 | 0.046456 |
| ENSG00000104915 | STX10 | 0.312762 | 0.046583 |
| ENSG00000164440 | TXLNB | −0.88266 | 0.046583 |
| ENSG00000237819 | LOC101927497 | −0.84081 | 0.046583 |
| ENSG00000131188 | PRR7 | 0.82053 | 0.04663 |
| ENSG00000111877 | MCM9 | −0.32868 | 0.046718 |
| ENSG00000004478 | FKBP4 | −0.26786 | 0.04677 |
| ENSG00000121152 | NCAPH | 0.317246 | 0.04677 |
| ENSG00000120800 | UTP20 | −0.33114 | 0.046815 |
| ENSG00000170949 | ZNF160 | −0.30726 | 0.046979 |
| ENSG00000092140 | G2E3 | −0.30438 | 0.047011 |
| ENSG00000254244 | | −0.32078 | 0.047124 |
| ENSG00000159423 | ALDH4A1 | 0.329673 | 0.04725 |
| ENSG00000267889 | | 0.797029 | 0.04725 |
| ENSG00000151233 | GXYLT1 | −0.29432 | 0.04727 |
| ENSG00000062370 | ZNF112 | −0.40156 | 0.047294 |
| ENSG00000164134 | NAA15 | −0.28539 | 0.047297 |
| ENSG00000169299 | PGM2 | 0.263156 | 0.047341 |
| ENSG00000198429 | ZNF69 | −0.63875 | 0.047341 |
| ENSG00000120899 | PTK2B | 0.284509 | 0.047406 |
| ENSG00000141564 | RPTOR | 0.289999 | 0.047406 |
| ENSG00000232626 | | 0.645127 | 0.047463 |
| ENSG00000038358 | EDC4 | 0.287393 | 0.047487 |
| ENSG00000177030 | DEAF1 | 0.305895 | 0.047533 |
| ENSG00000115421 | PAPOLG | −0.30024 | 0.047667 |
| ENSG00000138439 | FAM117B | −0.34657 | 0.047667 |
| ENSG00000064703 | DDX20 | −0.27217 | 0.047725 |
| ENSG00000065526 | SPEN | −0.30939 | 0.047817 |
| ENSG00000103168 | TAF1C | 0.324331 | 0.047868 |
| ENSG00000101017 | CD40 | 0.896776 | 0.048005 |
| ENSG00000112996 | MRPS30 | −0.28112 | 0.048282 |
| ENSG00000165671 | NSD1 | −0.30922 | 0.048303 |
| ENSG00000140988 | RPS2 | 0.257277 | 0.048352 |
| ENSG00000072736 | NFATC3 | −0.26318 | 0.048461 |
| ENSG00000132326 | PER2 | −0.31931 | 0.048461 |
| ENSG00000112234 | FBXL4 | −0.35476 | 0.048583 |
| ENSG00000125686 | MED1 | −0.31803 | 0.048583 |
| ENSG00000177374 | HIC1 | 0.720065 | 0.048598 |
| ENSG00000225791 | TRAM2-AS1 | −0.42449 | 0.048622 |
| ENSG00000108468 | CBX1 | −0.32884 | 0.048781 |
| ENSG00000257497 | | 0.773978 | 0.048831 |
| ENSG00000178999 | AURKB | 0.326077 | 0.048893 |
| ENSG00000135077 | HAVCR2 | −0.4042 | 0.048964 |
| ENSG00000272093 | | −0.53241 | 0.048971 |
| ENSG00000119403 | PHF19 | 0.344077 | 0.048978 |
| ENSG00000151067 | CACNA1C | −0.62253 | 0.048978 |
| ENSG00000197498 | RPF2 | −0.28368 | 0.048987 |
| ENSG00000198598 | MMP17 | 0.455932 | 0.048998 |
| ENSG00000164691 | TAGAP | 0.365079 | 0.049032 |
| ENSG00000101126 | ADNP | −0.27824 | 0.049042 |
| ENSG00000163611 | SPICE1 | −0.36633 | 0.049042 |
| ENSG00000167965 | MLST8 | 0.34623 | 0.049042 |
| ENSG00000169957 | ZNF768 | 0.290289 | 0.049042 |
| ENSG00000197013 | ZNF429 | −0.51202 | 0.049042 |
| ENSG00000165209 | STRBP | −0.28899 | 0.049066 |
| ENSG00000173141 | MRPL57 | 0.311246 | 0.049076 |
| ENSG00000179526 | SHARPIN | 0.332599 | 0.0491 |
| ENSG00000198019 | FCGR1B | 0.822081 | 0.049134 |
| ENSG00000147130 | ZMYM3 | −0.30395 | 0.049163 |
| ENSG00000243364 | EFNA4 | 0.486118 | 0.049336 |
| ENSG00000127995 | CASD1 | −0.32068 | 0.049528 |
| ENSG00000157107 | FCHO2 | −0.32542 | 0.049646 |
| ENSG00000174032 | SLC25A30 | −0.35014 | 0.049675 |
| ENSG00000123009 | | 0.284078 | 0.049793 |
| ENSG00000148426 | PROSER2 | −0.43254 | 0.049793 |
| ENSG00000180855 | ZNF443 | −0.53535 | 0.049793 |

SUPPLEMENTARY TABLE 1-continued

List of the identified differentially expressed transcripts
after DE analysis using DESeq2 and edgeR-

| ENSEMBL | Symbol | Log$_2$ Fold Change | False discovery rate |
|---|---|---|---|
| ENSG00000119707 | RBM25 | −0.26813 | 0.049862 |
| ENSG00000082258 | CCNT2 | −0.28419 | 0.049908 |
| ENSG00000151694 | ADAM17 | 0.34168 | 0.049944 |
| ENSG00000119314 | PTBP3 | −0.28674 | 0.049945 |
| ENSG00000131437 | KIF3A | −0.3975 | 0.04995 |
| ENSG00000160799 | CCDC12 | 0.310317 | 0.04999 |

SUPPLEMENTARY TABLE 2

GO biological processes identified as overrepresented in an overrepresentation analysis using the DE transcripts. The presented GO terms were called significant with a Bonferroni corrected P-value below 0.05. The corrected p-values are reported below. Number of mapped IDs from reference: 14774, unmapped IDs from reference: 12854; number of mapped IDs from DE transcripts: 3298, unmapped IDs from DE transcripts: 346.

| GO Biological Process | # of matches | Expected # of matches | Fold Enrichment | $P_{FWER}$-value |
|---|---|---|---|---|
| myeloid leukocyte activation (GO:0002274) | 46 | 19.59 | 2.35 | 1.74E−03 |
| leukocyte chemotaxis (GO:0030595) | 45 | 21.37 | 2.11 | 3.82E−02 |
| maintenance of location (GO:0051235) | 57 | 29.17 | 1.95 | 2.18E−02 |
| cell chemotaxis (GO:0060326) | 58 | 30.06 | 1.93 | 2.60E−02 |
| leukocyte migration (GO:0050900) | 89 | 49.43 | 1.8 | 1.52E−03 |
| positive regulation of MAP kinase activity (GO:0043406) | 71 | 39.63 | 1.79 | 2.89E−02 |
| regulation of angiogenesis (GO:0045765) | 69 | 38.52 | 1.79 | 3.93E−02 |
| regulation of vasculature development (GO:1901342) | 76 | 42.52 | 1.79 | 1.47E−02 |
| regulation of MAP kinase activity (GO:0043405) | 107 | 61.23 | 1.75 | 4.06E−04 |
| response to lipopolysaccharide (GO:0032496) | 102 | 60.11 | 1.7 | 3.08E−03 |
| positive regulation of cell migration (GO:0030335) | 125 | 74.14 | 1.69 | 2.27E−04 |
| positive regulation of cell motility (GO:2000147) | 128 | 76.37 | 1.68 | 2.14E−04 |
| positive regulation of cellular component movement (GO:0051272) | 131 | 78.37 | 1.67 | 1.72E−04 |
| inflammatory response (GO:0006954) | 140 | 84.16 | 1.66 | 7.58E−05 |
| positive regulation of locomotion (GO:0040017) | 130 | 78.15 | 1.66 | 2.53E−04 |
| response to molecule of bacterial origin (GO:0002237) | 103 | 62.56 | 1.65 | 1.01E−02 |
| regulation of cell migration (GO:0030334) | 202 | 125.79 | 1.61 | 7.49E−07 |
| positive regulation of MAPK cascade (GO:0043410) | 134 | 84.38 | 1.59 | 1.95E−03 |
| regulation of cell motility (GO:2000145) | 213 | 134.92 | 1.58 | 9.53E−07 |
| regulation of protein serine/threonine kinase activity (GO:0071900) | 143 | 91.28 | 1.57 | 1.66E−03 |
| regulation of locomotion (GO:0040012) | 218 | 139.82 | 1.56 | 1.63E−06 |
| regulation of cellular component movement (GO:0051270) | 225 | 145.61 | 1.55 | 1.78E−06 |
| blood vessel development (GO:0001568) | 131 | 85.49 | 1.53 | 1.57E−02 |
| taxis (GO:0042330) | 128 | 83.94 | 1.52 | 2.56E−02 |
| chemotaxis (GO:0006935) | 127 | 83.71 | 1.52 | 3.55E−02 |
| vasculature development (GO:0001944) | 135 | 89.06 | 1.52 | 1.88E−02 |
| negative regulation of programmed cell death (GO:0043069) | 225 | 151.17 | 1.49 | 3.86E−05 |
| negative regulation of apoptotic process (GO:0043066) | 221 | 148.95 | 1.48 | 6.76E−05 |
| regulation of MAPK cascade (GO:0043408) | 179 | 120.67 | 1.48 | 1.81E−03 |
| immune response (GO:0006955) | 280 | 191.03 | 1.47 | 2.06E−06 |
| positive regulation of immune system process (GO:0002684) | 240 | 164.76 | 1.46 | 6.93E−05 |
| cell activation (GO:0001775) | 158 | 108.65 | 1.45 | 2.67E−02 |
| negative regulation of cell death (GO:0060548) | 233 | 161.42 | 1.44 | 2.34E−04 |
| cell migration (GO:0016477) | 198 | 137.82 | 1.44 | 3.53E−03 |
| regulation of cell adhesion (GO:0030155) | 170 | 119.56 | 1.42 | 4.03E−02 |
| positive regulation of intracellular signal transduction (GO:1902533) | 230 | 162.31 | 1.42 | 1.15E−03 |
| regulation of immune system process (GO:0002682) | 366 | 259.38 | 1.41 | 2.85E−07 |
| response to lipid (GO:0033993) | 216 | 153.62 | 1.41 | 4.72E−03 |
| immune system process (GO:0002376) | 523 | 372.93 | 1.4 | 1.95E−11 |
| cellular response to oxygen-containing compound | | | | |

SUPPLEMENTARY TABLE 2-continued

GO biological processes identified as overrepresented in an overrepresentation analysis using the DE transcripts. The presented GO terms were called significant with a Bonferroni corrected P-value below 0.05. The corrected p-values are reported below. Number of mapped IDs from reference: 14774, unmapped IDs from reference: 12854; number of mapped IDs from DE transcripts: 3298, unmapped IDs from DE transcripts: 346.

| GO Biological Process | # of matches | Expected # of matches | Fold Enrichment | $P_{FWER}$-value |
|---|---|---|---|---|
| (GO:1901701) | 211 | 150.73 | 1.4 | 8.51E−03 |
| defense response (GO:0006952) | 290 | 207.95 | 1.39 | 1.09E−04 |
| response to oxygen-containing compound (GO:1901700) | 351 | 256.26 | 1.37 | 1.94E−05 |
| regulation of immune response (GO:0050776) | 217 | 158.74 | 1.37 | 2.84E−02 |
| positive regulation of protein phosphorylation (GO:0001934) | 216 | 158.97 | 1.36 | 4.36E−02 |
| regulation of cell proliferation (GO:0042127) | 368 | 272.07 | 1.35 | 2.98E−05 |
| locomotion (GO:0040011) | 256 | 189.91 | 1.35 | 1.06E−02 |
| positive regulation of phosphorus metabolic process (GO:0010562) | 249 | 185.24 | 1.34 | 1.80E−02 |
| positive regulation of phosphate metabolic process (GO:0045937) | 249 | 185.24 | 1.34 | 1.80E−02 |
| regulation of programmed cell death (GO:0043067) | 351 | 263.16 | 1.33 | 2.89E−04 |
| regulation of apoptotic process (GO:0042981) | 346 | 260.49 | 1.33 | 5.44E−04 |
| positive regulation of response to stimulus (GO:0048584) | 462 | 349.99 | 1.32 | 5.33E−06 |
| regulation of protein phosphorylation (GO:0001932) | 311 | 236.89 | 1.31 | 7.06E−03 |
| positive regulation of multicellular organismal process (GO:0051240) | 334 | 254.7 | 1.31 | 2.99E−03 |
| regulation of cell death (GO:0010941) | 365 | 278.75 | 1.31 | 9.41E−04 |
| response to external stimulus (GO:0009605) | 406 | 311.48 | 1.3 | 2.73E−04 |
| movement of cell or subcellular component (GO:0006928) | 309 | 237.11 | 1.3 | 1.40E−02 |
| regulation of phosphorylation (GO:0042325) | 329 | 255.15 | 1.29 | 1.55E−02 |
| positive regulation of signaling (GO:0023056) | 356 | 278.75 | 1.28 | 1.33E−02 |
| positive regulation of signal transduction (GO:0009967) | 330 | 258.49 | 1.28 | 3.38E−02 |
| positive regulation of cell communication (GO:0010647) | 354 | 277.41 | 1.28 | 1.54E−02 |
| regulation of intracellular signal transduction (GO:1902531) | 404 | 317.49 | 1.27 | 3.52E−03 |
| regulation of localization (GO:0032879) | 556 | 442.61 | 1.26 | 8.60E−05 |
| cellular response to organic substance (GO:0071310) | 435 | 346.65 | 1.25 | 5.14E−03 |
| cellular response to chemical stimulus (GO:0070887) | 528 | 421.91 | 1.25 | 3.55E−04 |
| response to organic substance (GO:0010033) | 578 | 468.22 | 1.23 | 4.35E−04 |
| regulation of response to stimulus (GO:0048583) | 824 | 670.15 | 1.23 | 3.62E−07 |
| regulation of signal transduction (GO:0009966) | 616 | 501.17 | 1.23 | 2.55E−04 |
| regulation of cell communication (GO:0010646) | 673 | 549.04 | 1.23 | 7.10E−05 |
| regulation of signaling (GO:0023051) | 682 | 558.16 | 1.22 | 8.92E−05 |
| regulation of multicellular organismal process (GO:0051239) | 571 | 470 | 1.21 | 4.01E−03 |
| regulation of molecular function (GO:0065009) | 637 | 525.21 | 1.21 | 9.02E−04 |
| regulation of developmental process (GO:0050793) | 499 | 412.78 | 1.21 | 4.11E−02 |
| regulation of catalytic activity (GO:0050790) | 521 | 431.26 | 1.21 | 2.62E−02 |
| response to chemical (GO:0042221) | 742 | 626.07 | 1.19 | 1.93E−03 |
| signal transduction (GO:0007165) | 911 | 779.69 | 1.17 | 5.08E−04 |
| negative regulation of biological process (GO:0048519) | 950 | 814.65 | 1.17 | 3.17E−04 |
| negative regulation of cellular process (GO:0048523) | 883 | 757.43 | 1.17 | 1.33E−03 |
| cell communication (GO:0007154) | 986 | 847.82 | 1.16 | 2.47E−04 |
| positive regulation of biological process (GO:0048518) | 1081 | 931.09 | 1.16 | 4.52E−05 |
| single organism signaling (GO:0044700) | 967 | 833.57 | 1.16 | 5.85E−04 |
| signaling (GO:0023052) | 967 | 834.24 | 1.16 | 6.78E−04 |
| positive regulation of cellular process (GO:0048522) | 970 | 844.04 | 1.15 | 2.98E−03 |
| cellular response to stimulus (GO:0051716) | 1171 | 1038.85 | 1.13 | 3.82E−03 |
| response to stimulus (GO:0050896) | 1439 | 1276.63 | 1.13 | 3.33E−05 |
| regulation of cellular metabolic process (GO:0031323) | 1174 | 1050.65 | 1.12 | 1.99E−02 |
| regulation of primary metabolic process (GO:0080090) | 1161 | 1041.52 | 1.11 | 3.71E−02 |
| regulation of metabolic process (GO:0019222) | 1230 | 1110.09 | 1.11 | 4.69E−02 |
| regulation of cellular process (GO:0050794) | 1968 | 1778.47 | 1.11 | 1.24E−07 |

SUPPLEMENTARY TABLE 2-continued

GO biological processes identified as overrepresented in an overrepresentation analysis using the DE transcripts. The presented GO terms were called significant with a Bonferroni corrected P-value below 0.05. The corrected p-values are reported below. Number of mapped IDs from reference: 14774, unmapped IDs from reference: 12854; number of mapped IDs from DE transcripts: 3298, unmapped IDs from DE transcripts: 346.

| GO Biological Process | # of matches | Expected # of matches | Fold Enrichment | $P_{FWER}$-value |
|---|---|---|---|---|
| regulation of biological process (GO:0050789) | 2064 | 1867.3 | 1.11 | 1.47E−08 |
| biological regulation (GO:0065007) | 2179 | 1972.39 | 1.1 | 5.32E−10 |
| cellular process (GO:0009987) | 2659 | 2522.76 | 1.05 | 4.59E−05 |
| biological process (GO:0008150) | 3011 | 2886.11 | 1.04 | 2.33E−08 |
| Unclassified (UNCLASSIFIED) | 287 | 411.89 | 0.7 | 0.00E+00 |
| sensory perception of chemical stimulus (GO:0007606) | 3 | 21.37 | <0.2 | 6.89E−3 |

EXAMPLE 2

The SenzaCell cell line may also be used together with a genomic biomarker signature for classification of respiratory sensitizers using the GARD platform, i.e. for identifying agents capable of inducing respiratory sensitization in a mammal.

The methods may be performed in line with the methodology discussed in the functional analysis section of Example 1 above for identifying skin sensitizers but adapted to use the biomarker signature of Table B and/or Table C below. See also the detailed methodology described specifically for identifying agents capable of inducing respiratory sensitization described in WO 2013/160882; WO 2016/083604; and Forreryd et al. (2015) Prediction of chemical Respiratory sensitizers using GARD, a novel in vitro assay based on a genomic biomarker signature. PLoS One 10(3)).

TABLE B

"Core", "preferred" and "optional" biomarkers from the GARD Respiratory Prediction Signature.

| | Gene Symbol | Entrez Gene ID | Affymetrix Probe Set ID | Validation Call Frequency |
|---|---|---|---|---|
| | (A) Core biomarkers | | | |
| 1. | OR5B21 | ENST00000360374 | 7948330 | 100 |
| 2. | SLC7A7 | ENST00000404278 | 7977786 | 95 |
| | (B) Preferred biomarkers | | | |
| 3. | PIP3-E | ENST00000265198 | 8130408 | 85 |
| 4. | BTNL8 | ENST00000400706 | 8116537 | 85 |
| 5. | CLEC4A | ENST00000360500 | 7953723 | 90 |
| 6. | HIST4H4 | ENST00000358064 | 7961483 | 80 |
| 7. | YKT6 | ENST00000223369 | 8132580 | 80 |
| 8. | FLJ32679 /// GOLGA8G /// GOLGA8E | ENST00000327271 | 7981895 | 85 |
| 9. | PACSIN3 | ENST00000298838 | 7947801 | 90 |
| 10. | PDE1B | ENST00000243052 | 7955943 | 80 |
| 11. | NQO1 | ENST00000320623 | 8002303 | 80 |
| 12. | CAMK1D | ENST00000378845 | 7926223 | 95 |
| 13. | MYB | ENST00000341911 | 8122202 | 95 |
| 14. | — | ENST00000387396 | 8065752 | 80 |
| 15. | GRK5 | ENST00000369106 | 7930894 | 90 |
| | (C) Optional biomarkers | | | |
| 16. | CD86 | ENST00000330540 | 8082035 | 100 |
| 17. | CD1A | ENST00000289429 | 7906339 | 85 |
| 18. | WWOX | ENST00000355860 | 7997352 | 85 |
| 19. | IKZF2 | ENST00000374319 | 8058670 | 85 |
| 20. | FUCA1 | ENST00000374479 | 7913694 | 80 |
| 21. | C10orf76 | ENST00000370033 | 7935951 | 80 |
| 22. | AMICA1 | ENST00000356289 | 7952022 | 80 |
| 23. | PDPK2 /// PDPK1 | ENST00000382326 | 7998825 | 80 |
| 24. | AZU1 | ENST00000334630 | 8024038 | 80 |
| 25. | ACN9 | ENST00000360382 | 8134415 | 80 |
| 26. | PDPN | ENST00000400804 | 7898057 | 75 |
| 27. | LOC642587 | NM_001104548 | 7909422 | 75 |
| 28. | SEC61A2 | ENST00000379051 | 7926189 | 75 |
| 29. | ELA2 | ENST00000263621 | 8024056 | 75 |
| 30. | BMP2K | ENST00000335016 | 8096004 | 75 |
| 31. | HCCS | ENST00000321143 | 8165995 | 75 |
| 32. | CXorf26 | ENST00000373358 | 8168447 | 75 |
| 33. | TYSND1 | ENST00000287078 | 7934114 | 70 |

TABLE B-continued

"Core", "preferred" and "optional" biomarkers
from the GARD Respiratory Prediction Signature.

| | Gene Symbol | Entrez Gene ID | Affymetrix Probe Set ID | Validation Call Frequency |
|---|---|---|---|---|
| 34. | CARS | ENST00000380525 | 7945803 | 70 |
| 35. | NECAP1 | ENST00000339754 | 7953715 | 70 |
| 36. | CDH26 | ENST00000348616 | 8063761 | 70 |
| 37. | SERPINB1 | ENST00000380739 | 8123598 | 70 |
| 38. | STEAP4 | ENST00000301959 | 8140840 | 70 |
| 39. | TXNIP | ENST00000369317 | 7904726 | 65 |
| 40. | — | ENST00000386628 | 7925821 | 65 |
| 41. | C12orf35 | ENST00000312561 | 7954711 | 65 |
| 42. | HMGA2 | ENST00000393578 | 7956867 | 65 |
| 43. | KRT16 | ENST00000301653 | 8015376 | 65 |
| 44. | GGTLC2 | ENST00000215938 | 8071662 | 65 |
| 45. | — | ENST00000386437 | 8089926 | 65 |
| 46. | OSBPL11 | ENST00000393455 | 8090277 | 65 |
| 47. | FAM71F1 | ENST00000315184 | 8135945 | 65 |
| 48. | ATP6V1B2 | ENST00000276390 | 8144931 | 65 |
| 49. | LOC128102 | AF252254 | 7904429 | 60 |
| 50. | TBX19 | ENST00000367821 | 7907146 | 60 |
| 51. | NID1 | ENST00000264187 | 7925320 | 60 |
| 52. | LPXN | ENST00000263845 | 7948332 | 60 |
| 53. | C15orf45 | AK057017 | 7982375 | 60 |
| 54. | RNF111 | ENST00000380504 | 7983953 | 60 |
| 55. | — | ENST00000386861 | 7993183 | 60 |
| 56. | CD33 | ENST00000262262 | 8030804 | 60 |
| 57. | TANK | ENST00000259075 | 8045933 | 60 |
| 58. | ANKRD44 | ENST00000282272 | 8057990 | 60 |
| 59. | WDFY1 | ENST00000233055 | 8059361 | 60 |
| 60. | SDC4 | ENST00000372733 | 8066513 | 60 |
| 61. | TMPRSS11B | ENST00000332644 | 8100701 | 60 |
| 62. | AFF4 | ENST00000265343 | 8114083 | 60 |
| 63. | HBEGF | ENST00000230990 | 8114572 | 60 |
| 64. | XK | ENST00000378616 | 8166723 | 60 |
| 65. | SLAMF7 | ENST00000368043 | 7906613 | 55 |
| 66. | S100A4 | ENST00000368715 | 7920271 | 55 |
| 67. | MPZL3 | ENST00000278949 | 7952036 | 55 |
| 68. | — | GENSCAN00000044853 | 7967586 | 55 |
| 69. | TRAV8-3 | ENST00000390435 | 7973298 | 55 |
| 70. | LOC100131497 | GENSCAN00000046821 | 7980481 | 55 |
| 71. | KIAA1468 | ENST00000299783 | 8021496 | 55 |
| 72. | SPHK2 | ENST00000245222 | 8030078 | 55 |
| 73. | — | ENST00000309260 | 8096554 | 55 |
| 74. | CCR6 | ENST00000283506 | 8123364 | 55 |
| 75. | GSTA3 | ENST00000370968 | 8127087 | 55 |
| 76. | RALA | ENST00000005257 | 8132406 | 55 |
| 77. | C7orf53 | ENST00000312849 | 8135532 | 55 |
| 78. | — | AF480566 | 8141421 | 55 |
| 79. | CERCAM | ENST00000372842 | 8158250 | 55 |
| 80. | — | hsa-mir-147 | 8163729 | 55 |
| 81. | NFYC | ENST00000372655 | 7900468 | 50 |
| 82. | CD53 | ENST00000271324 | 7903893 | 50 |
| 83. | PSEN2 | ENST00000366783 | 7910146 | 50 |
| 84. | CISD1 | ENST00000333926 | 7927649 | 50 |
| 85. | SCD | ENST00000370355 | 7929816 | 50 |
| 86. | MED19 | ENST00000337672 | 7948293 | 50 |
| 87. | SYT17 | ENST00000396244 | 7993624 | 50 |
| 88. | KRT16 /// LOC400578 /// MGC102966 | ENST00000399124 | 8013465 | 50 |
| 89. | C18orf51 | ENST00000400291 | 8023864 | 50 |
| 90. | CD79A | ENST00000221972 | 8029136 | 50 |
| 91. | C19orf56 | ENST00000222190 | 8034448 | 50 |
| 92. | AGFG1 | ENST00000409979 | 8048847 | 50 |
| 93. | FOXP1 | ENST00000318796 | 8088776 | 50 |
| 94. | TLR6 | ENST00000381950 | 8099841 | 50 |
| 95. | SUSD3 | ENST00000375472 | 8156393 | 50 |
| 96. | — | ENST00000387842 | 8176921 | 50 |
| 97. | — | ENST00000387842 | 8177424 | 50 |
| 98. | GPA33 | ENST00000367868 | 7922029 | 45 |
| 99. | CDC123 | ENST00000281141 | 7926207 | 45 |
| 100. | C10orf11 | ENST00000354343 | 7928534 | 45 |
| 101. | — | ENST00000322493 | 7937971 | 45 |
| 102. | PTMAP7 | AF170294 | 7976239 | 45 |
| 103. | ARRDC4 | ENST00000268042 | 7986350 | 45 |
| 104. | — | ENST00000388199 | 7997738 | 45 |
| 105. | — | ENST00000388437 | 8009299 | 45 |

TABLE B-continued

"Core", "preferred" and "optional" biomarkers
from the GARD Respiratory Prediction Signature.

| Gene Symbol | Entrez Gene ID | Affymetrix Probe Set ID | Validation Call Frequency |
|---|---|---|---|
| 106. KRT9 | ENST00000246662 | 8015357 | 45 |
| 107. — | ENST00000379371 | 8035868 | 45 |
| 108. HDAC4 | ENST00000345617 | 8060030 | 45 |
| 109. CD200 | ENST00000315711 | 8081657 | 45 |
| 110. PAPSS1 | ENST00000265174 | 8102214 | 45 |
| 111. ORAI2 | ENST00000356387 | 8135172 | 45 |
| 112. — | AK124536 | 8144569 | 45 |
| 113. ZBTB10 | ENST00000379091 | 8147040 | 45 |
| 114. — | ENST00000387422 | 8159963 | 45 |
| 115. RAB9A | ENST00000243325 | 8166098 | 45 |
| 116. — | — | 7895613 | 40 |
| 117. DRD5 | ENST00000304374 | 7905025 | 40 |
| 118. CNR2 | ENST00000374472 | 7913705 | 40 |
| 119. OIT3 | ENST00000334011 | 7928330 | 40 |
| 120. — | ENST00000386981 | 7933008 | 40 |
| 121. C10orf90 | ENST00000356858 | 7936996 | 40 |
| 122. OR52D1 | ENST00000322641 | 7938008 | 40 |
| 123. ZNF214 | ENST00000278314 | 7946288 | 40 |
| 124. — | ENST00000386959 | 7954690 | 40 |
| 125. ART4 | ENST00000228936 | 7961507 | 40 |
| 126. RCBTB2 | ENST00000344532 | 7971573 | 40 |
| 127. HOMER2 | ENST00000304231 | 7991034 | 40 |
| 128. WWP2 | ENST00000359154 | 7996976 | 40 |
| 129. WDR24 | ENST00000248142 | 7998280 | 40 |
| 130. MED31 | ENST00000225728 | 8011968 | 40 |
| 131. CALM2 | ENST00000272298 | 8052010 | 40 |
| 132. DLX2 | ENST00000234198 | 8056784 | 40 |
| 133. BTBD3 | ENST00000399006 | 8060988 | 40 |
| 134. — | ENST00000339367 | 8075817 | 40 |
| 135. TBCA | ENST00000380377 | 8112767 | 40 |
| 136. GIN1 | ENST00000399004 | 8113403 | 40 |
| 137. NOL7 | ENST00000259969 | 8116969 | 40 |
| 138. — | ENST00000402365 | 8117628 | 40 |
| 139. C7orf28B /// C7orf28A | ENST00000325974 | 8138128 | 40 |
| 140. DPP7 | ENST00000371579 | 8165438 | 40 |
| 141. hCG_1749005 | NR_003933 | 8167640 | 40 |
| 142. PNPLA4 | ENST00000381042 | 8171229 | 40 |
| 143. USP51 | ENST00000330856 | 8173174 | 40 |
| 144. HLA-DQA1 /// HLA-DRA | ENST00000383127 | 8178193 | 40 |
| 145. FAAH | ENST00000243167 | 7901229 | 35 |
| 146. GDAP2 | ENST00000369443 | 7918955 | 35 |
| 147. CD48 | ENST00000368046 | 7921667 | 35 |
| 148. PTPRJ | ENST00000278456 | 7939839 | 35 |
| 149. EXPH5 | ENST00000265843 | 7951545 | 35 |
| 150. RPS26 /// LOC728937 /// RPS26L /// hCG_2033311 | ENST00000393490 | 7956114 | 35 |
| 151. ALDH2 | ENST00000261733 | 7958784 | 35 |
| 152. CALM1 | ENST00000356978 | 7976200 | 35 |
| 153. NOX5 /// SPESP1 | ENST00000395421 | 7984488 | 35 |
| 154. RHBDL1 | ENST00000352681 | 7992010 | 35 |
| 155. CYLD | ENST00000311559 | 7995552 | 35 |
| 156. OSBPL1A | ENST00000357041 | 8022572 | 35 |
| 157. GYPC | ENST00000259254 | 8045009 | 35 |
| 158. RQCD1 | ENST00000295701 | 8048340 | 35 |
| 159. RBM44 | ENST00000316997 | 8049552 | 35 |
| 160. — | ENST00000384680 | 8051862 | 35 |
| 161. C3orf58 | ENST00000315691 | 8083223 | 35 |
| 162. MFSD1 | ENST00000264266 | 8083656 | 35 |
| 163. HACL1 | ENST00000321169 | 8085608 | 35 |
| 164. SATB1 | ENST00000338745 | 8085716 | 35 |
| 165. USP4 | ENST00000351842 | 8087380 | 35 |
| 166. — | ENST00000410125 | 8089928 | 35 |
| 167. — | ENST00000384055 | 8097445 | 35 |
| 168. IL7R | ENST00000303115 | 8104901 | 35 |
| 169. — | ENST00000364497 | 8117018 | 35 |
| 170. FAM135A | ENST00000370479 | 8120552 | 35 |
| 171. CD164 | ENST00000310786 | 8128716 | 35 |
| 172. DYNLT1 | ENST00000367088 | 8130499 | 35 |
| 173. NRCAM | ENST00000379027 | 8142270 | 35 |
| 174. ZNF596 | ENST00000308811 | 8144230 | 35 |

TABLE B-continued

"Core", "preferred" and "optional" biomarkers
from the GARD Respiratory Prediction Signature.

| | Gene Symbol | Entrez Gene ID | Affymetrix Probe Set ID | Validation Call Frequency |
|---|---|---|---|---|
| 175. | — | ENST00000332418 | 8170322 | 35 |
| 176. | TCEAL3 /// TCEAL6 | ENST00000372774 | 8174134 | 35 |
| 177. | SNAPIN | ENST00000368685 | 7905598 | 30 |
| 178. | DENND2D | ENST00000369752 | 7918487 | 30 |
| 179. | SAMD8 | ENST00000372690 | 7928516 | 30 |
| 180. | LHPP | ENST00000368842 | 7931204 | 30 |
| 181. | SLC37A2 | ENST00000298280 | 7944931 | 30 |
| 182. | FLI1 /// EWSR1 | ENST00000344954 | 7945132 | 30 |
| 183. | OR9G4 | ENST00000395180 | 7948157 | 30 |
| 184. | LOC338799 | ENST00000391388 | 7967210 | 30 |
| 185. | HEXDC | ENST00000337014 | 8010787 | 30 |
| 186. | NOTUM | ENST00000409678 | 8019334 | 30 |
| 187. | MCOLN1 | ENST00000394321 | 8025183 | 30 |
| 188. | PRKACA | ENST00000350356 | 8034762 | 30 |
| 189. | CRIM1 | ENST00000280527 | 8041447 | 30 |
| 190. | CECR5 | ENST00000336737 | 8074227 | 30 |
| 191. | RNF13 | ENST00000392894 | 8083310 | 30 |
| 192. | 40969 | ENST00000339875 | 8103508 | 30 |
| 193. | ZNF366 | ENST00000318442 | 8112584 | 30 |
| 194. | — | ENST00000410754 | 8120979 | 30 |
| 195. | GIMAP5 | ENST00000358647 | 8137257 | 30 |
| 196. | — | ENST00000362484 | 8147242 | 30 |
| 197. | TFE3 | ENST00000315869 | 8172520 | 30 |
| 198. | RHOU | ENST00000366691 | 7910387 | 25 |
| 199. | MED8 | ENST00000290663 | 7915516 | 25 |
| 200. | CASQ2 | ENST00000261448 | 7918878 | 25 |
| 201. | NUDT5 | ENST00000378940 | 7932069 | 25 |
| 202. | C11orf73 | ENST00000278483 | 7942932 | 25 |
| 203. | PAK1 | ENST00000356341 | 7950578 | 25 |
| 204. | PRSS21 | ENST00000005995 | 7992722 | 25 |
| 205. | — | ENST00000332418 | 7997907 | 25 |
| 206. | BTBD12 | ENST00000294008 | 7999008 | 25 |
| 207. | DHRS13 | ENST00000394901 | 8013804 | 25 |
| 208. | CCDC102B | ENST00000319445 | 8021685 | 25 |
| 209. | BCL2 | ENST00000398117 | 8023646 | 25 |
| 210. | ZNF211 /// ZNF134 | ENST00000396161 | 8031784 | 25 |
| 211. | NDUFV2 | ENST00000340013 | 8039068 | 25 |
| 212. | MYCN | ENST00000281043 | 8040419 | 25 |
| 213. | — | ENST00000385528 | 8045561 | 25 |
| 214. | — | ENST00000362957 | 8046522 | 25 |
| 215. | CASP8 | ENST00000264275 | 8047419 | 25 |
| 216. | RTN4 | ENST00000394611 | 8052204 | 25 |
| 217. | PLCG1 | ENST00000244007 | 8062623 | 25 |
| 218. | MGC42105 | ENST00000326035 | 8105146 | 25 |
| 219. | EMB | ENST00000303221 | 8112007 | 25 |
| 220. | — | ENST00000386433 | 8121249 | 25 |
| 221. | COL21A1 | ENST00000370817 | 8127201 | 25 |
| 222. | LRP12 | ENST00000276654 | 8152280 | 25 |
| 223. | LMNA | ENST00000368301 | 7906085 | 20 |
| 224. | — | ENST00000385567 | 7907535 | 20 |
| 225. | — | ENST00000362863 | 7926805 | 20 |
| 226. | ZNF503 | ENST00000372524 | 7934553 | 20 |
| 227. | NLRX1 | ENST00000397884 | 7944463 | 20 |
| 228. | — | ENST00000391173 | 7954775 | 20 |
| 229. | NDRG2 | ENST00000298687 | 7977621 | 20 |
| 230. | TRAF7 | ENST00000326181 | 7992529 | 20 |
| 231. | KRT40 | ENST00000400879 | 8015152 | 20 |
| 232. | KRT40 | ENST00000400879 | 8019604 | 20 |
| 233. | DRD5 | ENST00000304374 | 8053725 | 20 |
| 234. | ZC3H8 | ENST00000409573 | 8054664 | 20 |
| 235. | MMP9 | ENST00000372330 | 8063115 | 20 |
| 236. | PLTP | ENST00000372420 | 8066619 | 20 |
| 237. | — | ENST00000362686 | 8100476 | 20 |
| 238. | SPEF2 | ENST00000282469 | 8104856 | 20 |
| 239. | LRRC16A | ENST00000332168 | 8117243 | 20 |
| 240. | FBXO9 | AK095315 | 8120269 | 20 |
| 241. | EEPD1 | ENST00000242108 | 8132305 | 20 |
| 242. | FCN1 | ENST00000371807 | 8165011 | 20 |
| 243. | EFNA3 | ENST00000368408 | 7905918 | 15 |
| 244. | — | ENST00000314893 | 7910385 | 15 |
| 245. | TMEM19 | ENST00000266673 | 7957167 | 15 |
| 246. | PLXNC1 | ENST00000258526 | 7957570 | 15 |
| 247. | NHLRC3 | ENST00000379599 | 7968703 | 15 |
| 248. | MBNL2 | ENST00000397601 | 7969677 | 15 |

TABLE B-continued

"Core", "preferred" and "optional" biomarkers
from the GARD Respiratory Prediction Signature.

| | Gene Symbol | Entrez Gene ID | Affymetrix Probe Set ID | Validation Call Frequency |
|---|---|---|---|---|
| 249. | EIF5 | ENST00000216554 | 7977058 | 15 |
| 250. | PLEKHG4 | ENST00000360461 | 7996516 | 15 |
| 251. | COPS3 | ENST00000268717 | 8013094 | 15 |
| 252. | FAM171A2 | ENST00000398346 | 8016033 | 15 |
| 253. | LOC653653 /// AP1S2 | ENST00000380291 | 8017210 | 15 |
| 254. | VAPA | ENST00000340541 | 8020129 | 15 |
| 255. | MATK | ENST00000395040 | 8032682 | 15 |
| 256. | ACTR2 | ENST00000377982 | 8042337 | 15 |
| 257. | BPI | ENST00000262865 | 8062444 | 15 |
| 258. | ERG | ENST00000398905 | 8070297 | 15 |
| 259. | LAMB2 | ENST00000305544 | 8087337 | 15 |
| 260. | — | BC090058 | 8133752 | 15 |
| 261. | PHTF2 | ENST00000248550 | 8133818 | 15 |
| 262. | — | ENST00000333261 | 8133902 | 15 |
| 263. | C8orf55 | ENST00000336138 | 8148559 | 15 |
| 264. | PDE7A | ENST00000379419 | 8151074 | 15 |
| 265. | NAPRT1 | ENST00000340490 | 8153430 | 15 |
| 266. | HLA-DRA | ENST00000383127 | 8179481 | 15 |
| 267. | SLC22A15 | ENST00000369503 | 7904226 | 10 |
| 268. | FCGR1A /// FCGR1B /// FCGR1C | ENST00000369384 | 7905047 | 10 |
| 269. | SLC27A3 | ENST00000271857 | 7905664 | 10 |
| 270. | ID3 | ENST00000374561 | 7913655 | 10 |
| 271. | TBCEL | ENST00000284259 | 7944623 | 10 |
| 272. | FAM138D | ENST00000355746 | 7960172 | 10 |
| 273. | POMP | ENST00000380842 | 7968297 | 10 |
| 274. | SNN | ENST00000329565 | 7993259 | 10 |
| 275. | MED13 | ENST00000262436 | 8017312 | 10 |
| 276. | ZFP36L2 | ENST00000282388 | 8051814 | 10 |
| 277. | UXS1 | ENST00000409501 | 8054395 | 10 |
| 278. | CD40 | ENST00000279061 | 8063156 | 10 |
| 279. | — | ENST00000362620 | 8066960 | 10 |
| 280. | GGT5 | ENST00000327365 | 8074991 | 10 |
| 281. | — | BC035666 | 8103023 | 10 |
| 282. | G6PD | ENST00000393562 | 8176133 | 10 |
| 283. | — | ENST00000384272 | 7902365 | 5 |
| 284. | CLCC1 | ENST00000369971 | 7918255 | 5 |
| 285. | SCGB2A1 | ENST00000244930 | 7940626 | 5 |
| 286. | GAA | ENST00000302262 | 8010354 | 5 |
| 287. | SERPINB2 | ENST00000404622 | 8021635 | 5 |
| 288. | GPI | ENST00000356487 | 8027621 | 5 |
| 289. | LASS6 | ENST00000392687 | 8046086 | 5 |
| 290. | EIF4A2 | AB209021 | 8084704 | 5 |
| 291. | HLA-DRA | ENST00000383127 | 8118548 | 5 |
| 292. | — | ENST00000385586 | 8136889 | 5 |
| 293. | ANXA2P2 | M62898 /// NR_003573 | 8154836 | 5 |
| 294. | FANCG | ENST00000378643 | 8160935 | 5 |
| 295. | FAM53B | ENST00000337318 | 7936884 | 0 |
| 296. | RFXAP | ENST00000255476 | 7968653 | 0 |
| 297. | UBR1 | ENST00000382177 | 7987981 | 0 |
| 298. | TBC1D2B | ENST00000409931 | 7990657 | 0 |
| 299. | SERPINB10 | ENST00000397996 | 8021645 | 0 |
| 300. | SEC23B | ENST00000377481 | 8061186 | 0 |
| 301. | MN1 | ENST00000302326 | 8075126 | 0 |
| 302. | CRTAP | ENST00000320954 | 8078450 | 0 |

Table B. Genes are annotated with Entrez Gene ID where found (www.ncbi.nlm.nih.gov/gene). The Affymetrix Probe Set ID for the Human ST 1.0 Array are provided. The validation call frequency (%) is the occurrence of each gene in the 20 Validation Biomarker Signatures obtained during cross-validation.

TABLE C

| | Gene ID | Ensembl Transcript ID | Affymetrix | Validation |
|---|---|---|---|---|
| | Table C(i) - Core biomarkers | | | |
| 1. | TNFRSF19 | ENST00000403372 | 7968015 | 100 |
| 2. | SNORA74A | NR_002915 | 8108420 | 100 |
| 3. | SPAM1 | ENST00000340011 | 8135835 | 100 |
| | Table C(ii) - Preferred biomarkers | | | |
| 4. | ETID:ENST00000364621 | ENST00000364621 | 7917972 | 95 |
| 5. | HOMER3 | ENST00000392351 | 8035566 | 95 |
| 6. | CD1C | ENST00000368169 | 7906348 | 90 |
| 7. | IGHD /// IGHM | ENST00000390538 | 7981601 | 90 |
| 8. | SNRPN /// SNORD116-26 | NR_003340 | 7982000 | 90 |
| 9. | ETID:ENST00000364678 | ENST00000364678 | 7934896 | 85 |
| 10. | STRAP | ENST00000025399 | 7954173 | 85 |
| 11. | DIABLO | ENST00000267169 | 7967230 | 85 |
| 12. | ETID:ENST00000411349 | ENST00000411349 | 8151989 | 85 |
| 13. | ETID:ENST00000385497 | ENST00000385497 | 7923037 | 80 |
| 14. | OR51A2 | ENST00000380371 | 7946017 | 80 |
| 15. | MRPL21 | ENST00000362034 | 7949995 | 80 |
| 16. | PPP1R14A | ENST00000301242 | 8036473 | 80 |
| 17. | DEFB127 | ENST00000382388 | 8060314 | 80 |
| 18. | C9orf130 | ENST00000375268 | 8162562 | 80 |
| 19. | PRO2012 | BC019830 | 7924817 | 75 |
| 20. | LOC399898 | AK128188 | 7940116 | 75 |
| 21. | ETID:ENST00000387701 | ENST00000387701 | 7969914 | 75 |
| 22. | WDR68 | ENST00000310827 | 8009164 | 75 |
| 23. | NEU2 | ENST00000233840 | 8049243 | 75 |
| 24. | ETID:ENST00000386677 | ENST00000386677 | 8072575 | 75 |
| 25. | SPARC | ENST00000231061 | 8115327 | 75 |
| 26. | ETID:ENST00000390342 | ENST00000390342 | 8139107 | 75 |
| 27. | CRNN | ENST00000271835 | 7920178 | 70 |
| 28. | MMP12 | ENST00000326227 | 7951297 | 70 |
| 29. | ACVRL1 | ENST00000267008 | 7955562 | 70 |
| 30. | EIF4E2 | ENST00000258416 | 8049180 | 70 |
| 31. | RP11-191L9.1 | ENST00000380990 | 8076819 | 70 |
| 32. | PDCD6 /// AHRR | ENST00000264933 | 8104180 | 70 |
| 33. | ARRDC3 | ENST00000265138 | 8113073 | 70 |
| 34. | VWDE | ENST00000275358 | 8138258 | 70 |
| 35. | ZBTB34 | ENST00000319119 | 8157945 | 70 |
| 36. | ITGB1BP2 | ENST00000373829 | 8168291 | 70 |
| 37. | OR10K2 | ENST00000392265 | 7921356 | 65 |
| 38. | FLJ22596 | AK026249 | 7950442 | 65 |
| 39. | ETID:ENST00000306515 | ENST00000306515 | 8043572 | 65 |
| 40. | ACVR2A | ENST00000404590 | 8045587 | 65 |
| 41. | ETID:ENST00000385690 | ENST00000385690 | 8092312 | 65 |
| 42. | ETID:ENST00000386018 | ENST00000386018 | 8097945 | 65 |
| 43. | C6orf201 | ENST00000360378 | 8116696 | 65 |
| 44. | ETID:ENST00000385583 | ENST00000385583 | 8136932 | 65 |
| 45. | ETID:ENST00000385719 | ENST00000385719 | 8148515 | 65 |
| 46. | GPR20 | ENST00000377741 | 8153269 | 65 |
| 47. | ETID:ENST00000364357 | ENST00000364357 | 8163084 | 65 |
| 48. | ZCCHC13 | ENST00000339534 | 8168420 | 65 |
| 49. | GPR64 | ENST00000356606 | 8171624 | 65 |
| 50. | CD1D | ENST00000368171 | 7906330 | 60 |
| 51. | DUSP12 | ENST00000367943 | 7906810 | 60 |
| 52. | KLHL33 | ENST00000344581 | 7977567 | 60 |
| 53. | PSMB6 | ENST00000270586 | 8003953 | 60 |
| 54. | TMEM95 | ENST00000396580 | 8004364 | 60 |
| 55. | C1QBP | ENST00000225698 | 8011850 | 60 |
| 56. | EMILIN2 | ENST00000254528 | 8019912 | 60 |
| 57. | CD8A | ENST00000352580 | 8053584 | 60 |
| 58. | C20orf152 | ENST00000349339 | 8062237 | 60 |
| 59. | KCNJ4 | ENST00000303592 | 8076072 | 60 |
| 60. | ETID:ENST00000364163 | ENST00000364163 | 8078310 | 60 |
| 61. | FAM19A1 | ENST00000327941 | 8080918 | 60 |
| 62. | ETID:ENST00000384601 | ENST00000384601 | 8081233 | 60 |
| 63. | POLR2H | ENST00000296223 | 8084488 | 60 |
| 64. | AK000420 | AK000420 | 8110706 | 60 |
| 65. | ETID:ENST00000363354 | ENST00000363354 | 8120360 | 60 |
| 66. | APID:8121483 | — | 8121483 | 60 |
| 67. | EGFL6 | ENST00000361306 | 8166079 | 60 |
| 68. | POU3F4 | ENST00000373200 | 8168567 | 60 |

TABLE C-continued

| | Gene ID | Ensembl Transcript ID | Affymetrix | Validation |
|---|---|---|---|---|
| 69. | ETID:ENST00000385841 | ENST00000385841 | 7905629 | 55 |
| 70. | OR52A5 | ENST00000307388 | 7946023 | 55 |
| 71. | TIMM8B | ENST00000280354 | 7951679 | 55 |
| 72. | PEBP1 | ENST00000261313 | 7959070 | 55 |
| 73. | OR4F6 | ENST00000328882 | 7986530 | 55 |
| 74. | CDH15 | ENST00000289746 | 7997880 | 55 |
| 75. | TMEM199 | ENST00000292114 | 8005857 | 55 |
| 76. | ABI3 | ENST00000225941 | 8008185 | 55 |
| 77. | FU42842 | AK124832 | 8008540 | 55 |
| 78. | MC4R | ENST00000299766 | 8023593 | 55 |
| 79. | ETID:ENST00000410673 | ENST00000410673 | 8045931 | 55 |
| 80. | ISM1 | ENST00000262487 | 8061013 | 55 |
| 81. | LOC440957 | ENST00000307106 | 8080416 | 55 |
| 82. | KLB | ENST00000257408 | 8094679 | 55 |
| 83. | GM2A | ENST00000357164 | 8109344 | 55 |
| 84. | ANXA6 | ENST00000354546 | 8115234 | 55 |
| 85. | TAS2R40 | ENST00000408947 | 8136846 | 55 |
| 86. | APID:8142880 | — | 8142880 | 55 |
| 87. | RARRES2 | ENST00000223271 | 8143772 | 55 |
| 88. | SH2D4A | ENST00000265807 | 8144880 | 55 |
| 89. | PLP1 | ENST00000361621 | 8169061 | 55 |
| 90. | ATP1A2 | ENST00000392233 | 7906501 | 50 |
| 91. | ETID:ENST00000386800 | ENST00000386800 | 7932610 | 50 |
| 92. | MATIA | ENST00000372206 | 7934755 | 50 |
| 93. | TSGA10IP | ENST00000312452 | 7941469 | 50 |
| 94. | PRDM7 | ENST00000325921 | 8003571 | 50 |
| 95. | ETID:ENST00000390847 | ENST00000390847 | 8015739 | 50 |
| 96. | ETID:ENST00000255183 | ENST00000255183 | 8066444 | 50 |
| 97. | MRPL39 | ENST00000307301 | 8069620 | 50 |
| 98. | ETID:ENST00000386327 | ENST00000386327 | 8074884 | 50 |
| 99. | TIPARP | ENST00000295924 | 8083569 | 50 |
| 100. | HES1 | ENST00000232424 | 8084880 | 50 |
| 101. | ETID:ENST00000363502 | ENST00000363502 | 8089727 | 50 |
| 102. | PRDM9 | ENST00000253473 | 8104634 | 50 |
| 103. | ETID:ENST00000390917 | ENST00000390917 | 8137433 | 50 |
| 104. | KIAA1688 | ENST00000377307 | 8153876 | 50 |
| 105. | ETID:ENST00000391219 | ENST00000391219 | 8156759 | 50 |
| 106. | ETID:ENST00000387973 | ENST00000387973 | 8160782 | 50 |
| 107. | LOC100129534 | — | 7911718 | 45 |
| 108. | SLC2A1 | ENST00000397019 | 7915472 | 45 |
| 109. | AF116714 | AF116714 | 7935359 | 45 |
| 110. | EPS8L2 | ENST00000318562 | 7937443 | 45 |
| 111. | MGC3196 | ENST00000307366 | 7948836 | 45 |
| 112. | 7952733 | — | 7952733 | 45 |
| 113. | ETID:ENST00000384391 | ENST00000384391 | 7990031 | 45 |
| 114. | EME2 | ENST00000307394 | 7992379 | 45 |
| 115. | NETO1 | ENST00000299430 | 8023828 | 45 |
| 116. | NPHS1 | ENST00000353632 | 8036176 | 45 |
| 117. | ETID:ENST00000384109 | ENST00000384109 | 8047215 | 45 |
| 118. | ETID:ENST00000364143 | ENST00000364143 | 8059799 | 45 |
| 119. | ISX | ENST00000404699 | 8072636 | 45 |
| 120. | IL17RB | ENST00000288167 | 8080562 | 45 |
| 121. | PCOLCE2 | ENST00000295992 | 8091243 | 45 |
| 122. | LRIT3 | ENST00000409621 | 8096839 | 45 |
| 123. | ETID:ENST00000330110 | ENST00000330110 | 8104615 | 45 |
| 124. | ZNF354C | ENST00000315475 | 8110491 | 45 |
| 125. | ETID:ENST00000386444 | ENST00000386444 | 8162927 | 45 |
| 126. | OR2G3 | ENST00000320002 | 7911209 | 40 |
| 127. | GLUL | ENST00000331872 | 7922689 | 40 |
| 128. | CCKBR | ENST00000334619 | 7938090 | 40 |
| 129. | OR1S2 | ENST00000302592 | 7948312 | 40 |
| 130. | DCUN1D5 | ENST00000260247 | 7951325 | 40 |
| 131. | ETID:ENST00000388291 | ENST00000388291 | 7951420 | 40 |
| 132. | EMG1 | ENST00000261406 | 7953594 | 40 |
| 133. | PTHLH | ENST00000395868 | 7962000 | 40 |
| 134. | PTGES3 | ENST00000262033 | 7964250 | 40 |
| 135. | CIDEB | ENST00000258807 | 7978272 | 40 |
| 136. | ETID:ENST00000383863 | ENST00000383863 | 7985918 | 40 |
| 137. | ATP10A | ENST00000356865 | 7986789 | 40 |
| 138. | MYO5C | ENST00000261839 | 7988876 | 40 |
| 139. | ETID:ENST00000380078 | ENST00000380078 | 7989951 | 40 |
| 140. | PLA2G10 | ENST00000261659 | 7999588 | 40 |
| 141. | HSPE1 | ENST00000409729 | 8047223 | 40 |
| 142. | ETID:ENST00000388324 | ENST00000388324 | 8096249 | 40 |
| 143. | MYO6 | ENST00000369977 | 8120783 | 40 |
| 144. | C7orf30 | ENST00000287543 | 8131860 | 40 |
| 145. | ETID:ENST00000340779 | ENST00000340779 | 8139828 | 40 |

TABLE C-continued

| | Gene ID | Ensembl Transcript ID | Affymetrix | Validation |
|---|---|---|---|---|
| 146. | LOC441245 | AK090474 | 8139887 | 40 |
| 147. | CRIM2 | ENST00000297801 | 8142821 | 40 |
| 148. | XKR4 | ENST00000327381 | 8146475 | 40 |
| 149. | FAM110B | ENST00000361488 | 8146533 | 40 |
| 150. | PEBP4 | ENST00000256404 | 8149725 | 40 |
| 151. | LOC644714 | BC047037 | 8161943 | 40 |
| 152. | PAPPAS | AY623011 /// AY623012 | 8163672 | 40 |
| 153. | BEX4 | ENST00000372691 | 8169009 | 40 |
| 154. | HMGB4 | ENST00000323936 | 7899905 | 35 |
| 155. | ETID:BC028413 /// BC128516 | BC028413 /// BC128516 | 7911676 | 35 |
| 156. | ETID:ENST00000363919 | ENST00000363919 | 7928750 | 35 |
| 157. | ETID:ENST00000335621 | ENST00000335621 | 7958942 | 35 |
| 158. | SOX1 | ENST00000330949 | 7970146 | 35 |
| 159. | CTSG | ENST00000216336 | 7978351 | 35 |
| 160. | ETID:ENST00000362344 | ENST00000362344 | 7982100 | 35 |
| 161. | FLJ37464 | ENST00000398354 | 7996377 | 35 |
| 162. | RAX | ENST00000334889 | 8023549 | 35 |
| 163. | IL29 | ENST00000333625 | 8028613 | 35 |
| 164. | CEACAM20 | ENST00000316962 | 8037482 | 35 |
| 165. | ETID:ETID:ENST00000365557 | ENST00000365557 | 8044684 | 35 |
| 166. | SEC14L3 | ENST00000403066 | 8075375 | 35 |
| 167. | C3orf52 | ENST00000264848 | 8081645 | 35 |
| 168. | FETUB | ENST00000265029 | 8084657 | 35 |
| 169. | PIGY | ENST00000273968 | 8101718 | 35 |
| 170. | CDH12 | ENST00000284308 | 8111234 | 35 |
| 171. | LGSN | ENST00000370657 | 8127380 | 35 |
| 172. | ETID:ENST00000391031 | ENST00000391031 | 8129067 | 35 |
| 173. | HGC6.3 | AB016902 | 8130824 | 35 |
| 174. | tcag7.873 | NM_001126493 | 8138797 | 35 |
| 175. | T1560 | ENST00000379496 | 8146527 | 35 |
| 176. | EXOSC4 | ENST00000316052 | 8148710 | 35 |
| 177. | TRAM1 | ENST00000262213 | 8151281 | 35 |
| 178. | APID:8159371 | — | 8159371 | 35 |
| 179. | OR13C2 | ENST00000318797 | 8162936 | 35 |
| 180. | PLS3 | ENST00000289290 | 8169473 | 35 |
| 181. | TMEM53 | ENST00000372244 | 7915578 | 30 |
| 182. | CD1B | ENST00000368168 | 7921346 | 30 |
| 183. | SORCS3 | ENST00000393176 | 7930341 | 30 |
| 184. | OR52E8 | ENST00000329322 | 7946111 | 30 |
| 185. | FAM160A2 | ENST00000265978 | 7946128 | 30 |
| 186. | LOC649946 | BC017930 | 7952126 | 30 |
| 187. | FAM158A | ENST00000216799 | 7978114 | 30 |
| 188. | APID:7986637 | — | 7986637 | 30 |
| 189. | MYO1E | ENST00000288235 | 7989277 | 30 |
| 190. | NUPR1 | ENST00000395641 | 8000574 | 30 |
| 191. | APID:8005433 | — | 8005433 | 30 |
| 192. | SIGLEC15 | ENST00000389474 | 8021091 | 30 |
| 193. | 2-Mar | ENST00000393944 | 8025421 | 30 |
| 194. | LOC100131554 | — | 8041886 | 30 |
| 195. | GGTLC1 | ENST00000335694 | 8065427 | 30 |
| 196. | PSMA7 | ENST00000395567 | 8067382 | 30 |
| 197. | SLC25A18 | ENST00000399813 | 8071107 | 30 |
| 198. | C3orf14 | ENST00000232519 | 8080847 | 30 |
| 199. | CDX1 | ENST00000377812 | 8109226 | 30 |
| 200. | ETID:ENST00000386433 | ENST00000386433 | 8121249 | 30 |
| 201. | RRAGD | ENST00000359203 | 8128123 | 30 |
| 202. | SDK1 | ENST00000389531 | 8131205 | 30 |
| 203. | LOC168474 | NR_002789 | 8139826 | 30 |
| 204. | ETID:ENST00000384125 | ENST00000384125 | 8146120 | 30 |
| 205. | TRHR | ENST00000311762 | 8147877 | 30 |
| 206. | IL11RA | ENST00000378817 | 8154934 | 30 |
| 207. | MGC21881 /// LOC554249 | ENST00000377616 | 8155393 | 30 |
| 208. | ZNF483 | ENST00000358151 | 8157193 | 30 |
| 209. | C9orf69 | ENST00000400709 | 8159624 | 30 |
| 210. | MGC21881 /// LOC554249 | ENST00000377616 | 8161451 | 30 |
| 211. | ETID:ENST00000364507 | ENST00000364507 | 8168161 | 30 |
| 212. | ETID:ENST00000387003 | ENST00000387003 | 7914137 | 25 |
| 213. | ETID:ENST00000388083 | ENST00000388083 | 7929614 | 25 |
| 214. | ETID:ENST00000365084 | ENST00000365084 | 7934568 | 25 |
| 215. | FRG2 /// FRG2B /// FRG2C | ENST00000368515 | 7937251 | 25 |
| 216. | C14orf53 | ENST00000389594 | 7975154 | 25 |
| 217. | ODF3L1 | ENST00000332145 | 7985025 | 25 |
| 218. | FAM18A | ENST00000299866 | 7999412 | 25 |
| 219. | PRTN3 | ENST00000234347 | 8024048 | 25 |
| 220. | CFD | ENST00000327726 | 8024062 | 25 |
| 221. | TMED1 | ENST00000214869 | 8034101 | 25 |
| 222. | ETID:ENST00000387150 | ENST00000387150 | 8035937 | 25 |

TABLE C-continued

| | Gene ID | Ensembl Transcript ID | Affymetrix | Validation |
|---|---|---|---|---|
| 223. | HSD17B14 | ENST00000263278 | 8038213 | 25 |
| 224. | BOK | ENST00000318407 | 8049876 | 25 |
| 225. | ETID:ENST00000365609 | ENST00000365609 | 8050801 | 25 |
| 226. | SNRPB | ENST00000381342 | 8064502 | 25 |
| 227. | EPHA6 | ENST00000338994 | 8081138 | 25 |
| 228. | SCARNA22 | NR_003004 | 8093576 | 25 |
| 229. | FLJ35424 | ENST00000404649 | 8093821 | 25 |
| 230. | ETID:ENST00000387555 | ENST00000387555 | 8104723 | 25 |
| 231. | ETID:ENST00000388664 | ENST00000388664 | 8107115 | 25 |
| 232. | ETID:ENST00000363365 | ENST00000363365 | 8108566 | 25 |
| 233. | ETID:ENST00000362861 | ENST00000362861 | 8111358 | 25 |
| 234. | ETID:ENST00000363181 | ENST00000363181 | 8114581 | 25 |
| 235. | GRM6 | ENST00000319065 | 8116253 | 25 |
| 236. | LOC646093 | — | 8116400 | 25 |
| 237. | HIST1H1E | ENST00000304218 | 8117377 | 25 |
| 238. | TIAM2 | ENST00000367174 | 8122933 | 25 |
| 239. | ETID:ENST00000363074 | ENST00000363074 | 8128712 | 25 |
| 240. | ETID:ENST00000385777 | ENST00000385777 | 8148331 | 25 |
| 241. | MTUS1 | ENST00000400046 | 8149500 | 25 |
| 242. | MUC21 | ENST00000383351 | 8177931 | 25 |
| 243. | WDR8 | ENST00000378322 | 7911839 | 20 |
| 244. | LOC100131195 | AK097743 | 7933190 | 20 |
| 245. | OR4D10 | ENST00000378245 | 7940182 | 20 |
| 246. | C12orf63 | ENST00000342887 | 7957688 | 20 |
| 247. | ELA1 | ENST00000293636 | 7963304 | 20 |
| 248. | DNAJC14 /// CIP29 | ENST00000317269 | 7963935 | 20 |
| 249. | FLJ40176 | ENST00000322527 | 7972670 | 20 |
| 250. | ETID:ENST00000410207 | ENST00000410207 | 7985308 | 20 |
| 251. | PSME3 | ENST00000293362 | 8007397 | 20 |
| 252. | ETID:ENST00000405656 | ENST00000405656 | 8009515 | 20 |
| 253. | HN1 | ENST00000356033 | 8018305 | 20 |
| 254. | ETID:ENST00000335523 | ENST00000335523 | 8027385 | 20 |
| 255. | CYP2A7 /// CYP2A7P1 | ENST00000301146 | 8036981 | 20 |
| 256. | ATXN10 | ENST00000252934 | 8073799 | 20 |
| 257. | ZMAT5 | ENST00000397779 | 8075276 | 20 |
| 258. | ETID:ENST00000362493 | ENST00000362493 | 8084215 | 20 |
| 259. | FHIT | ENST00000341848 | 8088458 | 20 |
| 260. | FRG2 /// FRG2B /// FRG2C | ENST00000368515 | 8104124 | 20 |
| 261. | SNX18 | ENST00000381410 | 8105328 | 20 |
| 262. | ETID:ENST00000362433 | ENST00000362433 | 8128445 | 20 |
| 263. | DTX2 | ENST00000307569 | 8133736 | 20 |
| 264. | ASB4 | ENST00000325885 | 8134376 | 20 |
| 265. | ETID:ENST00000365242 | ENST00000365242 | 8147445 | 20 |
| 266. | ETID:ENST00000364204 | ENST00000364204 | 8156450 | 20 |
| 267. | COL5A1 | ENST00000355306 | 8159142 | 20 |
| 268. | LCAP | ENST00000357566 | 8170786 | 20 |
| 269. | APOO | ENST00000379226 | 8171823 | 20 |
| 270. | PTPRU | ENST00000373779 | 7899562 | 15 |
| 271. | IL28RA | ENST00000327535 | 7913776 | 15 |
| 272. | NEUROG3 | ENST00000242462 | 7934083 | 15 |
| 273. | VAX1 | ENST00000277905 | 7936552 | 15 |
| 274. | LOC440131 | ENST00000400540 | 7968323 | 15 |
| 275. | C13orf31 | ENST00000325686 | 7968883 | 15 |
| 276. | ADAMTS7 | ENST00000388820 | 7990736 | 15 |
| 277. | SMTNL2 | ENST00000338859 | 8003892 | 15 |
| 278. | LOC284112 | AK098506 | 8012004 | 15 |
| 279. | ETV2 | ENST00000402764 | 8027920 | 15 |
| 280. | FUT2 | ENST00000391876 | 8030094 | 15 |
| 281. | C2orf39 | ENST00000288710 | 8040672 | 15 |
| 282. | LOC200383 /// DNAH6 | ENST00000237449 | 8043071 | 15 |
| 283. | ETID:ENST00000385676 | ENST00000385676 | 8055204 | 15 |
| 284. | CCDC108 | ENST00000341552 | 8059028 | 15 |
| 285. | APID:8065011 | — | 8065011 | 15 |
| 286. | C22orf27 | BC042980 | 8072400 | 15 |
| 287. | ETID:ENST00000364444 | ENST00000364444 | 8103041 | 15 |
| 288. | PDLIM3 | ENST00000284767 | 8104022 | 15 |
| 289. | ETID:ENST00000330110 | ENST00000330110 | 8104613 | 15 |
| 290. | ETID:ENST00000384539 | ENST00000384539 | 8107125 | 15 |
| 291. | ETID:ENST00000390214 | ENST00000390214 | 8130372 | 15 |
| 292. | MGC72080 | BC029615 | 8141169 | 15 |
| 293. | C9orf128 | ENST00000377984 | 8161154 | 15 |
| 294. | RGAG4 | NM_001024455 | 8173503 | 15 |
| 295. | PIP5K1A | ENST00000409426 | 7905365 | 10 |
| 296. | GPR161 | ENST00000367838 | 7922108 | 10 |
| 297. | ETID:ENST00000385353 | ENST00000385353 | 7925434 | 10 |
| 298. | OR56A3 | ENST00000329564 | 7938066 | 10 |
| 299. | OR5A2 | ENST00000302040 | 7948377 | 10 |

TABLE C-continued

| | Gene ID | Ensembl Transcript ID | Affymetrix | Validation |
|---|---|---|---|---|
| 300. | WNT11 | ENST00000322563 | 7950534 | 10 |
| 301. | APID:7960259 | — | 7960259 | 10 |
| 302. | RAB37 | ENST00000340415 | 8009666 | 10 |
| 303. | LAIR1 | ENST00000391742 | 8039257 | 10 |
| 304. | ETID:ENST00000388385 | ENST00000388385 | 8041420 | 10 |
| 305. | CHAC2 | ENST00000295304 | 8041961 | 10 |
| 306. | ETID:ENST00000387574 | ENST00000387574 | 8062337 | 10 |
| 307. | ETID:ENST00000387884 | ENST00000387884 | 8062962 | 10 |
| 308. | BCL2L1 | ENST00000376062 | 8065569 | 10 |
| 309. | KDELR3 | ENST00000409006 | 8073015 | 10 |
| 310. | TMEM108 | ENST00000321871 | 8082767 | 10 |
| 311. | SPATA16 | ENST00000351008 | 8092187 | 10 |
| 312. | BTC | ENST00000395743 | 8101002 | 10 |
| 313. | SUPT3H | ENST00000371460 | 8126710 | 10 |
| 314. | EIF4B | ENST00000262056 | 8135268 | 10 |
| 315. | CHMP4C | ENST00000297265 | 8147057 | 10 |
| 316. | H2BFM | ENST00000243297 | 8169080 | 10 |
| 317. | APID:8180392 | — | 8180392 | 10 |
| 318. | NR5A2 | ENST00000367362 | 7908597 | 5 |
| 319. | TRIM49 | ENST00000332682 | 7939884 | 5 |
| 320. | MS4A6A | ENST00000323961 | 7948455 | 5 |
| 321. | C11orf10 | ENST00000257262 | 7948606 | 5 |
| 322. | HSPC152 | ENST00000308774 | 7949075 | 5 |
| 323. | RASAL1 | ENST00000261729 | 7966542 | 5 |
| 324. | ETID:ENST00000387531 | ENST00000387531 | 7975694 | 5 |
| 325. | PLDN | ENST00000220531 | 7983502 | 5 |
| 326. | PER1 | ENST00000354903 | 8012349 | 5 |
| 327. | ALS2CR12 | ENST00000286190 | 8058203 | 5 |
| 328. | C20orf142 | ENST00000396825 | 8066407 | 5 |
| 329. | ETID:ENST00000386848 | ENST00000386848 | 8073680 | 5 |
| 330. | LOC100129113 | AK094477 | 8074307 | 5 |
| 331. | CERK | ENST00000216264 | 8076792 | 5 |
| 332. | ETID:ENST00000385783 | ENST00000385783 | 8083937 | 5 |
| 333. | PROS1 | ENST00000407433 | 8089015 | 5 |
| 334. | PCDHGA | ENST00000378105 | 8108757 | 5 |
| 335. | MUC3B /// MUC3A | ENST00000332750 | 8135015 | 5 |
| 336. | ETID:ENST00000365355 | ENST00000365355 | 8142534 | 5 |
| 337. | APID:8156969 | — | 8156969 | 5 |
| 338. | ETID:ENST00000358047 | ENST00000410626 | 8163013 | 5 |
| 339. | FAM47C | ENST00000358047 | 8166703 | 5 |
| 340. | NXF4 | ENST00000360035 | 8168940 | 5 |
| 341. | PIWIL4 | ENST00000299001 | 7943240 | 0 |
| 342. | ETID:ENST00000384727 | ENST00000384727 | 7968732 | 0 |
| 343. | ALDH6A1 | ENST00000350259 | 7980098 | 0 |
| 344. | TMEM64 | ENST00000324979 | 8151747 | 0 |
| 345. | ETID:ENST00000364816 | ENST00000364816 | 8168079 | 0 |
| Table C(iii) - Optional biomarkers | | | | |
| 346. | C11orf73 | ENST00000278483 | 7942932 | 100 |
| 347. | OR5B21 | ENST00000278483 | 7948330 | 100 |
| 348. | NOX5 /// SPESP1 | ENST00000395421 | 7984488 | 100 |
| 349. | AMICA1 | ENST00000356289 | 7952022 | 95 |
| 350. | ETID:ENST00000387422 | ENST00000387422 | 8159963 | 90 |
| 351. | SERPINB1 | ENST00000380739 | 8123598 | 85 |
| 352. | ETID:ENST00000387396 | ENST00000387396 | 8065752 | 80 |
| 353. | CD1A | ENST00000289429 | 7906339 | 75 |
| 354. | RAB9A | ENST00000243325 | 8166098 | 75 |
| 355. | C10orf90 | ENST00000356858 | 7936996 | 70 |
| 356. | LPXN | ENST00000263845 | 7948332 | 65 |
| 357. | GGTLC2 | ENST00000215938 | 8071662 | 65 |
| 358. | ETID:ENST00000384680 | ENST00000384680 | 8051862 | 60 |
| 359. | PNPLA4 | ENST00000381042 | 8171229 | 60 |
| 360. | CAMK1D | ENST00000378845 | 7926223 | 55 |
| 361. | ETID:ENST00000410754 | ENST00000410754 | 8120979 | 55 |
| 362. | CDC123 | ENST00000281141 | 7926207 | 50 |
| 363. | WDFY1 | ENST00000233055 | 8059361 | 50 |
| 364. | hCG_1749005 | — | 8167640 | 50 |
| 365. | CD48 | ENST00000368046 | 7921667 | 45 |
| 366. | MED19 | ENST00000337672 | 7948293 | 45 |
| 367. | DRD5 | ENST00000304374 | 8053725 | 45 |
| 368. | APID:7967586 | — | 7967586 | 40 |
| 369. | VAPA | ENST00000340541 | 8020129 | 40 |
| 370. | FAM71F1 | ENST00000315184 | 8135945 | 40 |
| 371. | APID:8141421 | — | 8141421 | 35 |
| 372. | HCCS | ENST00000321143 | 8165995 | 35 |
| 373. | CNR2 | ENST00000374472 | 7913705 | 25 |
| 374. | OIT3 | ENST00000334011 | 7928330 | 25 |

TABLE C-continued

| | Gene ID | Ensembl Transcript ID | Affymetrix | Validation |
|---|---|---|---|---|
| 375. | BMP2K | ENST00000335016 | 8096004 | 25 |
| 376. | ZNF366 | ENST00000318442 | 8112584 | 25 |
| 377. | SYT17 | ENST00000396244 | 7993624 | 20 |
| 378. | CALM2 | ENST00000272298 | 8052010 | 20 |
| 379. | XK | ENST00000378616 | 8166723 | 20 |
| 380. | ART4 | ENST00000228936 | 7961507 | 15 |
| 381. | ETID:ENST00000332418 | ENST00000332418 | 7997907 | 15 |
| 382. | ZFP36L2 | ENST00000282388 | 8051814 | 15 |
| 383. | GSTA3 | ENST00000370968 | 8127087 | 15 |
| 384. | COL21A1 | ENST00000370817 | 8127201 | 15 |
| 385. | ETID:ENST00000332418 | ENST00000332418 | 8170322 | 15 |
| 386. | FUCA1 | ENST00000374479 | 7913694 | 5 |
| 387. | ETID:ENST00000386628 | ENST00000386628 | 7925821 | 5 |
| 388. | AZU1 | ENST00000334630 | 8024038 | 5 |
| 389. | IL7R | ENST00000303115 | 8104901 | 5 |

The table shows predictor genes in GRPS, identified by one-way ANOVA p-value filtering and Backward elimination. When possible, the Ensembl transcript ID was used as gene identifier. The Affymetrix Probe Set ID for the Human ST 1.0 Array are provided.

[1]Validation call frequency (%) describes the occurrence of each predictor transcript among the 20 biomarker signatures obtained by cross validation.

EXAMPLE 3

The SenzaCell cell line may also be used for classification of the potency of skin sensitizers using the GARD platform, i.e. for determining the skin sensitizing potency of test agents.

Such methods may be performed in line with those described in the functional analysis section of Example 1 above for identifying skin sensitizers but adapted to use the biomarker signature of Table D in order to determine potency. See also the specific methodology described in detail in Zeller et al. (2017) The GARD platform for potency assessment of skin sensitizing chemicals. ALTEX Online first published Apr. 12, 2017, version 2 https://doi.org/10.14573/altex.1701101, and also described in WO 2017/162773.

TABLE D

| Transcript cluster ID | VCF (%) | Gene Title | Gene Symbol | Gene assignment |
|---|---|---|---|---|
| | | Table D(i) | | |
| 8117594 | 93 | histone cluster 1, H2bm | HIST1H2BM | NM_003521 |
| 8124385 | 86 | histone cluster 1, H4b | HIST1H4B | NM_003544 |
| 8124430 | 81 | histone cluster 1, H1d | HIST1H1D | NM_005320 |
| 8095221 | 80 | phosphoribosylaminoimidazole carboxylase, phosphoribosylaminoimidazole succinocarboxamide synthetase | PAICS | NM_001079524 |
| 8124413 | 69 | histone cluster 1, H4d | HIST1H4D | NM_003539 |
| 8117608 | 56 | histone cluster 1, H2al /// histone cluster 1, H2bn | HIST1H2AL /// HIST1H2BN | NM_003511 |
| 7994109 | 51 | polo-like kinase 1 | PLK1 | NM_005030 |
| 7904433 | 44 | phosphoglycerate dehydrogenase | PHGDH | ENST00000369407 |
| 8082350 | 44 | minichromosome maintenance complex component 2 | MCM2 | NM_004526 |
| 8141395 | 43 | minichromosome maintenance complex component 7 | MCM7 | NM_001278595 |
| 7903893 | 41 | CD53 molecule | CD53 | NM_000560 |
| 8118669 | 41 | kinesin family member C1 | KIFC1 | NM_002263 |
| 7938348 | 40 | WEE1 G2 checkpoint kinase | WEE1 | NM_001143976 |
| 7957737 | 34 | thymopoietin | TMPO | NM_001032283 |
| 8146357 | 34 | minichromosome maintenance complex component 4 | MCM4 | NM_005914 |
| 7918300 | 33 | proline/serine-rich coiled-coil 1 | PSRC1 | NM_001005290 |
| 8054329 | 31 | ring finger protein 149 | RNF149 | NM_173647 |
| 8055426 | 31 | minichromosome maintenance complex component 6 | MCM6 | NM_005915 |
| 8072687 | 29 | minichromosome maintenance complex component 5 | MCM5 | NM_006739 |
| 8003503 | 20 | Fanconi anemia complementation group A | FANCA | NM_000135 |

TABLE D-continued

Table D(ii)

| Transcript cluster ID | VCF (%) | Gene Title | Gene Symbol | Gene assignment |
|---|---|---|---|---|
| 8040843 | 44 | carbamoyl-phosphate synthetase 2, aspartate transcarbamylase, and dihydroorotase | CAD | NM_004341 |
| 7898549 | 42 | MRT4 homolog, ribosome maturation factor | MRTO4 | NM_016183 |
| 7901091 | 41 | target of EGR1, member 1 (nuclear) | TOE1 | NM_025077 |
| 7900699 | 40 | cell division cycle 20 | CDC20 | NM_001255 |
| 8121087 | 36 | peptidase M20 domain containing 2 | PM20D2 | NM_00101085 |
| 8084630 | 35 | NmrA-like family domain containing 1 pseudogene | LOC344887 | NR_033752 |
| 7958455 | 30 | uracil DNA glycosylase | UNG | NM_003362 |
| 8119088 | 27 | cyclin-dependent kinase inhibitor 1A (p21, Cip1) | CDKN1A | NM_000389 |
| 8117395 | 26 | histone cluster 1, H2bf | HIST1H2BF | NM_003522 |
| 8124527 | 25 | histone cluster 1, H1b | HIST1H1B | NM_005322 |
| 7896697 | 21 | unknown | unknown | unknown |
| 8097417 | 20 | jade family PHD finger 1 | JADE1 | NM_001287441 |
| 7977445 | 18 | KIAA0125 | KIAA0125 | NR_026800 |
| 7985213 | 17 | cholinergic receptor, nicotinic alpha 5 | CHRNA5 | NM_000745 |
| 8068478 | 17 | chromatin assembly factor 1, subunit B (p60) /// MORC family CW-type zinc finger 3 | CHAF1B /// MORC3 | NM_005441 |
| 8099721 | 16 | sel-1 suppressor of lin-12-like 3 (C. elegans) | SEL1L3 | NM_015187 |
| 7948192 | 14 | structure specific recognition protein 1 | SSRP1 | NM_003146 |
| 7960340 | 14 | forkhead box M1 | FOXM1 | NM_001243088 |
| 8107706 | 14 | lamin B1 | LMNB1 | NM_001198557 |
| 8124524 | 14 | histone cluster 1, H2ak | HIST1H2AK | NM_003510 |
| 8040712 | 11 | centromere protein A | CENPA | NM_001042426 |
| 8043602 | 10 | non-SMC condensin I complex subunit H | NCAPH | NM_001281710 |
| 8124394 | 7 | histone cluster 1, H2bb | HIST1H2BB | NM_021062 |
| 8144931 | 7 | ATPase, H+ transporting, lysosomal 56/58 kDa, V1 subunit B2 | ATP6V1B2 | NM_001693 |
| 7999025 | 5 | TNF receptor-associated protein 1 | TRAP1 | NM_001272049 |

Table D(iii)

| Transcript cluster ID | VCF (%) | Gene Title | Gene Symbol | Gene assignment |
|---|---|---|---|---|
| 8004804 | 83 | phosphoribosylformylglycinamidine synthase | PFAS | NM_012393 |
| 8005839 | 63 | transmembrane protein 97 | TMEM97 | NM_014573 |
| 7916432 | 61 | 24-dehydrocholesterol reductase | DHCR24 | NM_014762 |
| 7948656 | 30 | ferritin, heavy polypeptide 1 | FTH1 | NM_002032 |
| 8117408 | 30 | histone cluster 1, H2ae | HIST1H2AE | NM_021052 |
| 8002303 | 17 | NAD(P)H dehydrogenase, quinone 1 | NQO1 | NM_000903 |
| 7939341 | 8 | CD44 molecule (Indian blood group) | CD44 | NM_000610 |

EXAMPLE 4

The SenzaCell cell line may also be used for identifying proteins which are allergenic in a mammal.

The methods may be performed in line with the functional analysis section of Example 1 above for identifying skin sensitizers but adapted to use the biomarker signature of Table E in order to identify allergenic proteins. See also the methodology described in Zeller et al. An alternative biomarker-based approach for the prediction of proteins known to sensitize the respiratory tract. Toxicol In Vitro, 2017 Oct. 7; 46:155-162.

A possible method of performing allergenic predictions on proteins is provided as follows. It is based on the GARD Protein Allergen Prediction Signature of Table E (herein referred to as "GARD PAPS"). The readout of GARD is a set of genomic predictors, referred to as the GARD Prediction Signature (GPS).

The genetic material of the cells are isolated from cell samples stimulated with the test substances. The transcriptional levels of the GARD PAPS are quantified and compared to a reference data set by the use of multivariate statistical prediction models. Each sample is assigned a decision value based on its transcriptional levels of the GARD PAPS, as measured by Affymetrix microarray technology. Final predictions are based on the mean value from biological triplicate samples.

All proteins are screened for cytotoxic effects and the GARD input concentration established for each protein.

LPS may be used as a negative control, ensuring that observed signals generated by samples are not due to endotoxin contaminants. Endotoxin contents of the samples may be quantified using a LAL test. The LPS concentration used as a negative control may be set to correspond to the highest endotoxin concentration present in a sample.

All test proteins and substances are assayed in biological triplicates. All replicates of test substances are assigned decision values using the GARD PAPS prediction model, as described (see materials and methods below).

Materials & Methods

The comprehensive materials and methods for the GARD testing strategy, used to generate data according to this example, is included below.

Deviations from Standard Protocols

The cytotoxic effects of the test proteins may be monitored in the concentration range 1-25 µg/ml. 25 µg/ml may be used as the GARD input concentration.

When stimulating the cells with the test substances, the proteins may first be dissolved in PBS to a concentration of 1000 μg/ml. 50 μl of the dissolved proteins then added to 1.95 ml of seeded cells. LPS may be diluted in PBS to a final concentration of 0.1 μg/ml and 2 μl added to 1.998 ml of cell suspension.

The cells are stimulated for 24 h after which they are lysed in TRIzol reagent. RNA is purified, labeled and hybridized to Affymetrix arrays.

The quantified transcription levels are single chain array normalized (SCAN) and the GARD PAPS extracted from the data set. Unstimulated samples, from the test samples and the reference samples used to build the prediction model, may be used to remove batch effects between data sets.

Final classifications are made using a support vector machine (SVM) which had been trained on the reference samples used to establish the GARD PAPS.

Cell Line Maintenance and Seeding of Cells for Stimulation

The SenzaCell cell line may be maintained in α-MEM (Thermo Scientific Hyclone, Logan, UT) supplemented with 20% (volume/volume) fetal calf serum (Life Technologies, Carlsbad, CA) and 40 ng/ml rhGM-CSF (Bayer HealthCare Pharmaceuticals, Seattle, WA), as described (Johansson et al., 2011). A media change during expansion is performed every 3-4 days, or when cell-density exceeds 5-600.000 cells/ml. Proliferating progenitor cells are used for the assay, with no further differentiation steps applied. During media exchange, cells are counted and suspended to 200.000 cells/ml. Working stocks of cultures are grown for a maximum of 20 passages or two months after thawing. For chemical stimulation of cells, 1.8 ml is seeded in 24-well plates at a concentration of 222.000 cells/ml. The compound to be used for stimulation is added in a volume of 200 μl, diluting the cell density to 200.000 cells/ml during incubation.

Phenotypic Analysis

Prior to any chemical stimulation, a qualitative phenotypic analysis is performed to ensure that proliferating cells are in an immature stage. All cell surface staining and washing steps are performed in PBS containing 1% BSA (w/v). Cells are incubated with specific mouse monoclonal antibodies (mAbs) for 15 min at 4° C. The following mAbs are used for flow cytometry: FITC-conjugated CD1a (Dako-Cytomation, Glostrup, Denmark), CD34, CD86, and HLA-DR (BD Biosciences, San Diego, CA), PE-conjugated CD14 (DakoCytomation), CD54 and CD80 (BD Biosciences). Mouse IgG1, conjugated to FITC or PE are used as isotype controls (BD Biosciences) and propidium iodide (PI) (BD Biosciences) is used to assess cell viability. FACSDiva software is used for data acquisition with FACSCanto II instrument (BD Bioscience). 10,000 events are acquired, gates are set based on light scatter properties to exclude debris and non-viable cells, and quadrants are set according to the signals from isotype controls. Further data analysis is performed, using FCS Express V3 (De Novo Software, Los Angeles, CA). For a reference phenotype of unstimulated cells, see Johansson et al., 2011.

Chemical Handling and Assessment of Cytotoxicity

All chemicals are stored according to instructions from the supplier, in order to ensure stability of compounds. Chemicals are dissolved in water when possible or DMSO for hydrophobic compounds. As many chemicals will have a toxic effect on the cells, cytotoxic effects of test substances are monitored. Some chemicals are poorly dissolved in cell media; therefore the maximum soluble concentration is assessed as well. The chemical that is to be tested is titrated to concentrations ranging from 1 μM to the maximum soluble concentration in cell media. For freely soluble compounds, 500 μM is set as the upper end of the titration range. For cell stimulations, chemicals are dissolved in its appropriate solvent as 1000× stocks of target in-well concentration, called stock A. A 10× stock, called stock B, is prepared by taking 10 μl of stock A to 990 μl of cell media. 200 μl of stock B is then added to the wells containing 1.8 ml seeded cells. For the samples dissolved in DMSO, the in-well concentration of DMSO will thus be 0.1%. Following incubation for 24 h at 37° C. and 5% CO2, harvested cells are stained with PI and analyzed with a flow cytometer. PI-negative cells are defined as viable, and the relative viability of cells stimulated with each concentration in the titration range is calculated as $$\text{Relative viability} = \frac{\text{fraction of viable stimulated cells}}{\text{fraction of viable unstimulated cells}} \cdot 100$$

For toxic compounds, the concentration yielding 90% relative viability (Rv90) is used for the GARD assay, the reason being that this concentration demonstrates bioavailability of the compound used for stimulation, while not impairing immunological responses. For non-toxic compounds, a concentration of 500 μM is used if possible. For non-toxic compounds that are insoluble at 500 μM in cell media, the highest soluble concentration is used.

Whichever of these three criteria is met, only one concentration will be used for the genomic assay. The concentration to be used for any given chemical is termed the 'GARD input concentration'.

Chemical Exposure of Cells for GARD

Once the GARD input concentration for chemicals to be assayed is established, the cells are stimulated again as described above, this time only using the GARD input concentration. All assessments of test substances are assayed in biological triplicates, performed at different time-points and using different cell cultures. Following incubation for 24 h at 37° C. and 5% CO2, cells from one well are lysed in 0.5 ml TRIzol reagent (Life Technologies) and stored at −20° C. until RNA is extracted. In parallel, a small sample of stimulated cells is taken for PI staining and analysis with flow cytometry, to ensure the expected relative viability of stimulated cells is reached.

Preparation of Benchmark Controls

In addition to any test substance(s) to be assayed within a campaign, a set of benchmark controls are performed, for the purpose of prediction model calibration and estimation of prediction performance. For details regarding benchmark controls used in each specific campaign, see the main document to which this appendix is attached.

Isolation of RNA and GPS Quantification Using Nanostring nCounter System

RNA isolation from lysed cells is performed using commercially available kits (Direct-Zol RNA MiniPrep, Zymo Research, Irvine, CA). Total RNA is quantified and quality controlled using BioAnalyzer equipment (Agilent, Santa Clara, CA). A total of 100 ng of RNA is used as sample input in a hybridization assay with GPS specific reporter probe CodeSet (Nanostring, Seattle, WA). The hybridized RNA-CodeSet sample is prepared on chip using nCounter Prepstation and individual transcripts of the GPS is quantified using Nanostring Digital Analyzer (Nanostring).

Data Acquisition and Normalization

Raw data is exported from the Digital Analyzer and counts of individual transcripts of the GPS are single-chip normalized with a count per total counts algorithm. Normalized data consists of a S by V matrix, where S denotes the number of samples in the GARD campaign, and V denotes the number of quantified transcripts of the GPS.

Data Analysis—Generation of Calibrated Support Vector Machine Decision Values

All further downstream analysis is performed using application-based software, developed in the open source statistical environment R. A support vector machine (SVM) is trained using historical data used for GPS establishment (Johansson et al., 2011). All samples from test substances and benchmark controls from the specific GARD campaign are predicted using the trained SVM, assigning each sample with a SVM decision value. The predictor performance is estimated by identification of the area under the receiver operating characteristic (ROC AUC) of the predicted class of benchmark controls.

GARD Classifications of Test Substance(s)

The GARD prediction model is defined as follows:

If the mean decision value of all available biological replicates of a test substance is greater than zero, the test substance is classified as a sensitizer.

Scripts

Listed below are details of the script, written in R code, which may be used to perform the method:

```
# Required files:
#   - GARD_PAPS.R
#   - raw affymetrix files of test samples in subdir: raw_affy/
#   - Annotation of the new data describing the unstimulated samples
      raw_affy/annotation.rds
#   - Historical data stored in trainingset.rds
# Load required dependencies
source('~/GARD_PAPS.R')
# Read Training Data
train = readRDS('~/trainingset.rds')
# Read new data and annotations
new_data = read_raw_affy('~/raw_affy/*.CEL')
new_data_ref = readRDS('~/raw_affy/annotation.rds')
# Normalize the new data
normalized_data = normalize_train_test(train = train, test =
new_data, test_reference = new_data_ref)
# Train model on historical data
model = train_svm(normalized_data$train)
# Predict New Samples
predictions = predict_test_samples(model = model,
data=normalized_data$test)
```

TABLE E

| Probe Set ID | Transcript ID | Transcript Description | Gene Title | Gene Symbol | |
|---|---|---|---|---|---|
| | | Table E(i) | | | |
| 8104107 | ENST00000326754 /// BC111959 /// NM_173553 | Tripartite motif family-like protein 2 gene:ENSG00000179046 /// Homo sapiens tripartite motif family-like 2, mRNA (cDNA clone MGC:138164 IMAGE:8327427), complete cds. /// Homo sapiens tripartite motif family-like 2 (TRIML2), mRNA. | tripartite motif family-like 2 | TRIML2 | 1 |
| 7984862 | ENST00000343932 /// M55053 /// NM_000761 | Isoform 2 of Cytochrome P4501A2 gene:ENSG00000140505 /// Human cytochrome P-3-450 mRNA, complete cds. /// Homo sapiens cytochrome P450, family 1, subfamily A, polypeptide 2 (CYP1A2), mRNA. | cytochrome P450, family 1, subfamily A, polypeptide 2 | CYP1A2 | 2 |
| 8103341 | ENST00000311277 /// ENST00000393836 /// ENST00000379248 /// ENST00000393834 /// AY690636 /// NM_001039580 | Isoform 1 of Microtubule-associated protein 9 gene:ENSG00000164114 /// Isoform 2 of Microtubule-associated protein 9 gene:ENSG00000164114 /// Putative uncharacterized protein MAP9 gene:ENSG00000164114 /// Putative uncharacterized protein MAP9 gene:ENSG00000164114 /// Homo sapiens ASAP mRNA, complete cds. /// Homo sapiens microtubule-associated protein 9 (MAP9), mRNA. | microtubule-associated protein 9 | MAP9 | 3 |
| 8021468 | GENSCAN00000031245 /// XM_001722472 | cdna:Genscan chromosome:NCBI36:18:55579770:55587249:1 /// PREDICTED: Homo sapiens similar to 40S ribosomal protein S26 (LOC100131971), mRNA. | similar to 40S ribosomal protein S26 | LOC100131971 | 4 |
| 8166945 | GENSCAN00000048751 /// ENST00000354794 | cdna:Genscan chromosome:NCBI36:X:44028478:44030436:1 /// cdna:pseudogene chromosome:NCBI36:X:44028257:44030436:1 gene:ENSG00000198414 | — | — | 5 |

TABLE E-continued

| Probe Set ID | Transcript ID | Transcript Description | Gene Title | Gene Symbol | |
|---|---|---|---|---|---|
| 8021461 | ENST00000256857 /// BC004488 /// NM_001012512 /// NM_001012513 /// NM_002091 | gastrin-releasing peptide isoform 1 preproprotein gene:ENSG00000134443 /// Homo sapiens gastrin-releasing peptide, mRNA (cDNA clone MGC:10712 IMAGE:3936083), complete cds. /// Homo sapiens gastrin-releasing peptide (GRP), transcript variant 2, mRNA. /// Homo sapiens gastrin-releasing peptide (GRP), transcript variant 3, mRNA. /// Homo sapiens gastrin-releasing peptide (GRP), transcript variant 1, mRNA. | gastrin-releasing peptide | GRP | 6 |
| 8088903 | GENSCAN00000015233 /// ENST00000358162 | cdna:Genscan chromosome:NCBI36:3:75557484:75756994:−1 /// cdna:pseudogene chromosome:NCBI36:3:75730726:75731229:−1 gene:ENSG00000196454 | — | — | 7 |
| 8053064 | ENST00000409969 /// ENST00000264089 /// ENST00000377668 /// AK001650 /// NM_018221 | cdna:known chromosome:NCBI36:2:74235673:74259503:−1 gene:ENSG00000114978 /// Isoform 1 of Mps one binder kinase activator-like 1B gene:ENSG00000114978 /// Putative uncharacterized protein MOBKL1B (Fragment) gene:ENSG00000114978 /// Homo sapiens cDNA FLJ10788 fis, clone NT2RP4000498, moderately similar to MOB1 PROTEIN. /// Homo sapiens MOB1, Mps One Binder kinase activator-like 1B (yeast) (MOBKL1B), mRNA. | MOB1, Mps One Binder kinase activator-like 1B (yeast) | MOBKL1B | 8 |
| 7945130 | ENST00000411383 /// ENST00000386420 | ncrna:misc_RNA chromosome:NCBI36:11:126782956:126783275:1 gene:ENSG00000223315 /// ncrna:snRNA_pseudogene chromosome:NCBI36:11:126782956:126783196:1 gene:ENSG00000209155 | — | — | 9 |
| 8160260 | ENST00000380672 /// ENST00000380667 /// ENST00000380666 /// AY438376 /// NM_017637 | Isoform 1 of Zinc finger protein basonuclin-2 gene:ENSG00000173068 /// Basonuclin 2 gene:ENSG00000173068 /// Isoform 2 of Zinc finger protein basonuclin-2 gene:ENSG00000173068 /// Homo sapiens basonuclin2 mRNA, complete cds. /// Homo sapiens basonuclin 2 (BNC2), mRNA. | basonuclin 2 | BNC2 | 10 |
| 7934708 | ENST00000372329 /// ENST00000372327 /// ENST00000372325 /// ENST00000398636 /// ENST00000372316 /// ENST00000372313 /// ENST00000372308 /// ENST00000394569 /// AK298029 /// AK298034 /// BC157866 /// BC157890 /// NM_006926 /// NM_001098668 /// NM_001093770 /// NM_005411 | Pulmonary surfactant-associated protein A2 gene:ENSG00000182314 /// cDNA FLJ54288, moderately similar to Pulmonary surfactant-associated protein A1 gene:ENSG00000185303 /// Pulmonary surfactant-associated protein A1 gene:ENSG00000185303 /// Pulmonary surfactant-associated protein A2 gene:ENSG00000122854 /// cDNA FLJ54288, moderately similar to Pulmonary surfactant-associated protein A1 gene:ENSG00000122852 /// Pulmonary surfactant-associated protein A1 gene:ENSG00000122852 /// | surfactant protein A1 /// surfactant protein A1B /// surfactant protein A2 /// surfactant protein A2B | SFTPA1 /// SFTPA1B /// SFTPA2 /// SFTPA2B | 11 |

TABLE E-continued

| Probe Set ID | Transcript ID | Transcript Description | Gene Title | Gene Symbol | |
|---|---|---|---|---|---|
| | | Pulmonary surfactant-associated protein A1 gene:ENSG00000122852 /// Homo sapiens cDNA FLJ51913 complete cds, highly similar to Pulmonary surfactant-associated protein A1 precursor. /// Homo sapiens cDNA FLJ50593 complete cds, moderately similar to Pulmonary surfactant-associated protein A1 precursor. /// Homo sapiens surfactant protein A2B, mRNA (cDNA clone MGC:189761 IMAGE:9057085), complete cds. /// Homo sapiens surfactant protein A2B, mRNA (cDNA clone MGC:189714 IMAGE:8862711), complete cds. /// Homo sapiens surfactant protein A2B (SFTPA2B), mRNA. /// Homo sapiens surfactant protein A2 (SFTPA2), mRNA. /// Homo sapiens surfactant protein A1 (SFTPA1), mRNA. /// Homo sapiens surfactant protein A1B (SFTPA1B), mRNA. | | | |
| 8068046 | ENST00000407713 /// AF304442 | B lymphocyte activation-related protein BC-1514 gene:ENSG00000219130 /// Homo sapiens B lymphocyte activation-related protein BC-1514 mRNA, complete cds. | chromosome 21 open reading frame 118 | C21orf118 | 12 |
| 8131301 | ENST00000365169 | ncrna:snRNA chromosome:NCBI36:7:5186218:5186319:1 gene:ENSG00000202039 | | | 13 |

Table E(ii)

| Probe Set ID | Transcript ID | Transcript Description | Gene Title | Gene Symbol | |
|---|---|---|---|---|---|
| 7934698 | ENST00000372329 /// ENST00000372327 /// ENST00000372325 /// ENST00000398636 /// ENST00000372316 /// ENST00000372313 /// ENST00000372308 /// ENST00000394569 /// AK298029 /// AK298034 /// BC157866 /// BC157890 /// NM_006926 /// NM_001098668 /// NM_001093770 /// NM_005411 | Pulmonary surfactant-associated protein A2 gene:ENSG00000182314 /// cDNA FLJ54288, moderately similar to Pulmonary surfactant-associated protein A1 gene:ENSG00000185303 /// Pulmonary surfactant-associated protein A1 gene:ENSG00000185303 /// Pulmonary surfactant-associated protein A1 gene:ENSG00000185303 /// Pulmonary surfactant-associated protein A2 gene:ENSG00000122854 /// cDNA FLJ54288, moderately similar to Pulmonary surfactant-associated protein A1 gene:ENSG00000122852 /// Pulmonary surfactant-associated protein A1 gene:ENSG00000122852 /// Pulmonary surfactant-associated protein A1 gene:ENSG00000122852 /// Homo sapiens cDNA FLJ51913 complete cds, highly similar to Pulmonary surfactant-associated protein A1 precursor. /// Homo sapiens cDNA FLJ50593 complete cds, moderately similar to Pulmonary surfactant-associated protein A1 precursor. /// Homo sapiens surfactant protein A2B, mRNA (cDNA clone MGC:189761 IMAGE:9057085), complete cds. /// Homo sapiens surfactant protein A2B, mRNA (cDNA clone MGC:189714 | surfactant protein A1 /// surfactant protein A1B /// surfactant protein A2 /// surfactant protein A2B | SFTPA1 /// SFTPA1B /// SFTPA2 /// SFTPA2B | 14 |

TABLE E-continued

| Probe Set ID | Transcript ID | Transcript Description | Gene Title | Gene Symbol | |
|---|---|---|---|---|---|
| | | IMAGE:8862711), complete cds. /// *Homo sapiens* surfactant protein A2B (SFTPA2B), mRNA. /// *Homo sapiens* surfactant protein A2 (SFTPA2), mRNA. /// *Homo sapiens* surfactant protein A1 (SFTPA1), mRNA. /// *Homo sapiens* surfactant protein A1B (SFTPA1B), mRNA. | | | |
| 7916882 | ENST00000262340 /// U18991 /// NM_000329 | Retinal pigment epithelium-specific 65 kDa protein gene:ENSG00000116745 /// Human retinal pigment epithelium-specific 61 kDa protein (RPE65) mRNA, complete cds. /// *Homo sapiens* retinal pigment epithelium-specific protein 6 kDa (RPE65), mRNA. | retinal pigment epithelium-specific protein 65 kDa | RPE65 | 15 |
| 8149324 | ENST00000284486 /// ENST00000398342 /// AL834122 /// NM_053279 | UPF0484 protein FAM167A gene:ENSG00000154319 /// FAM167A protein gene:ENSG00000154319 /// *Homo sapiens* mRNA; cDNA DKFZp761F1821 (from clone DKFZp761F1821). /// *Homo sapiens* family with sequence similarity 167, member A (FAM167A), mRNA. | family with sequence similarity 167, member A | FAM167A | 16 |
| 7914992 | ENST00000387309 | ncrna:rRNA_pseudogene chromosome:NCBI36:1:37502886:37502974:−1 gene:ENSG00000210044 | — | — | 17 |
| 8021774 | ENST00000405150 /// AK126293 | FLJ44313 protein gene:ENSG00000220032 /// *Homo sapiens* cDNA FLJ44313 fis, clone TRACH2025911. | FLJ44313 protein | FLJ44313 | 18 |
| 7965573 | ENST00000344911 /// ENST00000343702 /// AF278532 /// NM_021229 | Isoform 2 of Netrin-4 gene:ENSG00000074527 /// Isoform 1 of Netrin-4 gene:ENSG00000074527 /// *Homo sapiens* beta-netrin mRNA, complete cds. /// *Homo sapiens* netrin4 (NTN4), mRNA. | netrin 4 | NTN4 | 19 |
| 8057771 | ENST00000358470 /// ENST00000392320 /// BC031212 /// NM_003151 | Signal transducer and activator of transcription 4 gene:ENSG00000138378 /// Signal transducer and activator of transcription 4 gene:ENSG00000138378 /// *Homo sapiens* signal transducer and activator of transcription 4, mRNA (cDNA clone MGC:39492 IMAGE:4830583), complete cds. /// *Homo sapiens* signal transducer and activator of transcription 4 (STAT4), mRNA. | signal transducer and activator of transcription 4 | STAT4 | 20 |
| 8111417 | ENST00000342059 /// ENST00000296589 /// ENST00000382102 /// ENST00000345083 /// AF172849 /// NM_016180 /// NM_001012509 | Isoform AIM-1c of Membrane-associated transporter protein gene:ENSG00000164175 /// Isoform AIM-1a of Membrane-associated transporter protein gene:ENSG00000164175 /// membrane-associated transporter protein isoform b gene:ENSG00000164175 /// Isoform AIM-1b of Membrane-associated transporter protein gene:ENSG00000164175 /// *Homo sapiens* AIM-1 protein mRNA, complete cds. /// *Homo sapiens* solute carrier family 45, member 2 (SLC45A2), transcript variant 1, mRNA. /// *Homo sapiens* solute carrier family 45, member 2 (SLC45A2), transcript variant 2, mRNA. | solute carrier family 45, member 2 | SLC45A2 | 21 |

TABLE E-continued

| Probe Set ID | Transcript ID | Transcript Description | Gene Title | Gene Symbol | |
|---|---|---|---|---|---|
| 8161381 | ENST00000316269 /// AK125850 /// AL833349 | hypothetical protein gene:ENSG00000204831 /// *Homo sapiens* cDNA FLJ43862 fis, clone TESTI4007775. /// *Homo sapiens* mRNA; cDNA DKFZp686P0734 (from clone DKFZp686P0734). | hypothetical protein LOC100133036 /// family with sequence similarity 95, member B1 | LOC100133036 /// FAM95B1 | 22 |
| 8165032 | ENST00000371763 /// AY336054 /// NM_182974 | Glycosyltransferase 6 domain-containing protein 1 gene:ENSG00000204007 /// *Homo sapiens* gycosyltransferase family 6 like-protein mRNA, complete cds. /// *Homo sapiens* glycosyltransferase 6 domain containing 1 (GLT6D1), mRNA. | glycosyltransferase 6 domain containing 1 | GLT6D1 | 23 |
| 8113276 | AF119888 | *Homo sapiens* PRO2613 mRNA, complete cds. | — | — | 24 |
| 8116874 | ENST00000283141 /// ENST00000341041 /// AK128130 /// NM_001040274 | Isoform 1 of Synaptonemal complex protein 2-like gene:ENSG00000153157 /// Isoform 1 of Synaptonemal complex protein 2-like gene:ENSG00000153157 /// *Homo sapiens* cDNA FLJ46251 fis, clone TESTI4021713, weakly similar to *Homo sapiens* synaptonemal complex protein 2 (SYCP2). /// *Homo sapiens* synaptonemal complex protein 2-like (SYCP2L), mRNA. | synaptonemal complex protein 2-like | SYCP2L | 25 |
| 8030753 | ENST00000326003 /// ENST00000326052 /// ENST00000360617 /// BC005307 /// NM_001648 /// NM_001030047 /// NM_001030048 /// NM_001030049 /// NM_001030050 | Prostate-specific antigen gene:ENSG00000142515 /// prostate specific antigen isoform 5 preproprotein gene:ENSG00000142515 /// prostate specific antigen isoform 3 preproprotein gene:ENSG00000142515 /// *Homo sapiens* kallikrein-related peptidase 3, mRNA (cDNA clone MGC:12378 IMAGE:3950475), complete cds. /// *Homo sapiens* kallikrein-related peptidase 3 (KLK3), transcript variant 1, mRNA. /// *Homo sapiens* kallikrein-related peptidase 3 (KLK3), transcript variant 3, mRNA. /// *Homo sapiens* kallikrein-related peptidase 3 (KLK3), transcript variant 4, mRNA. /// *Homo sapiens* kallikrein-related peptidase 3 (KLK3), transcript variant 5, mRNA. /// *Homo sapiens* kallikrein-related peptidase 3 (KLK3), transcript variant 6, mRNA. | kallikrein-related peptidase 3 | KLK3 | 26 |
| 8098439 | GENSCAN00000042517 | cdna:Genscan chromosome:NCBI36:4:182680810:182745578:1 | — | — | 27 |
| 8076819 | ENST00000380990 /// AK128136 | Conserved hypothetical protein gene:ENSG00000205634 /// *Homo sapiens* cDNA FLJ46257 fis, clone TESTI4024240. | FLJ46257 protein | RP11-191L9.1 | 28 |

TABLE E-continued

| Probe Set ID | Transcript ID | Transcript Description | Gene Title | Gene Symbol | |
|---|---|---|---|---|---|
| 7957819 | ENST00000392989 /// ENST00000323346 /// AK128319 /// NM_139319 | Isoform 2 of Vesicular glutamate transporter 3 gene:ENSG00000179520 /// Isoform 1 of Vesicular glutamate transporter 3 gene:ENSG00000179520 /// Homo sapiens cDNA FLJ46460 fis, clone THYMU3021404, highly similar to Homo sapiens solute carrier family 17 (sodium-dependent inorganic phosphate cotransporter), member 8 (SLC17A8), mRNA. /// Homo sapiens solute carrier family 17 (sodium-dependent inorganic phosphate cotransporter), member 8 (SLC17A8), mRNA. | solute carrier family 17 (sodium-dependent inorganic phosphate cotransporter), member 8 | SLC17A8 | 29 |
| 7986229 | ENST00000268164 /// ENST00000378973 /// BC096202 /// NM_006011 | Alpha-2,8-sialyltransferase 8B gene:ENSG00000140557 /// ST8SIA2 protein gene:ENSG00000140557 /// Homo sapiens ST8 alpha-N-acetyl-neuraminide alpha-2,8-sialyltransferase 2, mRNA (cDNA clone MGC:116854 IMAGE:40004644), complete cds. /// Homo sapiens ST8 alpha-N-acetyl-neuraminide alpha-2,8-sialyltransferase 2 (ST8SIA2), mRNA. | ST8 alpha-N-acetyl-neuraminide alpha-2,8-sialyltransferase 2 | ST8SIA2 | 30 |
| 7995310 | ENST00000319817 | Putative uncharacterized protein MGC3480 gene:ENSG00000179755 | — | — | 31 |
| 8138920 | ENST00000387801 /// ENST00000387652 /// ENST00000387676 /// ENST00000387734 /// ENST00000386042 | ncrna:snRNA_pseudogene chromosome:NCBI36:12:62305744:62305830:-1 gene:ENSG00000210536 /// ncrna:snRNA_pseudogene chromosome:NCBI36:7:29701450:29701536:1 gene:ENSG00000210387 /// ncrna:snRNA_pseudogene chromosome:NCBI36:7:32724496:32724582:-1 gene:ENSG00000210411 /// ncrna:snRNA_pseudogene chromosome:NCBI36:7:35155590:35155669:-1 gene:ENSG00000210469 /// ncrna:snRNA_pseudogene chromosome:NCBI36:7:102669899:102669985:-1 gene:ENSG00000208777 | — | — | 32 |
| 8055492 | ENST00000385544 | ncrna:Mt_tRNA_pseudogene chromosome:NCBI36:2:140697147:140697215:-1 gene:ENSG00000208279 | — | — | 33 |
| 7995674 | ENST00000290552 /// AK125053 /// NM_024335 | Iroquois-class homeodomain protein IRX-6 gene:ENSG00000159387 /// Homo sapiens cDNA FLJ43063 fis, clone BRTHA3008310, moderately similar to Mus musculus mRNA for iroquois homeobox protein 6. /// Homo sapiens iroquois homeobox 6 (IRX6), mRNA. | iroquois homeobox 6 | IRX6 | 34 |
| 8155627 | ENST00000316269 /// AK125850 /// AL833349 | hypothetical protein gene:ENSG00000204831 /// Homo sapiens cDNA FLJ43862 fis, clone TESTI4007775. /// Homo sapiens mRNA; cDNA DKFZp686P0734 (from clone DKFZp686P0734). | hypothetical protein LOC100133036 /// family with sequence similarity 95, member B1 | LOC100133036 /// FAM95B1 | 35 |
| 7941608 | GENSCAN00000024384 /// ENST00000364863 | cdna:Genscan chromosome:NCBI36:11:65945227:65956926:1 /// ncrna:snoRNA chromosome:NCBI36:11:65956813:65956949:1 gene:ENSG00000201733 | — | — | 36 |
| 7957495 | ENST00000362375 | ncrna:misc_RNA chromosome:NCBI36:12:87348350:87348458:1 gene:ENSG00000199245 | — | — | 37 |

TABLE E-continued

| Probe Set ID | Transcript ID | Transcript Description | Gene Title | Gene Symbol | |
|---|---|---|---|---|---|
| 7961413 | ENST00000318426 /// BC101220 /// NM_182558 | Putative uncharacterized protein C12orf36 gene:ENSG00000180861 /// *Homo sapiens* chromosome 12 open reading frame 36, mRNA (cDNA clone MGC:120138 IMAGE:40022214), complete cds. /// *Homo sapiens* chromosome 12 open reading frame 36 (C12orf36), mRNA. | chromosome 12 open reading frame 36 | C12orf36 | 38 |
| 8055941 | ENST00000325926 /// BC002908 /// NM_019845 | Protein reprimo gene:ENSG00000177519 /// *Homo sapiens* reprimo, TP53 dependent G2 arrest mediator candidate, mRNA (cDNA clone MGC:11260 IMAGE:3942270), complete cds. /// *Homo sapiens* reprimo, TP53 dependent G2 arrest mediator candidate (RPRM), mRNA. | reprimo, TP53 dependent G2 arrest mediator candidate | RPRM | 39 |
| 7962792 | ENST00000310248 /// NM_001004134 | Olfactory receptor 10AD1 gene:ENSG00000172640 /// *Homo sapiens* olfactory receptor, family 10, subfamily AD, member 1 (OR10AD1), mRNA. | olfactory receptor, family 10, subfamily AD, member 1 | OR10AD1 | 40 |
| 7896756 | ENST00000326734 /// BC118644 | similar to hCG1735895 gene:ENSG00000177757 /// *Homo sapiens* cDNA clone IMAGE:40030978. | — | — | 41 |
| 8054939 | ENST00000411186 | ncrna:misc_RNA chromosome:NCBI36:2:124343303:124343617:-1 gene:ENSG00000223118 | — | — | 42 |
| 7976057 | ENST00000387641 | ncrna:snoRNA_pseudogene chromosome:NCBI36:14:81998185:81998284:1 gene:ENSG00000210376 | — | — | 43 |
| 7940002 | ENST00000332362 /// BC136737 /// NM_001005210 | Leucine rich repeat containing 55 gene:ENSG00000183908 /// *Homo sapiens* leucine rich repeat containing 55, mRNA (cDNA clone MGC:168350 IMAGE:9020727), complete cds. /// *Homo sapiens* leucine rich repeat containing 55 (LRRC55), mRNA. | leucine rich repeat containing 55 | LRRC55 | 44 |
| 7979204 | ENST00000395631 /// ENST00000343279 /// ENST00000341590 /// Z24725 /// NM_006832 /// NM_001134999 /// NM_001135000 | Isoform 1 of Fermitin family homolog 2 gene:ENSG00000073712 /// fermitin family homolog 2 isoform 2 gene:ENSG00000073712 /// Isoform 1 of Fermitin family homolog 2 gene:ENSG00000073712 /// *H. sapiens* mitogen inducible gene mig-2, complete CDS. /// *Homo sapiens* fermitin family homolog 2 (*Drosophila*) (FERMT2), transcript variant 1, mRNA. /// *Homo sapiens* fermitin family homolog 2 (*Drosophila*) (FERMT2), transcript variant 2, mRNA. /// *Homo sapiens* fermitin family homolog 2 (*Drosophila*) (FERMT2), transcript variant 3, mRNA. | fermitin family homolog 2 (*Drosophila*) | FERMT2 | 45 |
| 7981190 | AL834311 | *Homo sapiens* mRNA; cDNA DKFZp434O1614 (from clone DKFZp434O1614). | hypothetical LOC100130815 | LOC100130815 | 46 |
| 8092686 | ENST00000358241 /// BC068081 /// NM_001004312 | Receptor-transporting protein 2 gene:ENSG00000198471 /// *Homo sapiens* receptor (chemosensory) transporter protein 2, mRNA (cDNA clone MGC:78665 IMAGE:6212901), complete cds. /// *Homo sapiens* receptor (chemosensory) transporter protein 2 (RTP2), mRNA. | receptor (chemosensory) transporter protein 2 | RTP2 | 47 |

TABLE E-continued

| Probe Set ID | Transcript ID | Transcript Description | Gene Title | Gene Symbol | |
|---|---|---|---|---|---|
| 7961604 | ENST00000266505 /// ENST00000318197 /// AY035866 /// NM_033123 | Isoform 1 of 1-phosphatidylinositol-4,5-bisphosphate phosphodiesterase zeta-1 gene:ENSG00000139151 /// cDNA FLJ40236 fis, clone TESTI2023214, weakly similar to 1-PHOSPHATIDYLINOSITOL-4,5-BISPHOSPHATE PHOSPHODIESTERASE DELTA 1 gene:ENSG00000139151 /// Homo sapiens testis-development related NYD-SP27 mRNA, complete cds. /// Homo sapiens phospholipase C, zeta 1 (PLCZ1), mRNA. | phospholipase C, zeta 1 | PLCZ1 | 48 |
| 8026503 | ENST00000397365 /// ENST00000343017 /// NR_024335 /// NR_024336 | Putative uncharacterized protein FLJ25328 gene:ENSG00000167459 /// FLJ25328 protein (Fragment) gene:ENSG00000167459 /// Homo sapiens hypothetical LOC148231 (FLJ25328), transcript variant 1, non-coding RNA. /// Homo sapiens hypothetical LOC148231 (FLJ25328), transcript variant 2, non-coding RNA. | hypothetical LOC148231 | FLJ25328 | 49 |
| 8084887 | ENST00000411400 /// ENST00000385589 | ncrna:misc_RNA chromosome:NCBI36:3:195346160:195346450:1 gene:ENSG00000223332 /// ncrna:scRNA_pseudogene chromosome:NCBI36:3:195346161:195346454:1 gene:ENSG00000208324 | — | — | 50 |
| 7904417 | GENSCAN00000027599 /// ENST00000286193 | cdna:Genscan chromosome:NCBI36:1:119806478:119858791:1 /// cdna:pseudogene chromosome:NCBI36:1:119811367:119817360:1 gene:ENSG00000187481 | — | — | 51 |
| 8112666 | GENSCAN00000026551 /// ENST00000329491 | cdna:Genscan chromosome:NCBI36:5:74319149:74349847:−1 /// cdna:pseudogene chromosome:NCBI36:5:74321774:74322218:−1 gene:ENSG00000182383 | — | — | 52 |
| 8036969 | ENST00000301141 /// ENST00000301146 /// ENST00000291764 /// ENST00000359667 /// ENST00000330436 /// AF209774 /// M33317 /// M33318 /// NM_000764 /// NM_000762 /// NM_000766 /// NM_030589 | Cytochrome P450 2A6 gene:ENSG00000213052 /// Cytochrome P450 2A7 gene:ENSG00000198077 /// cytochrome P450, family 2, subfamily A, polypeptide 7 isoform 2 gene:ENSG00000198077 /// cdna:known chromosome:NCBI36:19:46107659:46108594:−1 gene:ENSG00000198251 /// Cytochrome P450 2A13 gene:ENSG00000197838 /// Homo sapiens cytochrome P450 2A13 (CYP2A13)mRNA, complete cds. /// Human cytochrome P450IIA4 (CYP2A4) mRNA, complete cds. /// Human cytochrome P450IIA3 (CYP2A3) mRNA, complete cds. /// Homo sapiens cytochrome P450, family 2, subfamily A, polypeptide 7 (CYP2A7), transcript variant 1, mRNA. /// Homo sapiens cytochrome P450, family 2, subfamily A, polypeptide 6 (CYP2A6), mRNA. /// Homo sapiens cytochrome P450, family 2, subfamily A, polypeptide 13 (CYP2A13), mRNA. /// Homo sapiens cytochrome P450, family 2, subfamily A, polypeptide 7 (CYP2A7), transcript variant 2, mRNA. | cytochrome P450, family 2, subfamily A, polypeptide 13 /// cytochrome P450, family 2, subfamily A, polypeptide 7 /// cytochrome P450, family 2, subfamily A, polypeptide 6 | CYP2A13 /// CYP2A7 /// CYP2A6 | 53 |

TABLE E-continued

| Probe Set ID | Transcript ID | Transcript Description | Gene Title | Gene Symbol | |
|---|---|---|---|---|---|
| 8176935 | ENST00000303804 /// ENST00000303728 /// ENST00000343584 /// ENST00000303593 /// ENST00000306589 /// ENST00000338673 /// AF000988 /// NM_001002758 /// NM_004676 | Isoform 1 of PTPN13-like protein, Y-linked gene:ENSG00000169807 /// Isoform 1 of PTPN13-like protein, Y-linked gene:ENSG00000169789 /// Isoform 1 of PTPN13-like protein, Y-linked gene:ENSG00000169763 /// Isoform 2 of PTPN13-like protein, Y-linked gene:ENSG00000169763 /// Isoform 1 of PTPN13-like protein, Y-linked gene:ENSG00000172283 /// Isoform 2 of PTPN13-like protein, Y-linked gene:ENSG00000172283 /// Homo sapiens testis-specific PTP-BL Related Y protein (PRY) mRNA, complete cds. /// Homo sapiens PTPN13-like, Y-linked 2 (PRY2), mRNA. /// Homo sapiens PTPN13-like, Y-linked (PRY), mRNA. | PTPN13-like, Y-linked /// PTPN13-like, Y-linked 2 | PRY /// PRY2 | 54 |
| 8044124 | ENST00000258456 /// U92642 /// NM_007227 | High-affinity lysophosphatidic acid receptor homolog gene:ENSG00000135973 /// Human high-affinity lysophosphatidic acid receptor homolog mRNA, complete cds. /// Homo sapiens G protein-coupled receptor 45 (GPR45), mRNA. | G protein-coupled receptor 45 | GPR45 | 55 |
| 8070930 | — | — | — | — | 56 |
| 8015037 | AK095738 | Homo sapiens cDNA FLJ38419 fis, clone FEBRA2009846. | — | — | 57 |
| 7969482 | ENST00000377462 | similar to hCG30005 gene:ENSG00000102794 | — | — | 58 |
| 8173524 | ENST00000373619 /// ENST00000246139 /// U65092 /// NM_004143 | Cbp/p300-interacting transactivator 1 gene:ENSG00000125931 /// Cbp/p300-interacting transactivator 1 gene:ENSG00000125931 /// Human melanocyte-specific gene 1 (msg1) mRNA, complete cds. /// Homo sapiens Cbp/p300-interacting transactivator, with Glu/Asp-rich carboxy-terminal domain, 1 (CITED1), mRNA. | Cbp/p300-interacting transactivator, with Glu/Asp-rich carboxy-terminal domain, 1 | CITED1 | 59 |
| 8143747 | ENST00000385536 | ncrna:tRNA_pseudogene chromosome:NCBI36:7:148966447:148966513:−1 gene:ENSG00000208271 | — | — | 60 |
| 8080781 | ENST00000356151 /// ENST00000302779 /// ENST00000383715 /// ENST00000383716 /// AY274811 /// NM_017771 | Isoform 1 of PX domain-containing protein kinase-like protein gene:ENSG00000168297 /// Isoform 4 of PX domain-containing protein kinase-like protein gene:ENSG00000168297 /// Isoform 2 of PX domain-containing protein kinase-like protein gene:ENSG00000168297 /// Isoform 6 of PX domain-containing protein kinase-like protein gene:ENSG00000168297 /// Homo sapiens PX serine/threonine kinase mRNA, complete cds. /// Homo sapiens PX domain containing serine/threonine kinase (PXK), mRNA. | PX domain containing serine/threonine kinase | PXK | 61 |
| 8111118 | ENST00000365399 | ncrna:snoRNA chromosome:NCBI36:5:15163895:15164029:−1 gene:ENSG00000202269 | — | — | 62 |
| 7934883 | ENST00000387878 | ncrna:scRNA_pseudogene chromosome:NCBI36:10:89582555:89582827:−1 gene:ENSG00000210613 | — | — | 63 |

TABLE E-continued

| Probe Set ID | Transcript ID | Transcript Description | Gene Title | Gene Symbol | |
|---|---|---|---|---|---|
| 8010113 | ENST00000374998 /// ENST00000374999 /// ENST00000301618 /// AB114297 /// NM_144677 /// NM_198955 | Isoform 3 of Alpha-1,6-mannosylglycoprotein 6-beta-N-acetylglucosaminyltransferase B gene:ENSG00000167889 /// Isoform 1 of Alpha-1,6-mannosylglycoprotein 6-beta-N-acetylglucosaminyltransferase B gene:ENSG00000167889 /// beta(1,6)-N-acetylglucosaminyltransferase V isoform 1 gene:ENSG00000167889 /// *Homo sapiens* hGnTVb mRNA for UDP-N-acetylglucosamine: alpha1,6-D-mannoside beta1,6-N-acetylglucosaminyltransferase b, complete cds. /// *Homo sapiens* mannosyl (alpha-1,6-)-glycoprotein beta-1,6-N-acetyl-glucosaminyltransferase, isozyme B (MGAT5B), transcript variant 1, mRNA. /// *Homo sapiens* mannosyl (alpha-1,6-)-glycoprotein beta-1,6-N-acetyl-glucosaminyltransferase, isozyme B (MGAT5B), transcript variant 2, mRNA. | mannosyl (alpha-1,6-)-glycoprotein beta-1,6-N-acetyl-glucosaminyl-transferase, isozyme B | MGAT5B | 64 |
| 8175524 | ENST00000370540 /// NM_001013403 | Uncharacterized protein LOC347487 gene:ENSG00000203933 /// *Homo sapiens* hypothetical LOC347487 (LOC347487), mRNA. | hypothetical LOC347487 | RP11-35F15.2 | 65 |
| 7997740 | ENST00000268607 /// BC045759 /// NM_022818 | Microtubule-associated proteins 1A/1B light chain 3B gene:ENSG00000140941 /// *Homo sapiens* microtubule-associated protein 1 light chain 3 beta, mRNA (cDNA clone MGC:48651 IMAGE:4828857), complete cds. /// *Homo sapiens* microtubule-associated protein 1 light chain 3 beta (MAP1LC3B), mRNA. | microtubule-associated protein 1 light chain 3 beta | MAP1LC3B | 66 |
| 8177395 | ENST00000303804 /// ENST00000303728 /// ENST00000343584 /// ENST00000303593 /// ENST00000306589 /// ENST00000338673 /// AF000988 /// NM_001002758 /// NM_004676 | Isoform 1 of PTPN13-like protein, Y-linked gene:ENSG00000169807 /// Isoform 1 of PTPN13-like protein, Y-linked gene:ENSG00000169789 /// Isoform 1 of PTPN13-like protein, Y-linked gene:ENSG00000169763 /// Isoform 2 of PTPN13-like protein, Y-linked gene:ENSG00000169763 /// Isoform 1 of PTPN13-like protein, Y-linked gene:ENSG00000172283 /// Isoform 2 of PTPN13-like protein, Y-linked gene:ENSG00000172283 /// *Homo sapiens* testis-specific PTP-BL Related Y protein (PRY) mRNA, complete cds. /// *Homo sapiens* PTPN13-like, Y-linked 2 (PRY2), mRNA. /// *Homo sapiens* PTPN13-like, Y-linked (PRY), mRNA. | PTPN13-like, Y-linked /// PTPN13-like, Y-linked 2 | PRY /// PRY2 | 67 |
| 7929478 | ENST00000371321 /// M61854 /// NM_000769 | Cytochrome P450 2C19 gene:ENSG00000165841 /// Human cytochrome P4502C19 (CYP2C19) mRNA, clone 11a. /// *Homo sapiens* cytochrome P450, family 2, subfamily C, polypeptide 19 (CYP2C19), mRNA. | cytochrome P450, family 2, subfamily C, polypeptide 19 | CYP2C19 | 68 |

TABLE E-continued

| Probe Set ID | Transcript ID | Transcript Description | Gene Title | Gene Symbol | |
|---|---|---|---|---|---|
| 8102781 | GENSCAN00000015129 /// XR_016991 | cdna:Genscan chromosome:NCBI36:4:1328637 36:133029672:−1 /// PREDICTED: *Homo sapiens* similar to hCG2026352 (LOC646187), mRNA. | similar to hCG2026352 | LOC646187 | 69 |
| 8155026 | ENST00000329395 /// BC031276 /// NR_003581 /// NR_003582 | Putative FetA-like protein gene:ENSG00000179766 /// *Homo sapiens* ATPase, Class I, type 8B family pseudogene, mRNA (cDNA clone MGC:39768 IMAGE:5295199), complete cds. /// *Homo sapiens* ATPase, Class I, type 8B family pseudogene (LOC158381), transcript variant 1, non-coding RNA. /// *Homo sapiens* ATPase, Class I, type 8B family pseudogene (LOC158381), transcript variant 2, non-coding RNA. | ATPase, Class I, type 8B family pseudogene | LOC158381 | 70 |
| 8146914 | ENST00000276603 /// ENST00000276602 /// U74382 /// NM_003218 /// NM_017489 | Isoform 1 of Telomeric repeat-binding factor 1 gene:ENSG00000147601 /// Isoform 2 of Telomeric repeat-binding factor 1 gene:ENSG00000147601 /// Human telomeric repeat DNA-binding protein (PIN2) mRNA, complete cds. /// *Homo sapiens* telomeric repeat binding factor (NIMA-interacting) 1 (TERF1), transcript variant 2, mRNA. /// *Homo sapiens* telomeric repeat binding factor (NIMA-interacting) 1 (TERF1), transcript variant 1, mRNA. | telomeric repeat binding factor (NIMA-interacting) 1 | TERF1 | 71 |
| 8169022 | ENST00000372661 /// ENST00000372656 /// BC023544 /// NM_001006612 /// NM_016303 /// NM_001006614 /// NM_001006613 | WW domain-binding protein 5 gene:ENSG00000185222 /// WW domain-binding protein 5 gene:ENSG00000185222 /// *Homo sapiens* WW domain binding protein 5, mRNA (cDNA clone MGC:15211 IMAGE:4122244), complete cds. /// *Homo sapiens* WW domain binding protein 5 (WBP5), transcript variant 2, mRNA. /// *Homo sapiens* WW domain binding protein 5 (WBP5), transcript variant 1, mRNA. /// *Homo sapiens* WW domain binding protein 5 (WBP5), transcript variant 4, mRNA. /// *Homo sapiens* WW domain binding protein 5 (WBP5), transcript variant 3, mRNA. | WW domain binding protein 5 | WBP5 | 72 |
| 7944952 | ENST00000340456 /// AK128036 | cdna:known chromosome:NCBI36:11:124488267:124501887:1 gene:ENSG00000187686 /// *Homo sapiens* cDNA FLJ46155 fis, clone TESTI4001517. | — | — | 73 |
| 8108199 | BC025747 | *Homo sapiens* similar to CG4995 gene product, mRNA (cDNA clone MGC:35539 IMAGE:5200129), complete cds. | similar to CG4995 gene product | LOC153328 | 74 |
| 8040618 | ENST00000264710 /// AK023223 /// NM_016131 | Ras-related protein Rab-10 gene:ENSG00000084733 /// *Homo sapiens* cDNA FLJ13161 fis, clone NT2RP3003589, highly similar to *Homo sapiens* ras-related GTP-binding protein mRNA. /// *Homo sapiens* RAB10, member RAS oncogene family (RAB10), mRNA. | RAB10, member RAS oncogene family | RAB10 | 75 |

TABLE E-continued

| Probe Set ID | Transcript ID | Transcript Description | Gene Title | Gene Symbol | |
|---|---|---|---|---|---|
| 7981326 | hsa-mir-1247 /// hsa-mir-1247 /// AF305836 /// AF469206 /// BC065701 | MI0006382 Homo sapiens miR-1247 stem-loop /// MI0006382 Homo sapiens miR-1247 stem-loop /// Homo sapiens uterine-derived 14 kDa protein mRNA, complete cds. /// Homo sapiens clone 8 DIO3AS mRNA, partial sequence; alternatively spliced. /// Homo sapiens deiodinase, iodothyronine, type /// opposite strand, mRNA (cDNA clone IMAGE:6205020). | DIO3 opposite strand (non-protein coding) | DIO3OS | 76 |
| 8057004 | ENST00000358450 /// ENST00000286063 /// ENST00000389683 /// ENST00000409504 /// AB036704 /// NM_001077358 /// NM_016953 /// NM_001077196 /// NM_001077197 | Isoform 2 of Dual 3',5'-cyclic-AMP and -GMP phosphodiesterase 11A gene:ENSG00000128655 /// Isoform 1 of Dual 3',5'-cyclic-AMP and -GMP phosphodiesterase 11A gene:ENSG00000128655 /// Isoform 4 of Dual 3',5'-cyclic-AMP and -GMP phosphodiesterase 11A gene:ENSG00000128655 /// cdna:known chromosome:NCBI36:2:178202021:178495768:−1 gene:ENSG00000128655 /// Homo sapiens HSPDE11A mRNA for phosphodiesterase 11A, complete cds. /// Homo sapiens phosphodiesterase 11A (PDE11A), transcript variant 2, mRNA. /// Homo sapiens phosphodiesterase 11A (PDE11A), transcript variant 4, mRNA. /// Homo sapiens phosphodiesterase 11A (PDE11A), transcript variant 1, mRNA. /// Homo sapiens phosphodiesterase 11A (PDE11A), transcript variant 3, mRNA. | phosphodiesterase 11A | PDE11A | 77 |
| 8108370 | ENST00000239938 /// M62829 /// NM_001964 | Early growth response protein 1 gene:ENSG00000120738 /// Human transcription factor ETR103 mRNA, complete cds. /// Homo sapiens early growth response 1 (EGR1), mRNA. | early growth response 1 | EGR1 | 78 |
| 8159078 | ENST00000316948 /// ENST00000291722 /// AK074852 /// NM_017586 /// NM_001135775 | Isoform 1 of Transmembrane protein C9orf7 gene:ENSG00000160325 /// Isoform 2 of Transmembrane protein C9orf7 gene:ENSG00000160325 /// Homo sapiens cDNA FLJ90371 fis, clone NT2RP2004524. /// Homo sapiens chromosome 9 open reading frame 7 (C9orf7), transcript variant 1, mRNA. /// Homo sapiens chromosome 9 open reading frame 7 (C9orf7), transcript variant 2, mRNA. | chromosome 9 open reading frame 7 | C9orf7 | 79 |
| 8035956 | ENST00000365097 | ncrna:misc_RNA chromosome:NCBI36:19:38045533:38045838:−1 gene:ENSG00000201967 | — | — | 80 |
| 7982868 | ENST00000249798 /// ENST00000397434 /// BC019625 /// NM_024111 | Cation transport regulator-like protein 1 gene:ENSG00000128965 /// Cation transport protein-like protein gene:ENSG00000128965 /// Homo sapiens ChaC, cation transport regulator homolog 1 (E. coli), mRNA (cDNA clone MGC:24988 IMAGE:4473135), complete cds. /// Homo sapiens ChaC, cation transport regulator homolog 1 (E. coli) (CHAC1), mRNA. | ChaC, cation transport regulator homolog 1 (E. coli) | CHAC1 | 81 |

TABLE E-continued

| Probe Set ID | Transcript ID | Transcript Description | Gene Title | Gene Symbol | |
|---|---|---|---|---|---|
| 8084878 | ENST00000384640 | ncrna:misc__RNA chromosome:NCBI36:3:194824672:194824784:1 gene:ENSG00000207370 | — | — | 82 |
| 7969959 | ENST00000375936 /// ENST00000329625 /// DQ343761 /// NM__172370 | Isoform 1 of D-amino acid oxidase activator gene:ENSG00000182346 /// Putative uncharacterized protein DAOA gene:ENSG00000182346 /// Homo sapiens schizophrenia and bipolar disorder associated protein G72 form A mRNA, complete cds, alternatively spliced. /// Homo sapiens D-amino acid oxidase activator (DAOA), mRNA. | D-amino acid oxidase activator | DAOA | 83 |
| 8137330 | ENST00000356058 /// AK128129 | cDNA FLJ46250 fis, clone TESTI4021569, moderately similar to ATP-binding cassette, sub-family B, member 8, mitochondrial gene:ENSG00000197150 /// Homo sapiens cDNA FLJ46250 fis, clone TESTI4021569, moderately similar to ATP-binding cassette, sub-family B, member 8, mitochondrial precursor. | — | — | 84 |
| 8160383 | ENST00000259555 /// ENST00000380220 /// ENST00000239347 /// M34913 /// V00542 /// NM__021057 /// NM__002172 | Interferon alpha-14 gene:ENSG00000186809 /// Interferon alpha-14 gene:ENSG00000186809 /// Interferon alpha-7 gene:ENSG00000214042 /// Human interferon-alpha-J1 (IFN-alpha-J1) mRNA, complete cds. /// Messenger RNA for human leukocyte (alpha) interferon. /// Homo sapiens interferon, alpha 7 (IFNA7), mRNA. /// Homo sapiens interferon, alpha 14 (IFNA14), mRNA. | interferon, alpha 7 /// interferon, alpha 14 | IFNA7 /// IFNA14 | 85 |
| 8071168 | ENST00000342005 /// ENST00000329949 /// ENST00000402027 /// ENST00000248992 /// AK292412 /// AK302597 /// AY358961 /// NR__003714 | cDNA FLJ60978, weakly similar to Nuclear envelope pore membrane protein POM 121 gene:ENSG00000182356 /// Putative uncharacterized protein ENSP00000383394 gene:ENSG00000217261 /// POM121-like 1 protein gene:ENSG00000183169 /// POM121-like gene:ENSG00000128262 /// Homo sapiens cDNA FLJ76724 complete cds. /// Homo sapiens cDNA FLJ60978 complete cds, weakly similar to Nuclear envelope pore membrane protein POM 121. /// Homo sapiens clone DNA107786 POM121-like (UNQ2565) mRNA, complete cds. /// Homo sapiens POM121-like protein (DKFZP434P211), non-coding RNA. | POM121 membrane glycoprotein-like 1 (rat) /// POM121 membrane glycoprotein-like 1 pseudogene /// POM121 membrane glycoprotein-like 1 pseudogene | POM121L1 /// DKFZp434K191 /// DKFZP434P211 | 86 |
| 8067965 | AF304443 | Homo sapiens B lymphocyte activation-related protein BC-2048 mRNA, complete cds. | — | — | 87 |
| 8175589 | ENST00000364415 | ncrna:rRNA chromosome:NCBI36:X:146897312:146897427:−1 gene:ENSG00000201285 | — | — | 88 |

TABLE E-continued

| Probe Set ID | Transcript ID | Transcript Description | Gene Title | Gene Symbol | |
|---|---|---|---|---|---|
| 7935990 | ENST00000406432 ///<br>ENST00000020673 ///<br>BC142643 ///<br>NM_002779 | Isoform 1 of PH and SEC7 domain-containing protein 1 gene:ENSG00000059915 /// Isoform 1 of PH and SEC7 domain-containing protein 1 gene:ENSG00000059915 /// Homo sapiens pleckstrin and Sec7 domain containing, mRNA (cDNA clone MGC:164849 | pleckstrin and Sec7 domain containing | PSD | 89 |
| | ENST00000388445 | gene:ENSG00000211166 /// ncrna:scRNA_pseudogene chromosome:NCBI36:11:112986610:112986679:1 gene:ENSG00000211180 | | | |
| 8135099 | ENST00000397927 ///<br>ENST00000313669 ///<br>BC110393 ///<br>NM_133457 | Isoform 1 of Collagen alpha-1(XXVI) chain gene:ENSG00000160963 /// Isoform 2 of Collagen alpha-1(XXVI) chain gene:ENSG00000160963 /// Homo sapiens EMI domain containing 2, mRNA (cDNA clone MGC:117329 IMAGE:5195867), complete cds. /// Homo sapiens EMI domain containing 2 (EMID2), mRNA. | EMI domain containing 2 | EMID2 | 96 |
| 7978801 | ENST00000399232 ///<br>ENST00000399222 ///<br>ENST00000357362 ///<br>AY369208 ///<br>NM_182830 ///<br>NM_001113498 | MAM domain-containing glycosylphosphatidylinositol anchor protein 2 gene:ENSG00000139915 /// MAM domain containing 1 isoform 2 gene:ENSG00000139915 /// MAM domain containing 1 isoform 2 gene:ENSG00000139915 /// Homo sapiens MAM domain-containing glycosylphosphatidylinositol anchor 2 (MDGA2) mRNA, complete cds. /// Homo sapiens MAM domain containing glycosylphosphatidylinositol anchor 2 (MDGA2), transcript variant 2, mRNA. /// Homo sapiens MAM domain containing glycosylphosphatidylinositol anchor 2 (MDGA2), transcript variant 1, mRNA. | MAM domain containing glycosyl-phosphatidylinositol anchor 2 | MDGA2 | 97 |
| 7971661 | hsa-mir-15a ///<br>hsa-mir-15a | MI0000069 Homo sapiens miR-15a stem-loop /// MI0000069 Homo sapiens miR-15a stem-loop | — | — | 98 |
| 8136709 | ENST00000397504 ///<br>BC111973 ///<br>NR_003715 | Putative maltase-glucoamylase-like protein LOC93432 gene:ENSG00000214088 /// Homo sapiens maltase-glucoamylase-like pseudogene, mRNA (cDNA clone IMAGE:8327441), complete cds. /// Homo sapiens maltase-glucoamylase-like pseudogene (LOC93432), non-coding RNA. | maltase-glucoamylase-like pseudogene | LOC93432 | 99 |
| 8139367 | ENST00000289547 ///<br>ENST00000381160 ///<br>ENST00000381159 ///<br>AF192522 ///<br>NM_013389 ///<br>NM_001101648 | Niemann-Pick C1-like protein 1 isoform 1 gene:ENSG00000015520 /// Isoform 2 of Niemann-Pick C1-like protein 1 gene:ENSG00000015520 /// Isoform 3 of Niemann-Pick C1-like protein 1 gene:ENSG00000015520 /// Homo sapiens Niemann-Pick C1-like protein 1 (NPC1L1) mRNA, complete cds. /// Homo sapiens NPC1 (Niemann-Pick disease, | NPC1 (Niemann-Pick disease, type C1, gene)-like 1 | NPC1L1 | 100 |

TABLE E-continued

| Probe Set ID | Transcript ID | Transcript Description | Gene Title | Gene Symbol | |
|---|---|---|---|---|---|
| | | type C1, gene)-like 1 (NPC1L1), transcript variant 1, mRNA. /// *Homo sapiens* NPC1 (Niemann-Pick disease, type C1, gene)-like 1 (NPC1L1), transcript variant 2, mRNA. | | | |
| 8055952 | ENST00000339562 /// ENST00000409572 /// ENST00000409108 /// BC009288 /// NM_006186 | Nuclear receptor subfamily 4 group A member 2 gene:ENSG00000153234 /// cdna:known chromosome:NCBI36:2:156889856:156907106:-1 gene:ENSG00000153234 /// cdna:known chromosome:NCBI36:2:156890502:156895465:-1 gene:ENSG00000153234 /// *Homo sapiens* nuclear receptor subfamily 4, group A, member 2, mRNA (cDNA clone MGC:14354 IMAGE:4298967), complete cds. /// *Homo sapiens* nuclear receptor subfamily 4, group A, member 2 (NR4A2), mRNA. | nuclear receptor subfamily 4, group A, member 2 | NR4A2 | 101 |
| 7942809 | BC008359 | *Homo sapiens* cDNA clone IMAGE:3606756. | — | — | 102 |
| 8120151 | ENST00000244799 /// ENST00000393699 /// ENST00000371211 /// ENST00000393696 /// BX647224 /// NM_181744 /// NM_001030051 | Opsin-5 gene:ENSG00000124818 /// Opsin-5 gene:ENSG00000124818 /// opsin 5 isoform 2 gene:ENSG00000124818 /// opsin 5 isoform 2 gene:ENSG00000124818 /// *Homo sapiens* mRNA; cDNA DKFZp686D0636 (from clone DKFZp686D0636). /// *Homo sapiens* opsin 5 (OPN5), transcript variant 1, mRNA. /// *Homo sapiens* opsin 5 (OPN5), transcript variant 2, mRNA. | opsin 5 | OPN5 | 103 |
| 8143710 | ENST00000385543 | ncrna:tRNA_pseudogene chromosome:NCBI36:7:148684678:148684753:-1 gene:ENSG00000208278 | — | — | 104 |
| 8091676 | ENST00000385921 /// ENST00000410743 | ncrna:rRNA_pseudogene chromosome:NCBI36:3:158374399:158374523:-1 gene:ENSG00000208656 /// ncrna:rRNA chromosome:NCBI36:3:158374401:158374523:-1 gene:ENSG00000222675 | — | — | 105 |
| 8083409 | ENST00000356517 /// BC065724 /// NM_207365 | Isoform 1 of Arylacetamide deacetylase-like 2 gene:ENSG00000197953 /// *Homo sapiens* arylacetamide deacetylase-like 2, mRNA (cDNA clone MGC:72001 IMAGE:6663150), complete cds. /// *Homo sapiens* arylacetamide deacetylase-like 2 (AADACL2), mRNA. | arylacetamide deacetylase-like 2 | AADACL2 | 106 |
| 7955119 | ENST00000380491 /// ENST00000314014 /// BC031670 | Isoform 2 of Uncharacterized protein C12orf54 gene:ENSG00000177627 /// Isoform 1 of Uncharacterized protein C12orf54 gene:ENSG00000177627 /// *Homo sapiens* chromosome 12 open reading frame 54, mRNA (cDNA clone MGC:35033 IMAGE:5165130), complete cds. | chromosome 12 open reading frame 54 | C12orf54 | 107 |
| 8005757 | ENST00000387268 | ncrna:Mt_tRNA_pseudogene chromosome:NCBI36:17:21952378:21952445:1 gene:ENSG00000210003 | — | — | 108 |
| 8129313 | ENST00000364509 | ncrna:snRNA chromosome:NCBI36:6:121905331:121905471:-1 gene:ENSG00000201379 | — | — | 109 |

TABLE E-continued

| Probe Set ID | Transcript ID | Transcript Description | Gene Title | Gene Symbol | |
|---|---|---|---|---|---|
| 8176806 | ENST00000303804 /// ENST00000341740 /// ENST00000338793 /// ENST00000303728 /// ENST00000343584 /// ENST00000303593 /// ENST00000306589 /// ENST00000338673 /// AF517635 /// NM_001002758 /// NM_004676 | Isoform 1 of PTPN13-like protein, Y-linked gene:ENSG00000169807 /// Isoform 2 of PTPN13-like protein, Y-linked gene:ENSG00000169807 /// Isoform 2 of PTPN13-like protein, Y-linked gene:ENSG00000169789 /// Isoform 1 of PTPN13-like protein, Y-linked gene:ENSG00000169789 /// Isoform 1 of PTPN13-like protein, Y-linked gene:ENSG00000169763 /// Isoform 2 of PTPN13-like protein, Y-linked gene:ENSG00000169763 /// Isoform 1 of PTPN13-like protein, Y-linked gene:ENSG00000172283 /// Isoform 2 of PTPN13-like protein, Y-linked gene:ENSG00000172283 /// Homo sapiens testis-specific PTP-BL related Y protein mRNA, complete cds, alternatively spliced. /// Homo sapiens PTPN13-like, Y-linked 2 (PRY2), mRNA. /// Homo sapiens PTPN13-like, Y-linked (PRY), mRNA. | PTPN13-like, Y-linked /// PTPN13-like, Y-linked 2 | PRY /// PRY2 | 110 |
| 8020842 | NR_003558 | Homo sapiens WW domain binding protein 11 pseudogene 1 (WBP11P1), non-coding RNA. | WW domain binding protein 11 pseudogene 1 | WBP11P1 | 111 |
| 8028389 | ENST00000396877 /// ENST00000338502 /// DQ323928 /// NM_001039616 /// NM_001042522 | sprouty-related, EVH1 domain containing 3 isoform b gene:ENSG00000188766 /// Sprouty-related, EVH1 domain-containing protein 3 gene:ENSG00000188766 /// Homo sapiens Spred3 mRNA, complete cds. /// Homo sapiens sprouty-related, EVH1 domain containing 3 (SPRED3), transcript variant 2, mRNA. /// Homo sapiens sprouty-related, EVH1 domain containing 3 (SPRED3), transcript variant 1, mRNA. | sprouty-related, EVH1 domain containing 3 | SPRED3 | 112 |
| 8007828 | ENST00000344290 /// ENST00000262410 /// ENST00000351559 /// ENST00000340799 /// ENST00000354326 /// ENST00000347967 /// ENST00000334239 /// BC114948 /// NM_001123067 /// NM_016835 /// NM_016834 /// NM_016841 /// NM_005910 /// NM_001123066 | Isoform Tau-G of Microtubule-associated protein tau gene:ENSG00000186868 /// Isoform PNS-tau of Microtubule-associated protein tau gene:ENSG00000186868 /// Isoform Tau-F of Microtubule-associated protein tau gene:ENSG00000186868 /// Isoform Tau-E of Microtubule-associated protein tau gene:ENSG00000186868 /// Isoform Tau-C of Microtubule-associated protein tau gene:ENSG00000186868 /// Isoform Tau-D of Microtubule-associated protein tau gene:ENSG00000186868 /// Isoform Tau-A of Microtubule-associated protein tau gene:ENSG00000186868 /// Homo sapiens microtubule-associated protein tau, mRNA (cDNA clone IMAGE:40007445), complete cds. /// Homo sapiens microtubule-associated protein | microtubule-associated protein tau | MAPT | 113 |

TABLE E-continued

| Probe Set ID | Transcript ID | Transcript Description | Gene Title | Gene Symbol | |
|---|---|---|---|---|---|
| | | tau (MAPT), transcript variant 5, mRNA. /// *Homo sapiens* microtubule-associated protein tau (MAPT), transcript variant 1, mRNA. /// *Homo sapiens* microtubule-associated protein tau (MAPT), transcript variant 3, mRNA. /// *Homo sapiens* microtubule-associated protein tau (MAPT), transcript variant 4, mRNA. /// *Homo sapiens* microtubule-associated protein tau (MAPT), transcript variant 2, mRNA. /// *Homo sapiens* microtubule-associated protein tau (MAPT), transcript variant 6, mRNA. | | | |
| 8058145 | — | — | — | — | 114 |
| 8055348 | ENST00000410136 | ncrna:misc_RNA chromosome:NCBI36:2:133865128:133865440:−1 gene:ENSG00000222068 | — | — | 115 |
| 7951165 | ENST00000263463 /// ENST00000325455 /// X51730 /// NM_000926 | Progesterone receptor, isoform CRA_c gene:ENSG00000082175 /// Isoform B of Progesterone receptor gene:ENSG00000082175 /// Human mRNA and promoter DNA for progesterone receptor. /// *Homo sapiens* progesterone receptor (PGR), mRNA. | progesterone receptor | PGR | 116 |
| 8141922 | ENST00000339444 /// ENST00000393735 /// ENST00000356767 /// ENST00000393730 /// ENST00000354356 /// ENST00000306312 /// ENST00000393732 /// ENST00000393729 /// ENST00000393723 /// ENST00000393727 /// ENST00000393722 /// AF523354 /// NM_206884 /// NM_198999 /// NM_206883 /// NM_206885 | Isoform 2 of Prestin gene:ENSG00000170615 /// Isoform 3 of Prestin gene:ENSG00000170615 /// Isoform 4 of Prestin gene:ENSG00000170615 /// SLC26A5 protein gene:ENSG00000170615 /// Prestin gene:ENSG00000170615 /// Isoform 1 of Prestin gene:ENSG00000170615 /// SLC26A5 protein gene:ENSG00000170615 /// SLC26A5 protein gene:ENSG00000170615 /// Prestin isoform SLC26A5e gene:ENSG00000170615 /// Prestin gene:ENSG00000170615 /// Putative uncharacterized protein SLC26A5 gene:ENSG00000170615 /// *Homo sapiens* prestin (PRES) mRNA, complete cds. /// *Homo sapiens* solute carrier family 26, member 5 (prestin) (SLC26A5), transcript variant c, mRNA. /// *Homo sapiens* solute carrier family 26, member 5 (prestin) (SLC26A5), transcript variant a, mRNA. /// *Homo sapiens* solute carrier family 26, member 5 (prestin) (SLC26A5), transcript variant b, mRNA. /// *Homo sapiens* solute carrier family 26, member 5 (prestin) (SLC26A5), transcript variant d, mRNA. | solute carrier family 26, member 5 (prestin) | SLC26A5 | 117 |
| 7934731 | ENST00000318965 /// ENST00000372288 /// ENST00000372287 /// ENST00000405868 /// XM_001723653 /// XM_926017 | cdna:pseudogene chromosome:NCBI36:10:32840249:32840671:−1 gene:ENSG00000181993 /// cdna:pseudogene chromosome:NCBI36:10:81774473:81774898:−1 gene:ENSG00000204042 /// cdna:pseudogene chromosome:NCBI36:10:81781704:81782129:−1 gene:ENSG00000204041 /// cdna:pseudogene | similar to hCG1791993 /// similar to hCG1791993 | LOC642538 /// LOC642521 | 118 |

TABLE E-continued

| Probe Set ID | Transcript ID | Transcript Description | Gene Title | Gene Symbol | |
|---|---|---|---|---|---|
| | | chromosome:NCBI36:10:81790363:81790779:−1 gene:ENSG00000217279 /// PREDICTED:*Homo sapiens* similar to hCG1791993 (LOC642538), mRNA. /// PREDICTED:*Homo sapiens* similar to hCG1791993 (LOC642521), mRNA. | | | |
| 7921449 | ENST00000255030 /// ENST00000368112 /// ENST00000368111 /// ENST00000368110 /// ENST00000343919 /// AK289443 /// NM_000567 | Isoform 1 of C-reactive protein gene:ENSG00000132693 /// Isoform 2 of C-reactive protein gene:ENSG00000132693 /// C-reactive protein, pentraxin-related gene:ENSG00000132693 /// C-reactive protein, pentraxin-related gene:ENSG00000132693 /// C-reactive protein, pentraxin-related gene:ENSG00000132693 /// *Homo sapiens* cDNA FLJ78115 complete cds, highly similar to *Homo sapiens* C-reactive protein, pentraxin-related (CRP), mRNA. /// *Homo sapiens* C-reactive protein, pentraxin-related (CRP), mRNA. | C-reactive protein, pentraxin-related | CRP | 119 |
| 8157818 | ENST00000373574 /// BC127949 /// NM_001045476 | WD repeat-containing protein 38 gene:ENSG00000136918 /// *Homo sapiens* WD repeat domain 38, mRNA (cDNA clone MGC:158102 IMAGE:40132852), complete cds. /// *Homo sapiens* WD repeat domain 38 (WDR38), mRNA. | WD repeat domain 38 | WDR38 | 120 |
| 7920264 | ENST00000359215 /// ENST00000368718 /// ENST00000368717 /// BC093955 /// NM_002962 | S100 calcium binding protein A5 gene:ENSG00000196420 /// S100 calcium binding protein A5 gene:ENSG00000196420 /// S100 calcium binding protein A5 gene:ENSG00000196420 /// *Homo sapiens* S100 calcium binding protein A5, mRNA (cDNA clone MGC:120990 IMAGE:7939800), complete cds. /// *Homo sapiens* S100 calcium binding protein A5 (S100A5), mRNA. | S100 calcium binding protein A5 | S100A5 | 121 |
| 8099362 | ENST00000411154 /// ENST00000387157 | ncrna:rRNA chromosome:NCBI36:4:9726478:9726606:−1 gene:ENSG00000223086 /// ncrna:rRNA_pseudogene chromosome:NCBI36:4:9726517:9726606:−1 gene:ENSG00000209892 | — | — | 122 |
| 8095412 | ENST00000381066 /// ENST00000354865 /// ENST00000246891 /// BC128227 /// NM_001025104 /// NM_001890 | Casein gene:ENSG00000126545 /// Isoform 3 of Alpha-S1-casein gene:ENSG00000126545 /// Isoform 1 of Alpha-S1-casein gene:ENSG00000126545 /// *Homo sapiens* casein alpha s1, mRNA (cDNA clone MGC:149367 IMAGE:40114618), complete cds. /// *Homo sapiens* casein alpha s1 (CSN1S1), transcript variant 2, mRNA. /// *Homo sapiens* casein alpha s1 (CSN1S1), transcript variant 1, mRNA. | casein alpha s1 | CSN1S1 | 123 |
| 8010622 | ENST00000384294 | ncrna:misc_RNA chromosome:NCBI36:17:77150953:77151065:1 gene:ENSG00000207021 | — | — | 124 |
| 8107421 | ENST00000316788 /// BC012614 /// NM_001284 | AP-3 complex subunit sigma-1 gene:ENSG00000177879 /// *Homo sapiens* adaptor-related protein complex 3, sigma 1 subunit, mRNA (cDNA clone IMAGE:4281620). /// *Homo sapiens* adaptor-related protein complex 3, sigma 1 subunit (AP3S1), mRNA. | adaptor-related protein complex 3, sigma 1 subunit | AP3S1 | 125 |

TABLE E-continued

| Probe Set ID | Transcript ID | Transcript Description | Gene Title | Gene Symbol | |
|---|---|---|---|---|---|
| 8126750 | ENST00000230565 /// ENST00000371383 /// BX647968 /// NM_021572 | Ectonucleotide pyrophosphatase/phosphodiesterase family member 5 gene:ENSG00000112796 /// Ectonucleotide pyrophosphatase/phosphodiesterase family member 5 gene:ENSG00000112796 /// *Homo sapiens* mRNA; cDNA DKFZp686E1552 (from clone DKFZp686E1552). /// *Homo sapiens* ectonucleotide pyrophosphatase/phosphodiesterase 5 (putative function) (ENPP5), mRNA. | ectonucleotide pyrophosphatase/ phosphodiesterase 5 (putative function) | ENPP5 | 126 |
| 8027770 | ENST00000270310 /// BC018619 /// NM_022006 | FXYD domain-containing ion transport regulator 7 gene:ENSG00000126258 /// *Homo sapiens* FXYD domain containing ion transport regulator 7, mRNA (cDNA clone MGC:31815 IMAGE:3626060), complete cds. /// *Homo sapiens* FXYD domain containing ion transport regulator 7 (FXYD7), mRNA. | FXYD domain containing ion transport regulator 7 | FXYD7 | 127 |
| 8088491 | ENST00000383710 /// ENST00000383709 /// ENST00000283269 /// ENST00000357948 /// ENST00000360097 /// AF458662 /// NM_183393 /// NM_003716 /// NM_183394 | Isoform 1 of Calcium-dependent secretion activator 1 gene:ENSG00000163618 /// Isoform 4 of Calcium-dependent secretion activator 1 gene:ENSG00000163618 /// Isoform 3 of Calcium-dependent secretion activator 1 gene:ENSG00000163618 /// Isoform 2 of Calcium-dependent secretion activator 1 gene:ENSG00000163618 /// Isoform 5 of Calcium-dependent secretion activator 1 gene:ENSG00000163618 /// *Homo sapiens* calcium-dependent activator protein for secretion protein mRNA, complete cds. /// *Homo sapiens* Ca++-dependent secretion activator (CADPS), transcript variant 3, mRNA. /// *Homo sapiens* Ca++-dependent secretion activator (CADPS), transcript variant 1, mRNA. /// *Homo sapiens* Ca++-dependent secretion activator (CADPS), transcript variant 2, mRNA. | Ca++-dependent secretion activator | CADPS | 128 |
| 8161192 | ENST00000377877 /// ENST00000357058 /// ENST00000350199 /// ENST00000377885 /// ENST00000377876 /// ENST00000353739 /// ENST00000259605 /// ENST00000377870 /// AF394047 /// NM_022781 /// NM_194328 /// NM_194329 /// NM_194330 /// NM_194332 | Ring finger protein 38 gene:ENSG00000137075 /// ring finger protein 38 isoform 2 gene:ENSG00000137075 /// ring finger protein 38 isoform 2 gene:ENSG00000137075 /// ring finger protein 38 isoform 2 gene:ENSG00000137075 /// ring finger protein 38 isoform 2 gene:ENSG00000137075 /// Isoform 2 of RING finger protein 38 gene:ENSG00000137075 /// Isoform 1 of RING finger protein 38 gene:ENSG00000137075 /// Ring finger protein 38 gene:ENSG00000137075 /// *Homo sapiens* RING finger protein 38 (RNF38) mRNA, complete cds. /// *Homo sapiens* ring finger protein 38 (RNF38), transcript variant 1, mRNA. /// *Homo sapiens* ring finger protein | ring finger protein 38 | RNF38 | 129 |

TABLE E-continued

| Probe Set ID | Transcript ID | Transcript Description | Gene Title | Gene Symbol | |
|---|---|---|---|---|---|
| | | 38 (RNF38), transcript variant 2, mRNA. /// *Homo sapiens* ring finger protein 38 (RNF38), transcript variant 3, mRNA. /// *Homo sapiens* ring finger protein 38 (RNF38), transcript variant 5, mRNA. /// *Homo sapiens* ring finger protein 38 (RNF38), transcript variant 6, mRNA. | | | |
| 8124634 | ENST00000404200 /// ENST00000401594 /// ENST00000366307 | cdna:pseudogene chromosome:NCBI36:c6 COX:29249580:29250516:−1 gene:ENSG00000219452 /// cdna:pseudogene chromosome:NCBI36:c6 QBL:29248513:29249449:−1 gene:ENSG00000216296 /// cdna:pseudogene chromosome:NCBI36:6:29213626:29214572:−1 gene:ENSG00000203492 | — | — | 130 |
| 8007584 | ENST00000293414 /// BC075088 /// NM_080863 | Ankyrin repeat and SOCS box protein 16 gene:ENSG00000161664 /// *Homo sapiens* ankyrin repeat and SOCS box-containing 16, mRNA (cDNA clone MGC:103981 IMAGE:30915388), complete cds. /// *Homo sapiens* ankyrin repeat and SOCS box-containing 16 (ASB16), mRNA. | ankyrin repeat and SOCS box-containing 16 | ASB16 | 131 |
| 7964660 | ENST00000299178 /// AY322550 /// NM_000706 | Vasopressin V1a receptor gene:ENSG00000166148 /// *Homo sapiens* arginine vasopressin receptor 1A mRNA, complete cds. /// *Homo sapiens* arginine vasopressin receptor 1A (AVPR1A), mRNA. | arginine vasopressin receptor 1A | AVPR1A | 132 |
| 7980003 | ENST00000387477 | ncrna:snRNA_pseudogene chromosome:NCBI36:14:72783233:72783340:−1 gene:ENSG00000210212 | — | — | 133 |
| 8135458 | ENST00000222597 /// AK026762 /// NM_024814 /// NR_024199 | E3 ubiquitin-protein ligase Hakai gene:ENSG00000105879 /// *Homo sapiens* cDNA:FLJ23109 fis, clone LNG07754. /// *Homo sapiens* Cas-Br-M (murine) ecotropic retroviral transforming sequence-like 1 (CBLL1), transcript variant 1, mRNA. /// *Homo sapiens* Cas-Br-M (murine) ecotropic retroviral transforming sequence-like 1 (CBLL1), transcript variant 2, transcribed RNA. | Cas-Br-M (murine) ecotropic retroviral transforming sequence-like 1 | CBLL1 | 134 |
| 7991512 | ENST00000352519 /// ENST00000341853 /// AK302717 /// NR_003260 | Uncharacterized protein C15orf51 (Fragment) gene:ENSG00000182397 /// UPF0621 protein C15orf51 gene:ENSG00000182397 /// *Homo sapiens* cDNA FLJ54911 complete cds. /// *Homo sapiens* chromosome 15 open reading frame 51 (C15orf51), non-coding RNA. | chromosome 15 open reading frame 51 | C15orf51 | 135 |
| 8029693 | ENST00000353609 /// BC036724 /// NM_006732 /// NM_001114171 | Protein fosB gene:ENSG00000125740 /// *Homo sapiens* FBJ murine osteosarcoma viral oncogene homolog B, mRNA (cDNA clone MGC:39968 IMAGE:5212854), complete cds. /// *Homo sapiens* FBJ murine osteosarcoma viral oncogene homolog B (FOSB), transcript variant 1, mRNA. /// *Homo sapiens* FBJ murine osteosarcoma viral oncogene homolog B (FOSB), transcript variant 2, mRNA. | FBJ murine osteosarcoma viral oncogene homolog B | FOSB | 136 |

TABLE E-continued

| Probe Set ID | Transcript ID | Transcript Description | Gene Title | Gene Symbol | |
|---|---|---|---|---|---|
| 7981773 | ENST00000384559 | ncrna:snRNA chromosome:NCBI36:15:19204036:19204142:1 gene:ENSG00000207289 | — | — | 137 |
| 7934729 | GENSCAN00000036525 /// ENST00000318965 /// ENST00000372288 /// ENST00000372287 /// ENST00000405868 /// XM_001723653 /// XM_926017 | cdna:Genscan chromosome:NCBI36:10:81732033:81798683:−1 /// cdna:pseudogene chromosome:NCBI36:10:32840249:32840671:−1 gene:ENSG00000181993 /// cdna:pseudogene chromosome:NCBI36:10:81774473:81774898:−1 gene:ENSG00000204042 /// cdna:pseudogene chromosome:NCBI36:10:81781704:81782129:−1 gene:ENSG00000204041 /// cdna:pseudogene chromosome:NCBI36:10:81790363:81790779:−1 gene:ENSG00000217279 /// PREDICTED:*Homo sapiens* similar to hCG1791993 (LOC642538), mRNA. /// PREDICTED:*Homo sapiens* similar to hCG1791993 (LOC642521), mRNA. | similar to hCG1791993 /// similar to hCG1791993 | LOC642538 /// LOC642521 | 138 |
| 7936996 | ENST00000356858 /// ENST00000284694 /// ENST00000368674 /// ENST00000392694 /// AK297577 /// NM_001004298 | Novel protein gene:ENSG00000154493 /// cDNA FLJ60307 gene:ENSG00000154493 /// Novel protein gene:ENSG00000154493 /// Novel protein gene:ENSG00000154493 /// *Homo sapiens* cDNA FLJ60307 complete cds. /// *Homo sapiens* chromosome 10 open reading frame 90 (C10orf90), mRNA. | chromosome 10 open reading frame 90 | C10orf90 | 139 |
| 7906205 | ENST00000329117 /// ENST00000361588 /// ENST00000255029 /// AY358372 /// NM_021948 /// NM_198427 | Isoform 1 of Brevican core protein gene:ENSG00000132692 /// Isoform 2 of Brevican core protein gene:ENSG00000132692 /// Hyaluronan binding protein (Fragment) gene:ENSG00000132692 /// *Homo sapiens* clone DNA98565 Brevican Core Pro (UNQ2525) mRNA, complete cds. /// *Homo sapiens* brevican (BCAN), transcript variant 1, mRNA. /// *Homo sapiens* brevican (BCAN), transcript variant 2, mRNA. | brevican | BCAN | 140 |
| 8100990 | BC132938 /// L10403 | *Homo sapiens* pro-platelet basic protein-like 2, mRNA (cDNA clone MGC:164569 IMAGE:40146960), complete cds. /// *Homo sapiens* DNA binding protein for surfactant protein B mRNA, complete cds. | pro-platelet basic protein-like 2 | PPBPL2 | 141 |
| 8156846 | GENSCAN00000020848 /// ENST00000409669 /// ENST00000410082 /// ENST00000409686 | cdna:Genscan chromosome:NCBI36:9:101107215:101108714:1 /// cdna:pseudogene chromosome:NCBI36:9:101107215:101108714:1 gene:ENSG00000222026 /// cdna:pseudogene chromosome:NCBI36:9:101107215:101108714:1 gene:ENSG00000222034 /// cdna:pseudogene chromosome:NCBI36:9:101107215:101108714:1 gene:ENSG00000222039 | — | — | 142 |
| 8044563 | ENST00000341010 /// ENST00000337569 /// ENST00000393197 /// AY029413 /// NM_032556 /// NM_173161 | Isoform 1 of Interleukin-1 family member 10 gene:ENSG00000136697 /// Isoform 2 of Interleukin-1 family member 10 gene:ENSG00000136697 /// Isoform 1 of Interleukin-1 family member 10 gene:ENSG00000136697 /// *Homo sapiens* interleukin-1 receptor antagonist-like FIL1 theta | interleukin 1 family, member 10 (theta) | IL1F10 | 143 |

TABLE E-continued

| Probe Set ID | Transcript ID | Transcript Description | Gene Title | Gene Symbol | |
|---|---|---|---|---|---|
| | | (FIL1-theta) mRNA, complete cds. /// *Homo sapiens* interleukin 1 family, member 10 (theta) (IL1F10), transcript variant 1, mRNA. /// *Homo sapiens* interleukin 1 family, member 10 (theta) (IL1F10), transcript variant 2, mRNA. | | | |
| 7932964 | ENST00000355848 /// ENST00000410067 /// BC005235 /// NM_006333 /// NM_173177 | Nuclear nucleic acid-binding protein C1D gene:ENSG00000197223 /// cdna:known chromosome:NCBI36:2:68123292:68143661:−1 gene:ENSG00000197223 /// *Homo sapiens* nuclear DNA-binding protein, mRNA (cDNA clone MGC:12261 IMAGE:3930648), complete cds. /// *Homo sapiens* nuclear DNA-binding protein (C1D), transcript variant 1, mRNA. /// *Homo sapiens* nuclear DNA-binding protein (C1D), transcript variant 2, mRNA. | nuclear DNA-binding protein | C1D | 144 |
| 7912606 | ENST00000361079 /// ENST00000330881 /// ENST00000357367 /// NM_001012277 /// NM_001012276 | PRAME family member 7 gene:ENSG00000204510 /// PRAME family member 7 gene:ENSG00000204510 /// PRAME family member 8 gene:ENSG00000182330 /// *Homo sapiens* PRAME family member 7 (PRAMEF7), mRNA. /// *Homo sapiens* PRAME family member 8 (PRAMEF8), mRNA. | PRAME family member 7 /// PRAME family member 8 | PRAMEF7 /// PRAMEF8 | 145 |
| 8099713 | ENST00000387283 | ncrna:Mt_tRNA_pseudogene chromosome:NCBI36:4:25328670:25328727:−1 gene:ENSG00000210018 | — | — | 146 |
| 8139723 | ENST00000324256 /// BC011872 /// NR_003949 | Putative FK506-binding protein 9-like protein gene:ENSG00000176826 /// *Homo sapiens* FK506 binding protein 9-like, mRNA (cDNA clone MGC:20531 IMAGE:3028515), complete cds. /// *Homo sapiens* FK506 binding protein 9-like (FKBP9L), non-coding RNA. | FK506 binding protein 9-like | FKBP9L | 147 |
| 8109159 | hsa-mir-145 /// hsa-mir-145 /// AK093957 | MI0000461 *Homo sapiens* miR-145 stem-loop /// MI0000461 *Homo sapiens* miR-145 stem-loop /// *Homo sapiens* cDNA FLJ36638 fis, clone TRACH2018950. | hypothetical protein LOC728264 | LOC728264 | 148 |
| 7906197 | ENST00000255039 /// AB049054 /// NM_021817 | Hyaluronan and proteoglycan link protein 2 gene:ENSG00000132702 /// *Homo sapiens* BRAL1 mRNA for brain link protein-1, complete cds. /// *Homo sapiens* hyaluronan and proteoglycan link protein 2 (HAPLN2), mRNA. | hyaluronan and proteoglycan link protein 2 | HAPLN2 | 149 |
| 7912591 | ENST00000361079 /// ENST00000330881 /// ENST00000357367 /// NM_001012277 /// NM_001012276 | PRAME family member 7 gene:ENSG00000204510 /// PRAME family member 7 gene:ENSG00000204510 /// PRAME family member 8 gene:ENSG00000182330 /// *Homo sapiens* PRAME family member 7 (PRAMEF7), mRNA. /// *Homo sapiens* PRAME family member 8 (PRAMEF8), mRNA. | PRAME family member 7 /// PRAME family member 8 | PRAMEF7 /// PRAMEF8 | 150 |
| 7986291 | AY358254 | *Homo sapiens* clone DNA172197 IFMQ9370 (UNQ9370) mRNA, complete cds. | IFMQ9370 | UNQ9370 | 151 |
| 7925504 | ENST00000357246 /// BC132986 /// NM_001004343 | Microtubule-associated proteins 1A/1B light chain 3C gene:ENSG00000197769 /// *Homo sapiens* microtubule-associated protein 1 light chain 3 | microtubule-associated protein 1 light chain 3 gamma | MAP1LC3C | 152 |

TABLE E-continued

| Probe Set ID | Transcript ID | Transcript Description | Gene Title | Gene Symbol | |
|---|---|---|---|---|---|
| | | gamma, mRNA (cDNA clone MGC:164617 IMAGE:40147008), complete cds. /// *Homo sapiens* microtubule-associated protein 1 light chain 3 gamma (MAP1LC3C), mRNA. | | | |
| 7897991 | ENST00000361079 /// ENST00000330881 /// ENST00000357367 /// NM_001012277 /// NM_001012276 | PRAME family member 7 gene:ENSG00000204510 /// PRAME family member 7 gene:ENSG00000204510 /// PRAME family member 8 gene:ENSG00000182330 /// *Homo sapiens* PRAME family member 7 (PRAMEF7), mRNA. /// *Homo sapiens* PRAME family member 8 (PRAMEF8), mRNA. | PRAME family member 7 /// PRAME family member 8 | PRAMEF7 /// PRAMEF8 | 153 |
| 7972461 | ENST00000376503 /// ENST00000313260 /// ENST00000376494 /// U21936 /// NM_005073 | Solute carrier family 15 member 1 gene:ENSG00000088386 /// pH-sensing regulatory factor of peptide transporter gene:ENSG00000088386 /// Solute carrier family 15 (Oligopeptide transporter), member 1 gene:ENSG00000088386 /// Human peptide transporter (HPEPT1) mRNA, complete cds. /// *Homo sapiens* solute carrier family 15 (oligopeptide transporter), member 1 (SLC15A1), mRNA. | solute carrier family 15 (oligopeptide transporter), member 1 | SLC15A1 | 154 |
| 8146857 | ENST00000388545 | ncrna:rRNA_pseudogene chromosome:NCBI36:8:69770442:69770521:1 gene:ENSG00000211280 | — | — | 155 |
| 7925846 | AF220183 /// BC104155 | *Homo sapiens* uncharacterized hypothalamus protein HT009 mRNA, complete cds. /// *Homo sapiens* chromosome 10 open reading frame 110, mRNA (cDNA clone IMAGE:40029412), complete cds. | chromosome 10 open reading frame 110 | C10orf110 | 156 |
| 8059026 | hsa-mir-375 /// hsa-mir-375 | MI0000783 *Homo sapiens* miR-375 stem-loop /// MI0000783 *Homo sapiens* miR-375 stem-loop | — | — | 157 |
| 8071274 | L20860 | Human glycoprotein Ib beta mRNA, complete cds. | glycoprotein Ib (platelet), beta polypeptide | GP1BB | 158 |
| 8050113 | AK125905 | *Homo sapiens* cDNA FLJ43917 fis, clone TESTI4011505. | hypothetical LOC100129581 | LOC100129581 | 159 |
| 8170159 | ENST00000370648 /// L08893 /// NM_001727 | Bombesin receptor subtype-3 gene:ENSG00000102239 /// Human bombesin receptor subtype-3 mRNA, complete cds. /// *Homo sapiens* bombesin-like receptor 3 (BRS3), mRNA. | bombesin-like receptor 3 | BRS3 | 160 |
| 7958711 | ENST00000308208 /// BC044815 /// NM_152591 | Coiled-coil domain-containing protein 63 gene:ENSG00000173093 /// *Homo sapiens* coiled-coil domain containing 63, mRNA (cDNA clone IMAGE:5166270), complete cds. /// *Homo sapiens* coiled-coil domain containing 63 (CCDC63), mRNA. | coiled-coil domain containing 63 | CCDC63 | 161 |
| 8021357 | ENST00000262095 /// NM_004852 | one cut domain, family member 2 gene:ENSG00000119547 /// *Homo sapiens* one cut homeobox 2 (ONECUT2), mRNA. | one cut homeobox 2 | ONECUT2 | 162 |
| 8095161 | ENST00000387825 | ncrna:snRNA_pseudogene chromosome:NCBI36:4:56359561:56359653:1 gene:ENSG00000210560 | — | — | 163 |
| 7960861 | ENST00000364793 | ncrna:misc_RNA chromosome:NCBI36:12:7894580:7894681:−1 gene:ENSG00000201663 | — | — | 164 |

TABLE E-continued

| Probe Set ID | Transcript ID | Transcript Description | Gene Title | Gene Symbol | |
|---|---|---|---|---|---|
| 8127932 | ENST00000330469 /// ENST00000369663 /// BC132715 /// NM_001080508 | TBX18 protein (Fragment) gene:ENSG00000112837 /// T-box transcription factor TBX18 gene:ENSG00000112837 /// *Homo sapiens* T-box 18, mRNA (cDNA clone MGC:164346 IMAGE:40146737), complete cds. /// *Homo sapiens* T-box 18 (TBX18), mRNA. | T-box 18 | TBX18 | 165 |
| 8116607 | ENST00000399551 /// AK123663 /// BC108683 | hypothetical protein gene:ENSG00000215076 /// *Homo sapiens* cDNA FLJ41669 fis, clone FEBRA2028618. /// *Homo sapiens* cDNA clone IMAGE:5212284. | hypothetical LOC401232 | DKFZP686I15217 | 166 |
| 8164766 | ENST00000298545 /// BC050576 /// NM_152572 | Isoform 1 of Putative adenylate kinase-like protein C9orf98 gene:ENSG00000165695 /// *Homo sapiens* chromosome 9 open reading frame 98, mRNA (cDNA clone MGC:57797 IMAGE:5744517), complete cds. /// *Homo sapiens* chromosome 9 open reading frame 98 (C9orf98), mRNA. | chromosome 9 open reading frame 98 | C9orf98 | 167 |
| 8012726 | ENST00000379814 /// ENST00000226207 /// AF111785 /// NM_005963 | MYH1 protein (Fragment) gene:ENSG00000109061 /// Myosin-1 gene:ENSG00000109061 /// *Homo sapiens* myosin heavy chain IIx/d mRNA, complete cds. /// *Homo sapiens* myosin, heavy chain 1, skeletal muscle, adult (MYH1), mRNA. | myosin, heavy chain 1, skeletal muscle, adult | MYH1 | 168 |
| 7906552 | ENST00000368078 /// ENST00000368079 /// BC022289 /// NM_001231 | Calsequestrin gene:ENSG00000143318 /// Calsequestrin-1 gene:ENSG00000143318 /// *Homo sapiens* calsequestrin 1 (fast-twitch, skeletal muscle), mRNA (cDNA clone MGC:22462 IMAGE:4338020), complete cds. /// *Homo sapiens* calsequestrin 1 (fast-twitch, skeletal muscle) (CASQ1), nuclear gene encoding mitochondrial protein, mRNA. | calsequestrin 1 (fast-twitch, skeletal muscle) | CASQ1 | 169 |
| 8115831 | ENST00000239223 /// BC022463 /// NM_004417 | Dual specificity protein phosphatase 1 gene:ENSG00000120129 /// *Homo sapiens* dual specificity phosphatase 1, mRNA (cDNA clone MGC:26153 IMAGE:4794895), complete cds. /// *Homo sapiens* dual specificity phosphatase 1 (DUSP1), mRNA. | dual specificity phosphatase 1 | DUSP1 | 170 |
| 8143708 | AK125575 | *Homo sapiens* cDNA FLJ43587 fis, clone SKNMC2009450. | — | — | 171 |
| 8036430 | ENST00000358582 /// BC108687 /// NM_152605 | Isoform 2 of Zinc finger protein 781 gene:ENSG00000196381 /// *Homo sapiens* zinc finger protein 781, mRNA (cDNA clone MGC:131783 IMAGE:6148649), complete cds. /// *Homo sapiens* zinc finger protein 781 (ZNF781), mRNA. | zinc finger protein 781 | ZNF781 | 172 |
| 7937975 | ENST00000354690 | cdna:pseudogene chromosome:NCBI36:11:4809975:4810860:1 gene:ENSG00000197984 | — | — | 173 |
| 7973054 | ENST00000363355 | ncrna:rRNA chromosome:NCBI36:14:19952986:19953103:1 gene:ENSG00000200225 | — | — | 174 |

TABLE E-continued

| Probe Set ID | Transcript ID | Transcript Description | Gene Title | Gene Symbol | |
|---|---|---|---|---|---|
| 8052698 | ENST00000355848 /// ENST00000407324 /// ENST00000410067 /// ENST00000409302 /// BC005235 /// NM_006333 /// NM_173177 | Nuclear nucleic acid-binding protein C1D gene:ENSG00000197223 /// 20 kDa protein gene:ENSG00000197223 /// cdna:known chromosome:NCBI36:2:68123292:68143661:−1 gene:ENSG00000197223 /// cdna:known chromosome:NCBI36:2:68123313:68143645:−1 gene:ENSG00000197223 /// *Homo sapiens* nuclear DNA-binding protein, mRNA (cDNA clone MGC:12261 IMAGE:3930648), complete cds. /// *Homo sapiens* nuclear DNA-binding protein (C1D), transcript variant 1, mRNA. /// *Homo sapiens* nuclear DNA-binding protein (C1D), transcript variant 2, mRNA. | nuclear DNA-binding protein | C1D | 175 |
| 8113352 | ENST00000388656 | ncrna:Mt_tRNA_pseudogene chromosome:NCBI36:5:99414667:99414734:−1 gene:ENSG00000211391 | — | — | 176 |
| 8077499 | AF086709 /// AK054898 /// BC016278 | *Homo sapiens* NAG-7 protein (NAG-7) mRNA, complete cds. /// *Homo sapiens* cDNA FLJ30336 fis, clone BRACE2007358, moderately similar to *Homo sapiens* NAG-7 protein (NAG-7) mRNA. /// *Homo sapiens* loss of heterozygosity, 3, chromosomal region 2, gene A, mRNA (cDNA clone MGC:8781 IMAGE:3915957), complete cds. | loss of heterozygosity, 3, chromosomal region 2, gene A | LOH3CR2A | 177 |
| 8104074 | ENST00000307161 /// BC126297 /// NM_005958 | Melatonin receptor type 1A gene:ENSG00000168412 /// *Homo sapiens* melatonin receptor 1A, mRNA (cDNA clone MGC:161575 IMAGE:8992013), complete cds. /// *Homo sapiens* melatonin receptor 1A (MTNR1A), mRNA. | melatonin receptor 1A | MTNR1A | 178 |
| 7951701 | ENST00000388431 /// ENST00000388445 | ncrna:scRNA_pseudogene chromosome:NCBI36:11:112053855:112053924:−1 gene:ENSG00000211166 /// ncrna:scRNA_pseudogene chromosome:NCBI36:11:112986610:112986679:1 gene:ENSG00000211180 | — | — | 179 |
| 8157092 | ENST00000374692 /// ENST00000374689 /// ENST00000374688 /// BC000049 /// NM_018112 | Trimeric intracellular cation channel type B gene:ENSG00000095209 /// Putative uncharacterized protein TMEM38B gene:ENSG00000095209 /// 26 kDa protein gene:ENSG00000095209 /// *Homo sapiens* transmembrane protein 38B, mRNA (cDNA clone MGC:960 IMAGE:3506969), complete cds. /// *Homo sapiens* transmembrane protein 38B (TMEM38B), mRNA. | transmembrane protein 38B | TMEM38B | 180 |
| 7942814 | ENST00000387816 | ncrna:Mt_tRNA_pseudogene chromosome:NCBI36:11:80940435:80940502:1 gene:ENSG00000210551 | — | — | 181 |
| 8090366 | ENST00000290868 /// ENST00000383579 /// BC115405 /// NM_144639 | Probable urocanate hydratase gene:ENSG00000159650 /// Urocanase family protein gene:ENSG00000159650 /// *Homo sapiens* urocanase domain containing 1, mRNA (cDNA clone MGC:135007 IMAGE:40076084), complete cds. /// *Homo sapiens* urocanase domain containing 1 (UROC1), mRNA. | urocanase domain containing 1 | UROC1 | 182 |

TABLE E-continued

| Probe Set ID | Transcript ID | Transcript Description | Gene Title | Gene Symbol | |
|---|---|---|---|---|---|
| 8036300 | ENST00000363309 | ncrna:misc_RNA chromosome:NCBI36:19:41386089:41386201:−1 gene:ENSG00000200179 | — | — | 183 |
| 8036403 | ENST00000316807 | Putative uncharacterized protein LOC400692 gene:ENSG00000180458 | — | — | 184 |
| 7971644 | ENST00000378195 /// ENST00000361840 /// AF334405 /// NM_020456 /// NM_001127482 /// NR_023351 | Isoform 2 of Chronic lymphocytic leukemia deletion region gene 6 protein gene:ENSG00000123178 /// Isoform 1 of Chronic lymphocytic leukemia deletion region gene 6 protein gene:ENSG00000123178 /// Homo sapiens CLLL6 protein (CLLD6) mRNA, complete cds. /// Homo sapiens chromosome 13 open reading frame 1 (C13orf1), transcript variant 1, mRNA. /// Homo sapiens chromosome 13 open reading frame 1 (C13orf1), transcript variant 2, mRNA. /// Homo sapiens chromosome 13 open reading frame 1 (C13orf1), transcript variant 3, transcribed RNA. | chromosome 13 open reading frame 1 | C13orf1 | 185 |
| 8157216 | ENST00000374279 /// BC038711 /// NM_003358 | Ceramide glucosyltransferase gene:ENSG00000148154 /// Homo sapiens UDP-glucose ceramide glucosyltransferase, mRNA (cDNA clone MGC:33797 IMAGE:5295561), complete cds. /// Homo sapiens UDP-glucose ceramide glucosyltransferase (UGCG), mRNA. | UDP-glucose ceramide glucosyltransferase | UGCG | 186 |
| 8074714 | ENST00000342005 /// ENST00000329949 /// ENST00000402027 /// ENST00000248992 /// AK292412 /// AK302597 /// AY358961 /// NR_003714 | cDNA FLJ60978, weakly similar to Nuclear envelope pore membrane protein POM 121 gene:ENSG00000182356 /// Putative uncharacterized protein ENSP00000383394 gene:ENSG00000217261 /// POM121-like 1 protein gene:ENSG00000183169 /// POM121-like gene:ENSG00000128262 /// Homo sapiens cDNA FLJ76724 complete cds. /// Homo sapiens cDNA FLJ60978 complete cds, weakly similar to Nuclear envelope pore membrane protein POM 121. /// Homo sapiens clone DNA107786 POM121-like (UNQ2565) mRNA, complete cds. /// Homo sapiens POM121-like protein (DKFZP434P211), non-coding RNA. | POM121 membrane glycoprotein-like 1 (rat) /// POM121 membrane glycoprotein-like 1 pseudogene /// POM121 membrane glycoprotein-like 1 pseudogene | POM121L1 /// DKFZp434K191 /// DKFZP434P211 | 187 |
| 8065758 | AK096092 | Homo sapiens cDNA FLJ38773 fis, clone KIDNE2018071. | hypothetical protein FLJ38773 | FLJ38773 | 188 |
| 8049530 | ENST00000308482 /// NM_001137550 | leucine rich repeat (in FLII) interacting protein 1 isoform 1 gene:ENSG00000124831 /// Homo sapiens leucine rich repeat (in FLII) interacting protein 1 (LRRFIP1), transcript variant 1, mRNA. | leucine rich repeat (in FLII) interacting protein 1 | LRRFIP1 | 189 |
| 7906475 | ENST00000321935 /// ENST00000368106 /// ENST00000339348 /// ENST00000392235 /// AK131201 /// NM_001004310 | Isoform 2 of Fc receptor-like protein 6 gene:ENSG00000181036 /// Isoform 1 of Fc receptor-like protein 6 gene:ENSG00000181036 /// Isoform 3 of Fc receptor-like protein 6 gene:ENSG00000181036 /// Isoform 4 of Fc receptor-like protein 6 | Fc receptor-like 6 | FCRL6 | 190 |

TABLE E-continued

| Probe Set ID | Transcript ID | Transcript Description | Gene Title | Gene Symbol | |
|---|---|---|---|---|---|
| | | gene:ENSG00000181036 /// *Homo sapiens* cDNA FLJ16056 fis, clone SPLEN2010588, weakly similar to CELL SURFACE GLYCOPROTEIN GP42 PRECURSOR. /// *Homo sapiens* Fc receptor-like 6 (FCRL6), mRNA. | | | |
| 7989476 | ENST00000304813 /// ENST00000299125 /// AK096042 | cdna:known chromosome:NCBI36:15:60322074:60323649:−1 gene:ENSG00000220356 /// Isoform 1 of Golgin subfamily A member 2-like protein 4 gene:ENSG00000166104 /// *Homo sapiens* cDNA FLJ38723 fis, clone KIDNE2010137, weakly similar to GOLGIN-95. | hypothetical FLJ38723 | FLJ38723 | 191 |
| 8103722 | ENST00000325407 /// AY956762 | Heat shock protein 90Af gene:ENSG00000181359 /// *Homo sapiens* heat shock protein 90Af (HSP90Af) mRNA, complete cds. | heat shock protein 90 kDa alpha (cytosolic), class A member 6 (pseudogene) | HSP90AA6P | 192 |
| 8035146 | ENST00000409035 /// ENST00000269881 /// BC014595 /// NM_145046 | cdna:known chromosome:NCBI36:19:16450878:16600015:−1 gene:ENSG00000141979 /// Calreticulin-3 gene:ENSG00000141979 /// *Homo sapiens* calreticulin 3, mRNA (cDNA clone MGC:26577 IMAGE:4822010), complete cds. /// *Homo sapiens* calreticulin 3 (CALR3), mRNA. | calreticulin 3 | CALR3 | 193 |
| 8150722 | ENST00000276480 /// AB011107 /// NM_014682 | Suppression of tumorigenicity protein 18 gene:ENSG00000147488 /// *Homo sapiens* mRNA for KIAA0535 protein, complete cds. /// *Homo sapiens* suppression of tumorigenicity 18 (breast carcinoma) (zinc finger protein) (ST18), mRNA. | suppression of tumorigenicity 18 (breast carcinoma) (zinc finger protein) | ST18 | 194 |
| 8053715 | GENSCAN00000025928 /// ENST00000312946 /// ENST00000402897 | cdna:Genscan chromosome:NCBI36:2:89209283:89223706:−1 /// cdna:pseudogene chromosome:NCBI36:2:89209304:89210080:−1 gene:ENSG00000204732 /// cdna:pseudogene chromosome:NCBI36:2:89728732:89729523:1 gene:ENSG00000218041 | — | — | 195 |
| 7922976 | ENST00000367468 /// AY151286 /// NM_000963 | Prostaglandin G/H synthase 2 gene:ENSG00000073756 /// *Homo sapiens* cyclooxygenase 2b mRNA, complete cds; alternatively spliced. /// *Homo sapiens* prostaglandin-endoperoxide synthase 2 (prostaglandin G/H synthase and cyclooxygenase) (PTGS2), mRNA. | prostaglandin-endoperoxide synthase 2 (prostaglandin G/H synthase and cyclooxygenase) | PTGS2 | 196 |
| 8087433 | ENST00000273588 /// ENST00000395338 /// ENST00000273598 /// AF538150 /// D13811 /// NM_000481 /// NM_032316 | Aminomethyltransferase, mitochondrial gene:ENSG00000145020 /// Aminomethyltransferase gene:ENSG00000145020 /// Isoform 1 of Nicolin-1 gene:ENSG00000145029 /// *Homo sapiens* NPCEDRGP (NPCEDRG) mRNA, NPCEDRG-s allele, complete cds. /// *Homo sapiens* mRNA for glycine cleavage system T-protein, complete cds. /// *Homo sapiens* aminomethyltransferase (AMT), mRNA. /// *Homo sapiens* nicolin 1 (NICN1), mRNA. | nicolin 1 /// aminomethyl-transferase | NICN1 /// AMT | 197 |

TABLE E-continued

| Probe Set ID | Transcript ID | Transcript Description | Gene Title | Gene Symbol | |
|---|---|---|---|---|---|
| 8075142 | ENST00000397906 /// ENST00000266082 /// AB028966 /// BC016465 | Tetratricopeptide repeat protein 28 gene:ENSG00000100154 /// Tetratricopeptide repeat protein 28 gene:ENSG00000100154 /// *Homo sapiens* mRNA for KIAA1043 protein, partial cds. /// *Homo sapiens* tetratricopeptide repeat domain 28, mRNA (cDNA clone MGC:18145 IMAGE:4154050), complete cds. | tetratricopeptide repeat domain 28 | TTC28 | 198 |
| 7919751 | ENST00000307940 /// ENST00000369026 /// BC017197 /// NM_182763 /// NM_021960 | Isoform 2 of Induced myeloid leukemia cell differentiation protein Mcl-1 gene:ENSG00000143384 /// Isoform 1 of Induced myeloid leukemia cell differentiation protein Mcl-1 gene:ENSG00000143384 /// *Homo sapiens* myeloid cell leukemia sequence 1 (BCL2-related), mRNA (cDNA clone MGC:1839 IMAGE:3138465), complete cds. /// *Homo sapiens* myeloid cell leukemia sequence 1 (BCL2-related) (MCL1), transcript variant 2, mRNA. /// *Homo sapiens* myeloid cell leukemia sequence 1 (BCL2-related) (MCL1), transcript variant 1, mRNA. | myeloid cell leukemia sequence 1 (BCL2-related) | MCL1 | 199 |
| 8000590 | ENST00000314752 /// ENST00000395609 /// ENST00000395607 /// ENST00000350842 /// AB209149 /// NM_177529 /// NM_177530 /// NM_177536 /// NM_001055 /// NM_177534 | Sulfotransferase 1A1 gene:ENSG00000196502 /// Sulfotransferase 1A1 gene:ENSG00000196502 /// Sulfotransferase 1A1 gene:ENSG00000196502 /// sulfotransferase family, cytosolic, 1A, phenol-preferring, member 1 isoform b gene:ENSG00000196502 /// *Homo sapiens* mRNA for Phenol-sulfating phenol sulfotransferase 1 variant protein. /// *Homo sapiens* sulfotransferase family, cytosolic, 1A, phenol-preferring, member 1 (SULT1A1), transcript variant 2, mRNA. /// *Homo sapiens* sulfotransferase family, cytosolic, 1A, phenol-preferring, member 1 (SULT1A1), transcript variant 3, mRNA. /// *Homo sapiens* sulfotransferase family, cytosolic, 1A, phenol-preferring, member 1 (SULT1A1), transcript variant 5, mRNA. /// *Homo sapiens* sulfotransferase family, cytosolic, 1A, phenol-preferring, member 1 (SULT1A1), transcript variant 1, mRNA. /// *Homo sapiens* sulfotransferase family, cytosolic, 1A, phenol-preferring, member 1 (SULT1A1), transcript variant 4, mRNA. | sulfotransferase family, cytosolic, 1A, phenol-preferring, member 1 | SULT1A1 | 200 |
| 7973444 | ENST00000386719 /// ENST00000410999 | ncrna:snRNA_pseudogene chromosome:NCBI36:14:23330971:23331182:1 gene:ENSG00000209454 /// ncrna:misc_RNA chromosome:NCBI36:14:23330979:23331267:1 gene:ENSG00000222931 | — | — | 201 |
| 8072004 | ENST00000382738 /// NM_001013618 | immunoglobulin lambda-like polypeptide 3 gene:ENSG00000206066 /// *Homo sapiens* immunoglobulin lambda-like polypeptide 3 (IGLL3), mRNA. | immunoglobulin lambda-like polypeptide 3 | IGLL3 | 202 |

TABLE E-continued

| Probe Set ID | Transcript ID | Transcript Description | Gene Title | Gene Symbol | |
|---|---|---|---|---|---|
| 7982574 | ENST00000397609 /// ENST00000305752 /// AK095745 /// NM_173611 /// NM_001042429 | family with sequence similarity 98, member B isoform 1 gene:ENSG00000171262 /// Protein FAM98B gene:ENSG00000171262 /// *Homo sapiens* cDNA FLJ38426 fis, clone FEBRA2012507. /// *Homo sapiens* family with sequence similarity 98, member B (FAM98B), transcript variant 1, mRNA. /// *Homo sapiens* family with sequence similarity 98, member B (FAM98B), transcript variant 2, mRNA. | family with sequence similarity 98, member B | FAM98B | 203 |
| 8135436 | ENST00000265715 /// AF030880 /// NM_000441 | Pendrin gene:ENSG00000091137 /// *Homo sapiens* pendrin (PDS) mRNA, complete cds. /// *Homo sapiens* solute carrier family 26, member 4 (SLC26A4), mRNA. | solute carrier family 26, member 4 | SLC26A4 | 204 |
| 8180281 | — | — | — | — | 205 |
| 8080676 | ENST00000311180 /// AK300374 /// NM_177966 | Isoform 1 of 2',5'-phosphodiesterase 12 gene:ENSG00000174840 /// *Homo sapiens* cDNA FLJ54489 complete cds, highly similar to *Homo sapiens* 2'-phosphodiesterase (2-PDE), mRNA. /// *Homo sapiens* phosphodiesterase 12 (PDE12), mRNA. | phosphodiesterase 12 | PDE12 | 206 |
| 8154135 | ENST00000262352 /// ENST00000381910 /// BC033040 /// NM_004170 | Excitatory amino acid transporter 3 gene:ENSG00000106688 /// Solute carrier family 1 (Neuronal/epithelial high affinity glutamate transporter, system Xag), member 1 gene:ENSG00000106688 /// *Homo sapiens* solute carrier family 1 (neuronal/epithelial high affinity glutamate transporter, system Xag), member 1, mRNA (cDNA clone MGC:33786 IMAGE:5261168), complete cds. /// *Homo sapiens* solute carrier family 1 (neuronal/epithelial high affinity glutamate transporter, system Xag), member 1 (SLC1A1), mRNA. | solute carrier family 1 (neuronal/epithelial high affinity glutamate transporter, system Xag), member 1 | SLC1A1 | 207 |
| 8091306 | ENST00000354952 /// ENST00000383083 /// AF199023 /// NM_001128305 /// NM_020353 /// NM_001128304 /// NM_001128306 | Phospholipid scramblase 4 gene:ENSG00000114698 /// phospholipid scramblase 4 isoform b gene:ENSG00000114698 /// *Homo sapiens* phospholipid scramblase 4 mRNA, complete cds. /// *Homo sapiens* phospholipid scramblase 4 (PLSCR4), transcript variant 3, mRNA. /// *Homo sapiens* phospholipid scramblase 4 (PLSCR4), transcript variant 2, mRNA. /// *Homo sapiens* phospholipid scramblase 4 (PLSCR4), transcript variant 1, mRNA. /// *Homo sapiens* phospholipid scramblase 4 (PLSCR4), transcript variant 4, mRNA. | phospholipid scramblase 4 | PLSCR4 | 208 |
| 7971375 | ENST00000379056 /// ENST00000379060 /// ENST00000379055 /// ENST00000309246 /// BC040008 /// NM_003295 | Tumor protein, translationally-controlled 1, isoform CRA a gene:ENSG00000133112 /// Translationally-controlled tumor protein gene:ENSG00000133112 /// Tumor protein, translationally-controlled 1, isoform CRA a gene:ENSG00000133112 /// | tumor protein, translationally-controlled 1 | TPT1 | 209 |

TABLE E-continued

| Probe Set ID | Transcript ID | Transcript Description | Gene Title | Gene Symbol | |
|---|---|---|---|---|---|
| | | Tumor protein, translationally-controlled 1 gene:ENSG00000133112 /// *Homo sapiens* tumor protein, translationally-controlled 1, mRNA (cDNA clone IMAGE:5219529), complete cds. /// *Homo sapiens* tumor protein, translationally-controlled 1 (TPT1), mRNA. | | | |
| 7981998 | NR_003339 | *Homo sapiens* small nucleolar RNA, C/D box 116-25 (SNORD116-25), non-coding RNA. | small nuclear ribonucleoprotein polypeptide N /// small nucleolar RNA, C/D box 116-25 | SNRPN /// SNORD11 6-25 | 210 |
| 7905077 | BC068044 | *Homo sapiens* cDNA clone IMAGE:6380649, containing frame-shift errors. | | | 211 |
| 7912349 | ENST00000377008 /// ENST00000377004 /// AK094437 /// AK095152 /// BC126349 | Isoform 1 of Uncharacterized protein C1orf127 gene:ENSG00000175262 /// Isoform 2 of Uncharacterized protein C1orf127 gene:ENSG00000175262 /// *Homo sapiens* cDNA FLJ37118 fis, clone BRACE2022328. /// *Homo sapiens* cDNA FLJ37833 fis, clone BRSSN2009702. /// *Homo sapiens* chromosome 1 open reading frame 127, mRNA (cDNA clone MGC:161627 IMAGE:8992065), complete cds. | chromosome 1 open reading frame 127 | C1orf127 | 212 |
| 8091097 | XR_040865 | PREDICTED:*Homo sapiens* misc_RNA (FLJ11827), miscRNA. | hypothetical protein FLJ11827 | FLJ11827 | 213 |
| 7904287 | ENST00000369478 /// ENST00000369477 /// BC033583 /// NM_001767 | T-cell surface antigen CD2 gene:ENSG00000116824 /// CD2 molecule gene:ENSG00000116824 /// *Homo sapiens* CD2 molecule, mRNA (cDNA clone MGC:34621 IMAGE:5227138), complete cds. /// *Homo sapiens* CD2 molecule (CD2), mRNA. | CD2 molecule | CD2 | 214 |
| 8043100 | ENST00000233143 /// BC107889 /// NM_021103 | Thymosin beta-10 gene:ENSG00000034510 /// *Homo sapiens* cDNA clone IMAGE:6651898. /// *Homo sapiens* thymosin beta 10 (TMSB10), mRNA. | thymosin beta 10 | TMSB10 | 215 |
| 8177323 | ENST00000303804 /// ENST00000341740 /// ENST00000338793 /// ENST00000303728 /// ENST00000343584 /// ENST00000303593 /// ENST00000306589 /// ENST00000338673 /// AF517635 /// NM_001002758 /// NM_004676 | Isoform 1 of PTPN13-like protein, Y-linked gene:ENSG00000169807 /// Isoform 2 of PTPN13-like protein, Y-linked gene:ENSG00000169807 /// Isoform 2 of PTPN13-like protein, Y-linked gene:ENSG00000169789 /// Isoform 1 of PTPN13-like protein, Y-linked gene:ENSG00000169789 /// Isoform 1 of PTPN13-like protein, Y-linked gene:ENSG00000169763 /// Isoform 2 of PTPN13-like protein, Y-linked gene:ENSG00000169763 /// Isoform 1 of PTPN13-like protein, Y-linked gene:ENSG00000172283 /// Isoform 2 of PTPN13-like protein, Y-linked gene:ENSG00000172283 /// *Homo sapiens* testis-specific PTP-BL related Y protein mRNA, complete cds, alternatively spliced. /// *Homo sapiens* | PTPN13-like, Y-linked /// PTPN13-like, Y-linked 2 | PRY /// PRY2 | 216 |

… TABLE E-continued

| Probe Set ID | Transcript ID | Transcript Description | Gene Title | Gene Symbol | |
|---|---|---|---|---|---|
| | | PTPN13-like, Y-linked 2 (PRY2), mRNA. /// Homo sapiens PTPN13-like, Y-linked (PRY), mRNA. | | | |
| 7920633 | ENST00000368399 /// ENST00000341298 /// ENST00000368400 /// AK293625 /// NM_153741 /// NM_018973 | cDNA FLJ60436, highly similar to Homo sapiens dolichyl-phosphate mannosyltransferase polypeptide 3, transcript variant 1, mRNA gene:ENSG00000179085 /// Isoform 1 of Dolichol-phosphate mannosyltransferase subunit 3 gene:ENSG00000179085 /// Isoform 1 of Dolichol-phosphate mannosyltransferase subunit 3 gene:ENSG00000179085 /// Homo sapiens cDNA FLJ60436 complete cds, highly similar to Homo sapiens dolichyl-phosphate mannosyltransferase polypeptide 3, transcript variant 1, mRNA. /// Homo sapiens dolichyl-phosphate mannosyltransferase polypeptide 3 (DPM3), transcript variant 2, mRNA. /// Homo sapiens dolichyl-phosphate mannosyltransferase polypeptide 3 (DPM3), transcript variant 1, mRNA | dolichyl-phosphate mannosyltransferase polypeptide 3 | DPM3 | 217 |
| 8110916 | ENST00000382550 /// AK124118 | cDNA FLJ42124 fis, clone TESTI2009477, weakly similar to TRICHOHYALIN gene:ENSG00000205976 /// Homo sapiens cDNA FLJ42124 fis, clone TESTI2009477, weakly similar to TRICHOHYALIN. | similar to hypothetical protein FLJ36144 | LOC442132 | 218 |
| 7943051 | ENST00000321955 /// ENST00000375944 /// BC096316 /// NM_005467 | N-acetylated-alpha-linked acidic dipeptidase 2 gene:ENSG00000077616 /// NAALAD2 protein gene:ENSG00000077616 /// Homo sapiens N-acetylated alpha-linked acidic dipeptidase 2, mRNA (cDNA clone MGC:116994 IMAGE:40007638), complete cds. /// Homo sapiens N-acetylated alpha-linked acidic dipeptidase 2 (NAALAD2), mRNA. | N-acetylated alpha-linked acidic dipeptidase 2 | NAALAD2 | 219 |
| 7938951 | ENST00000324559 /// AL833271 /// NM_213599 | Anoctamin-5 gene:ENSG00000171714 /// Homo sapiens mRNA; cDNA DKFZp451A148 (from clone DKFZp451A148). /// Homo sapiens anoctamin 5 (ANO5), mRNA. | anoctamin 5 | ANO5 | 220 |
| 8083839 | ENST00000402305 /// ENST00000355897 /// BC000181 /// NM_014373 | Probable G-protein coupled receptor 160 gene:ENSG00000173890 /// Probable G-protein coupled receptor 160 gene:ENSG00000173890 /// Homo sapiens G protein-coupled receptor 160, mRNA (cDNA clone MGC:5003 IMAGE:3048193), complete cds. /// Homo sapiens G protein-coupled receptor 160 (GPR160), mRNA. | G protein-coupled receptor 160 | GPR160 | 221 |
| 8046020 | ENST00000375437 /// ENST00000357398 /// ENST00000283256 /// ENST00000375427 /// AB208888 /// NM_021007 /// NM_001040142 /// NM_001040143 | Isoform 1 of Sodium channel protein type 2 subunit alpha gene:ENSG00000136531 /// Isoform 2 of Sodium channel protein type 2 subunit alpha gene:ENSG00000136531 /// Isoform 1 of Sodium channel protein type 2 subunit alpha gene:ENSG00000136531 /// Isoform 2 of Sodium channel protein type 2 subunit alpha gene:ENSG00000136531 /// | sodium channel, voltage-gated, type II, alpha subunit | SCN2A | 222 |

TABLE E-continued

| Probe Set ID | Transcript ID | Transcript Description | Gene Title | Gene Symbol | |
|---|---|---|---|---|---|
| | | Homo sapiens mRNA for Sodium channel protein type II alpha subunit variant protein. /// Homo sapiens sodium channel, voltage-gated, type II, alpha subunit (SCN2A), transcript variant 1, mRNA. /// Homo sapiens sodium channel, voltage-gated, type II, alpha subunit (SCN2A), transcript variant 2, mRNA. /// Homo sapiens sodium channel, voltage-gated, type II, alpha subunit (SCN2A), transcript variant 3, mRNA. | | | |
| 8127658 | ENST00000364421 | ncrna:snRNA chromosome:NCBI36:6:76240174:76240330:−1 gene:ENSG00000201291 | — | — | 223 |
| 8129097 | AK096882 | Homo sapiens cDNA FLJ39563 fis, clone SKMUS2001164. | TSPY-like 1 | TSPYL1 | 224 |
| 7903079 | ENST00000370272 /// ENST00000370267 /// BC035507 /// NM_001938 | Protein Dr1 gene:ENSG00000117505 /// Protein Dr1 gene:ENSG00000117505 /// Homo sapiens down-regulator of transcription 1, TBP-binding (negative cofactor 2), mRNA (cDNA clone MGC:29766 IMAGE:4555131), complete cds. /// Homo sapiens down-regulator of transcription 1, TBP-binding (negative cofactor 2) (DR1), mRNA. | down-regulator of transcription 1, TBP-binding (negative cofactor 2) | DR1 | 225 |
| 8110104 | ENST00000410179 | ncrna:misc_RNA chromosome:NCBI36:5:174987797:174988108:1 gene:ENSG00000222111 | — | — | 226 |
| 8127145 | ENST00000304434 /// ENST00000370918 /// AF338241 /// NM_021814 | Elongation of very long chain fatty acids protein 5 gene:ENSG00000012660 /// 35 kDa protein gene:ENSG00000012660 /// Homo sapiens elongation of very long chain fatty acids protein-like protein 2 (ELOVL2) mRNA, complete cds. /// Homo sapiens ELOVL family member 5, elongation of long chain fatty acids (FEN1/Elo2, SUR4/Elo3-like, yeast) (ELOVL5), mRNA. | ELOVL family member 5, elongation of long chain fatty acids (FEN1/Elo2, SUR4/Elo3-like, yeast) | ELOVL5 | 227 |
| 8175299 | ENST00000391440 /// BC086860 /// NM_001078173 | Protein FAM127C gene:ENSG00000212747 /// Homo sapiens cDNA clone IMAGE:6153002. /// Homo sapiens family with sequence similarity 127, member C (FAM127C), mRNA. | family with sequence similarity 127, member C | FAM127C | 228 |
| 8033248 | ENST00000245912 /// AF064090 /// NM_172014 /// NM_003807 | tumor necrosis factor ligand superfamily, member 14 isoform 1 precursor gene:ENSG00000125735 /// Homo sapiens ligand for herpesvirus entry mediator (HVEM-L) mRNA, complete cds. /// Homo sapiens tumor necrosis factor (ligand) superfamily, member 14 (TNFSF14), transcript variant 2, mRNA. /// Homo sapiens tumor necrosis factor (ligand) superfamily, member 14 (TNFSF14), transcript variant 1, mRNA. | tumor necrosis factor (ligand) superfamily, member 14 | TNFSF14 | 229 |
| 7933075 | ENST00000374694 /// AB043703 /// NM_031866 | Frizzled-8 gene:ENSG00000177283 /// Homo sapiens FZD8 mRNA for seven-transmembrane receptor Frizzled-8, complete cds. /// Homo sapiens frizzled homolog 8 (Drosophila) (FZD8), mRNA. | frizzled homolog 8 (Drosophila) | FZD8 | 230 |

TABLE E-continued

| Probe Set ID | Transcript ID | Transcript Description | Gene Title | Gene Symbol | |
|---|---|---|---|---|---|
| 7915870 | ENST00000371937 /// ENST00000329231 /// BC008498 /// NM_022745 /// NM_001042546 | ATP synthase mitochondrial F1 complex assembly factor 1 gene:ENSG00000123472 /// ATP synthase mitochondrial F1 complex assembly factor 1 isoform 2 precursor gene:ENSG00000123472 /// Homo sapiens ATP synthase mitochondrial F1 complex assembly factor 1, mRNA (cDNA clone MGC:14830 IMAGE:4281102), complete cds. /// Homo sapiens ATP synthase mitochondrial F1 complex assembly factor 1 (ATPAF1), nuclear gene encoding mitochondrial protein, transcript variant 1, mRNA. /// Homo sapiens ATP synthase mitochondrial F1 complex assembly factor 1 (ATPAF1), nuclear gene encoding mitochondrial protein, transcript variant 2, mRNA. | ATP synthase mitochondrial F1 complex assembly factor 1 | ATPAF1 | 231 |
| 8121064 | ENST00000388700 /// ENST00000411294 | ncrna:scRNA_pseudogene chromosome:NCBI36:6:88612087:88612384:1 gene:ENSG00000211435 /// ncrna:misc_RNA chromosome:NCBI36:6:88612087:88612382:1 gene:ENSG00000223226 | — | — | 232 |
| 8161437 | GENSCAN00000015556 /// ENST00000407551 /// XM_001714380 | cdna:Genscan chromosome:NCBI36:9:46007163:46060142:−1 /// cdna:pseudogene chromosome:NCBI36:9:46277008:46277218:1 gene:ENSG00000216653 /// PREDICTED:Homo sapiens similar to hCG1656091 (LOC100132357), mRNA. | similar to hCG1656091 | LOC100132357 | 233 |
| 8008980 | ENST00000335108 /// BC046200 | Putative uncharacterized protein C17orf82 gene:ENSG00000187013 /// Homo sapiens chromosome 17 open reading frame 82, mRNA (cDNA clone MGC:57831 IMAGE:6152618), complete cds. | chromosome 17 open reading frame 82 | C17orf82 | 234 |
| 8154563 | ENST00000340967 /// ENST00000380376 /// BC092487 /// NM_001010887 | Isoform 1 of Alkaline ceramidase 2 gene:ENSG00000177076 /// Isoform 3 of Alkaline ceramidase 2 gene:ENSG00000177076 /// Homo sapiens N-acylsphingosine amidohydrolase 3-like, mRNA (cDNA clone MGC:104688 IMAGE:30528463), complete cds. /// Homo sapiens N-acylsphingosine amidohydrolase 3-like (ASAH3L), mRNA. | alkaline ceramidase 2 | ACER2 | 235 |
| 8161426 | GENSCAN00000015556 /// ENST00000407551 /// XM_001714380 | cdna:Genscan chromosome:NCBI36:9:46007163:46060142:−1 /// cdna:pseudogene chromosome:NCBI36:9:46277008:46277218:1 gene:ENSG00000216653 /// PREDICTED:Homo sapiens similar to hCG1656091 (LOC100132357), mRNA. | similar to hCG1656091 | LOC100132357 | 236 |
| 8083223 | ENST00000315691 /// BC037293 /// NM_173552 /// NM_001134470 | UPF0672 protein C3orf58 gene:ENSG00000181744 /// Homo sapiens chromosome 3 open reading frame 58, mRNA (cDNA clone MGC:33365 IMAGE:5267770), complete cds. /// Homo sapiens chromosome 3 open reading frame 58 (C3orf58), transcript variant 1, mRNA. /// Homo sapiens chromosome 3 open reading frame 58 (C3orf58), transcript variant 2, mRNA. | chromosome 3 open reading frame 58 | C3orf58 | 237 |

TABLE E-continued

| Probe Set ID | Transcript ID | Transcript Description | Gene Title | Gene Symbol | |
|---|---|---|---|---|---|
| 8001329 | ENST00000219197 /// M58583 /// NM_004352 | Cerebellin-1 gene:ENSG00000102924 /// Human precerebellin and cerebellin mRNA, complete cds. /// *Homo sapiens* cerebellin 1 precursor (CBLN1), mRNA. | cerebellin 1 precursor | CBLN1 | 238 |
| 8165575 | ENST00000371457 /// ENST00000277531 /// ENST00000406427 /// ENST00000371451 /// ENST00000371450 /// ENST00000371446 /// AK297623 /// NM_152286 /// NM_001098537 | cDNA FLJ45411 fis, clone BRHIP3032374, moderately similar to *Homo sapiens* neuropathy target esterase gene:ENSG00000130653 /// Isoform 1 of Patatin-like phospholipase domain-containing protein 7 gene:ENSG00000130653 /// patatin-like phospholipase domain containing 7 isoform a gene:ENSG00000130653 /// Putative uncharacterized protein PNPLA7 gene:ENSG00000130653 /// Isoform 2 of Patatin-like phospholipase domain-containing protein 7 gene:ENSG00000130653 /// 23 kDa protein gene:ENSG00000130653 /// *Homo sapiens* cDNA FLJ55553 complete cds. /// *Homo sapiens* patatin-like phospholipase domain containing 7 (PNPLA7), transcript variant 2, mRNA. /// *Homo sapiens* patatin-like phospholipase domain containing 7 (PNPLA7), transcript variant 1, mRNA. | patatin-like phospholipase domain containing 7 | PNPLA7 | 239 |
| 7971731 | ENST00000400366 /// ENST00000344297 /// ENST00000242839 /// ENST00000400370 /// U11700 /// NM_000053 /// NM_001005918 | Isoform 3 of Copper-transporting ATPase 2 gene:ENSG00000123191 /// Isoform 2 of Copper-transporting ATPase 2 gene:ENSG00000123191 /// Isoform 1 of Copper-transporting ATPase 2 gene:ENSG00000123191 /// ATP7B protein gene:ENSG00000123191 /// Human copper transporting ATPase mRNA, complete cds. /// *Homo sapiens* ATPase, Cu++ transporting, beta polypeptide (ATP7B), transcript variant 1, mRNA. /// *Homo sapiens* ATPase, Cu++ transporting, beta polypeptide (ATP7B), transcript variant 2, mRNA. | ATPase, Cu++ transporting, beta polypeptide | ATP7B | 240 |
| 8028600 | ENST00000339852 /// BC092493 /// NM_001001414 | FBA domain-containing protein LOC342897 gene:ENSG00000188505 /// *Homo sapiens* similar to F-box only protein 2, mRNA (cDNA clone MGC:104713 IMAGE:30337042), complete cds. /// *Homo sapiens* nonspecific cytotoxic cell receptor protein 1 homolog (zebrafish) (NCCRP1), mRNA. | non-specific cytotoxic cell receptor protein 1 homolog (zebrafish) | NCCRP1 | 241 |
| 8155569 | ENST00000407551 /// XM_001714380 | cdna:pseudogene chromosome:NCBI36:9:46277008:46277218:1 gene:ENSG00000216653 /// PREDICTED:*Homo sapiens* similar to hCG1656091 (LOC100132357), mRNA. | similar to hCG1656091 | LOC100132357 | 242 |

TABLE E-continued

| Probe Set ID | Transcript ID | Transcript Description | Gene Title | Gene Symbol | |
|---|---|---|---|---|---|
| 8039605 | ENST00000342088 /// AK023017 /// NM_001005850 | Zinc finger protein 835 gene:ENSG00000127903 /// Homo sapiens cDNA FLJ12955 fis, clone NT2RP2005496, moderately similar to ZINC FINGER PROTEIN 135. /// Homo sapiens zinc finger protein 835 (ZNF835), mRNA. | zinc finger protein 835 | ZNF835 | 243 |
| 7937971 | ENST00000322493 | cdna:pseudogene chromosome:NCBI36:11:4764560:4765496:1 gene:ENSG00000176951 | — | — | 244 |
| 8137925 | ENST00000384168 | ncrna:misc_RNA chromosome:NCBI36:7:4817345:4817446:−1 gene:ENSG00000206895 | — | — | 245 |
| 7915408 | ENST00000372572 /// ENST00000372571 /// ENST00000372573 /// ENST00000361346 /// ENST00000361776 /// BC152441 /// NM_014947 | Isoform 1 of Forkhead box protein J3 gene:ENSG00000198815 /// 15 kDa protein gene:ENSG00000198815 /// Isoform 1 of Forkhead box protein J3 gene:ENSG00000198815 /// Isoform 1 of Forkhead box protein J3 gene:ENSG00000198815 /// Isoform 2 of Forkhead box protein J3 gene:ENSG00000198815 /// Homo sapiens forkhead box J3, mRNA (cDNA clone MGC:176686 IMAGE:8862565), complete cds. /// Homo sapiens forkhead box J3 (FOXJ3), mRNA. | forkhead box J3 | FOXJ3 | 246 |
| 8014891 | ENST00000394189 /// ENST00000377944 /// ENST00000348427 /// ENST00000346872 /// ENST00000377958 /// ENST00000293068 /// ENST00000351680 /// ENST00000350532 /// ENST00000377945 /// ENST00000346243 /// ENST00000377952 /// AY377981 /// NM_183230 /// NM_183231 /// NM_183232 /// NM_012481 /// NM_183228 /// NM_183229 | Aiolos isoform hAio-del gene:ENSG00000161405 /// Aiolos isoform hAio-del gene:ENSG00000161405 /// Isoform 2 of Zinc finger protein Aiolos gene:ENSG00000161405 /// Isoform 5 of Zinc finger protein Aiolos gene:ENSG00000161405 /// Aiolos isoform hAio-del gene:ENSG00000161405 /// Isoform 1 of Zinc finger protein Aiolos gene:ENSG00000161405 /// Isoform 3 of Zinc finger protein Aiolos gene:ENSG00000161405 /// Isoform 4 of Zinc finger protein Aiolos gene:ENSG00000161405 /// Aiolos isoform hAio-del gene:ENSG00000161405 /// Isoform 6 of Zinc finger protein Aiolos gene:ENSG00000161405 /// Aiolos isoform hAio-del gene:ENSG00000161405 /// Homo sapiens aiolos isoform hAio-ALT (ZNFN1A3) mRNA, complete cds, alternatively spliced. /// Homo sapiens IKAROS family zinc finger 3 (Aiolos) (IKZF3), transcript variant 4, mRNA. /// Homo sapiens IKAROS family zinc finger 3 (Aiolos) (IKZF3), transcript variant 5, mRNA. /// Homo sapiens IKAROS family zinc finger 3 (Aiolos) (IKZF3), transcript variant 6, mRNA. /// Homo sapiens IKAROS family zinc finger 3 (Aiolos) (IKZF3), transcript variant 1, mRNA. /// Homo sapiens IKAROS family zinc finger 3 (Aiolos) (IKZF3), transcript variant 2, mRNA. /// Homo sapiens IKAROS family zinc finger 3 (Aiolos) (IKZF3), transcript variant 3, mRNA. | IKAROS family zinc finger 3 (Aiolos) | IKZF3 | 247 |
| 7999406 | ENST00000386866 | ncrna:Mt_tRNA_pseudogene chromosome:NCBI36:16:10722924:10722982:−1 gene:ENSG00000209601 | — | — | 248 |

TABLE E-continued

| Probe Set ID | Transcript ID | Transcript Description | Gene Title | Gene Symbol | |
|---|---|---|---|---|---|
| 8128087 | ENST00000369451 /// BC130344 /// NM_002042 | gamma-aminobutyric (GABA) receptor, rho 1 gene:ENSG00000146276 /// Homo sapiens gamma-aminobutyric acid (GABA) receptor, rho 1, mRNA (cDNA clone MGC:163216 IMAGE:40146375), complete cds. /// Homo sapiens gamma-aminobutyric acid (GABA) receptor, rho 1 (GABRR1), mRNA. | gamma-aminobutyric acid (GABA) receptor, rho 1 | GABRR1 | 249 |
| 8011968 | ENST00000225728 /// AF151883 /// NM_016060 | Mediator of RNA polymerase II transcription subunit 31 gene:ENSG00000108590 /// Homo sapiens CGI-125 protein mRNA, complete cds. /// Homo sapiens mediator complex subunit 31 (MED31), mRNA. | mediator complex subunit 31 | MED31 | 250 |
| 7950555 | ENST00000404995 /// ENST00000407242 /// ENST00000260061 /// BC070079 /// NM_005512 /// NM_001128922 | Leucine-rich repeat-containing protein 32 gene:ENSG00000137507 /// Leucine-rich repeat-containing protein 32 gene:ENSG00000137507 /// Leucine-rich repeat-containing protein 32 gene:ENSG00000137507 /// Homo sapiens leucine rich repeat containing 32, mRNA (cDNA clone MGC:87399 IMAGE:30344529), complete cds. /// Homo sapiens leucine rich repeat containing 32 (LRRC32), transcript variant 1, mRNA. /// Homo sapiens leucine rich repeat containing 32 (LRRC32), transcript variant 2, mRNA. | leucine rich repeat containing 32 | LRRC32 | 251 |
| 8012535 | ENST00000329805 /// AY129026 /// NM_152599 | UPF0537 transmembrane protein gene:ENSG00000185156 /// Homo sapiens clone FP7072 unknown mRNA. /// Homo sapiens major facilitator superfamily domain containing 6-like (MFSD6L), mRNA. | major facilitator superfamily domain containing 6-like | MFSD6L | 252 |
| 7988767 | ENST00000396402 /// ENST00000396404 /// ENST00000260433 /// ENST00000405913 /// AK291778 /// NM_031226 /// NM_000103 | Cytochrome P450 19A1 gene:ENSG00000137869 /// Cytochrome P450 19A1 gene:ENSG00000137869 /// Cytochrome P450 19A1 gene:ENSG00000137869 /// CYP19A1 protein gene:ENSG00000137869 /// Homo sapiens cDNA FLJ75846 complete cds, highly similar to Homo sapiens cytochrome P450, family 19, subfamily A, polypeptide 1 (CYP19A1), transcript variant 1, mRNA. /// Homo sapiens cytochrome P450, family 19, subfamily A, polypeptide 1 (CYP19A1), transcript variant 2, mRNA. /// Homo sapiens cytochrome P450, family 19, subfamily A, polypeptide 1 (CYP19A1), transcript variant 1, mRNA. | cytochrome P450, family 19, subfamily A, polypeptide 1 | CYP19A1 | 253 |

TABLE E-continued

| Probe Set ID | Transcript ID | Transcript Description | Gene Title | Gene Symbol | |
|---|---|---|---|---|---|
| 8036291 | ENST00000355114 /// ENST00000392173 /// ENST00000304116 /// BC068453 /// NM_001042474 /// NM_152477 | cDNA FLJ32728 fis, clone TESTI2001049, highly similar to Zinc finger protein 565 gene:ENSG00000196357 /// Zinc finger protein 565 gene:ENSG00000196357 /// Zinc finger protein 565 gene:ENSG00000196357 /// *Homo sapiens* zinc finger protein 565, mRNA (cDNA clone IMAGE:30343899). /// *Homo sapiens* zinc finger protein 565 | zinc finger protein 565 | ZNF565 | 254 |
| 8095331 | ENST00000365299 | ncrna:misc_RNA chromosome:NCBI36:4:62454626:62454721:1 gene:ENSG00000202169 | — | — | 257 |
| 8180232 | — | — | — | — | 258 |
| 8105040 | ENST00000274276 /// U60805 /// NM_003999 | Isoform 1 of Oncostatin-M specific receptor subunit beta gene:ENSG00000145623 /// Human oncostatin-M specific receptor beta subunit (OSMRB) mRNA, complete cds. /// *Homo sapiens* oncostatin M receptor (OSMR), mRNA. | oncostatin M receptor | OSMR | 259 |
| 8122684 | ENST00000326669 /// AY340238 /// NM_001002255 | SMT3 suppressor of mif two 3 homolog 4 gene:ENSG00000177688 /// *Homo sapiens* small ubiquitin-like protein 4 mRNA, complete cds. /// *Homo sapiens* SMT3 suppressor of mif two 3 homolog 4 (*S. cerevisiae*) (SUMO4), mRNA. | SMT3 suppressor of mif two 3 homolog 4 (*S. cerevisiae*) | SUMO4 | 261 |
| 7940622 | ENST00000306238 /// BC062693 /// NM_006552 | Secretoglobin family 1D member 1 gene:ENSG00000168515 /// *Homo sapiens* secretoglobin, family 1D, member 1, mRNA (cDNA clone MGC:71958 IMAGE:30327780), complete cds. /// *Homo sapiens* secretoglobin, family 1D, member 1 (SCGB1D1), mRNA. | secretoglobin, family 1D, member 1 | SCGB1D1 | 262 |
| 8092654 | ENST00000296277 /// BC012328 /// NM_052969 | 60S ribosomal protein L39-like gene:ENSG00000163923 /// *Homo sapiens* ribosomal protein L39-like, mRNA (cDNA clone MGC:20168 IMAGE:4555759), complete cds. /// *Homo sapiens* ribosomal protein L39-like (RPL39L), mRNA. | ribosomal protein L39-like | RPL39L | 263 |
| 7944867 | ENST00000363408 | ncrna:rRNA chromosome:NCBI36:11:124011565:124011685:1 gene:ENSG00000200278 | — | — | 264 |
| 7925087 | ENST00000384108 | ncrna:snRNA chromosome:NCBI36:1:231034386:231034556:-1 gene:ENSG00000206835 | — | — | 265 |
| 7985920 | ENST00000341735 /// BC111413 /// NM_001039958 | mesoderm posterior 2 homolog gene:ENSG00000188095 /// *Homo sapiens* mesoderm posterior 2 homolog (mouse), mRNA (cDNA clone MGC:133018 IMAGE:40004357), complete cds. /// *Homo sapiens* mesoderm posterior 2 homolog (mouse) (MESP2), mRNA. | mesoderm posterior 2 homolog (mouse) | MESP2 | 266 |
| 7939314 | ENST00000257831 /// AF203977 /// NM_012153 | Isoform 1 of ETS homologous factor gene:ENSG00000135373 /// *Homo sapiens* ETS-family transcription factor EHF (EHF) mRNA, complete cds. /// *Homo sapiens* ets homologous factor (EHF), mRNA. | ets homologous factor | EHF | 267 |

TABLE E-continued

| Probe Set ID | Transcript ID | Transcript Description | Gene Title | Gene Symbol | |
|---|---|---|---|---|---|
| 7979179 | ENST00000395686 /// ENST00000359133 /// AF081886 /// NM_014584 | Putative uncharacterized protein ERO1L gene:ENSG00000197930 /// ERO1-like protein alpha gene:ENSG00000197930 /// Homo sapiens ERO1-like protein (ERO1-L) mRNA, complete cds. /// Homo sapiens ERO1-like (S. cerevisiae) (ERO1L), mRNA. | ERO1-like (S. cerevisiae) | ERO1L | 268 |
| 8123819 | ENST00000379715 /// BC005291 /// NM_004280 /// NM_001135650 | Eukaryotic translation elongation factor 1 epsilon-1 gene:ENSG00000124802 /// Homo sapiens eukaryotic translation elongation factor 1 epsilon 1, mRNA (cDNA clone MGC:12352 IMAGE:3685030), complete cds. /// Homo sapiens eukaryotic translation elongation factor 1 epsilon 1 (EEF1E1), | eukaryotic translation elongation factor 1 epsilon 1 | EEF1E1 | 269 |
| 8173414 | ENST00000298085 /// ENST00000374299 /// BC033816 /// NM_032803 /// NM_001048164 | Cationic amino acid transporter 3 gene:ENSG00000165349 /// Cationic amino acid transporter 3 gene:ENSG00000165349 /// Homo sapiens solute carrier family 7 (cationic amino acid transporter, y+ system), member 3, mRNA (cDNA clone MGC:44839 IMAGE:5206252), complete cds. /// Homo sapiens solute carrier family 7 (cationic amino acid transporter, y+ system), member 3 (SLC7A3), transcript variant 1, mRNA. /// Homo sapiens solute carrier family 7 (cationic amino acid transporter, y+ system), member 3 (SLC7A3), transcript variant 2, mRNA. | solute carrier family 7 (cationic amino acid transporter, y+ system), member 3 | SLC7A3 | 270 |
| 7952797 | ENST00000299140 /// BC058039 /// NM_174927 | Spermatogenesis-associated protein 19, mitochondrial gene:ENSG00000166118 /// Homo sapiens spermatogenesis associated 19, mRNA (cDNA clone MGC:62071 IMAGE:6619434), complete cds. /// Homo sapiens spermatogenesis associated 19 (SPATA19), mRNA. | spermatogenesis associated 19 | SPATA19 | 271 |
| 8031387 | ENST00000291890 /// ENST00000338835 /// ENST00000350790 /// ENST00000357397 /// BC064806 /// NM_004829 | Isoform 1 of Natural cytotoxicity triggering receptor 1 gene:ENSG00000189430 /// Isoform 2 of Natural cytotoxicity triggering receptor 1 gene:ENSG00000189430 /// Isoform 3 of Natural cytotoxicity triggering receptor 1 gene:ENSG00000189430 /// Isoform 5 of Natural cytotoxicity triggering receptor 1 gene:ENSG00000189430 /// Homo sapiens natural cytotoxicity triggering receptor 1, mRNA (cDNA clone MGC:65100 IMAGE:5218848), complete cds. /// Homo sapiens natural cytotoxicity triggering receptor 1 (NCR1), mRNA. | natural cytotoxicity triggering receptor 1 | NCR1 | 272 |
| 8038655 | ENST00000324041 /// AF113140 /// NM_004917 | Kallikrein-4 gene:ENSG00000167749 /// Homo sapiens serine protease prostase mRNA, complete cds. /// Homo sapiens kallikrein-related peptidase 4 (KLK4), mRNA. | kallikrein-related peptidase 4 | KLK4 | 273 |

TABLE E-continued

| Probe Set ID | Transcript ID | Transcript Description | Gene Title | Gene Symbol | |
|---|---|---|---|---|---|
| 8074106 | ENST00000252783 /// ENST00000395676 /// BC009980 /// NM_138433 | Kelch domain-containing protein 7B gene:ENSG00000130487 /// kelch domain containing 7B gene:ENSG00000130487 /// *Homo sapiens* kelch domain containing 7B, mRNA (cDNA clone MGC:16635 IMAGE:4121528), complete cds. | kelch domain containing 7B | KLHDC7B | 274 |
| 8166382 | ENST00000379484 /// ENST00000365779 /// AK292933 /// NM_015884 | Membrane-bound transcription factor site-2 protease gene:ENSG00000012174 /// 36 kDa protein gene:ENSG00000012174 /// *Homo sapiens* cDNA FLJ75833 complete cds, highly similar to *Homo sapiens* membrane-bound transcription factor peptidase, site 2 (MBTPS2), mRNA. /// *Homo sapiens* membrane-bound transcription factor peptidase, site 2 (MBTPS2), mRNA. | membrane-bound transcription factor peptidase, site 2 | MBTPS2 | 275 |
| 7965884 | ENST00000307000 /// U49897 /// NM_000277 | Phenylalanine-4-hydroxylase gene:ENSG00000171759 /// *Homo sapiens* phenylalanine hydroxylase (PAH) mRNA, complete cds. /// *Homo sapiens* phenylalanine hydroxylase (PAH), mRNA. | phenylalanine hydroxylase | PAH | 276 |
| 8103684 | ENST00000261511 /// BC010367 /// NM_017867 | UPF0609 protein C4orf27 gene:ENSG00000056050 /// *Homo sapiens* chromosome 4 open reading frame 27, mRNA (cDNA clone MGC:13432 IMAGE:4334172), complete cds. /// *Homo sapiens* chromosome 4 open reading frame 27 (C4orf27), mRNA. | chromosome 4 open reading frame 27 | C4orf27 | 277 |
| 8139592 | ENST00000258774 /// AF076844 /// NM_004507 | Checkpoint protein HUS1 gene:ENSG00000136273 /// *Homo sapiens* Hus1-like protein (HUS1) mRNA, complete cds. /// *Homo sapiens* HUS1 checkpoint homolog (*S. pombe*) (HUS1), mRNA. | HUS1 checkpoint homolog (*S. pombe*) | HUS1 | 278 |
| 8004957 | ENST00000361801 /// ENST00000262442 /// ENST00000396001 /// AJ404468 /// NM_001372 /// NM_004662 | dynein, axonemal, heavy chain 9 isoform 1 gene:ENSG00000007174 /// Isoform 1 of Dynein heavy chain 9, axonemal gene:ENSG00000007174 /// dynein, axonemal, heavy chain 9 isoform 1 gene:ENSG00000007174 /// *Homo sapiens* mRNA for dynein heavy chain 9 (DNAH9 gene). /// *Homo sapiens* dynein, axonemal, heavy chain 9 (DNAH9), transcript variant 2, mRNA. /// *Homo sapiens* dynein, axonemal, heavy chain 9 (DNAH9), transcript variant 1, mRNA. | dynein, axonemal, heavy chain 9 | DNAH9 | 279 |
| 8130553 | AK130765 | *Homo sapiens* cDNA FLJ27255 fis, clone SYN09519. | hypothetical LOC401281 | FLJ27255 | 280 |
| 8094830 | ENST00000264452 /// AY659966 /// NM_018126 | Transmembrane protein 33 gene:ENSG00000109133 /// *Homo sapiens* SHINC3 (SHINC3) mRNA, complete cds. /// *Homo sapiens* transmembrane protein 33 (TMEM33), mRNA. | transmembrane protein 33 | TMEM33 | 281 |
| 8149438 | ENST00000329135 /// ENST00000382080 /// AY028700 /// NM_139167 | Zeta-sarcoglycan gene:ENSG00000185053 /// sarcoglycan zeta gene:ENSG00000185053 /// *Homo sapiens* zeta-sarcoglycan mRNA, complete cds. /// *Homo sapiens* sarcoglycan zeta (SGCZ), mRNA. | sarcoglycan zeta | SGCZ | 282 |

TABLE E-continued

| Probe Set ID | Transcript ID | Transcript Description | Gene Title | Gene Symbol | |
|---|---|---|---|---|---|
| 8180029 | ENST00000399426 ///<br>ENST00000399424 ///<br>ENST00000399427 ///<br>ENST00000383099 ///<br>ENST00000383245 ///<br>ENST00000323109 ///<br>ENST00000399658 ///<br>ENST00000399661 ///<br>ENST00000323143 ///<br>ENST00000399053 ///<br>ENST00000374931 ///<br>ENST00000374934 ///<br>AK098007 ///<br>NR_003937 | Major histocompatibility complex, class II, DQ beta 2 gene:ENSG00000215008 /// Major histocompatibility complex, class II, DQ beta 2 gene:ENSG00000215008 /// Major histocompatibility complex, class II, DQ beta 2 gene:ENSG00000215008 /// Major histocompatibility complex, class II, DQ beta 2 gene:ENSG00000215008 /// Major histocompatibility complex, class II, DQ beta 2 gene:ENSG00000196610 /// Major histocompatibility complex, class II, DQ beta 2 gene:ENSG00000196610 /// Major histocompatibility complex, class II, DQ beta 2 gene:ENSG00000196610 /// cdna:known chromosome:NCBI36:c6_QBL:32795451:32802909:-1 gene:ENSG00000196610 /// Major histocompatibility complex, class II, DQ beta 2 gene:ENSG00000204275 /// Major histocompatibility complex, class II, DQ beta 2 gene:ENSG00000204275 /// Major histocompatibility complex, class II, DQ beta 2 gene:ENSG00000204275 /// Major histocompatibility complex, class II, DQ beta 2 gene:ENSG00000204275 /// *Homo sapiens* cDNA FLJ40688 fis, clone THYMU2024185, highly similar to HLA class II histocompatibility antigen, DX beta chain precursor. /// *Homo sapiens* major histocompatibility complex, class II, DQ beta2 (HLA-DQB2), non-coding RNA. | major histocompatibility complex, class II, DQ beta 2 | HLA-DQB2 | 283 |
| 8015060 | ENST00000264651 ///<br>AK000268 ///<br>NM_019016 | Keratin, type I cytoskeletal 24 gene:ENSG00000167916 /// *Homo sapiens* cDNA FLJ20261 fis, clone COLF7630. /// *Homo sapiens* keratin 24 (KRT24), mRNA. | keratin 24 | KRT24 | 284 |
| 8066384 | ENST00000373005 ///<br>ENST00000373003 ///<br>BC040049 ///<br>NM_176791 ///<br>NM_001008901 | gametocyte specific factor 1-like isoform 2 gene:ENSG00000124196 /// Gametocyte-specific factor 1-like gene:ENSG00000124196 /// *Homo sapiens* gametocyte specific factor 1-like, mRNA (cDNA clone MGC:50820 | gametocyte specific factor 1-like | GTSF1L | 285 |
| 8001197 | ENST00000303155 ///<br>AY358718 ///<br>NM_018092 | Isoform 1 of Neuropilin and tolloid-like protein 2 gene:ENSG00000171208 /// *Homo sapiens* clone DNA84912 Neto2 (UNQ1926) mRNA, complete cds. /// *Homo sapiens* neuropilin (NRP) and tolloid (TLL)-like 2 (NETO2), mRNA. | neuropilin (NRP) and tolloid (TLL)-like 2 | NETO2 | 286 |
| 8177195 | ENST00000253323 ///<br>ENST00000253325 ///<br>AF332238 ///<br>NR_001530 ///<br>NR_002159 | Putative transcript Y 9 protein gene:ENSG00000131007 /// Putative transcript Y 9 protein gene:ENSG00000131009 /// *Homo sapiens* testis transcript Y 9 (TTY9) mRNA, complete cds. /// *Homo sapiens* testis-specific transcript, Y-linked 9A (TTTY9A), | testis-specific transcript, Y-linked 9A /// testis-specific transcript, Y-linked 9B | TTTY9A ///<br>TTTY9B | 287 |

TABLE E-continued

| Probe Set ID | Transcript ID | Transcript Description | Gene Title | Gene Symbol | |
|---|---|---|---|---|---|
| | | non-coding RNA. /// Homo sapiens testis-specific transcript, Y-linked 9B (TTTY9B), non-coding RNA. | | | |
| 8008885 | hsa-mir-21 /// hsa-mir-21 /// AY699265 | MI0000077 Homo sapiens miR-21 stem-loop /// MI0000077 Homo sapiens miR-21 stem-loop /// Homo sapiens microRNA pri-miR-21, complete sequence. | microRNA 21 | MIR21 | 288 |
| 8176692 | ENST00000253323 /// ENST00000253325 /// AF332238 /// NR_001530 /// NR_002159 | Putative transcript Y 9 protein gene:ENSG00000131007 /// Putative transcript Y 9 protein gene:ENSG00000131009 /// Homo sapiens testis transcript Y 9 (TTY9) mRNA, complete cds. /// Homo sapiens testis-specific transcript, Y-linked 9A (TTTY9A), non-coding RNA. /// Homo sapiens testis-specific transcript, Y-linked 9B (TTTY9B), non-coding RNA. | testis-specific transcript, Y-linked 9A /// testis-specific transcript, Y-linked 9B | TTTY9A /// TTTY9B | 289 |
| 8056959 | ENST00000308618 /// NM_001080458 | Homeobox even-skipped homolog protein 2 gene:ENSG00000174279 /// Homo sapiens even-skipped homeobox 2 (EVX2), mRNA. | even-skipped homeobox 2 | EVX2 | 290 |
| 7974562 | ENST00000363948 | ncrna:snRNA chromosome:NCBI36:14:56361457:56361563:1 gene:ENSG00000200818 | — | — | 291 |
| 8136557 | ENST00000336425 /// ENST00000263552 /// BC014117 /// NM_001130966 /// NM_001061 /// NM_030984 | thromboxane A synthase 1 isoform TXS-I gene:ENSG00000059377 /// thromboxane A synthase 1 isoform TXS-II gene:ENSG00000059377 /// Homo sapiens thromboxane A synthase 1 (platelet), mRNA (cDNA clone MGC:20885 IMAGE:4548935), complete cds. /// Homo sapiens thromboxane A synthase 1 (platelet) (TBXAS1), transcript variant TXS-III, mRNA. /// Homo sapiens thromboxane A | thromboxane A synthase 1 (platelet) | TBXAS1 | 292 |
| 7936968 | ENST00000368679 /// ENST00000368683 /// ENST00000368676 /// AF023476 /// NM_003474 /// NM_021641 | Isoform 1 of ADAM 12 gene:ENSG00000148848 /// Isoform 4 of ADAM 12 gene:ENSG00000148848 /// Isoform 2 of ADAM 12 gene:ENSG00000148848 /// Homo sapiens meltrin-L precursor (ADAM12) mRNA, complete cds, alternatively spliced. /// Homo sapiens ADAM metallopeptidase domain 12 (ADAM12), transcript variant 1, mRNA. /// Homo sapiens ADAM metallopeptidase domain 12 (ADAM12), transcript variant 2, mRNA. | ADAM metallopeptidase domain 12 | ADAM12 | 293 |
| 8019478 | ENST00000312648 /// AY935535 /// NM_006137 | T-cell antigen CD7 gene:ENSG00000173762 /// Homo sapiens clone 14 CD7 antigen mRNA, complete cds. /// Homo sapiens CD7 molecule (CD7), mRNA. | CD7 molecule | CD7 | 294 |
| 8073799 | ENST00000252934 /// ENST00000396011 /// ENST00000381061 /// ENST00000402380 /// BC007508 /// NM_013236 | Ataxin-10 gene:ENSG00000130638 /// HUMEEP gene:ENSG00000130638 /// Putative uncharacterized protein ATXN10 gene:ENSG00000130638 /// Ataxin 10 | ataxin 10 | ATXN10 | 295 |

TABLE E-continued

| Probe Set ID | Transcript ID | Transcript Description | Gene Title | Gene Symbol | |
|---|---|---|---|---|---|
| | | gene:ENSG00000130638 /// *Homo sapiens* ataxin 10, mRNA (cDNA clone MGC:4152 IMAGE:3030062), complete cds. /// *Homo sapiens* ataxin 10 (ATXN10), mRNA. | | | |
| 8035789 | ENST00000358224 /// BC016785 /// NM_001039884 | Zinc finger protein 826 gene:ENSG00000178604 /// *Homo sapiens* zinc finger protein 826, mRNA (cDNA clone IMAGE:4096414), complete cds. /// *Homo sapiens* zinc finger protein 826 (ZNF826), mRNA. | zinc finger protein 826 | ZNF826 | 296 |
| 7951485 | ENST00000265836 /// ENST00000375682 /// AK128062 /// NM_017515 | Isoform 1 of Solute carrier family 35 member F2 gene:ENSG00000110660 /// Putative uncharacterized protein SLC35F2 (Fragment) gene:ENSG00000110660 /// *Homo sapiens* cDNA FLJ46182 fis, clone TESTI4004539. /// *Homo sapiens* solute carrier family 35, member F2 (SLC35F2), mRNA. | solute carrier family 35, member F2 | SLC35F2 | 297 |
| 8114805 | ENST00000359370 /// ENST00000378046 /// ENST00000337706 /// ENST00000360966 /// ENST0000040 | Heparin-binding growth factor 1 gene:ENSG00000113578 /// Heparin-binding growth factor 1 gene:ENSG00000113578 /// Heparin-binding growth factor 1 gene:ENSG00000113578 /// fibroblast growth factor 1 (acidic) isoform 2 precursor gene:ENSG00000113578 /// | fibroblast growth factor 1 (acidic) | FGF1 | 298 |
| 8095680 | ENST00000401931 /// ENST00000307407 /// ENST00000395775 /// M17017 /// NM_000584 | 11 kDa protein gene:ENSG00000169429 /// Isoform 1 of lnterleukin-8 gene:ENSG00000169429 /// 15 kDa protein gene:ENSG00000169429 /// Human beta-thromboglobulin-like protein mRNA, complete cds. /// *Homo sapiens* interleukin 8 (IL8), mRNA. | interleukin 8 | IL8 | 299 |
| 8017827 | ENST00000364677 | ncrna:misc_RNA chromosome:NCBI36:17:62835352:62835459:-1 gene:ENSG00000201547 | — | — | 300 |
| 8083034 | ENST00000332210 /// AY753303 /// NM_022131 | Calsyntenin-2 gene:ENSG00000158258 /// *Homo sapiens* alcadein gamma mRNA, complete cds. /// *Homo sapiens* calsyntenin 2 (CLSTN2), mRNA. | calsyntenin 2 | CLSTN2 | 301 |
| 8131140 | ENST00000313156 /// AK024457 | FLJ00049 protein (Fragment) gene:ENSG00000175873 /// *Homo sapiens* mRNA for FLJ00049 protein, partial cds. | FLJ00049 protein | FLJ00049 | 302 |
| 7977003 | ENST00000262241 /// AF155595 /// NM_015156 | REST corepressor 1 gene:ENSG00000089902 /// *Homo sapiens* CoREST protein (COREST) mRNA, complete cds. /// *Homo sapiens* REST corepressor 1 (RCOR1), mRNA. | REST corepressor 1 | RCOR1 | 303 |
| 8144774 | ENST00000324815 /// ENST00000324849 /// BC067754 /// NM_152415 | Isoform 3 of Vacuolar protein sorting-associated protein 37A gene:ENSG00000155975 /// Isoform 1 of Vacuolar protein sorting-associated protein 37A gene:ENSG00000155975 /// *Homo sapiens* vacuolar protein sorting 37 homolog A (*S. cerevisiae*), mRNA (cDNA clone MGC:87029 IMAGE:5275060), | vacuolar protein sorting 37 homolog A (*S. cerevisiae*) | VPS37A | 304 |
| 8172266 | hsa-mir-221 /// hsa-mir-221 | MI0000298 *Homo sapiens* miR-221 stem-loop /// MI0000298 *Homo sapiens* miR-221 stem-loop | — | — | 305 |

TABLE E-continued

| Probe Set ID | Transcript ID | Transcript Description | Gene Title | Gene Symbol | |
|---|---|---|---|---|---|
| 8091186 | — | — | — | — | 306 |
| 8076298 | ENST00000386767 | ncrna:scRNA_pseudogene chromosome:NCBI36:22:39776868:39776953:−1 gene:ENSG00000209502 | — | — | 307 |
| 8094704 | ENST00000295963 /// ENST00000261427 /// U58522 /// NM_001111112 /// NM_001111113 /// NM_005339 | Isoform 2 of Ubiquitin-conjugating enzyme E2 K gene:ENSG00000078140 /// Isoform 1 of Ubiquitin-conjugating enzyme E2 K gene:ENSG00000078140 /// Human huntingtin interacting protein (HIP2) mRNA, complete cds. /// *Homo sapiens* ubiquitin-conjugating enzyme E2K (UBC1 homolog, yeast) (UBE2K), transcript variant 2, mRNA. /// *Homo sapiens* ubiquitin-conjugating enzyme E2K (UBC1 homolog, yeast) (UBE2K), transcript variant 3, mRNA. /// *Homo sapiens* ubiquitin-conjugating enzyme E2K (UBC1 homolog, yeast) (UBE2K), transcript variant 1, mRNA. | ubiquitin-conjugating enzyme E2K (UBC1 homolog, yeast) | UBE2K | 308 |
| 8089329 | ENST00000273353 /// AK126801 /// NM_014981 | Myosin-15 gene:ENSG00000144821 /// *Homo sapiens* cDNA FLJ44851 fis, clone BRACE3051819, moderately similar to Myosin heavy chain, cardiac muscle alpha isoform. /// *Homo sapiens* myosin, heavy chain 15 (MYH15), mRNA. | myosin, heavy chain 15 | MYH15 | 309 |
| 8116548 | ENST00000344450 /// BC022847 /// NM_020185 | Isoform 1 of Dual specificity protein phosphatase 22 gene:ENSG00000112679 /// *Homo sapiens* dual specificity phosphatase 22, mRNA (cDNA clone MGC:15090 IMAGE:3942055), complete cds. /// *Homo sapiens* dual specificity phosphatase 22 (DUSP22), mRNA. | dual specificity phosphatase 22 | DUSP22 | 310 |
| 7903294 | ENST00000370152 /// AK057172 /// NM_033055 | Hippocampus abundant transcript 1 protein gene:ENSG00000156875 /// *Homo sapiens* cDNA FLJ32610 fis, clone STOMA2000055, highly similar to Mouse mRNA for tetracycline transporter-like protein. /// *Homo sapiens* hippocampus abundant transcript 1 (HIAT1), mRNA. | hippocampus abundant transcript 1 | HIAT1 | 311 |
| 7977567 | ENST00000344581 /// BC146951 | similar to hCG2036672 gene:ENSG00000185271 /// *Homo sapiens* kelch-like 33 (*Drosophila*), mRNA (cDNA clone | kelch-like 33 (*Drosophila*) | KLHL33 | 312 |
| 7902685 | ENST00000411322 | ncrna:misc_RNA chromosome:NCBI36:1:85502567:85502673:1 gene:ENSG00000223254 | — | — | 313 |
| 8137219 | ENST00000343855 /// AL832660 /// NM_138434 | Uncharacterized protein C7orf29 gene:ENSG00000188707 /// *Homo sapiens* mRNA; cDNA DKFZp313D2012 (from clone DKFZp313D2012). /// *Homo sapiens* chromosome 7 open reading frame 29 (C7orf29), mRNA. | chromosome 7 open reading frame 29 | C7orf29 | 314 |
| 7927153 | ENST00000387115 /// ENST00000408541 | ncrna:snRNA_pseudogene chromosome:NCBI36:10:43157240:43157363:1 gene:ENSG00000209850 /// ncrna:snRNA chromosome:NCBI36:10:43157240:43157364:1 gene:ENSG00000221468 | — | — | 315 |
| 7919572 | ENST00000386002 | ncrna:tRNA_pseudogene chromosome:NCBI36:1:147478572:147478645:−1 gene:ENSG00000208737 | — | — | 316 |

TABLE E-continued

| Probe Set ID | Transcript ID | Transcript Description | Gene Title | Gene Symbol | |
|---|---|---|---|---|---|
| 8073544 | hsa-mir-33a /// hsa-mir-33a | MI0000091 *Homo sapiens* miR-33a stem-loop /// MI0000091 *Homo sapiens* miR-33a stem-loop | — | — | 317 |
| 8090091 | ENST00000383657 /// BC049369 /// NM_198402 | Protein-tyrosine phosphatase-like member B gene:ENSG00000206527 /// *Homo sapiens* protein tyrosine phosphatase-like (proline instead of catalytic arginine), member b, mRNA (cDNA clone MGC:57203 IMAGE:5286864), complete cds. /// *Homo sapiens* protein tyrosine phosphatase-like (proline instead of catalytic arginine), member b (PTPLB), mRNA. | protein tyrosine phosphatase-like (proline instead of catalytic arginine), member b | PTPLB | 318 |
| 8045889 | ENST00000263635 /// AK128859 /// NM_033394 | Isoform 1 of Protein TANC1 gene:ENSG00000115183 /// *Homo sapiens* cDNA FLJ46667 fis, clone TRACH3007689. /// *Homo sapiens* tetratricopeptide repeat, ankyrin repeat and coiled-coil containing 1 (TANC1), mRNA. | tetratricopeptide repeat, ankyrin repeat and coiled-coil containing 1 | TANC1 | 319 |
| 7974689 | ENST00000395151 /// ENST00000335867 /// ENST00000395153 /// AF251079 /// NM_001079520 /// NM_016651 | 60 kDa protein gene:ENSG00000165617 /// Dapper homolog 1 gene:ENSG00000165617 /// dapper 1 isoform 2 gene:ENSG00000165617 /// *Homo sapiens* heptacellular carcinoma novel gene-3 protein mRNA, complete cds. /// *Homo sapiens* dapper, antagonist of beta-catenin, homolog 1 (*Xenopus laevis*) (DACT1), transcript variant 2, mRNA. /// *Homo sapiens* dapper, antagonist of beta-catenin, homolog 1 (*Xenopus laevis*) (DACT1), transcript variant 1, mRNA. | dapper, antagonist of beta-catenin, homolog 1 (*Xenopus laevis*) | DACT1 | 320 |
| 8160040 | ENST00000346816 /// ENST00000381196 /// ENST00000356435 /// ENST00000358503 /// ENST00000360074 /// ENST00000397617 /// ENST00000397611 /// ENST00000355233 /// ENST00000397606 /// AB211400 /// NM_130393 /// NM_130392 /// NM_130391 /// NM_002839 /// NM_001040712 | Isoform 3 of Receptor-type tyrosine-protein phosphatase delta gene:ENSG00000153707 /// Isoform 1 of Receptor-type tyrosine-protein phosphatase delta gene:ENSG00000153707 /// Isoform 1 of Receptor-type tyrosine-protein phosphatase delta gene:ENSG00000153707 /// 214 kDa protein gene:ENSG00000153707 /// Protein tyrosine phosphatase receptor type D gene:ENSG00000153707 /// 215 kDa protein gene:ENSG00000153707 /// 170 kDa protein gene:ENSG00000153707 /// PTPRD protein gene:ENSG00000153707 /// PTPRD protein gene:ENSG00000153707 /// *Homo sapiens* PTPRD mRNA for protein tyrosine phosphatase receptor type D, complete cds. /// *Homo sapiens* protein tyrosine phosphatase, receptor type, D (PTPRD), transcript variant 4, mRNA. /// *Homo sapiens* protein tyrosine phosphatase, receptor type, D (PTPRD), transcript variant 3, mRNA. /// *Homo sapiens* protein tyrosine phosphatase, receptor type, D (PTPRD), transcript variant 2, mRNA. /// *Homo sapiens* protein tyrosine phosphatase, receptor type, D (PTPRD), transcript | protein tyrosine phosphatase, receptor type, D | PTPRD | 321 |

TABLE E-continued

| Probe Set ID | Transcript ID | Transcript Description | Gene Title | Gene Symbol | |
|---|---|---|---|---|---|
| | | variant 1, mRNA. /// Homo sapiens protein tyrosine phosphatase, receptor type, D (PTPRD), transcript variant 5, mRNA. | | | |
| 8142878 | AF503918 | Homo sapiens CDC26 subunit of anaphase promoting complex (CDC26) mRNA, complete cds. | cell division cycle 26 homolog (S. cerevisiae) | CDC26 | 322 |
| 8065603 | BC101556 /// NR_002781 | Homo sapiens TSPY-like 3 (pseudogene), mRNA (cDNA clone MGC:126605 IMAGE:8069062), complete cds. /// Homo sapiens TSPY-like 3 (pseudogene) (TSPYL3), non-coding RNA. | TSPY-like 3 (pseudogene) | TSPYL3 | 323 |
| 8104781 | ENST00000330120 /// D88437 /// NM_016568 | Relaxin-3 receptor 1 gene:ENSG00000182631 /// Homo sapiens mRNA for G-protein coupled receptor SALPR, complete cds. /// Homo sapiens relaxin/insulin-like family peptide receptor 3 (RXFP3), mRNA. | relaxin/insulin-like family peptide receptor 3 | RXFP3 | 324 |
| 7959012 | ENST00000410526 /// ENST00000386460 | ncrna:misc_RNA chromosome:NCBI36:12:114639906:114640199:1 gene:ENSG00000222458 /// ncrna:scRNA_pseudogene chromosome:NCBI36:12:114639907:114640200:1 gene:ENSG00000209195 | — | — | 325 |
| 7954692 | ENST00000313737 /// AK023286 | Putative uncharacterized protein FLJ13224 gene:ENSG00000177340 /// Homo sapiens cDNA FLJ13224 fis, clone OVARC1000008. | hypothetical protein FLJ13224 | FLJ13224 | 326 |
| 7951038 | AK128061 /// NR_002973 | Homo sapiens cDNA FLJ46181 fis, clone TESTI4004210. /// Homo sapiens small nucleolar RNA, H/ACA box 40 (SNORA40), non-coding RNA. | TATA box binding protein (TBP)-associated factor, RNA polymerase I, D, 41 kDa /// small nucleolar RNA, H/ACA box 40 | TAF1D /// SNORA40 | 327 |
| 8169984 | ENST00000370796 /// ENST00000298556 /// M31642 /// NM_000194 | Putative uncharacterized protein HPRT1 gene:ENSG00000165704 /// Hypoxanthine-guanine phosphoribosyltransferase gene:ENSG00000165704 /// Homo sapiens hypoxanthine phosphoribosyltransferase 1 (HPRT1) mRNA, complete cds. /// Homo sapiens hypoxanthine phosphoribosyltransferase 1 (HPRT1), mRNA. | hypoxanthine phosphoribosyl-transferase 1 | HPRT1 | 328 |
| 7933204 | ENST00000298295 /// AB022718 /// NM_007021 | Protein DEPP gene:ENSG00000165507 /// Homo sapiens mRNA for DEPP (decidual protein induced by progesterone), complete cds. /// Homo sapiens chromosome 10 open reading frame 10 (C10orf10), mRNA. | chromosome 10 open reading frame 10 | C10orf10 | 329 |
| 7953747 | ENST00000364910 | ncrna:snRNA chromosome:NCBI36:12:8528609:8528715:1 gene:ENSG00000201780 | — | — | 330 |
| 8175256 | uc004exm.1 /// GENSCAN00000003290 /// BC007360 /// XM_001715787 /// XM_001128419 /// XM_001715872 | /// cdna:Genscan chromosome:NCBI36:X:133504408:133568038:−1 /// Homo sapiens hypothetical protein MGC16121, mRNA (cDNA clone IMAGE:3627113), complete cds. /// PREDICTED: Homo sapiens hypothetical protein MGC16121 (MGC16121), mRNA. /// PREDICTED: Homo sapiens hypothetical protein MGC16121 (MGC16121), mRNA. /// PREDICTED: Homo sapiens hypothetical protein MGC16121 (MGC16121), mRNA. | hypothetical protein MGC16121 | MGC16121 | 331 |

TABLE E-continued

| Probe Set ID | Transcript ID | Transcript Description | Gene Title | Gene Symbol | |
|---|---|---|---|---|---|
| 8180344 | — | — | — | — | 332 |
| 8013517 | ENST00000387217 | ncrna:Mt_tRNA_pseudogene chromosome:NCBI36:17:21942958:21943026:−1 gene:ENSG00000209952 | — | — | 333 |
| 8155802 | ENST00000376993 /// ENST00000376989 /// ENST00000358399 /// ENST00000238018 /// AF019638 /// NM_004293 | Guanine deaminase gene:ENSG00000119125 /// Guanine deaminase gene:ENSG00000119125 /// Guanine aminohydrolase gene:ENSG00000119125 /// cDNA FLJ60569, highly similar to Guanine deaminase gene:ENSG00000119125 /// Homo sapiens nedasin s-form mRNA, complete cds. /// Homo sapiens guanine deaminase (GDA), mRNA. | guanine deaminase | GDA | 334 |
| 8114468 | NR_002913 | Homo sapiens small nucleolar RNA, C/D box 63 (SNORD63), non-coding RNA. | small nucleolar RNA, C/D box 63 | SNORD63 | 335 |
| 8140398 | ENST00000307630 /// BC020963 /// NM_012479 | 14-3-3 protein gamma gene:ENSG00000170027 /// Homo sapiens tyrosine 3-monooxygenase/tryptophan 5-monooxygenase activation protein, gamma polypeptide, mRNA (cDNA clone MGC:8908 IMAGE:3915246), complete cds. /// Homo sapiens tyrosine 3-monooxygenase/tryptophan 5-monooxygenase activation protein, gamma polypeptide (YWHAG), mRNA. | tyrosine 3-monooxygenase/ tryptophan 5-monooxygenase activation protein, gamma polypeptide | YWHAG | 336 |
| 7982000 | NR_003340 | Homo sapiens small nucleolar RNA, C/D box 116-26 (SNORD116-26), non-coding RNA. | small nuclear ribonucleoprotein polypeptide N /// small nucleolar RNA, C/D box 116-26 | SNRPN /// SNORD116-26 | 337 |
| 8141150 | ENST00000394309 /// ENST00000175506 /// ENST00000394308 /// BC008723 /// NM_133436 /// NM_001673 /// NM_183356 | Asparagine synthetase [glutamine-hydrolyzing] gene:ENSG00000070669 /// Asparagine synthetase [glutamine-hydrolyzing] gene:ENSG00000070669 /// Asparagine synthetase [glutamine-hydrolyzing] gene:ENSG00000070669 /// Homo sapiens asparagine synthetase, mRNA (cDNA clone MGC:8639 IMAGE:2961551), complete cds. /// Homo sapiens asparagine synthetase (ASNS), transcript variant 1, mRNA. /// Homo sapiens asparagine synthetase (ASNS), transcript variant 2, mRNA. /// Homo sapiens asparagine synthetase (ASNS), transcript variant 3, mRNA. | asparagine synthetase | ASNS | 338 |
| 8055265 | ENST00000385636 | ncrna:Mt_tRNA_pseudogene chromosome:NCBI36:2:131846208:131846265:−1 gene:ENSG00000208371 | — | — | 339 |
| 8105607 | ENST00000389074 | UPF0514 membrane protein FAM159B gene:ENSG00000145642 | — | — | 340 |
| 8099130 | ENST00000363891 | ncrna:misc_RNA chromosome:NCBI36:4:4973381:4973692:−1 gene:ENSG00000200761 | — | — | 341 |
| 8015456 | ENST00000319121 /// BC034470 /// NM_018143 | Kelch-like protein 11 gene:ENSG00000178502 /// Homo sapiens kelch-like 11 (Drosophila), mRNA (cDNA clone MGC:26174 IMAGE:4822768), complete cds. /// Homo sapiens kelch-like 11 (Drosophila) (KLHL11), mRNA. | kelch-like 11 (Drosophila) | KLHL11 | 342 |

TABLE E-continued

| Probe Set ID | Transcript ID | Transcript Description | Gene Title | Gene Symbol | |
|---|---|---|---|---|---|
| 8028332 | ENST00000263372 /// AF117708 /// NM_004823 | Isoform 1 of Potassium channel subfamily K member 6 gene:ENSG00000099337 /// Homo sapiens tandem pore domain potassium channel TWIK-2 (KCNK6) mRNA, complete cds. /// Homo sapiens potassium channel, subfamily K, member 6 (KCNK6), mRNA. | potassium channel, subfamily K, member 6 | KCNK6 | 343 |
| 7947147 | ENST00000354193 /// AL833119 /// NM_148893 | Small VCP/p97-interacting protein gene:ENSG00000198168 /// Homo sapiens mRNA; cDNA DKFZp313A2432 (from clone DKFZp313A2432). /// Homo sapiens small VCP/p97-interacting protein (SVIP), mRNA. | small VCP/p97-interacting protein | SVIP | 344 |
| 7961198 | ENST00000023165 /// ENST00000341141 /// AK296103 /// NM_006611 | killer cell lectin-like receptor subfamily A, member 1 gene:ENSG00000021602 /// KLRA1 gene:ENSG00000021602 /// Homo sapiens cDNA FLJ59270 complete cds, highly similar to Homo sapiens killer cell lectin-like receptor subfamily A, member 1 (KLRA1), mRNA. /// Homo sapiens killer cell lectin-like receptor subfamily A, member 1 (KLRA1), mRNA. | killer cell lectin-like receptor subfamily A, member 1 | KLRA1 | 345 |
| 7957008 | ENST00000266679 /// ENST00000351671 /// BC000714 /// NM_007007 | Isoform 2 of Cleavage and polyadenylation specificity factor subunit 6 gene:ENSG00000111605 /// Isoform 1 of Cleavage and polyadenylation specificity factor subunit 6 gene:ENSG00000111605 /// Homo sapiens cleavage and polyadenylation specific factor 6, 68 kDa, mRNA (cDNA clone MGC:1242 IMAGE:3506481), complete cds. /// Homo sapiens cleavage and polyadenylation specific factor 6, 68 kDa (CPSF6), mRNA. | cleavage and polyadenylation specific factor 6, 68 kDa | CPSF6 | 346 |
| 8046790 | ENST00000384449 | ncrna:snRNA chromosome:NCBI36:2:183446814:183446920:1 gene:ENSG00000207178 | — | — | 347 |
| 8049375 | ENST00000389758 /// ENST00000396517 /// ENST00000327506 | similar to hCG2012694 gene:ENSG00000185038 /// similar to hCG2012694 gene:ENSG00000185038 /// similar to hCG2012694 gene:ENSG00000185038 | — | — | 348 |
| 8122732 | GENSCAN00000041083 /// ENST00000309074 | cdna:Genscan chromosome:NCBI36:6:150340754:150341242:1 /// cdna:pseudogene chromosome:NCBI36:6:150340754:150341242:1 gene:ENSG00000173909 | — | — | 349 |
| 7907024 | ENST00000367876 /// ENST00000367875 /// AB040946 /// NM_017542 | Pogo transposable element with KRAB domain gene:ENSG00000143157 /// Pogo transposable element with KRAB domain gene:ENSG00000143157 /// Homo sapiens mRNA for KIAA1513 protein, partial cds. /// Homo sapiens pogo transposable element with KRAB domain (POGK), mRNA. | pogo transposable element with KRAB domain | POGK | 350 |
| 8161774 | ENST00000376870 /// ENST00000360774 /// ENST00000361255 /// ENST00000376872 /// ENST00000376871 /// ENST00000376864 /// | Isoform M6-kinase 3 of Transient receptor potential cation channel subfamily M member 6 gene:ENSG00000119121 /// Isoform TRPM6a of Transient receptor potential cation channel | transient receptor potential cation channel, subfamily M, member 6 | TRPM6 | 351 |

TABLE E-continued

| Probe Set ID | Transcript ID | Transcript Description | Gene Title | Gene Symbol | |
|---|---|---|---|---|---|
| | ENST00000312449 /// ENST00000359047 /// AF350881 /// NM_017662 | subfamily M member 6 gene:ENSG00000119121 /// Putative uncharacterized protein TRPM6 gene:ENSG00000119121 /// Isoform M6-kinase 1 of Transient receptor potential cation channel subfamily M member 6 gene:ENSG00000119121 /// Isoform M6-kinase 2 of Transient receptor potential cation channel subfamily M member 6 gene:ENSG00000119121 /// Isoform TRPM6t of Transient receptor potential cation channel subfamily M member 6 gene:ENSG00000119121 /// Isoform TRPM6t of Transient receptor potential cation channel subfamily M member 6 gene:ENSG00000119121 /// Transient receptor potential cation channel, subfamily M, member 6, isoform CRAJ gene:ENSG00000119121 /// *Homo sapiens* channel kinase 2 (CHAK2) mRNA, complete cds. /// *Homo sapiens* transient receptor potential cation channel, subfamily M, member 6 (TRPM6), mRNA. | | | |
| 8157144 | ENST00000322940 /// ENST00000374621 /// ENST00000374624 /// BC015795 /// NM_017832 | UPF0436 protein C9orf6 gene:ENSG00000119328 /// Putative uncharacterized protein C9orf6 (Fragment) gene:ENSG00000119328 /// 13 kDa protein gene:ENSG00000119328 /// *Homo sapiens* chromosome 9 open reading frame 6, mRNA (cDNA clone MGC:8859 IMAGE:3910513), complete cds. /// *Homo sapiens* chromosome 9 open reading frame 6 (C9orf6), mRNA. | chromosome 9 open reading frame 6 | C9orf6 | 352 |
| 8018377 | ENST00000411285 /// ENST00000388598 | ncrna:snRNA chromosome:NCBI36:17:70916762:70916860:-1 gene:ENSG00000223217 /// ncrna:snRNA_pseudogene chromosome:NCBI36:17:70916768:70916864:-1 gene:ENSG00000211333 | — | — | 353 |
| 8146564 | ENST00000262646 /// ENST00000396697 /// ENST00000396696 /// BC008929 /// NM_002865 | Ras-related protein Rab-2A gene:ENSG00000104388 /// 24 kDa protein gene:ENSG00000104388 /// Putative uncharacterized protein RAB2A gene:ENSG00000104388 /// *Homo sapiens* RAB2A, member RAS oncogene family, mRNA (cDNA clone MGC:1656 IMAGE:2966694), complete cds. /// *Homo sapiens* RAB2A, member RAS oncogene family (RAB2A), mRNA. | RAB2A, member RAS oncogene family | RAB2A | 354 |
| 7957298 | ENST00000266692 /// ENST00000228327 /// ENST00000397909 /// ENST00000378640 /// BC017667 /// NM_014903 | Isoform 3 of Neuron navigator 3 gene:ENSG00000067798 /// Isoform 1 of Neuron navigator 3 gene:ENSG00000067798 /// Isoform 2 of Neuron navigator 3 gene:ENSG00000067798 /// 253 kDa protein gene:ENSG00000067798 /// *Homo sapiens* neuron navigator 3, mRNA (cDNA clone IMAGE:3914378), partial cds. /// *Homo sapiens* neuron navigator 3 (NAV3), mRNA. | neuron navigator 3 | NAV3 | 355 |

TABLE E-continued

| Probe Set ID | Transcript ID | Transcript Description | Gene Title | Gene Symbol | |
|---|---|---|---|---|---|
| 8091118 | — | — | — | — | 356 |
| 8107909 | ENST00000200652 /// BC028313 /// NM_003059 | Solute carrier family 22 member 4 gene:ENSG00000197208 /// Homo sapiens solute carrier family 22 (organic cation/ergothioneine transporter), member 4, mRNA (cDNA clone MGC:34546 IMAGE:5186192), complete cds. /// Homo sapiens solute carrier family 22 (organic cation/ergothioneine transporter), member 4 (SLC22A4), mRNA. | solute carrier family 22 (organic cation/ergothioneine transporter), member 4 | SLC22A4 | 357 |
| 8101723 | ENST00000323061 /// BC104883 /// NM_153757 | Nucleosome assembly protein 1-like 5 gene:ENSG00000177432 /// Homo sapiens nucleosome assembly protein 1-like 5, mRNA (cDNA clone MGC:132543 IMAGE:8143886), complete cds. /// Homo sapiens nucleosome assembly protein 1-like 5 (NAP1L5), mRNA. | nucleosome assembly protein 1-like 5 | NAP1L5 | 358 |
| 8053311 | ENST00000363618 | ncrna:misc_RNA chromosome:NCBI36:2:76525713:76526044:−1 gene:ENSG00000200488 | — | — | 359 |
| 8054364 | ENST00000393359 /// ENST00000258449 /// BC020548 /// NM_004257 | Transforming growth factor-beta receptor-associated protein 1 gene:ENSG00000135966 /// Transforming growth factor-beta receptor-associated protein 1 gene:ENSG00000135966 /// Homo sapiens transforming growth factor, beta receptor associated protein 1, mRNA (cDNA clone MGC:21319 IMAGE:4420120), complete cds. /// Homo sapiens transforming growth factor, beta receptor associated protein 1 (TGFBRAP1), mRNA. | transforming growth factor, beta receptor associated protein 1 | TGFBRAP1 | 360 |
| 7938295 | ENST00000314138 /// NM_000990 | 60S ribosomal protein L27a gene:ENSG00000166441 /// Homo sapiens ribosomal protein L27a (RPL27A), mRNA. | ribosomal protein L27a | RPL27A | 361 |
| 7995267 | ENST00000315486 /// ENST00000341305 /// ENST00000398682 /// ENST00000354614 /// ENST00000398680 /// ENST00000398667 /// ENST00000398666 /// ENST00000360260 /// ENST00000398664 /// ENST00000380147 /// ENST00000380148 /// AB023508 /// NM_016212 /// NM_001099687 | Isoform 1 of TP53-target gene 3 protein gene:ENSG00000180598 /// Isoform 2 of TP53-target gene 3 protein gene:ENSG00000180598 /// Isoform 2 of TP53-target gene 3 protein gene:ENSG00000183632 /// Isoform 3 of TP53-target gene 3 protein gene:ENSG00000183632 /// Isoform 1 of TP53-target gene 3 protein gene:ENSG00000183632 /// Isoform 2 of TP53-target gene 3 protein gene:ENSG00000205457 /// Isoform 1 of TP53-target gene 3 protein gene:ENSG00000205457 /// Isoform 3 of TP53-target gene 3 protein gene:ENSG00000205457 /// Isoform 2 of TP53-target gene 3 protein gene:ENSG00000205456 /// Isoform 1 of TP53-target gene 3 protein gene:ENSG00000205456 /// Isoform 3 of TP53-target gene 3 protein gene:ENSG00000205456 /// Homo sapiens mRNA for TP53TG3b, complete cds. /// Homo sapiens TP53 target 3 (TP53TG3), mRNA. /// Homo sapiens similar to TP53TG3 protein (LOC729355), mRNA. | TP53 target 3 /// similar to TP53TG3 protein | TP53TG3 /// LOC729355 | 362 |
| 8032465 | ENST00000300961 /// BC021201 /// NM_144616 | Junctional sarcoplasmic reticulum protein 1 gene:ENSG00000167476 /// Homo sapiens junctional sarcoplasmic reticulum protein 1, mRNA (cDNA clone MGC:13120 | junctional sarcoplasmic reticulum protein 1 | JSRP1 | 363 |

TABLE E-continued

| Probe Set ID | Transcript ID | Transcript Description | Gene Title | Gene Symbol | |
|---|---|---|---|---|---|
| | | IMAGE:4106867), complete cds. /// Homo sapiens junctional sarcoplasmic reticulum protein 1 (JSRP1), mRNA. | | | |
| 8167953 | ENST00000411174 /// ENST00000388411 | ncrna:misc_RNA chromosome:NCBI36:X:63347296:63347591:1 gene:ENSG00000223106 /// ncrna:scRNA_pseudogene chromosome:NCBI36:X:63347296:63347593:1 gene:ENSG00000211146 | — | — | 364 |
| 8102643 | ENST00000274026 /// AK291931 /// NM_001237 | Cyclin-A2 gene:ENSG00000145386 /// Homo sapiens cDNA FLJ77347 complete cds, highly similar to Homo sapiens cyclin A2 (CCNA2), mRNA. /// Homo sapiens cyclin A2 (CCNA2), mRNA. | cyclin A2 | CCNA2 | 365 |
| 7897960 | ENST00000332530 /// ENST00000359318 /// NM_001103169 /// NM_001103170 | arylacetamide deacetylase-like 3 isoform 2 gene:ENSG00000188984 /// Arylacetamide deacetylase-like 3 gene:ENSG00000188984 /// Homo sapiens arylacetamide deacetylase-like 3 (AADACL3), transcript variant 2, mRNA. /// Homo sapiens arylacetamide deacetylase-like 3 (AADACL3), transcript variant 1, mRNA. | arylacetamide deacetylase-like 3 | AADACL3 | 366 |
| 8055424 | ENST00000363794 | ncrna:misc_RNA chromosome:NCBI36:2:136284209:136284319:-1 gene:ENSG00000200664 | — | — | 367 |
| 8097704 | ENST00000296582 /// BC046128 /// NM_018241 | Isoform 1 of Transmembrane protein 184C gene:ENSG00000164168 /// Homo sapiens transmembrane protein 184C, mRNA (cDNA clone MGC:57601 IMAGE:5750613), complete cds. /// Homo sapiens transmembrane protein 184C (TMEM184C), mRNA. | transmembrane protein 184C | TMEM184C | 368 |
| 8106820 | ENST00000399107 /// AK295434 /// NM_006467 | DNA-directed RNA polymerase /// subunit G gene:ENSG00000113356 /// Homo sapiens cDNA FLJ60555 complete cds, highly similar to DNA-directed RNA polymerase /// subunit G (EC2.7.7.6). /// Homo sapiens polymerase (RNA) /// (DNA directed) polypeptide G (32kD) (POLR3G), mRNA. | polymerase (RNA) /// (DNA directed) polypeptide G (32kD) | POLR3G | 369 |
| 7992782 | ENST00000396927 /// AK091002 /// AY390431 /// NM_020982 | Claudin-9 gene:ENSG00000213937 /// Homo sapiens cDNA FLJ33683 fis, clone BRAWH2002623, highly similar to CLAUDIN-9. /// Homo sapiens HCTP4-binding protein mRNA, complete cds. /// Homo sapiens claudin 9 (CLDN9), mRNA. | claudin 9 /// HCTP4-binding protein | CLDN9 /// LOC100134406 | 370 |
| 8089830 | ENST00000295628 /// NM_001099678 | Leucine-rich repeat-containing protein 58 gene:ENSG00000163428 /// Homo sapiens leucine rich repeat containing 58 (LRRC58), mRNA. | leucine rich repeat containing 58 | LRRC58 | 371 |
| 7998629 | GENSCAN00000001581 | cdna:Genscan chromosome:NCBI36:16:1831818:1893847:-1 | — | — | 372 |
| 7943736 | hsa-mir-34b /// hsa-mir-34b | MI0000742 Homo sapiens miR-34b stem-loop /// MI0000742 Homo sapiens miR-34b stem-loop | — | — | 373 |

TABLE E-continued

| Probe Set ID | Transcript ID | Transcript Description | Gene Title | Gene Symbol | |
|---|---|---|---|---|---|
| 7921356 | ENST00000392265 /// ENST00000314902 /// NM_001004476 | Seven transmembrane helix receptor gene:ENSG00000180708 /// Olfactory receptor 10K2 gene:ENSG00000180708 /// Homo sapiens olfactory receptor, family 10, subfamily K, member 2 (OR10K2), mRNA. | olfactory receptor, family 10, subfamily K, member 2 | OR10K2 | 374 |
| 8052413 | GENSCAN00000048378 /// ENST00000404638 | cdna:Genscan chromosome:NCBI36:2:60815529:60816357:−1 /// cdna:pseudogene chromosome:NCBI36:2:60815529:60816366:−1 gene:ENSG00000217407 | — | — | 375 |
| 7961865 | ENST00000256078 /// ENST00000311936 /// ENST00000395977 /// M54968 /// NM_004985 /// NM_033360 | Isoform 2A of GTPase KRas gene:ENSG00000133703 /// Isoform 2B of GTPase KRas gene:ENSG00000133703 /// Isoform 2A of GTPase KRas gene:ENSG00000133703 /// Homo sapiens K-ras oncogene protein (KRAS) mRNA, complete cds. /// Homo sapiens v-Ki-ras2 Kirsten rat sarcoma viral oncogene homolog (KRAS), transcript variant b, mRNA. /// Homo sapiens v-Ki-ras2 Kirsten rat sarcoma viral oncogene homolog (KRAS), transcript variant a, mRNA. | v-Ki-ras2 Kirsten rat sarcoma viral oncogene homolog | KRAS | 376 |
| 8142019 | ENST00000297431 /// AK302122 /// NM_002553 /// NM_181747 | Origin recognition complex subunit 5 gene:ENSG00000164815 /// Homo sapiens cDNA FLJ53851 complete cds, highly similar to Origin recognition complex subunit 5. /// Homo sapiens origin recognition complex, subunit 5-like (yeast) (ORC5L), transcript variant 1, mRNA. /// Homo sapiens origin recognition complex, subunit 5-like (yeast) (ORC5L), transcript variant 2, mRNA. | origin recognition complex, subunit 5-like (yeast) | ORC5L | 377 |
| 8009873 | ENST00000325720 /// AF418286 /// NR_003587 | cdna:known chromosome:NCBI36:17:71097148:71101765:1 gene:ENSG00000204326 /// Homo sapiens clone 1 myosin XVBP (MYO15B) pseudogene, partial sequence. /// Homo sapiens myosin XVB pseudogene (MYO15B) on chromosome 17. | myosin XVB pseudogene | MYO15B | 378 |
| 8149749 | ENST00000312584 /// AY358285 /// NM_003840 | Tumor necrosis factor receptor superfamily member 10D gene:ENSG00000173530 /// Homo sapiens clone DNA35663 DCR2-TNFR (UNQ251) mRNA, complete cds. /// Homo sapiens tumor necrosis factor receptor superfamily, member 10d, decoy with truncated death domain (TNFRSF10D), mRNA. | tumor necrosis factor receptor superfamily, member 10d, decoy with truncated death domain | TNFRSF10D | 379 |
| 7986665 | ENST00000337451 /// ENST00000359727 /// ENST00000398014 /// ENST00000398013 /// BC011775 /// NM_030922 /// NM_001008892 /// NM_001008894 /// NM_001008860 | Non-imprinted in Prader-Willi/Angelman syndrome region protein 2 gene:ENSG00000140157 /// non imprinted in Prader-Willi/Angelman syndrome 2 isoform b gene:ENSG00000140157 /// Non-imprinted in Prader-Willi/Angelman syndrome region protein 2 | non imprinted in Prader-Willi/Angelman syndrome 2 | NIPA2 | 380 |

TABLE E-continued

| Probe Set ID | Transcript ID | Transcript Description | Gene Title | Gene Symbol | |
|---|---|---|---|---|---|
| | | gene:ENSG00000140157 /// Non-imprinted in Prader-Willi/Angelman syndrome region protein 2 gene:ENSG00000140157 /// *Homo sapiens* non imprinted in Prader-Willi/Angelman syndrome 2, mRNA (cDNA clone MGC:19609 IMAGE:3640970), complete cds. /// *Homo sapiens* non imprinted in Prader-Willi/Angelman syndrome 2 (NIPA2), transcript variant 1, mRNA. /// *Homo sapiens* non imprinted in Prader-Willi/Angelman syndrome 2 (NIPA2), transcript variant 3, mRNA. /// *Homo sapiens* non imprinted in Prader-Willi/Angelman syndrome 2 (NIPA2), transcript variant 4, mRNA. /// *Homo sapiens* non imprinted in Prader-Willi/Angelman syndrome 2 (NIPA2), transcript variant 2, mRNA. | | | |
| 8163015 | ENST00000386231 /// ENST00000411190 | ncrna:scRNA_pseudogene chromosome:NCBI36:9:109613716:109614016:−1 gene:ENSG00000208966 /// ncrna:misc_RNA chromosome:NCBI36:9:109613719:109614016:−1 gene:ENSG00000223122 | — | — | 381 |
| 8007548 | AF143236 | *Homo sapiens* apoptosis related protein APR-2 mRNA, complete cds. | chromosome 17 open reading frame 88 | C17orf88 | 382 |
| 7923659 | ENST00000367188 /// BC065280 /// NM_032833 | Protein phosphatase 1 regulatory subunit 15B gene:ENSG00000158615 /// *Homo sapiens* protein phosphatase 1, regulatory (inhibitor) subunit 15B, mRNA (cDNA clone MGC:74824 IMAGE:6172811), complete cds. /// *Homo sapiens* protein phosphatase 1, regulatory (inhibitor) subunit 15B (PPP1R15B), mRNA. | protein phosphatase 1, regulatory (inhibitor) subunit 15B | PPP1R15B | 383 |
| 8001666 | ENST00000262506 /// M55268 /// NM_001896 | Casein kinase II subunit alpha' gene:ENSG00000070770 /// Human casein kinase II alpha' subunit mRNA, complete cds. /// *Homo sapiens* casein kinase 2, alpha prime polypeptide (CSNK2A2), mRNA. | casein kinase 2, alpha prime polypeptide | CSNK2A2 | 384 |
| 8155418 | ENST00000316269 /// AK125850 /// AL833349 | hypothetical protein gene:ENSG00000204831 /// *Homo sapiens* cDNA FLJ43862 fis, clone TESTI4007775. /// *Homo sapiens* mRNA; cDNA DKFZp686P0734 (from clone DKFZp686P0734). | hypothetical protein LOC100133036 /// family with sequence similarity 95, member B1 | LOC100133036 /// FAM95B1 | 385 |
| 7952046 | ENST00000278937 /// BC017774 /// NM_144765 /// NM_005797 | Myelin protein zero-like protein 2 gene:ENSG00000149573 /// *Homo sapiens* myelin protein zero-like 2, mRNA (cDNA clone MGC:22243 IMAGE:4692569), complete cds. /// *Homo sapiens* myelin protein zero-like 2 (MPZL2), transcript variant 2, mRNA. /// *Homo sapiens* myelin protein zero-like 2 (MPZL2), transcript variant 1, mRNA. | myelin protein zero-like 2 | MPZL2 | 386 |

TABLE E-continued

| Probe Set ID | Transcript ID | Transcript Description | Gene Title | Gene Symbol | |
|---|---|---|---|---|---|
| 8141843 | uc003vad.1 /// XM_001725218 /// XM_001718200 | /// PREDICTED:*Homo sapiens* similar to HSPC047 protein (LOC100134722), mRNA. /// PREDICTED:*Homo sapiens* similar to RAS p21 protein activator 4 (LOC100133005), mRNA. | similar to HSPC047 protein /// similar to RAS p21 protein activator 4 | LOC100134722 /// LOC100133005 | 387 |
| 8023175 | ENST00000256433 /// AK027108 /// NM_016097 | Immediate early response 3-interacting protein 1 gene:ENSG00000134049 /// *Homo sapiens* cDNA:FLJ23455 fis, clone HSI07063, highly similar to AF125100 *Homo sapiens* HSPC039 protein mRNA. /// *Homo sapiens* immediate early response 3 interacting protein 1 (IER3IP1), mRNA. | immediate early response 3 interacting protein 1 | IER3IP1 | 388 |
| 8072153 | ENST00000249064 /// BC053874 /// NM_173510 | Isoform 1 of Coiled-coil domain-containing protein 117 gene:ENSG00000159873 /// *Homo sapiens* coiled-coil domain containing 117, mRNA (cDNA clone MGC:61737 IMAGE:5531689), complete cds. /// *Homo sapiens* coiled-coil domain containing 117 (CCDC117), mRNA. | coiled-coil domain containing 117 | CCDC117 | 389 |
| 7928308 | ENST00000307365 /// BC007714 /// NM_019058 | DNA-damage-inducible transcript 4 protein gene:ENSG00000168209 /// *Homo sapiens* DNA-damage-inducible transcript 4, mRNA (cDNA clone MGC:12610 IMAGE:4302878), complete cds. /// *Homo sapiens* DNA-damage-inducible transcript 4 (DDIT4), mRNA. | DNA-damage-inducible transcript 4 | DDIT4 | 390 |
| 8108099 | ENST00000322887 /// ENST00000398844 /// ENST00000265341 /// AK304060 /// NM_021982 | Isoform 2 of Protein transport protein Sec24A gene:ENSG00000113615 /// Isoform 1 of Protein transport protein Sec24A gene:ENSG00000113615 /// cDNA FLJ61651, highly similar to Protein transport protein Sec24A gene:ENSG00000113615 /// *Homo sapiens* cDNA FLJ61651 complete cds, highly similar to Protein transport protein Sec24A. /// *Homo sapiens* SEC24 family, member A (*S. cerevisiae*) (SEC24A), mRNA. | SEC24 family, member A (*S. cerevisiae*) | SEC24A | 391 |

REFERENCES

1. Peiser, M., T. Tralau, J. Heidler, A. M. Api, J. H. Arts, D. A. Basketter, J. English, T. L. Diepgen, R. C. Fuhlbrigge, A. A. Gaspari, J. D. Johansen, A. T. Karlberg, I. Kimber, J. P. Lepoittevin, M. Liebsch, H. I. Maibach, S. F. Martin, H. F. Merk, T. Platzek, T. Rustemeyer, A. Schnuch, R. J. Vandebriel, I. R. White, and A. Luch. 2012. Allergic contact dermatitis: epidemiology, molecular mechanisms, in vitro methods and regulatory aspects. Current knowledge assembled at an international workshop at BfR, Germany. *Cellular and molecular life sciences: CMLS* 69: 763-781.
2. Martin, S. F. 2012. Allergic contact dermatitis: xenoinflammation of the skin. *Current opinion in immunology* 24: 720-729.
3. Martin, S. F. 2015. New concepts in cutaneous allergy. *Contact Dermatitis* 72: 2-10.
4. McFadden, J. P., P. Puangpet, D. A. Basketter, R. J. Dearman, and I. Kimber. 2013. Why does allergic contact dermatitis exist? *Br J Dermatol* 168: 692-699.
5. Thyssen, J. P., E. Gimenez-Arnau, J. P. Lepoittevin, T. Menne, A. Boman, and A. Schnuch. 2012. The critical review of methodologies and approaches to assess the inherent skin sensitization potential (skin allergies) of chemicals. Part I. Contact Dermatitis 66 Suppl 1: 11-24.
6. Reisinger, K., S. Hoffmann, N. Alépée, T. Ashikaga, J. Barroso, C. Elcombe, N. Gellatly, V. Galbiati, S. Gibbs, H. Groux, J. Hibatallah, D. Keller, P. Kern, M. Klaric, S. Kolle, J. Kuehnl, N. Lambrechts, M. Lindstedt, M. Millet, S. Martinozzi-Teissier, A. Natsch, D. Petersohn, I. Pike, H. Sakaguchi, A. Schepky, M. Tailhardat, M. Templier, E. van Vliet, and G. Maxwell. 2015. Systematic evaluation of non-animal test methods for skin sensitisation safety assessment. *Toxicology in Vitro* 29: 259-270.

7. Steiling, W. 2016. Safety Evaluation of Cosmetic Ingredients Regarding Their Skin Sensitization Potential. *Cosmetics* 3: 14.
8. Masterson, A. J., C. C. Sombroek, T. D. De Gruijl, Y. M. Graus, H. J. van der Vliet, S. M. Lougheed, A. J. van den Eertwegh, H. M. Pinedo, and R. J. Scheper. 2002. MUTZ-3, a human cell line model for the cytokine-induced differentiation of dendritic cells from CD34+ precursors. *Blood* 100: 701-703.
9. Johansson, H., A.-S. Albrekt, C. A. K. Borrebaeck, and M. Lindstedt. 2013. The GARD assay for assessment of chemical skin sensitizers. *Toxicology in Vitro* 27: 1163-1169.
10. Johansson, H., M. Lindstedt, A.-S. Albrekt, and C. A. Borrebaeck. 2011. A genomic biomarker signature can predict skin sensitizers using a cell-based in vitro alternative to animal tests. *BMC Genomics* 12: 1-19.
11. Geraghty, R. J., A. Capes-Davis, J. M. Davis, J. Downward, R. I. Freshney, I. Knezevic, R. Lovell-Badge, J. R. W. Masters, J. Meredith, G. N. Stacey, P. Thraves, and M. Vias. 2014. Guidelines for the use of cell lines in biomedical research. *British Journal of Cancer* 111: 1021-1046.
12. Dumont, J., D. Euwart, B. Mei, S. Estes, and R. Kshirsagar. 2015. Human cell lines for biopharmaceutical manufacturing: history, status, and future perspectives. *Critical Reviews in Biotechnology*: 1-13.
13. Kaur, G., and J. M. Dufour. 2012. Cell lines: Valuable tools or useless artifacts. *Spermatogenesis* 2: 1-5.
14. Hughes, P., D. Marshall, Y. Reid, H. Parkes, and C. Gelber. 2007. The costs of using unauthenticated, over-passaged cell lines: how much more data do we need? *BioTechniques* 43: 575, 577-578, 581-572 passim.
15. Team, R. C. 2015. R: A language and environment for statistical computing. {R Foundation for Statistical Computing.
16. Hennig, C. 2105. fpc: Flexible Procedures for Clustering.
17. McKenna, A., M. Hanna, E. Banks, A. Sivachenko, K. Cibulskis, A. Kernytsky, K. Garimella, D. Altshuler, S. Gabriel, M. Daly, and M. A. DePristo. 2010. The Genome Analysis Toolkit: a MapReduce framework for analyzing next-generation DNA sequencing data. *Genome Res* 20.
18. Van der Auwera, G. A., M. O. Carneiro, C. Hartl, R. Poplin, G. del Angel, A. Levy-Moonshine, T. Jordan, K. Shakir, D. Roazen, J. Thibault, E. Banks, K. V. Garimella, D. Altshuler, S. Gabriel, and M. A. DePristo. 2013. From FastQ data to high confidence variant calls: the Genome Analysis Toolkit best practices pipeline. *Current protocols in bioinformatics/editoral board, Andreas D. Baxevanis . . . [et al.]* 11: 11.10.11-11.10.33.
19. Cingolani, P., A. Platts, L. Wang Ie, M. Coon, T. Nguyen, L. Wang, S. J. Land, X. Lu, and D. M. Ruden. 2012. A program for annotating and predicting the effects of single nucleotide polymorphisms, SnpEff: SNPs in the genome of *Drosophila melanogaster* strain w1118; iso-2; iso-3. *Fly* 6: 80-92.
20. Cingolani, P., V. M. Patel, M. Coon, T. Nguyen, S. J. Land, D. M. Ruden, and X. Lu. 2012. Using *Drosophila melanogaster* as a Model for Genotoxic Chemical Mutational Studies with a New Program, SnpSift. *Frontiers in genetics* 3: 35.
21. Carson, A. R., E. N. Smith, H. Matsui, S. K. Brækkan, K. Jepsen, J.-B. Hansen, and K. A. Frazer. 2014. Effective filtering strategies to improve data quality from population-based whole exome sequencing studies. *BMC Bioinformatics* 15: 1-15.
22. Mi, H., A. Muruganujan, J. T. Casagrande, and P. D. Thomas. 2013. Large-scale gene function analysis with the PANTHER classification system. *Nat. Protocols* 8: 1551-1566.
23. Trapnell, C., L. Pachter, and S. L. Salzberg. 2009. TopHat: discovering splice junctions with RNA-Seq. *Bioinformatics* (Oxford, England) 25: 1105-1111.
24. Li, H., B. Handsaker, A. Wysoker, T. Fennell, J. Ruan, N. Homer, G. Marth, G. Abecasis, and R. Durbin. 2009. The Sequence Alignment/Map format and SAMtools. *Bioinformatics* (Oxford, England) 25: 2078-2079.
25. Anders, S., P. T. Pyl, and W. Huber. 2015. HTSeq—a Python framework to work with high-throughput sequencing data. *Bioinformatics* (Oxford, England) 31: 166-169.
26. Robinson, M. D., D. J. McCarthy, and G. K. Smyth. 2010. edgeR: a Bioconductor package for differential expression analysis of digital gene expression data. *Bioinformatics* (Oxford, England) 26: 139-140.
27. Love, M. I., W. Huber, and S. Anders. 2014. Moderated estimation of fold change and dispersion for RNA-Seq data with DESeq2. *bioRxiv*.
28. Tarca, A. L., S. Draghici, P. Khatri, S. S. Hassan, P. Mittal, J.-s. Kim, C. J. Kim, J. P. Kusanovic, and R. Romero. 2009. A novel signaling pathway impact analysis. *Bioinformatics* (Oxford, England) 25: 75-82.
29. Kanehisa, M., and S. Goto. 2000. KEGG: kyoto encyclopedia of genes and genomes. *Nucleic acids research* 28: 27-30.
30. Kanehisa, M., Y. Sato, M. Kawashima, M. Furumichi, and M. Tanabe. 2016. KEGG as a reference resource for gene and protein annotation. *Nucleic acids research* 44: D457-462.
31. Kwiecien, R., A. Kopp-Schneider, and M. Blettner. 2011. Concordance Analysis: Part 16 of a Series on Evaluation of Scientific Publications. *Deutsches Ärzteblatt International* 108: 515-521.
32. David Meyer, E. D., Kurt Hornik, Andreas Weingessel and Friedrich Leisch. 2015. e1071: Misc Functions of the Department of Statistics, Probability.
33. Haneke, K. E., R. R. Tice, B. L. Carson, B. H. Margolin, and W. S. Stokes. 2001. ICCVAM evaluation of the murine local lymph node assay. Data analyses completed by the National Toxicology Program Interagency Center for the Evaluation of Alternative Toxicological Methods. *Regul Toxicol Pharmacol* 34: 274-286.
34. Urbisch, D., A. Mehling, K. Guth, T. Ramirez, N. Honarvar, S. Kolle, R. Landsiedel, J. Jaworska, P. S. Kern, F. Gerberick, A. Natsch, R. Emter, T. Ashikaga, M. Miyazawa, and H. Sakaguchi. 2015. Assessing skin sensitization hazard in mice and men using non-animal test methods. *Regulatory Toxicology and Pharmacology* 71: 337-351.
35. Santegoets, S. J. A. M., A. J. Masterson, P. C. van der Sluis, S. M. Lougheed, D. M. Fluitsma, A. J. M. van den Eertwegh, H. M. Pinedo, R. J. Scheper, and T. D. de Gruijl. 2006. A CD34+ human cell line model of myeloid dendritic cell differentiation: evidence for a CD14+ CD11b+ Langerhans cell precursor. *Journal of Leukocyte Biology* 80: 1337-1344.
36. Kim, K. D., S.-C. Choi, Y.-W. Noh, J. W. Kim, S.-G. Paik, Y. Yang, K. I. Kim, and J.-S. Lim. 0000. Impaired responses of leukemic dendritic cells derived from a human myeloid cell line to LPS stimulation. *Exp Mol Med* 38: 72-84.

37. Rasaiyaah, J., M. Noursadeghi, P. Kellam, and B. Chain. 2009. Transcriptional and functional defects of dendritic cells derived from the MUTZ-3 leukaemia line. *Immunology* 127: 429-441.
38. Fanger, N. A., K. Wardwell, L. Shen, T. F. Tedder, and P. M. Guyre. 1996. Type I (CD64) and type II (CD32) Fc gamma receptor-mediated phagocytosis by human blood dendritic cells. *The Journal of Immunology* 157: 541-548.
39. Iwasaki, A., and R. Medzhitov. 2004. Toll-like receptor control of the adaptive immune responses. *Nat Immunol* 5: 987-995.
40. Medzhitov, R., P. Preston-Hurlburt, and C. A. Janeway. 1997. A human homologue of the *Drosophila* Toll protein signals activation of adaptive immunity. *Nature* 388: 394-397.
41. Takeda, K., and S. Akira. 2005. Toll-like receptors in innate immunity. *International Immunology* 17: 1-14.
42. Gadhoum, S. Z., and R. Sackstein. 2008. Lewis x/CD15 expression in human myeloid cell differentiation is regulated by sialidase activity. *Nature chemical biology* 4: 751-757.
43. The Genomes Project, C. 2015. A global reference for human genetic variation. *Nature* 526: 68-74.
44. Nugoli, M., P. Chuchana, J. Vendrell, B. Orsetti, L. Ursule, C. Nguyen, D. Birnbaum, E. J. Douzery, P. Cohen, and C. Theillet. 2003. Genetic variability in MCF-7 sublines: evidence of rapid genomic and RNA expression profile modifications. *BMC Cancer* 3: 1-12.
45. Ramsay, R. G., and T. J. Gonda. 2008. MYB function in normal and cancer cells. *Nature reviews. Cancer* 8: 523-534.
46. Logan, C. Y., and R. Nusse. 2004. The Wnt signaling pathway in development and disease. *Annual review of cell and developmental biology* 20: 781-810.
47. Nusse, R. 2008. Wnt signaling and stem cell control. *Cell research* 18: 523-527.
48. Polakis, P. 2000. Wnt signaling and cancer. *Genes & development* 14: 1837-1851.
49. Consortium, T. G. O. 2015. Gene Ontology Consortium: going forward. *Nucleic acids research* 43: D1049-D1056.
50. Pearson, G., F. Robinson, T. Beers Gibson, B. E. Xu, M. Karandikar, K. Berman, and M. H. Cobb. 2001. Mitogen-activated protein (MAP) kinase pathways: regulation and physiological functions. *Endocrine reviews* 22: 153-183.
51. Lawrence, T. 2009. The Nuclear Factor NF-κB Pathway in Inflammation. *Cold Spring Harbor Perspectives in Biology* 1: a001651.

The invention claimed is:

1. A non-naturally occurring dendritic-like myeloid leukaemia cell according to ATCC Patent Deposit Designation PTA-123875.

2. A cell culture comprising a population of cells according to claim 1.

* * * * *